United States Patent
Gege et al.

(10) Patent No.: US 9,458,104 B2
(45) Date of Patent: Oct. 4, 2016

(54) CARBOXAMIDE OR SULFONAMIDE SUBSTITUTED NITROGEN-CONTAINING 5-MEMBERED HETEROCYCLES AS MODULATORS FOR THE ORPHAN NUCLEAR RECEPTOR RORγ

(71) Applicant: PHENEX PHARMACEUTICALS AG, Ludwigshafen (DE)

(72) Inventors: Christian Gege, Ehingen (DE); Olaf Kinzel, Heidelberg (DE); Christoph Steeneck, Dossenheim (DE); Gerald Kleymann, Bad Salzuflen (DE); Thomas Hoffmann, Viernheim (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 0 days.

(21) Appl. No.: 14/419,468

(22) PCT Filed: May 29, 2013

(86) PCT No.: PCT/EP2013/001594
§ 371 (c)(1),
(2) Date: Feb. 3, 2015

(87) PCT Pub. No.: WO2014/023367
PCT Pub. Date: Feb. 13, 2014

(65) Prior Publication Data
US 2015/0344423 A1    Dec. 3, 2015

Related U.S. Application Data

(60) Provisional application No. 61/681,296, filed on Aug. 9, 2012.

(30) Foreign Application Priority Data

Aug. 9, 2012 (EP) .................... 12005789

(51) Int. Cl.

| | | |
|---|---|---|
| *C07D 231/14* | (2006.01) | |
| *C07D 207/34* | (2006.01) | |
| *C07D 403/04* | (2006.01) | |
| *C07D 403/06* | (2006.01) | |
| *C07D 403/12* | (2006.01) | |
| *C07D 405/12* | (2006.01) | |
| *C07D 405/14* | (2006.01) | |
| *C07D 409/12* | (2006.01) | |
| *C07D 401/06* | (2006.01) | |
| *C07D 491/107* | (2006.01) | |
| *C07D 495/10* | (2006.01) | |
| *C07D 413/12* | (2006.01) | |
| *C07D 401/04* | (2006.01) | |
| *C07D 405/04* | (2006.01) | |
| *C07D 249/10* | (2006.01) | |

(52) U.S. Cl.
CPC ........... *C07D 207/34* (2013.01); *C07D 231/14* (2013.01); *C07D 249/10* (2013.01); *C07D401/04* (2013.01); *C07D 401/06* (2013.01); *C07D 403/04* (2013.01); *C07D 403/06* (2013.01); *C07D 403/12* (2013.01); *C07D 405/04* (2013.01); *C07D 405/12* (2013.01); *C07D 405/14* (2013.01); *C07D 409/12* (2013.01); *C07D 413/12* (2013.01); *C07D 491/107* (2013.01); *C07D 495/10* (2013.01)

(58) Field of Classification Search
CPC   C07D 231/14; C07D 207/34; C07D 403/04; C07D 403/06; C07D 403/12
See application file for complete search history.

(56) References Cited

U.S. PATENT DOCUMENTS

| | | | |
|---|---|---|---|
| 5,776,954 | A | 7/1998 | de Laszlo et al. |
| 7,951,956 | B2 | 5/2011 | Urade et al. |
| 2004/0192667 | A1 | 9/2004 | Makriyannis et al. |
| 2005/0113283 | A1 | 5/2005 | Solow-Cordero et al. |
| 2006/0100208 | A1 | 5/2006 | Makriyannis et al. |
| 2006/0189591 | A1 | 8/2006 | Okayama et al. |
| 2012/0322837 | A1 | 12/2012 | Maeba et al. |
| 2014/0163001 | A1 | 6/2014 | Yamamoto et al. |
| 2014/0228409 | A1 | 8/2014 | Yamamoto et al. |

FOREIGN PATENT DOCUMENTS

| | | | |
|---|---|---|---|
| CA | 2736441 | A1 | 10/2012 |
| CN | 101544631 | A | 9/2009 |
| EP | 0908456 | B1 | 12/2003 |
| EP | 1433788 | A1 | 6/2004 |
| EP | 1 946 778 | A1 | 7/2008 |
| KR | 2009044924 | A | 5/2009 |
| TW | 201130802 | A1 | 9/2011 |
| WO | WO 91/19708 | A1 | 12/1991 |
| WO | WO 96/01254 | A1 | 1/1996 |
| WO | WO 00/24739 | A1 | 5/2000 |
| WO | WO 01/29007 | A1 | 4/2001 |
| WO | WO 01/64669 | A1 | 9/2001 |
| WO | WO 03/002567 | A1 | 1/2003 |
| WO | WO 03/020217 | A2 | 3/2003 |
| WO | WO 03/037335 | A1 | 5/2003 |
| WO | WO 2004/010945 | A2 | 2/2004 |
| WO | WO 2004/014368 | A1 | 2/2004 |
| WO | WO 2004/060870 | A1 | 7/2004 |
| WO | WO 2004/092140 | A1 | 10/2004 |
| WO | WO 2004/094407 | A1 | 11/2004 |
| WO | WO 2005/016929 | A1 | 2/2005 |
| WO | WO 2005/108393 | A1 | 11/2005 |
| WO | WO 2006/004984 | A1 | 1/2006 |
| WO | WO 2006/021881 | A2 | 3/2006 |
| WO | WO 2006/125211 | A1 | 11/2006 |
| WO | WO 2006/133926 | A1 | 12/2006 |
| WO | WO 2007/002559 | A1 | 1/2007 |
| WO | WO 2007/007778 | A1 | 1/2007 |
| WO | WO 2007/024744 | A2 | 3/2007 |
| WO | WO 2008/017932 | A2 | 2/2008 |
| WO | WO 2008/075012 | A1 | 6/2008 |
| WO | WO 2008/075013 | A1 | 6/2008 |
| WO | WO 2008/092942 | A2 | 8/2008 |
| WO | WO 2009/011850 | A2 | 1/2009 |
| WO | WO 2009/037247 | A1 | 3/2009 |
| WO | WO 2009/080227 | A2 | 7/2009 |
| WO | WO 2009/097486 | A1 | 8/2009 |
| WO | WO 2010/038948 | A2 | 4/2010 |
| WO | WO 2010/048559 | A2 | 4/2010 |
| WO | WO 2010/075376 | A2 | 7/2010 |
| WO | WO 2011/020615 | A1 | 2/2011 |
| WO | WO 2011/042477 | A1 | 4/2011 |
| WO | WO 2011/092187 | A1 | 8/2011 |

| | | |
|---|---|---|
| WO | WO 2011/107248 A1 | 9/2011 |
| WO | WO 2011/112263 A1 | 9/2011 |
| WO | WO 2011/112264 A1 | 9/2011 |
| WO | WO 2011/115892 A1 | 9/2011 |
| WO | WO 2012/027965 A1 | 3/2012 |
| WO | WO 2012/028100 A1 | 3/2012 |
| WO | WO 2012/064631 A1 | 5/2012 |
| WO | WO 2012/064744 A2 | 5/2012 |
| WO | WO 2012/074547 A2 | 6/2012 |
| WO | WO 2012/100732 A1 | 8/2012 |
| WO | WO 2012/100734 A1 | 8/2012 |
| WO | WO 2012/101261 A1 | 8/2012 |
| WO | WO 2012/101263 A1 | 8/2012 |
| WO | WO 2012/106995 A1 | 8/2012 |
| WO | WO 2012/139775 A1 | 10/2012 |
| WO | WO 2012/139930 A1 | 10/2012 |
| WO | WO 2012/145254 A2 | 10/2012 |
| WO | WO 2012/147916 A1 | 11/2012 |
| WO | WO 2012/158784 A2 | 11/2012 |
| WO | WO 2013/000869 A1 | 1/2013 |
| WO | WO 2013/000871 A1 | 1/2013 |
| WO | WO 2013/014204 A2 | 1/2013 |
| WO | WO 2013/018695 A1 | 2/2013 |
| WO | WO 2013/019621 A1 | 2/2013 |
| WO | WO 2013/019626 A1 | 2/2013 |
| WO | WO 2013/019635 A1 | 2/2013 |
| WO | WO 2013/019653 A1 | 2/2013 |
| WO | WO 2013/019682 A1 | 2/2013 |
| WO | WO 2013/029338 A2 | 3/2013 |
| WO | WO 2013/036912 A2 | 3/2013 |
| WO | WO 2013/041519 A1 | 3/2013 |
| WO | WO 2013/042782 A1 | 3/2013 |
| WO | WO 2013/045431 A1 | 4/2013 |
| WO | WO 2013/079223 A1 | 6/2013 |
| WO | WO 2013/178362 A1 | 12/2013 |

OTHER PUBLICATIONS

West, Anthony R., Solid State Chemistry and Its Applications, Wiley, New York, 1988, 358.*

André et al., "A novel isoform of the orphan nuclear receptor RORβ is specifically expressed in pineal gland and retina," *Gene 216*: 277-283, 1998.

André et al., "Disruption of retinoid-related orphan receptor β changes circadian behavior, causes retinal degeneration and leads to vacillans phenotype in mice," *The EMBO Journal 17*(14): 3867-1877, 1998.

Awasthi et al., "T$_h$17 cells: from precursors to players in inflammation and infection," *International Immunology 21*(5): 489-498, 2009.

Becker-André et al., "Identification of Nuclear Receptor mRNAs by RT-PCR Amplification of Conserved Zinc-finger Motif Sequences," *Biochemical and Biophysical Research Communications 194*(3): 1371-1379, Aug. 16, 1993.

Crome et al., "Translational Mini-Review Series on TH17 Cells: Function and regulation of human T helper 17 cells in health and disease," *Clinicial and Exerimental Immunology 159*: 109-119, 2009.

Dyer et al., "A Noncommercial Dual Luciferase Enzyme Assay System for Reporter Gene Analysis," *Analytical Biochemistry 282*: 158-161, 2000.

Eberl et al., "The role of the nuclear hormone receptor RORγt in the development of lymph nodes and Peyer's patches," *Immunological Reviews 195*: 81-90, 2003.

Eberl et al., "Thymic Origin of Intestinal αβ T Cells Revealed by Fate Mapping of RORγt$^+$ Cells," *Science 305*: 248-251, Jul. 9, 2004.

Evans, "The Steroid and Thyroid Hormone Receptor Superfamily," *Science 240*: 889-895, May 13, 1988.

Giguère et al., "The Orphan Nuclear Receptor RORα (RORA) Maps to a Conserved Region of Homology on Human Chromosome 15q21-q22 and Mouse Chromosome 9," *Genomics 28*: 596-598, 1995.

Gu et al., "Interleukin 10 suppresses TH17 cytokines secreted by macrophages and T cells," *Eur. J. Immunol. 38*: 1807-1813, 2008.

Hamilton et al., "Disruption of the nuclear hormone receptor RORα in staggerer mice," *Nature 379*: 736-739, Feb. 22, 1996.

He et al., "RORγt, a Novel Isoform of an Orphan Receptor, Negatively Regulates Fas Ligand Expression and IL-2 Production in T Cells," *Immunity 9*: 797-806, Dec. 1998.

He et al., "Down-Regulation of the Orphan Nuclear Receptor RORγt Is Essential for T Lymphocyte Maturation," *The Journal of Immunology 164*: 5668-5674, 2000.

Hopfer et al., "Characterization of the renal CD4$^+$ T-cell response in experimental autoimmune glomerulonephritis," *Kidney International 82*: 60-71, 2012.

Houck et al., "T0901317 is a dual LXR/FXR agonist," *Molecular Genetics and Metabolism 83*: 184-187, 2004.

Ivanov et al., "The Orphan Nuclear Receptor RORγt Directs the Differentiation Program of Proinflammatory IL-17+ T Helper Cells," *Cell 126*: 1121-1133, Sep. 22, 2006.

Kallen et al., "X-Ray Structure of the hRORα LBD at 1.63 Å: Structural and Functional Data that Cholesterol or a Cholesterol Derivative Is the Natural Ligand of RORα," *Structure 10*: 1697-1707, Dec. 2002.

Kumar et al., "The Benzenesulfoamide T0901317 [*N*-(2,2,2-Trifluoroethyl)-*N*-[4-[2,2,2-trifluoro-1-hydroxy-1-(trifluoromethyl)ethyl]phenyl]-benzenesulfonamide] Is a Novel Retinoic Acid Receptor-Related Orphan Receptor-α/γ Inverse Agonist," *Molecular Pharmacology 77*(2): 228-236, 2010.

Lau et al., "The Orphan Nuclear Receptor, RORα, Regulates Gene Expression That Controls Lipid Metabolism," *Journal of Biological Chemistry 283*(26): 18411-18421, Jun. 27, 2008.

Mangelsdorf et al., "The Nuclear Receptor Superfamily: The Second Decade," *Cell 83*: 835-839, Dec. 15, 1995.

McKenna et al., "Nuclear Receptor Coregulators: Cellular and Molecular Biology," *Endocrine Reviews 20*(3): 321-344, 1999.

Missbach et al., "Thiazolidine Diones, Specific Ligands of the Nuclear Receptor Retinoid Z Receptor/Retinoid Acid Receptor-related Orphan Receptor α with Potent Antiarthritic Activity," *The Journal of Biological Chemistry 271*(23): 13515-13522, Jun. 7, 1996.

Paust et al., "Chemokines play a critical role in the cross-regulation of Th1 and Th17 immune responses in murine crescentic glomerulonephritis," *Kidney International 82*: 72-83, 2012.

Stehlin-Gaon et al., "All-trans retinoic acid is a ligand for the orphan nuclear receptor RORβ," *Nature Structural Biology 10*(10): 820-825, Oct. 2003.

Sun et al., "Requirement for RORγ in Thymocyte Survival and Lymphoid Organ Development," *Science 288*: 2369-2373, Jun. 30, 2000.

Tesmer et al., "Th17 cells in human disease," *Immunological Reviews 223*: 87-113, 2008.

Tilley et al., "Retinoid-Related Orphan Receptor γ Controls Immunoglobulin Production and Th1/Th2 Cytokine Balance in the Adaptive Immune Response to Allergen," *The Journal of Immunology 178*: 3208-3218, 2007.

Vanacker et al., "Transcriptional Activities of the Orphan Nuclear Receptor ERRα (Estrogen Receptor-Related Receptor-α)," *Molecular Endocrinology 13*: 764-773, 1999.

Velden et al., "Renal IL-17 expression in human ANCA-associated glomerulonephritis," *Am. J. Physiol. Renal Physiol. 302*: P1663-F1673, 2012.

Villey et al., "RORγT, a thymus-specific isoform of the orphan nuclear receptor RORγ/TOR, is up-regulated by signaling through the pre-T cell receptor and binds to the TEA promoter," *Eur. J. Immunol. 29*: 4072-4080, 1999.

Wang et al., "Modulation of Retinoic Acid Receptor-related Orphan Receptor α and γ Activity by 7-Oxygenated Sterol Ligands," *Journal of Biological Chemistry 285*(7): 5013-5025, Feb. 12, 2010.

Wiesenberg et al., "Transcriptional activation of the nuclear receptor RZRα by the pineal gland hormone melatonin and identification of CGP 52608 as a synthetic ligand," *Nucleic Acids Research 23*(3): 327-333, 1995.

Wilson et al., "The Orphan Receptors NGFI-B and Steroidogenic Factor 1 Establish Monomer Binding as a Third Paradigm of Nuclear Receptor-DNA Interaction," *Molecular and Cellular Biology 13*(9): 5794-5804, Sep. 1993.

Xue et al., "Crystal structure of the PXR-T1317 complex provides a scaffold to examine the potential for receptor antagonism," *Bioorganic & Medicinal Chemistry 15*: 2156-2166, 2007.

Zhou et al., "Transcriptional regulatory networks in Th17 cell differentiation," *Curr. Opin. Immunol. 21*(2): 146-152, Apr. 2009.

International Search Report mailed Oct. 14, 2013, for PCTAN PCT/EP2013/001594, 6 pages.

Official Action from European Patent Office re extended European search report, dated Oct. 30, 2012, for Patent Application No. 12005789.8, 5 pages.

Official Action from Taiwan Intellectual Property Office, dated Apr. 9, 2014, for Patent Application No. 102119213, 9 pages.

CAS Registry No. 1350165-67-1, Dec. 7, 2011, 4 pages.

CAS Registry No. 1189927-96-5, Oct. 25, 2009, 4 pages.

Official Action from Intellectual Property Australia, dated Nov. 18, 2015, for Patent Application No. 2013301914, 13 pages.

Huang et al., "Retinoid-related orphan receptor γt is a potential therapeutic target for controlling inflammatory autoimmunity," *Expert Opin. Ther. Targets 11*(6): 737-743, 2007.

Korn et al., "IL-17 and Th17 Cells," *Annu. Rev. Immunol. 27*: 485-517, 2009.

Leonardi et al., "Anti-Interleukin-17 Monoclonal Antibody Ixekizumab in Chronic Plaque Psoriasis," *N. Engl. J. Med. 366*(13): 1190-1199, Mar. 29, 2012.

Papp et al., "Brodalumab, an Anti-Interleukin-17-Receptor Antibody for Psoriasis," *N. Engl. J. Med. 366*(13): 1181-1189, Mar. 29, 2012.

Translation of Official Action from the State Intellectual Property Office of the People's Republic of China, dated Feb. 14, 2016, for Chinese Patent Application No. 201380042113.1, 9 pages.

Search Report from the Intellectual Property Office of Singapore, mailed Apr. 26, 2016, for Singapore Application No. 11201500955R, 1 page.

Official Action from Intellectual Property Office of New Zealand, dated May 20, 2016, for Patent Application No. 717154, 4 pages.

\* cited by examiner

*Primary Examiner* — Erich A Leeser

(74) *Attorney, Agent, or Firm* — Seed IP Law Group PLLC

(57) ABSTRACT

The invention provides modulators for the orphan nuclear receptor RORγ and methods for treating RORγ mediated diseases by administering these novel RORγ modulators to a human or a mammal in need thereof. Specifically, the present invention provides carboxamide containing cyclic compounds of Formula (1) to Formula (5) and the enantiomers, diastereomers, tautomers, /V-oxides, solvates and pharmaceutically acceptable salts thereof.

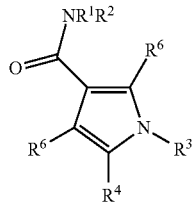

(1)

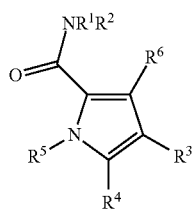

(2)

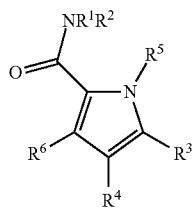

(3)

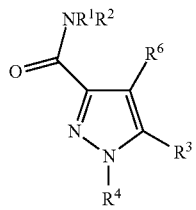

(4)

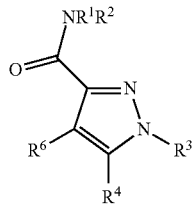

(5)

23 Claims, No Drawings

CARBOXAMIDE OR SULFONAMIDE SUBSTITUTED NITROGEN-CONTAINING 5-MEMBERED HETEROCYCLES AS MODULATORS FOR THE ORPHAN NUCLEAR RECEPTOR RORγ

The invention provides carboxamide or sulfonamide substituted nitrogen-containing 5-membered heterocylic compounds, preferably pyrroles and pyrrazoles, as modulators for the orphan nuclear receptor RORγ and methods for treating RORγ mediated chronic inflammatory and autoimmune diseases by administering these novel RORγ modulators to a human or a mammal in need thereof.

The retinoid-receptor related orphan receptors consist of three family members, namely RORα (Beckerandre et al., Biochem. Biophys. Res. Commun. 1993, 194:1371), RORβ (Andre et al., Gene 1998, 516:277) and RORγ (He et al., Immunity 1998, 9:797) and constitute the NR1F (ROR/RZR) subgroup of the nuclear receptor superfamily (Mangelsdorf et al., Cell 1995, 83:835).

The nuclear receptor superfamily shares common modular structural domains consisting of a hypervariable N-terminal domain, a conserved DNA binding domain (DBD), a hinge region, and a conserved ligand-binding domain (LBD). The DBD targets the receptor to specific DNA sequences (nuclear hormone response elements or NREs), and the LBD functions in the recognition of endogenous or exogenous chemical ligands. A constitutive transcriptional activation domain is found at the N-terminus (AF1) and a ligand regulated transcriptional activation domain is embedded within the C-terminal LBD of typical NRs. The nuclear receptors can exist in a transcriptional activating or repressing state when bound to their target NREs. The basic mechanism of gene activation involves ligand dependent exchange of co-regulatory proteins, namely co-activators and co-repressors (McKenna et al., Endocrine Rev. 1999, 20:321). A NR in the repressing state is bound to its DNA recognition element and is associated with co-repressor proteins that recruit histone-deacetylases (HDACs). In the presence of an agonist, co-repressors are exchanged for coactivators that recruit transcription factors, which contribute to assembling of a chromatin-remodelling complex, which relieves transcriptional repression and stimulates transcriptional initiation via histone acetylation. The AF-2 domain of the LBD acts as a ligand dependant molecular switch presenting interaction surfaces for co-repressor or coactivator proteins and providing with a conserved mechanism for gene activation or repression that is shared by the members of the nuclear receptor superfamily.

The members of the NR1F family of nuclear receptors (such as RORγ) have been considered to be constitutively active transcription factors in the absence of known ligands, which is similar to the estrogen-related receptor alpha (Vanacker et al., Mol. Endocrinol. 1999, 13:764). Most recently, 7-oxygenated oxysterols were identified to be high affinity ligands for RORα and RORγ (Wang et al., J. Biol. Chem. 2010, 285:5013). 7-Hydroxycholesterol is a key metabolite during the conversion of cholesterol into bile acids, but to date it is not clear whether it is a true endogenous ligand for the RORs. In any case it can be expected that inverse agonists of RORγ should reduce the transcriptional activity of RORγ and influence the biological pathways controlled by RORγ.

The RORs are expressed as isoforms arising from differential splicing or alternative transcriptional start sites. So far, isoforms have been described that differ only in their N-terminal domain (A/B-domain). In humans, four different RORα isoforms have been identified (RORα 1-4) while only two isoforms are known for both RORβ (1 and 2) and RORγ (1 and 2) (Andre et al., Gene 1998, 216:277; Villey et al., Eur. J. Immunol. 1999, 29:4072). RORγ is used herein as a term describing both, RORγ1 and/or RORγ2 (also called RORγt).

The ROR isoforms show different tissue expression patterns and regulate different target genes and physiological pathways. For example, the RORγt is highly restricted to CD4$^+$CD8$^+$ thymocytes and to interleukin-17 (IL-17) producing T cells while other tissues express RORγ1 (Eberl et al., Science 2004, 305:248, Zhou and Littmann, Curr. Opin. Immunol. 2009, 21:146).

RORs exhibit a structural architecture that is typical of nuclear receptors. RORs contain four major functional domains: an amino-terminal (NB) domain, a DNA-binding domain, a hinge domain, and a ligand-binding domain (Evans et al., Science 1988, 240:889). The DBD consists of two highly conserved zinc finger motifs involved in the recognition of ROR response elements (ROREs) which consist of the consensus motif AGGTCA preceded by an AT-rich sequence (Andre et al., Gene 1998, 216:277) which is similar to that of the nuclear receptors Rev-ErbAα and Rev-Erbβ (NR1D1 and D2, respectively) (Giguere et al., Genomics 1995, 28:596). These recognition elements do also show high similarity to those identified for the estrogen related receptors and in particular ERRα (ERRs, NR3B1, -2, -3) (Vanacker et al., Mol. Endocrinol. 1999, 13:764), steroidogenic factor 1 (SF-1, NR5A) and NGFI-B (NR4A1, -2, -3) (Wilson et al., Mol. Cell. Biol. 1993, 13:5794).

RORα is highly expressed in different brain regions and most highly in cerebellum and thalamus. RORα knock-out mice show ataxia with strong cerebellar atrophy, highly similar to the symptoms displayed in the so-called staggerer mutant mouse (RORα$^{sg/sg}$). This mouse carries mutations in RORα that results in a truncated RORα which does not contain a LBD (Hamilton et al., Nature 1996, 379:736).

Analysis of RORα$^{sg/sg}$ staggerer-mice have revealed a strong impact on lipid metabolism beyond the CNS defects, namely significant decreases in serum and liver triglyceride, reduced serum HDL cholesterol levels and reduced adiposity. SREBP1c and the cholesterol transporters ABCA1 and ABCG1 are reduced in livers of staggerer mice and CHIP analysis suggest that RORα is directly recruited to and regulates the SREBP1c promoter. In addition, PGC1α, PGC1β, lipin1 and β2-adrenergic receptor were found to be increased in tissues such as liver or white and brown adipose tissue, which may help to explain the observed resistance to diet-induced obesity in staggerer mice (Lau et al., J. Biol. Chem. 2008, 283:18411).

RORβ expression is mainly restricted to the brain and most abundantly found in the retina. RORβ knock-out mice display a duck-like gait and retinal degeneration which leads to blindness (Andre et al., EMBO J. 1998, 17:3867). The molecular mechanisms behind this retinal degeneration are still poorly understood.

RORγ (particularly RORγt) null-mutant mice lack lymph nodes and Peyer's patches (Eberl and Littmann, Immunol. Rev. 2003, 195:81) and lymphatic tissue inducer (LTi) cells are completely absent from spleen mesentery and intestine. In addition, the size of the thymus and the number of thymocytes is greatly reduced in RORγ null mice (Sun et al., Science 2000, 288:2369) due to a reduction in double-positive CD4$^+$CD8$^+$ and single positive CD4$^-$CD8$^+$ or CD4$^+$CD8$^-$ cells suggesting a very important role of RORγt in thymocyte development.

Thymocyte development follows a complex program involving coordinated cycles of proliferation, differentiation, cell death and gene recombination in cell populations dedicated by their microenvironment. Pluripotent lymphocyte progenitors migrating from fetal liver or adult bone marrow to the thymus are being committed to the T-cell lineage. They develop through a series of steps from CD4$^-$CD8$^-$ double negative cells to CD4+CD8$^+$ cells and those with low affinity towards self-MHC peptides are eliminated by negative selection. These develop further into CD4$^-$CD8$^+$ (killer) or CD4$^+$CD8$^-$ (helper) T-cell lineages. RORγt is not expressed in double negative and little expressed in immature single negative thymocytes (He et al., *J. Immunol.* 2000, 164:5668), while highly upregulated in double-positive thymocytes and downregulated during differentiation in single-positive thymocytes. RORγ deficiency results in increased apoptosis in CD4$^+$CD8$^+$ cells and the number of peripheral blood thymocytes is decreased by 6-fold (10-fold CD4$^+$ and 3-fold CD8$^+$ thymocytes).

Recent experiments in a model of ovalbumin (OVA)-induced inflammation in mice, as a model for allergic airway disease, demonstrated a severe impairment of the development of the allergic phenotype in the RORγ KO mice with decreased numbers of CD4$^+$ cells and lower Th2 cytokine/chemokine protein and mRNA expression in the lungs after challenge with OVA (Tilley et al., *J. Immunol.* 2007, 178:3208). IFN-γ and IL-10 production were increased in splenocytes following re-stimulation with the OVA antigen compared to wt splenocytes suggesting a shift towards a Th1 type immune response on cost of a reduction of Th2 type response. This suggests that down-modulation of RORγ transcriptional activity with a ligand could result in a similar shift of the immune response towards a Th1 type response, which could be beneficial in the treatment of certain pulmonary diseases like asthma, chronic obstructive pulmonary disease (COPD) or allergic inflammatory conditions. T-helper cells were previously considered to consist of Th1 and Th2 cells. However, a new class of Th cells, the Th17 cells, which produce IL-17, were also identified as a unique class of T-cells that are considered to be pro-inflammatory. They are recognized as key players in autoimmune and inflammatory diseases since IL-17 expression has been associated with many inflammatory diseases such as rheumatoid arthritis, systemic lupus erythematosus (SLE) and allograft rejection. (Tesmer et al., *Immunol. Rev.* 2008, 223:87).

RORγt is exclusively expressed in cells of the immune system and has been identified as a master regulator of Th17 cell differentiation. Expression of RORγt is induced by TGF-beta or IL-6 and overexpression of RORγt results in increased Th17 cell lineage and IL-17 expression. RORγt KO mice show very little Th17 cells in the intestinal lamina propria and demonstrate an attenuated response to challenges that usually lead to autoimmune disease (Ivanov et al., *Cell* 2006, 126:1121).

Inhibition of IL-17 production via inhibition of Th17 cell development may also be advantageous in atopic dermatitis and psoriasis where IL-17 is deeply involved. Interestingly, recent evidence was presented that IL-10 suppresses the expression of IL-17 secreted by both, macrophages and T-cells. In addition, the expression of the Th17 transcription factor RORγt was suppressed (Gu et al., *Eur. J. Immunol.* 2008, 38:1807). Moreover, IL-10 deficient mice provide a good model for inflammatory bowel disease (IBD) where a shift towards a Th1 type inflammatory response is frequently observed. Oral IL-10 delivery poses a potential treatment option for IBD.

The proinflammatory actions of IL-17 producing Th17 cells are counteracted by another T-helper cell type, so-called regulatory T-cells or Tregs. Naïve T-cells are differentiated into Tregs upon stimulation by TGFβ. This results in upregulation of the transcriptional modulator FoxP3 resulting in CD4$^+$FoxP3$^+$ Tregs. In case the nave T-cells are co-stimulated by IL-6, FoxP3 expression is suppressed and RORγt expression is induced. These CD4$^+$FoxP3$^-$RORγt$^+$ T-helper cells then differentiate into IL-17 producing Th17 cells. (reviewed in Awasthi and Kuchroo, *Int. Immunol.* 2009, 21:489, and Zhou and Littmann, *Curr. Opin. Immunol.* 2009, 21:146). Several lines of evidence suggest that these Th17 cells are responsible for the etiology of a whole range of autoimmune diseases such as multiple sclerosis, rheumatoid arthritis, ankylosing spondylitis, psoriasis, Crohn's disease and other types of inflammatory bowel disease, lupus erythematosus and asthma. The severity of disease seems to correlate with the presence of IL-17$^+$ Th17 cells and it is believed that interception of RORγt by a small molecule inverse agonist or antagonist should result in a reduction of these IL-17$^+$ Th17 cells ultimately leading to alleviation of disease symptoms and outcome (Crome et al., *Clin. Exp. Immunol.* 2010, 159:109).

Th1 and Th17 subtype effector CD4$^+$ T cells are thought to play a critical role in the pathogenesis of human and experimental crescentic glomerulonephritis (Paust et al., *Kidney Int.* 2012, doi: 10.1038/ki.2012.101). IL-17 modulators may thus be beneficial for treating acute glomerulonephritis (Velden et al., *Am. J. Physiol. Renal Physiol.* 2012, in press; Hopfer et al., *Kidney Int.* 2012, doi:10.1038/ki.2012.73).

Ligands for the RORs:

It was reported that cholesterol and its sulfated derivatives might function as RORα ligands and in particular cholesterol-sulfate could restore transcriptional activity of RORα in cholesterol-depleted cells (Kallen et al., *Structure* 2002, 10:1697). Previously, melatonin (Missbach et al., *J. Biol. Chem.* 1998, 271:13515) and thiazolidinediones were suggested to bind to RORα (Wiesenberg et al., *Nucleic Acid Res.* 1995, 23:327). However, none of these have been shown to be functional ligands of RORα or of any other of the RORs. Certain retinoids including all-trans retinoid acid have been demonstrated to bind to RORβ and function as partial antagonists for RORβ but not RORα (Stehlin-Gaon et al., *Nat. Struct. Biol.* 2003, 10:820).

Recently, 7-oxygenated sterols such as 7-hydroxy-cholesterol and 7-keto-cholesterol were identified as highly potent modulators of RORγ activity (Wang et al., *J. Biol. Chem.* 2010, 285:5013) in in vitro assays. The same group of investigators also found that a known LXR agonist, T0901317 ([N-(2,2,2-trifluoroethyl)-N-[4-[2,2,2-trifluoro-1-hydroxy-1-(trifluoro-methyl)ethyl]phenyl]-benzenesulfonamide]) acts as a RORγ inverse agonist at submicromolar potency (Kumar et al., *Mol. Pharmacol.* 2010, 77:228). In neither case, however, in vivo data were obtained that demonstrate a beneficial impact of these RORγ modulating compounds. In case of the 7-oxysterols their endogenous presence as metabolites naturally produced by the body itself as well as their rapid turnover and their biological activities on many cellular proteins prevent a meaningful animal study that allows drawing conclusions on the role of RORγ. In case of the Ser. No. 10/901,317 its polypharmacodynamic properties, acting on at least six different nuclear receptors (LXRα/β, FXR, PXR, RORα/γ) prevents its usefulness as a drug candidate for the development in an autoimmune disease application (Houck et al., *Mol. Genet. Metab.* 2004, 83:184; Xue et al., *Bioorg. Med. Chem.* 2007, 15:2156).

In WO2010/075376 compounds of general structure (A) for inhibiting replication of Hepatitis C virus are described. A₁ is defined to be a 3-14 membered carbo- or heterocycle, T can be e.g. CONR⁶ and SO₂NR⁶ while A₂ can be a carbo- or heterocycle. However, no pyrrole or pyrazole is described in the examples—a typical example is structure (A1), wherein the ring A₁ from general structure (A) is marked.

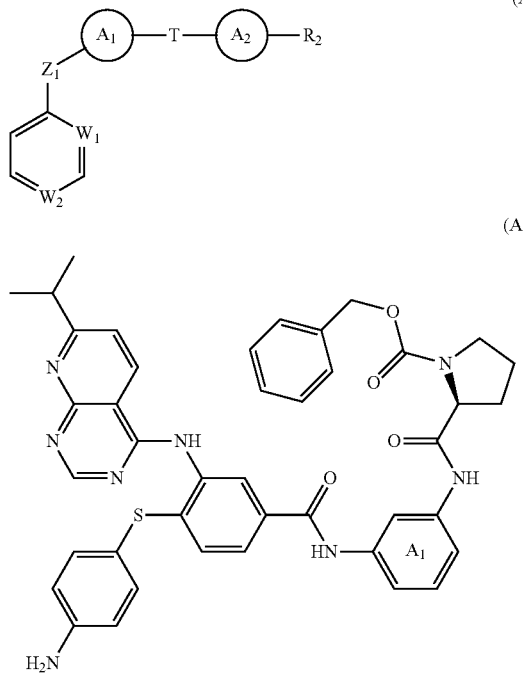

US2005/113283 claims a method of modulating an Edg-4-receptor mediated biological activity, wherein the modulator is a compound of structural formula (B) as presented in claim 40:

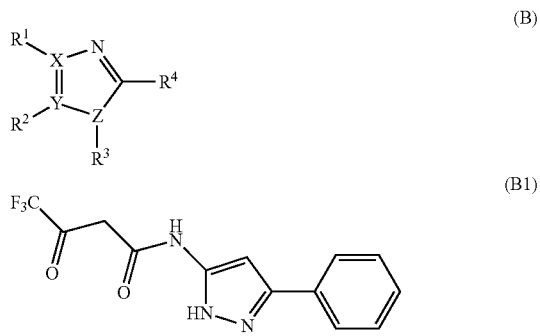

R¹ to R⁴ is selected from CONHR, CONR₂, phenyl, (CH₂)$_{m=0\ to\ 8}$—R⁵ (R⁵ e.g. cycloalkyl) beside others. However no pyrrole or pyrazole carboxamide is shown in the examples, only an inverse amide of structure (B1) is disclosed.

WO2005/016929 and WO2003/002567 describe compounds of general structure (C) and (C') as glutamate racemate inhibitors, wherein R⁴ is broadly defined to be a monocyclic or bicyclic, saturated or unsaturated ring system, which may contain from 5 to 12 ring atoms, 0 to 4 of which are heteroatoms independently selected from N, O or S and therefor also comprise pyrroles and pyrazoles. However no compounds were disclosed therein R⁴ is a pyrrole or pyrazole, substituted with a carboxamide moiety.

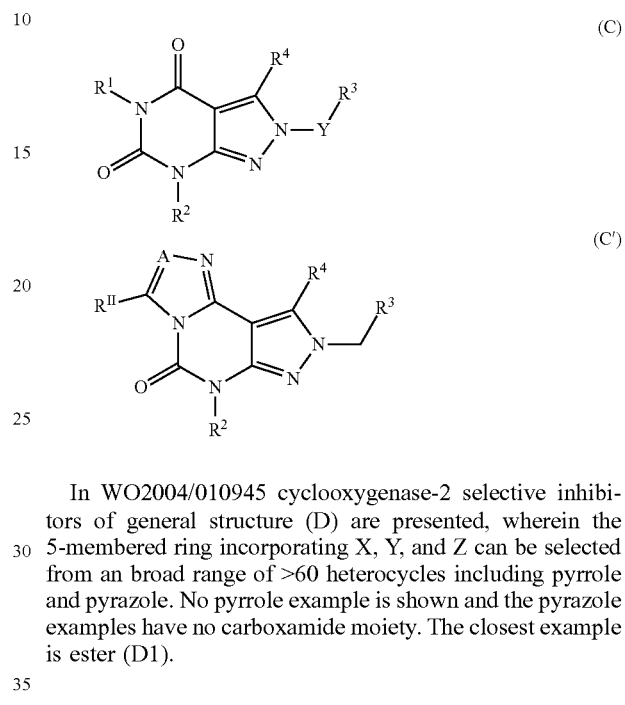

In WO2004/010945 cyclooxygenase-2 selective inhibitors of general structure (D) are presented, wherein the 5-membered ring incorporating X, Y, and Z can be selected from an broad range of >60 heterocycles including pyrrole and pyrazole. No pyrrole example is shown and the pyrazole examples have no carboxamide moiety. The closest example is ester (D1).

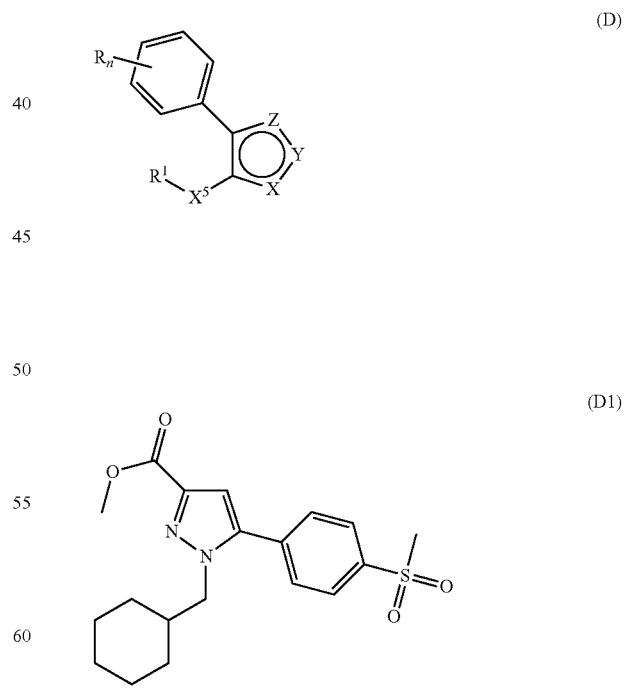

WO2000/024739 describes insecticides and acaricides of formula (E), wherein HET can be chosen from a large variety of heterocycles. However no pyrrole or pyrazole carboxamide example is presented.

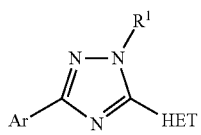

(E)

EP908456 discloses pyrrolo derivatives (X=NH, NMe) as cardiovascular agents of structure (F), wherein $R^1$ can be selected from cycloalkylalkyl and $R^{1a}$ can be selected from a broad spectrum of substituents including substituted carboxamides. However no pyrroles with $R^{1a}$ equals a substituted carboxamide are disclosed in the examples.

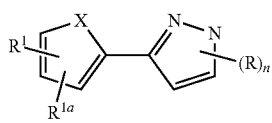

(F)

U.S. Pat. No. 5,776,954 describes pyrrolo derivatives of formula (G) as inhibitors of the biosynthesis and action of TNF-α and IL 1, wherein HAr is broadly defined as a heteroaryl group, preferably pyridyl, which is optionally substituted with $R^a$ residues. From a broad range of substituents, $R^1$ can be H or alkyl, $R^2$ can be e.g. an optionally substituted carboxamide, $R^3$ can be selected from H, halogen or alkyl and $R^4$ can be a $C_1$-alkylene-cycloalkyl or CO-cycloalkyl. However, no compounds are exemplified, which fall within the generic scope of the present invention, that is, no compounds are disclosed with $R^2$ is a substituted carboxamide.

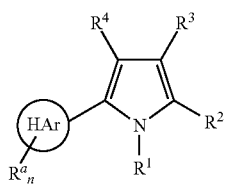

(G)

WO2011/042477 describes substituted pyrroles and imidazoles as estrogen receptor ligands, represented by structure (H). However no pyrroles are disclosed, which have a $C_1$-alkylene-cycloalkyl, CO-cycloalkyl or $SO_2$-cycloalkyl group as $R^{3D}$ in 2-position to the pyrrolo nitrogen.

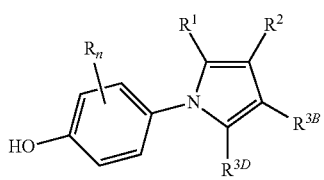

(H)

In WO2004/014368 3-pyrrolylpyridopyrazoles and 3-pyrrolylindazoles of structure (J) are described as protein kinase inhibitors, however no pyrrolyl carboxamide example is presented, which contains an $C_1$-alkyl-cycloalkyl, CO-cycloalkyl or $SO_2$-cycloalkyl moiety.

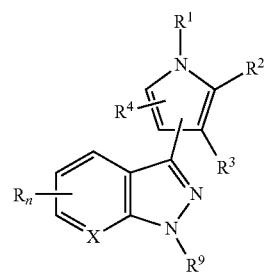

(J)

WO2012/064631 discloses pyridyl ureas as mineralcorticoid receptor antagonists of structure (K), wherein $R^4$ is selected from several pyrazolo isomers (beside others) including the $R^4$ residues depicted below. From a very broad range of substituents, M can be selected to be cycloalkylalkyl, $R^5$ to be e.g hydrogen, halogen and alkyl, and $R^6$ to be e.g. a substituted carboxamide (and vice versa for $R^5/R^6$). However, no pyrazole derivative with an optionally substituted carboxamide nor an optionally substituted $C_1$-alkylene-cycloalkyl or $SO_2$-cycloalkyl is disclosed in the examples.

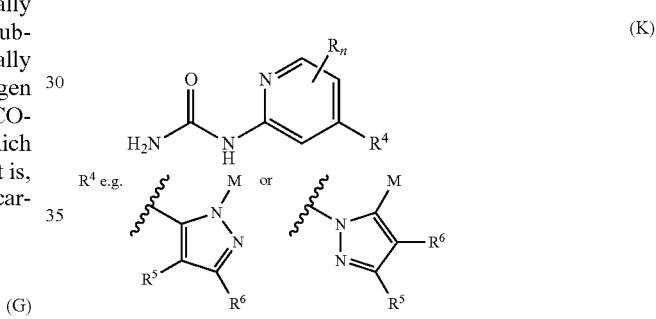

(K)

In WO2010/048559 phenylpyrazoles of structure (L) are described for the use as modulators of store-operated calcium channel activity, wherein A has to be a (hetero)aryl substituted carboxamide. From a broad range of possible substituents, X can be selected to be cycloalkylalkyl, $R^4$ to be hydrogen, halogen or alkyl and finally Y to be a optionally substituted carboxamide. However the only pyrazolo substituents exemplified are phenyl, Me, Et, $CF_3$, $CO_2Me$ and $CO_2Et$.

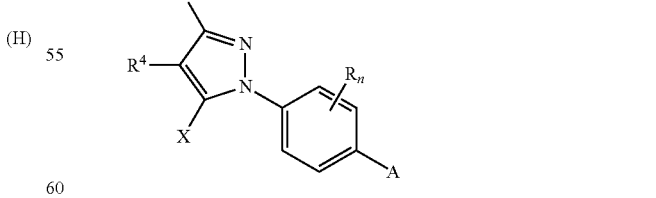

(L)

KR2009/044924 discloses 3-carboxamide substituted pyrazolo derivatives as T-type calcium channel antagonists, however no examples with a $C_1$-alkylene-cycloalkyl or $SO_2$-cycloalkyl substituent are disclosed and the carboxamide substituent is a complex moiety having a 6-membered aromatic ring.

In WO2009/037247 pyrazine derivatives of general structure (M) as potassium channel modulating agents are described. 'Het' represents a heterocyclic group which can also be pyrazolyl. The 'Het' moiety is optionally substituted e.g. with cycloalkyl-alkyl, amino-carbonyl and N,N-dialkyl-amino-carbonyl. No pyrazole examples, which are substituted with a carboxamide, are presented.

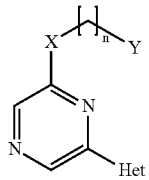
(M)

WO2008/092942 describes pyridinyl-pyrazole derivatives as potassium channel modulators of structure (N) wherein $R^1$ can be e.g. an aminocarbonyl or N,N-dialkylaminocarbonyl residue, $R^2$ can be hydrogen, halogen or alkyl and finally $R^3$ can be e.g. cycloalkyl-alkyl. Though no examples are shown with such a substitution pattern (i.e. no $C_1$-alkylene-cycloalkyl or $SO_2$-cycloalkyl substituent).

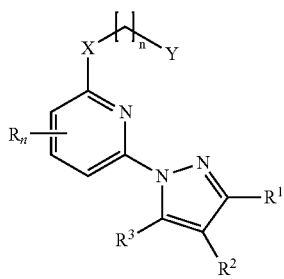
(N)

WO2008/075013 describes pyrazole carboxamides of formula (P) as CB1 receptor modulators, wherein the following substituents are possible: $R^1$ is a bond, $A^1$ is alkyl or hydrogen, $R^2$ is a bond, alkylene or cycloalkylene, $A^2$ is a acid or tetrazole, $R^3$ is hydrogen or (optionally substituted) alkyl, q=0, p=1 and finally $A^3$ is cycloalkyl. However all examples shown have q=p=0 and $A^3$ is an halogenated phenyl. Similar, in WO2008/075012 more substituents are allowed for $R^1$, however again all examples shown have q=p=0 and $A^3$ is a halogenated phenyl. In WO2006/133926 the only example wherein $A^3$ is not a phenyl is structure (P1).

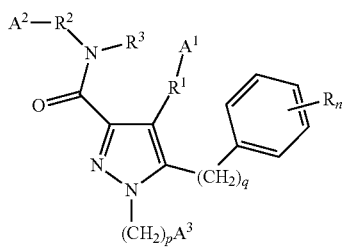
(P)

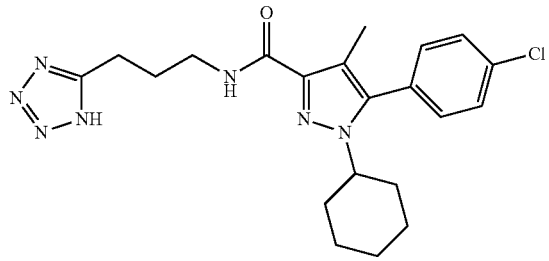
(P1)

WO2007/024744 mentions in claim 12ff pyrazolo carboxamides of structure (Q), wherein $R^5$ can be selected to be (hetero)aryl, $R^4$ to be alkyl, substituted with cycloalkyl, $R^1$ to be CN, halogen, alkyl and $R^7$ to be optionally substituted alkyl. However in all examples presented, $R^4$ is always a substituted aryl and never a cycloalkylalkyl.

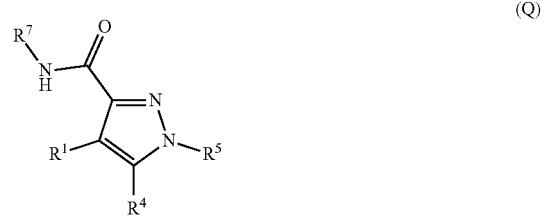
(Q)

In WO2007/002559 pyrazolo compounds of structure (Ra) and (Rd) as LXR modulators are described, wherein from an extremely broad range of substituents, $R^1$ can be generated to be cycloalkylalkyl, $R^2$ to be optionally substituted carboxamide, $R^{21}$ to be CN, halogen, alkyl and G to be optionally substituted (heteroaryl). However, from the >1800 pyrazolo compounds shown in the application, in all 208 compounds with $R^2$ is a optionally substituted carboxamide the $R^1$ residue is always an optionally substituted (hetero)aryl and never a cycloalkylalkyl. In summary, all 1H-pyrrazolo-3-carboxamides are substituted with two (hetero)aryls.

(Ra)

(Rb)

WO2006/125211 pyrazolo nucleosides with structure (S) as agonists for A1 adenosine receptor are described, wherein $R^1$ can be an optionally substituted carboxamide, $R^4$ can be hydrogen or alkyl and $R^3$ can be an alkyl, which is substituted with cycloalkyl. However no 1H-pyrrazolo-3-carboxamide example wherein $R^3$ is a cycloalkylalkyl is shown.

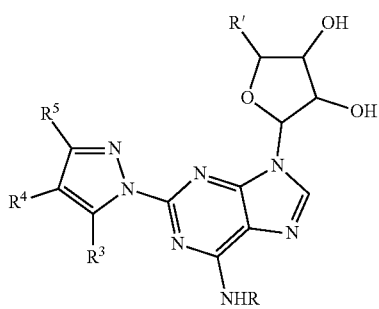

(S)

In US2006/0100208 (and related applications US2004/0192667, WO2003/020217 and WO2001/029007) arylpyrazole carboxamides as CB1 cannabinoid receptor antoganists are presented having general formula (T). From a broad range of substituents, the following can be selected: $NR^2R^5$ is an optionally substituted alkylamine or dialkylamine, A is a bond, $R^1$ and $R^4$ is either a substituted aryl or alkyl substituted with cycloalkyl (and vive versa), and last but not least $R^3$ can be hydrogen, halogen or alkyl. However, there are no 1H-pyrrazolo-3-carboxamides shown, wherein either $R^1$ or $R^4$ is a cycloalkylalkyl.

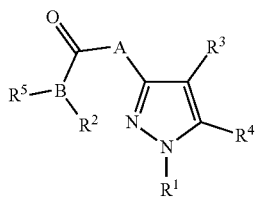

(T)

WO2006/021881 describes pyrazole-substituted pyrimidyl or pyridyl compounds of structure (U) as c-Met protein kinase inhibitors. $R^1$ is described to be any pyrazole isomer, which is optionally substituted with aryl, alkyl substituted with cycloalkyl or a substituted carboxamide. Yet, there are no 1H-pyrrazolo-3-carboxamides exemplified.

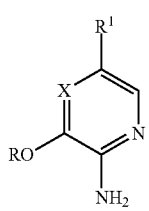

(U)

In WO2004/092140 biaryl-substituted pyrazoles as sodium channel blockers of structure (V) are shown, wherein $R^1$ can be selected from a very broad range of substitutent, including optionally substituted carboxamides. With $R^2$ equals $C_{1-4}$-alkyl-cycloalkyl and $R^3$ equals e.g. hydrogen or alkyl compounds within the present invention can be generated, however the closest shown 1H-pyrrazolo-3-carboxamide (V1) has only an alkyl residue in 5-position instead of $C_1$-alkyl-cycloalkyl.

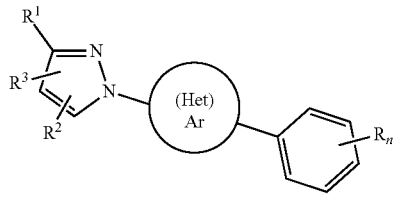

(V)

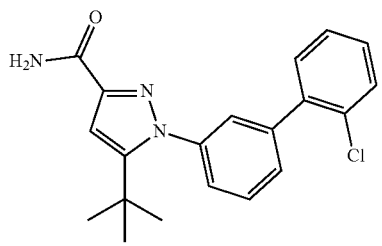

(V1)

EP1433788 describes pyrazole carboxamides as factor Xa inhibitors of structure (W), with Q equals a bond or any spacer and $R^0$ equals an optionally substituted aryl or heteroaryl group. However no substituted 1H-pyrrazolo-3-carboxamides are shown, which contain either a (hetero)aryl or $C_1$-alkyl-cycloalkyl residue in 1-position of the pyrazole. The closest analogue (W1) has a substituted benzyl in that position.

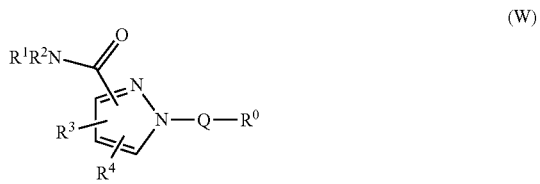

(W)

WO2003/037335 and WO2001/064669 describes (hetero)aryl substituted pyrazoles as selective COX-2 inhibitors of general structure (X), wherein B can be e.g. $SO_2$ (but not alkylene), $R^3$ can be cycloalkyl, $R^1$ can be selected from hydrogen, CN or alkyl and $R^2$ can be selected from a broad range of substituents including substituted carboxamides. However in both cases no substituted 1H-pyrrazolo-3-carboxamides are exemplified.

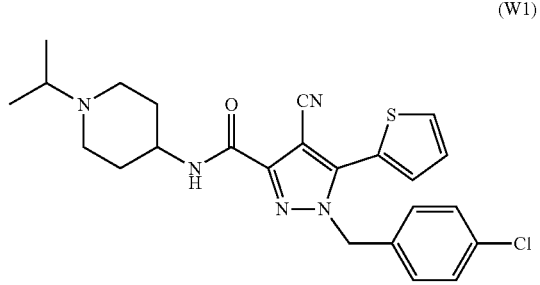

(W1)

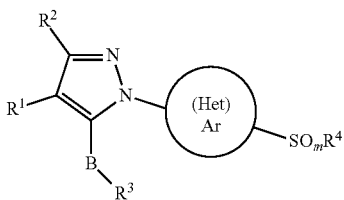
(X)

WO1996/001254 presents pyrazole derivatives for structure (Y) as herbicides, wherein W is an aromatic system, $R^1$ e.g. a carboxamide and R e.g. cycloalkylalkyl. However no pyrrazolocarboxamides are exemplified, the closest structure is ester (Y1).

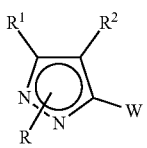
(Y)

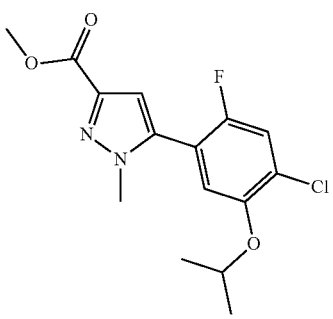
(Y1)

WO2013/014204 describes heterocyclic carboxamides as inhibitors of the protease cathepsin A, including compounds of structure (Z). However no examples, wherein $R^{10}$ is a X-cycloalkyl residue (with X=optionally substituted carbon, oxygen, sulfur) are shown.

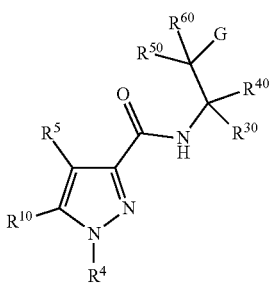
(Z)

In the similar application WO2011/092187, 3-heteroaroyl derivatives as inhibitors of the protease cathepsin A are described, including compounds of structure (AA), wherein $R^{10}$ can be O-cycloalkyl. An example is shown in structure (AA1).

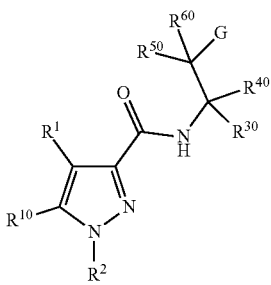
(AA)

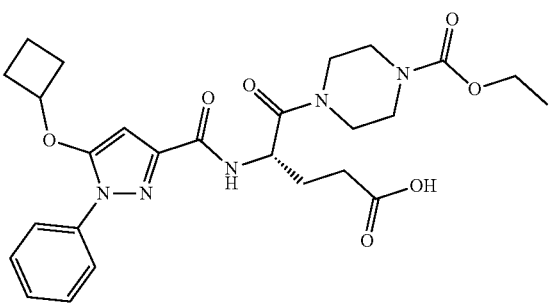
(AA1)

WO2009/080227 describes pyrazolo-carboxamides as $P_2Y_{12}$ antangonists for treating cardiovascular discorders with a broad range of residues. Again, structure (AA1) is mentioned as example.

In WO2012/139930 pyrazolopyrimidine derivatives of structure (AB) for the use as protein kinase modulators are presented, wherein $R^2$ can be selected from a broad range of substituents including cycloalkylalkyl and $R^3$ from an optionally substituted amide. However no examples, wherein $R^3$ is linked to the pyrazole nitrogen and wherein $R^3$ is a X-cycloalkyl moiety (with X=optionally substituted carbon, oxygen, sulfur) are shown.

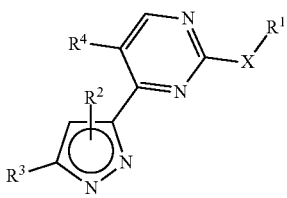
(AB)

In CA 2736441 pyrazolylthiazole compounds of structure (AC) are claimed, wherein $R^2$ can be an alkyl, which is substituted with cycloalkyl and X can be an optionally substituted amine. Albeit, no example, wherein $R^2$ is a cycloalkyl-alkyl moiety is shown.

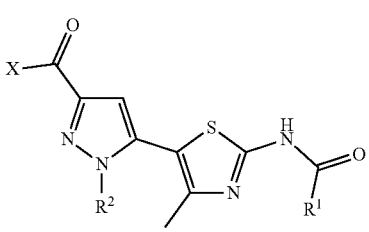
(AC)

In WO2013/029338 similar RORγ receptor modulators are described of structure (AD), wherein ring A, B and C is broadly defined as phenyl or heteroaryl and $R^2$ can be selected from e.g. $C_{1-6}$-alkylene-cycloalkyl, heterocycloalkyl, O-heteroaryl. In the examples ring B is limited to 6-membered (hetero)aryl.

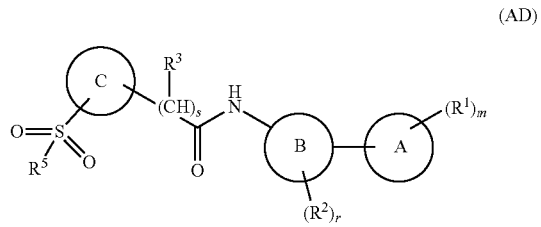

(AD)

The Chemical Abstracts database mentions compound (AE) with no accompanying literature reference, which is excluded via proviso from the presented claims.

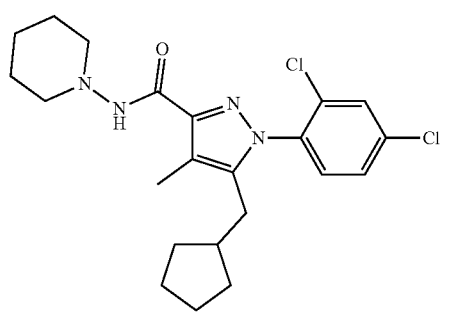

(AE)

Modulators of the RORγ receptor were recently disclosed in WO2011/107248, WO2011/112263, WO2011/112264, WO2011/115892, WO2012/027965, WO2012/028100, WO2012/064744, WO2012/074547, WO2012/100732, WO2012/100734, WO2012/101261, WO2012/101263, WO2012/106995, WO2012/139775, WO2012/145254, WO2012/147916, WO2012/158784, WO2013/000869, WO2013/000871, WO2013/018695, WO2013/019621, WO2013/019626, WO2013/019635, WO2013/019653, WO2013/019682, WO2013/036912, WO2013/041519, WO2013/042782, WO2013/045431 which are based upon other structural classes.

SUMMARY OF THE INVENTION

It is therefore the object of the present invention to provide compounds, which bind to the orphan nuclear receptors RORγ1 and/or RORγt and, thus, to open new methods for treating diseases associated with the modulation of RORγ, such as autoimmune diseases, inflammatory skin diseases or multiple sclerosis.

This object is solved by claims 1 to 22.

Thus, the present invention provides carboxamide containing cyclic compounds as RORγ modulators, which can be used for treating or preventing a disease or disorder associated with the inactivation or activation of the RORγ receptor.

The present invention relates to a RORγ modulator which is based on a cyclic scaffold for use in the treatment or prophylaxis of a disease or disorder associated with the inhibition or activation of RORγ.

When treating the disease or disorder associated with the modulation of the RORγ receptor, the activity of said receptor is preferably reduced.

Preferably, the disease or disorder is selected from the group consisting of autoimmune diseases. Autoimmune diseases comprise a group of diseases with a similar etiology of an overshooting immune response against endogenous targets resulting in chronic inflammation and physical disabilities or other severe symptoms. Autoimmune diseases comprise e.g. rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thromobotic purpura, myasthenia gravis, Sjorgren's syndrome, scleroderma, ulcerative colitis, epidermal hyperplasia, glomerulonephritis, chronic obstructive pulmonary disease (COPD) and amyotrophic lateral sclerosis.

The present invention provides novel compounds to be used in the treatment of diseases or disorders associated with the inactivation or activation of the RORγ receptor.

Further, the present invention relates to a method for treating autoimmune diseases comprising rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thromobotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis, said method comprising administering a sufficient amount of a compound according to Formula (1) to (9) as shown below to a mammal in need thereof.

DETAILED DESCRIPTION OF THE INVENTION

In a first alternative, the present invention provides a compound represented by Formula (1) to Formula (5)

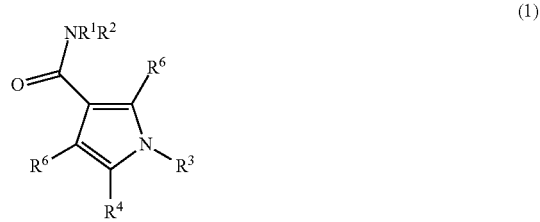

(1)

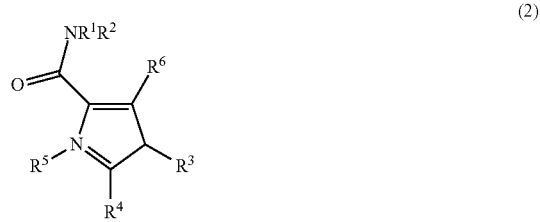

(2)

-continued

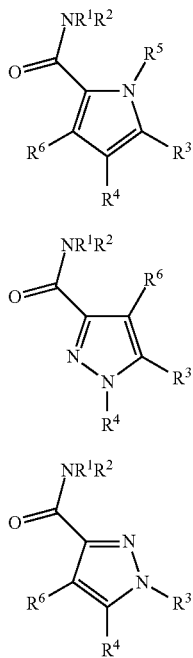

an enantiomer, diastereomer, tautomer, N-oxide, solvate, formulation and pharmaceutically acceptable salt thereof, wherein $R^1$ is independently selected from $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

$R^2$ is $R^1$ or H;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^3$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl is optionally substituted with 1 to 5 substituents independently selected from halogen, $C_{1-6}$-alkyl, $C_{1-6}$-alkenyl, $C_{1-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{31}$, $C_{0-6}$-alkylene-CN, $C_{0-6}$-alkylene-$N(R^{31})_2$, O—$C_{3-10}$-cycloalkyl, O—$C_{1-6}$-alkylene-O—$R^{31}$, O—$C_{3-10}$-heterocycloalkyl, $C_{0-6}$-alkylene-$COOR^{31}$, $C_{0-6}$-alkylene-$C(O)R^{31}$, $C_{0-6}$-alkylene-$C(O)N(R^{31})_2$, $C_{0-6}$-alkylene-$N(R^{31})C(O)R^{31}$, $C_{0-6}$-alkylene-SO—$R^{31}$, $C_{0-6}$-alkylene-$SO_2$—$R^{31}$, $C_{0-6}$-alkylene-$SO_2$—$N(R^{31})_2$, $C_{0-6}$-alkylene-$N(R^{31})SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkyl, alkenyl, alkynyl, alkylene, cycloalkyl, heterocycloalkyl and the 5- or 6-membered heteroaryl is optionally substituted by 1 to 4 substituents independently selected from the group consisting of halogen, CN, halo-$C_{1-3}$-alkyl, OH, oxo, =N—$OR^{32}$, O—$C_{1-3}$-alkyl and O-halo-$C_{1-3}$-alkyl, or wherein two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 7 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl;

$R^4$ is $(CR^8R^9)R^{40}$, $(C=O)R^{40}$, $(C=O)NR^{13}R^{14}$, O—$R^{40}$, $C_{3-10}$-cycloalkylidenemethyl, $C_3$-cycloalkylene-$R^{40}$ or $SO_y$—$R^7$;

$R^5$ is H, $C_{1-3}$-alkyl, $C_{3-6}$-cycloalkyl or halo-$C_{1-3}$-alkyl, wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

$R^6$ is independently H, halogen, CN, $C_{1-3}$-alkyl, $C_{3-6}$-cycloalkyl, halo-$C_{1-3}$-alkyl or $CONHR^{61}R^{62}$, wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

$R^7$ is $C_{3-10}$-cycloalkyl or $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-7}$-cycloalkyl and 3 to 7-membered heterocycloalkyl;

$R^8$ is H, F, $C_{1-3}$-alkyl, halo-$C_{1-3}$-alkyl, OH, O—$C_{1-3}$-alkyl or O-halo-$C_{1-3}$-alkyl;

$R^9$ is H, F, $C_{1-3}$-alkyl or halo-$C_{1-3}$-alkyl;

$R^{11}$ is independently selected from H, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}$-alkyl), $N(C_{1-3}$-alkyl$)_2$, $C_{3-6}$-heterocycloalkyl, $C_{3-6}$-cycloalkyl and $SO_2$—$C_{1-3}$-alkyl, wherein cycloalkyl and heterocycloalkyl is unsubstituted or substituted with 1 to 3 substituents independently selected from the group consisting of F, OH, oxo, Me and $CF_3$;

$R^{12}$ is independently selected from H, $C_{1-6}$-alkyl, halo-$C_{1-6}$-alkyl and $C_{3-6}$-cycloalkyl;

$R^{13}$ and $R^{14}$ taken together with the nitrogen to which they are attached complete a 3- to 10-membered ring containing carbon atoms, wherein this ring is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl and $C_{3-6}$-cycloalkyl;

$R^{31}$ is independently selected from H, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, =N—$OR^{32}$, $C_{1-3}$-alkyl, halo-$C_{1-3}$-alkyl, O-halo-$C_{1-3}$-alkyl and $SO_2$—$C_{1-3}$-alkyl;

and optionally when two $R^{31}$ are attached to a nitrogen atom, they may complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;

$R^{32}$ is independently selected from H, $C_{1-6}$-alkyl, halo-$C_{1-6}$-alkyl and $C_{3-6}$-cycloalkyl;

$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, halo-$C_{1-6}$-alkyl, $C_{1-6}$-cycloalkyl and $C_{3-8}$-heterocycloalkyl;

$R^{61}$ and $R^{62}$ are independently selected from the group consisting of H, $C_{1-3}$-alkyl and halo-$C_{1-3}$-alkyl;

x and y is independently selected from 0, 1 and 2;

with the proviso that compound 5-(cyclopentylmethyl)-1-(2,4-dichlorophenyl)-4-methyl-N-(piperidin-1-yl)-1H-pyrazole-3-carboxamide is excluded and compounds of Formula (5), wherein $R^4$ is $OR^{40}$ are excluded.

In an alternative preferred embodiment of the first alternative the compound is represented by Formula (1) to Formula (5)

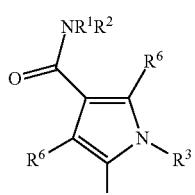

(1)

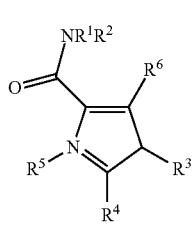

(2)

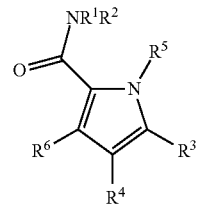

(3)

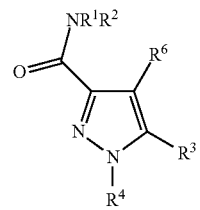

(4)

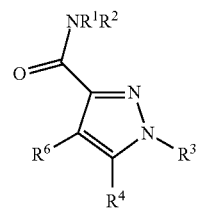

(5)

an enantiomer, diastereomer, tautomer, solvate, formulation and pharmaceutically acceptable salt thereof, wherein $R^1$ is independently selected from $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl containing 1 or 2 heteroatoms independently selected from the group consisting of N, O, S, SO and $SO_2$, $C_{0-10}$-alkylene-(5-membered monocyclic heteroaryl) or $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from the group consisting of oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$; $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$;

$R^2$ is $R^1$ or H;

or $R^1$ and $R^2$ when taken together with the nitrogen to which they are attached complete a 3- to 8-membered ring containing carbon atoms and optionally containing 1 or 2 heteroatoms selected from the group consisting of O, S or N, wherein the ring is unsubstituted or substituted with 1 to 4 substituents independently selected from the group consisting of halogen, oxo, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $CONR^{11}SO_2R^{12}$, $COR^{11}$, $NR^{11}$—CO—$NR^{11}R^{12}$, $SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 3 substituents independently selected from the group consisting of oxo, OH, $CH_3$, $CF_3$ and fluoro;

$R^3$ is a 6-10 membered mono- or bicyclic aryl or a 5-14 membered mono-, bi- or tricyclic heteroaryl containing 1 to 5 heteroatoms independently selected from the group consisting of N, O and S wherein aryl and heteroaryl are unsubstituted or substituted with 1 to 5 substituents independently selected from the group consisting of halogen, CN, $C_{2-6}$-alkenyl, $C_{2-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR$^{31}$, $C_{0-6}$-alkylene-C(O)R$^{31}$, $C_{0-6}$-alkylene-C(O)N(R$^{31}$)$_2$, $C_{0-6}$-alkylene-N(R$^{31}$)$_2$, $C_{0-6}$-alkylene-SO$_2$—N(R$^{31}$)$_2$, $C_{0-6}$-alkylene-SO$_2$—R$^{31}$, $C_{0-6}$-alkylene-(5-membered heteroaryl) and $C_{0-6}$-alkylene-(6-membered heteroaryl), wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—OR$^{32}$, N(R$^{31}$)$_2$, O—$C_{1-6}$-alkyl, O-halo-$C_{1-6}$-alkyl, COOH, CON(R$^{31}$)$_2$, CN, NR$^{31}$—COR$^{31}$, $C_{3-10}$-cycloalkyl, $C_{3-10}$-heterocycloalkyl, 6-10-membered mono- or bicyclic aryl and 6-10-membered mono- or bicyclic heteroaryl, or wherein two adjacent substituents may complete a 4- to 8-membered saturated or partially unsaturated ring containing carbon atoms and optionally containing 1 to 3 members selected from the group consisting of O, S, SO, SO$_2$ and NR$^{31}$, wherein the ring is unsubstituted or substituted with one to four substituents independently selected from the group consisting of halogen, oxo, =N—OR$^{32}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;

R$^4$ is (CR$^8$R$^9$)R$^{40}$, (C=O)R$^{13}$R$^{14}$, $C_{3-10}$-cycloalkylidenemethyl, $C_3$-cycloalkylene-R$^{40}$ or SO$_y$—R$^7$;

R$^5$ is H, $C_{1-3}$-alkyl, $C_{3-6}$-cycloalkyl or halo-$C_{1-3}$-alkyl,
wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

R$^6$ is independently H, halogen, CN, $C_{1-3}$-alkyl, $C_{3-6}$-cycloalkyl, halo-$C_{1-3}$-alkyl or CONHR$^{61}$R$^{62}$,
wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

R$^7$ is $C_{3-10}$-cycloalkyl or $C_{3-10}$-heterocycloalkyl,
wherein cycloalkyl and heterocycloalkyl are unsubstituted or substituted with 1 to 3 substituents independently selected from the group consisting of halogen, OH, oxo, $C_{1-6}$-alkyl, O-halo-$C_{1-6}$-alkyl, $C_{1-6}$-alkyl, halo-$C_{1-6}$-alkyl, $C_{3-7}$-cycloalkyl and 3 to 7-membered heterocycloalkyl;

R$^8$ is H, F, $C_{1-3}$-alkyl, halo-$C_{1-3}$-alkyl, OH, O—$C_{1-3}$-alkyl or O-halo-$C_{1-3}$-alkyl;

R$^9$ is H, F, $C_{1-3}$-alkyl or halo-$C_{1-3}$-alkyl;

R$^{11}$ and R$^{31}$ are independently selected from the group consisting of H, $C_{3-10}$-cycloalkyl, $C_{3-10}$-heterocycloalkyl, phenyl, 5-6-membered heteroaryl containing 1 to 4 heteroatoms independently selected from the group consisting of N, O and S wherein alkyl, cycloalkyl and heterocycloalkyl are unsubstituted or substituted with 1 to 5 substituents selected from the group consisting of $C_{1-6}$-alkyl, halo-$C_{1-6}$-alkyl, OH, O—$C_{1-6}$-alkyl, O-halo-$C_{1-6}$-alkyl, phenyl, heteroaryl, halogen, NH$_2$, NH($C_{1-6}$-alkyl), N($C_{1-6}$-alkyl)$_2$, $C_{3-10}$-heterocycloalkyl, $C_{3-10}$-cycloalkyl, COOH, SO$_2$—$C_{1-3}$-alkyl, SO$_2$—$C_{1-3}$-fluoroalkyl, oxo and CN, wherein cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 6-membered heteroaryl, halogen, NH$_2$, NH($C_{1-6}$-alkyl), N($C_{1-6}$-alkyl)$_2$ and $C_{3-10}$-cycloalkyl, and wherein phenyl and heteroaryl are unsubstituted or substituted with 1 to 4 substituents independently selected from the group consisting of OH, O—$C_{1-6}$-alkyl, O-halo-$C_{1-6}$-alkyl, halogen, $C_{1-6}$-alkyl, halo-$C_{1-6}$-alkyl, NH$_2$, NH($C_{1-6}$-alkyl), N($C_{1-6}$-alkyl)$_2$ and $C_{3-10}$-cycloalkyl;

R$^{12}$ and R$^{32}$ are independently selected from the group consisting of H, $C_{1-6}$-alkyl, halo-$C_{1-6}$-alkyl and $C_{3-10}$-cycloalkyl;

R$^{13}$ and R$^{14}$ taken together with the nitrogen to which they are attached complete a 3- to 10-membered ring containing carbon atoms, wherein this ring is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl and halo-$C_{1-6}$-alkyl;

R$^{40}$ is $C_{3-10}$-cycloalkyl, which is unsubstituted or substituted with 1 to 5 substituents independently selected from the group consisting of halogen, OH, oxo, O-halo-$C_{16}$-alkyl, and halo-$C_{1-6}$-alkyl;

R$^{61}$ and R$^{62}$ are independently selected from the group consisting of H, $C_{1-3}$-alkyl and halo-$C_{1-3}$-alkyl; and y is independently selected from 0, 1 and 2.

In a preferred embodiment in combination with any of the above or below embodiments of the first alternative R$^5$ is H or $C_{1-3}$-alkyl; and R$^6$ is H, F, Cl, CN, $C_{1-3}$-alkyl or halo-$C_{1-3}$-alkyl.

In a more preferred embodiment in combination with any of the above or below embodiments of the first alternative R$^5$ is H or methyl; and R$^6$ is H, F, Cl or methyl.

In an even more preferred embodiment in combination with any of the above or below embodiments of the first alternative the compound is represented by the following Formula:

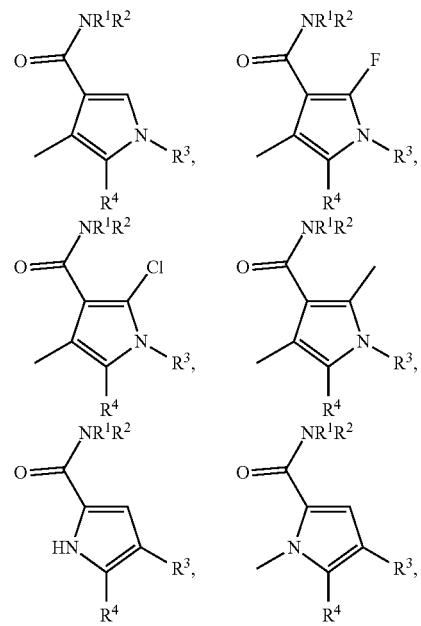

-continued

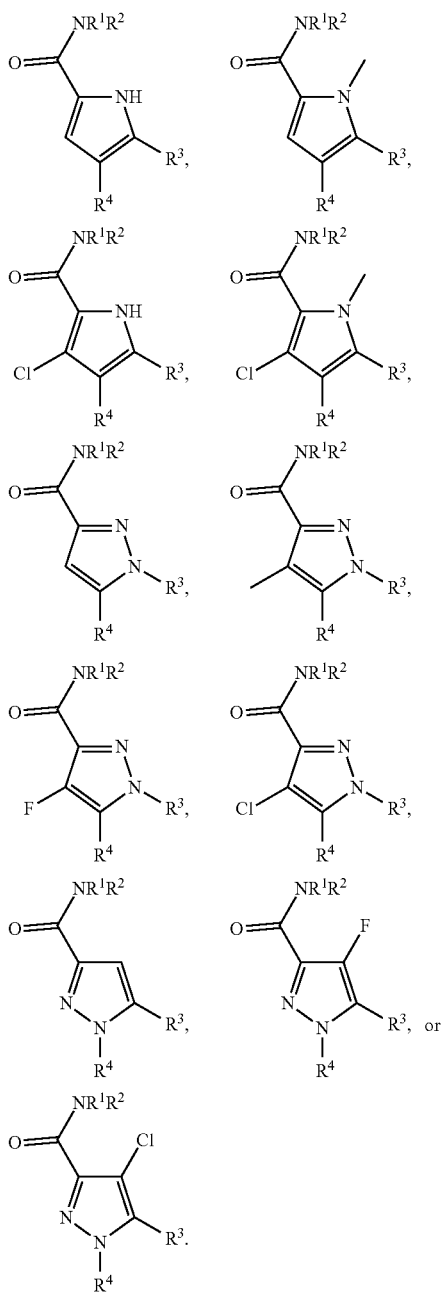

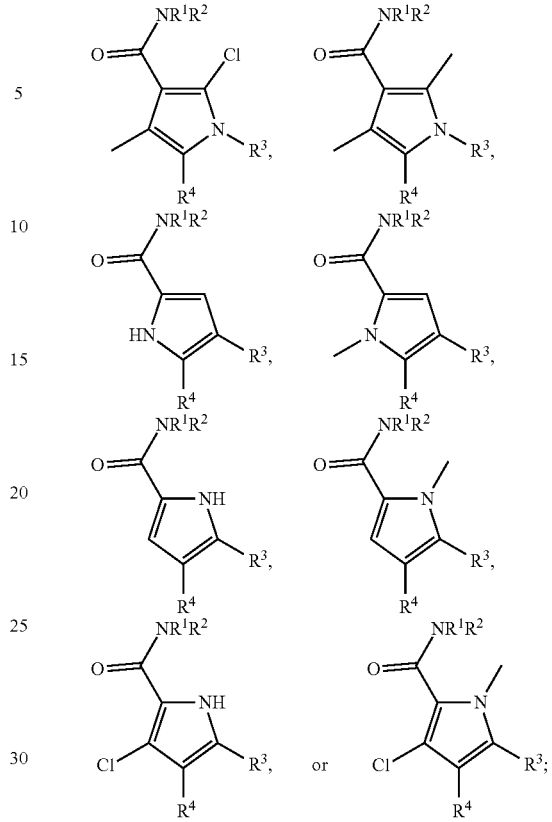

and even more preferred by Formula

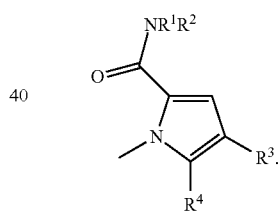

In a preferred embodiment in combination with any of the above or below embodiments of the first alternative $R^4$ is $CH_2R^{40}$, $CHMeR^{40}$, $OR^{40}$ or $(C=O)R^{40}$; wherein $R^{40}$ is $C_{3-8}$-cycloalkyl, which is unsubstituted or substituted with 1 to 3 substituents independently selected from the group consisting of F, $CH_3$ and $CF_3$.

In a more preferred embodiment in combination with any of the above or below embodiments of the first alternative $R^4$ is $CH_2R^{40}$, $CHMeR^{40}$ or $(C=O)R^{40}$; wherein $R^{40}$ is $C_{3-8}$-cycloalkyl, which is unsubstituted or substituted with 1 to 3 substituents independently selected from the group consisting of F, $CH_3$ and $CF_3$.

In an even more preferred embodiment in combination with any of the above or below embodiments of the first alternative $R^4$ is selected from $(CH_2)$—$C_{3-8}$-cycloalkyl, wherein cycloalkyl is unsubstituted or substituted with 1 to 3 substituents independently selected from the group consisting of F, $CH_3$ and $CF_3$.

In a most preferred embodiment in combination with any of the above or below embodiments of the first alternative $R^4$ is selected from In a most preferred embodiment in combination with any of the above or below embodiments of the first alternative the compound is represented by the following Formula:

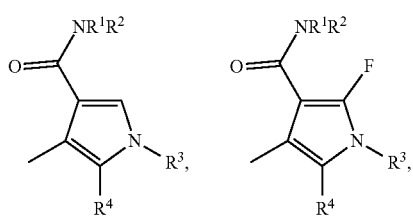

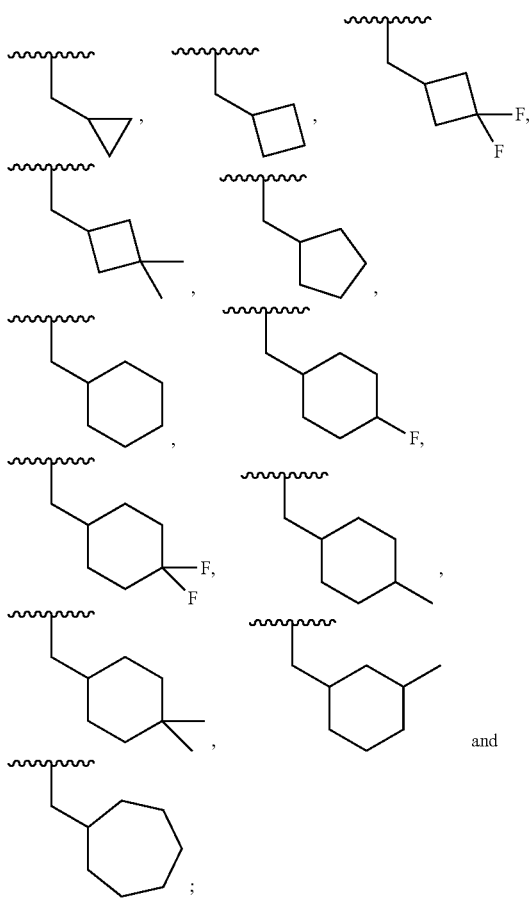

even more preferred $R^4$ is $(CH_2)$-cyclohexyl.

In a preferred embodiment in combination with any of the above or below embodiments of the first alternative $R^1$ is selected from $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl), wherein alkyl, alkylene, cycloalkyl, heterocycloalkyl and heteroaryl is unsubstituted or substituted with 1 to 7 substituents independently selected from oxo, $R^{12}$, CN, $OR^{11}$, O—$C_{2-6}$-alkylene-$OR^{11}$, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

$R^2$ is selected from H, halo-$C_{1-6}$-alkyl and hydroxy-$C_{1-6}$-alkyl;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-5}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl, OH, 0-$C_{1-3}$-alkyl, O-halo-$C_{1-3}$-alkyl, $SO_2$—$C_{1-3}$-alkyl, COOH and oxo.

In an alternative preferred embodiment in combination with any of the above or below embodiments of the first alternative $R^1$ is $C_{1-10}$-alkyl, $C_{0-10}$-alkylene-$C_{3-10}$-cycloalkyl or $C_{0-10}$-alkylene-$C_{3-10}$-heterocycloalkyl, wherein alkyl, alkylene, cycloalkyl and heterocycloalkyl are unsubstituted or substituted with 1 to 7 substituents independently selected from the group consisting of oxo, $OR^{11}$, $C_{1-6}$-alkyl, halo-$C_{1-6}$-alkyl, halogen, $CO_2R^{11}$, $CONR^{11}R^{12}$, $CONR^{11}SO_2R^{12}$, $COR^{11}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl and O—$C_{3-6}$-heterocycloalkyl;

$R^2$ is H, $C_{1-6}$-alkyl or halo-$C_{1-6}$-alkyl;

or $R^1$ and $R^2$ when taken together with the nitrogen to which they are attached complete a 3- to 8-membered ring containing carbon atoms and optionally containing 1 or 2 heteroatoms independently selected from the group consisting of O, S or N, wherein the ring is unsubstituted or substituted with 1 to 4 substituents independently selected from the group consisting of F, oxo and $C_{1-6}$-alkyl.

In a preferred embodiment in combination with any of the above or below embodiments of the first alternative $NR^1R^2$ is selected from NHMe, NHEt, NH$^i$Pr, NH$^t$Bu, NHCH$_2$CONH$_2$, NHCH$_2$CONMe$_2$, NHCH$_2$CH$_2$OH, NHCH$_2$CH$_2$OMe, NHCH$_2$CH$_2$SO$_2$Me, NHCH$_2$CH$_2$SO$_2$NH$_2$, NH(CH$_2$)$_3$OH, NH(CH$_2$)$_3$OMe, NH(CH$_2$)$_4$OH, NH(CH$_2$)$_4$OMe, NH(CH$_2$)$_5$OH, NH(CH$_2$)$_2$CO$_2$H, NH(CH$_2$)$_3$CO$_2$H, NH(CH$_2$)$_4$CO$_2$H, NH(CH$_2$)$_5$CO$_2$H, NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHCH(Me)CMe$_2$OH, NHCH$_2$CMe$_2$OMe, NHCH$_2$CMe$_2$CO$_2$H, NHCH$_2$CMe$_2$CONHMe, NHCH$_2$CMe$_2$CONMe$_2$, NHCH$_2$CMe$_2$NHSO$_2$Me, NH(CH$_2$)$_3$SOMe, NH(CH$_2$)$_5$SO$_2$Me, NH(CH$_2$)$_5$SO$_2$NH$_2$, NH(CH$_2$)$_3$NHSO$_2$Me, NH(CH$_2$)$_2$O(CH$_2$)$_2$OH, NHCH$_2$CHMeOH, NH(CH$_2$)$_5$SOMe, NH(CH$_2$)$_3$SO$_2$Me, NHC(CH$_2$OH)$_3$, NHCH$_2$CH(OH)CH$_2$OH, N(CH$_2$CH$_2$OH)$_2$,

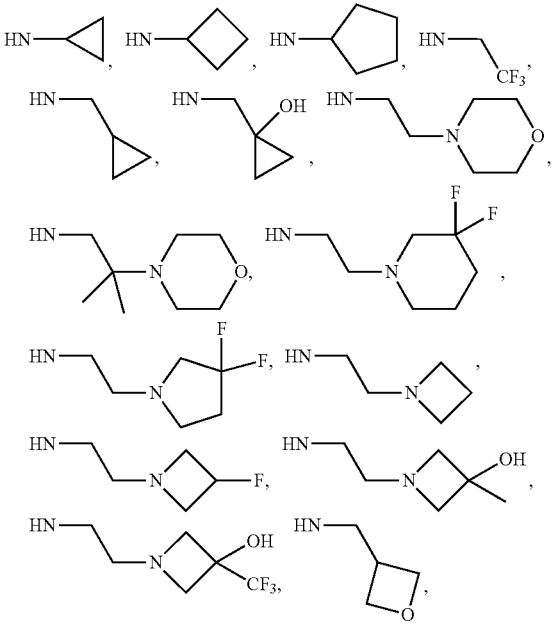

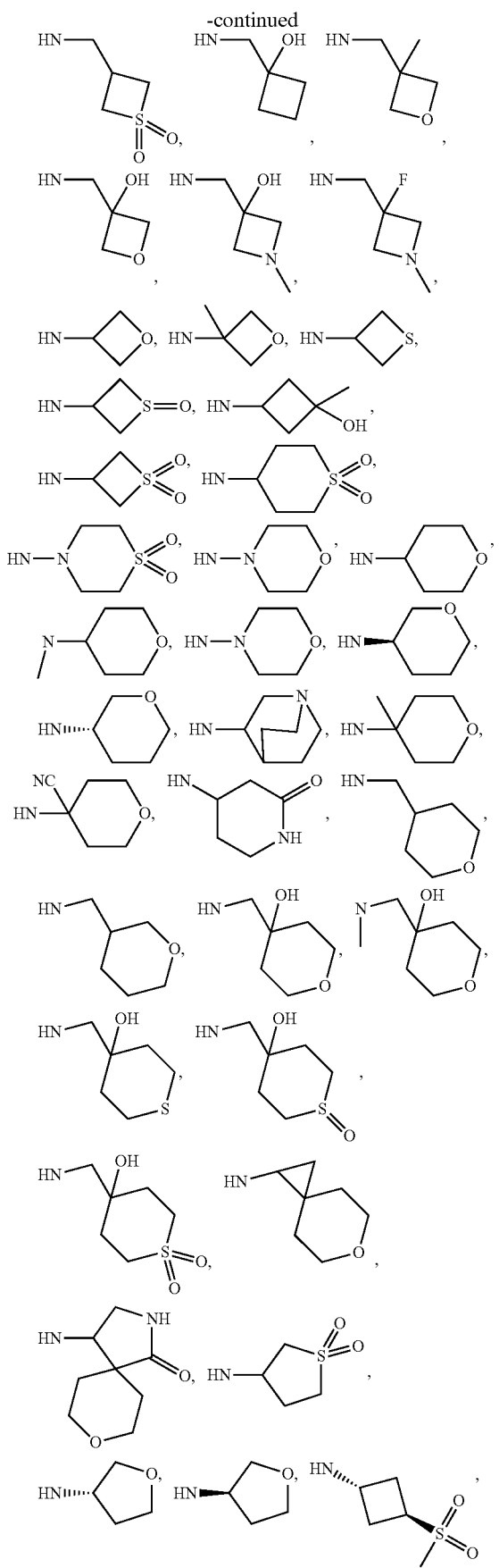
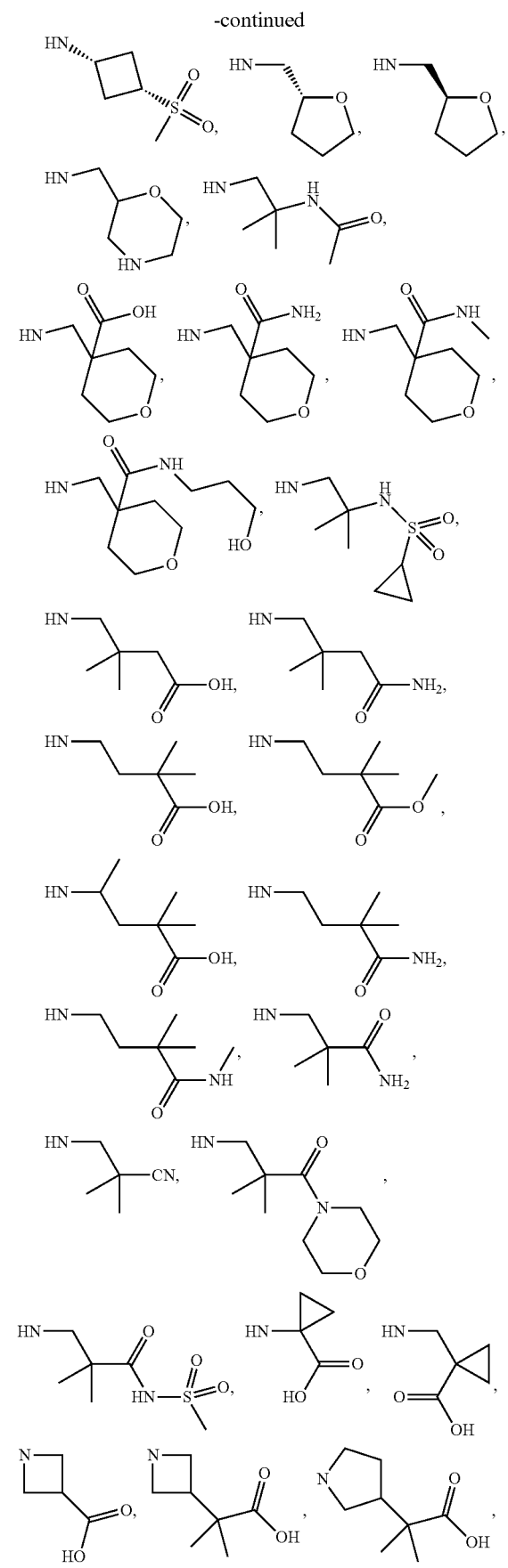

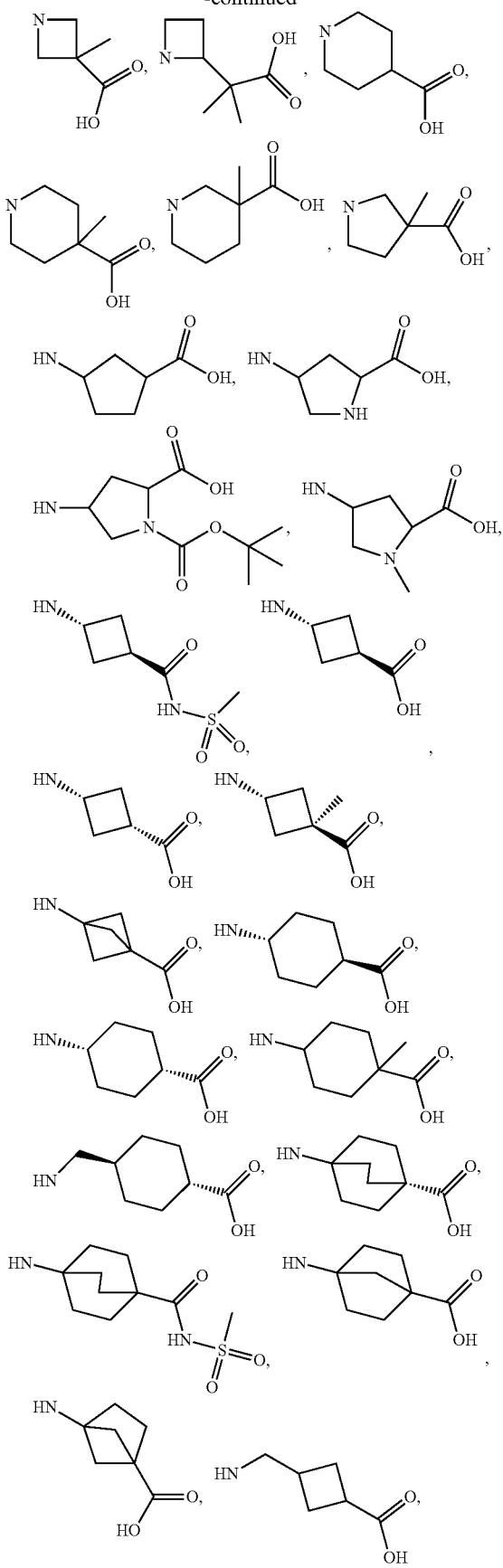
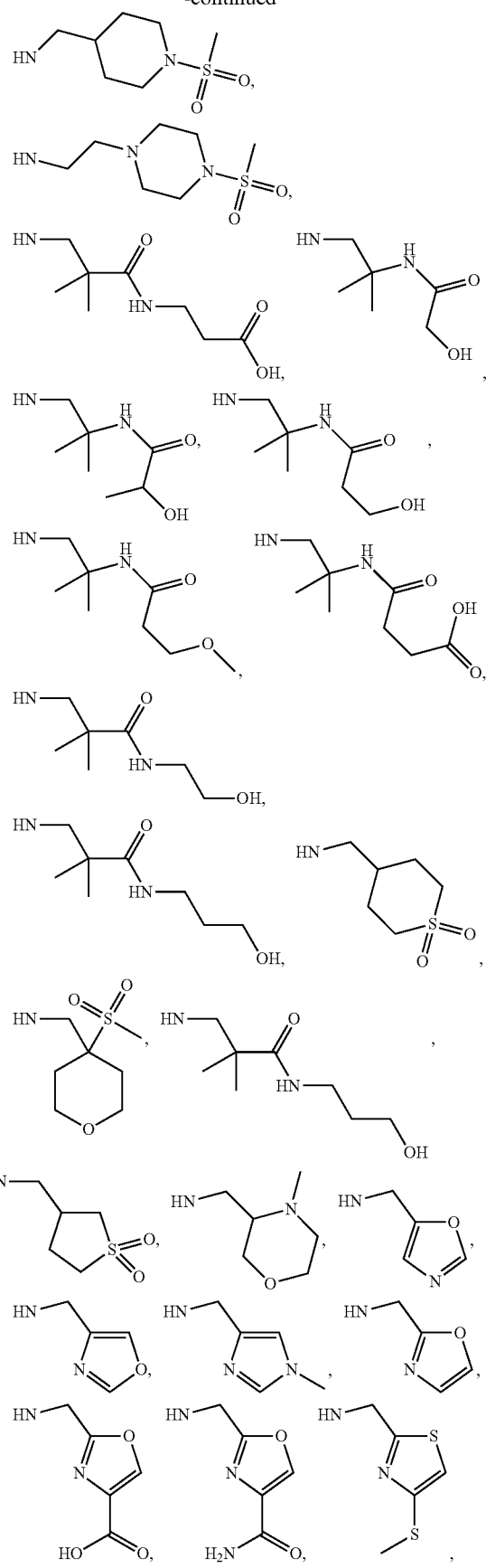

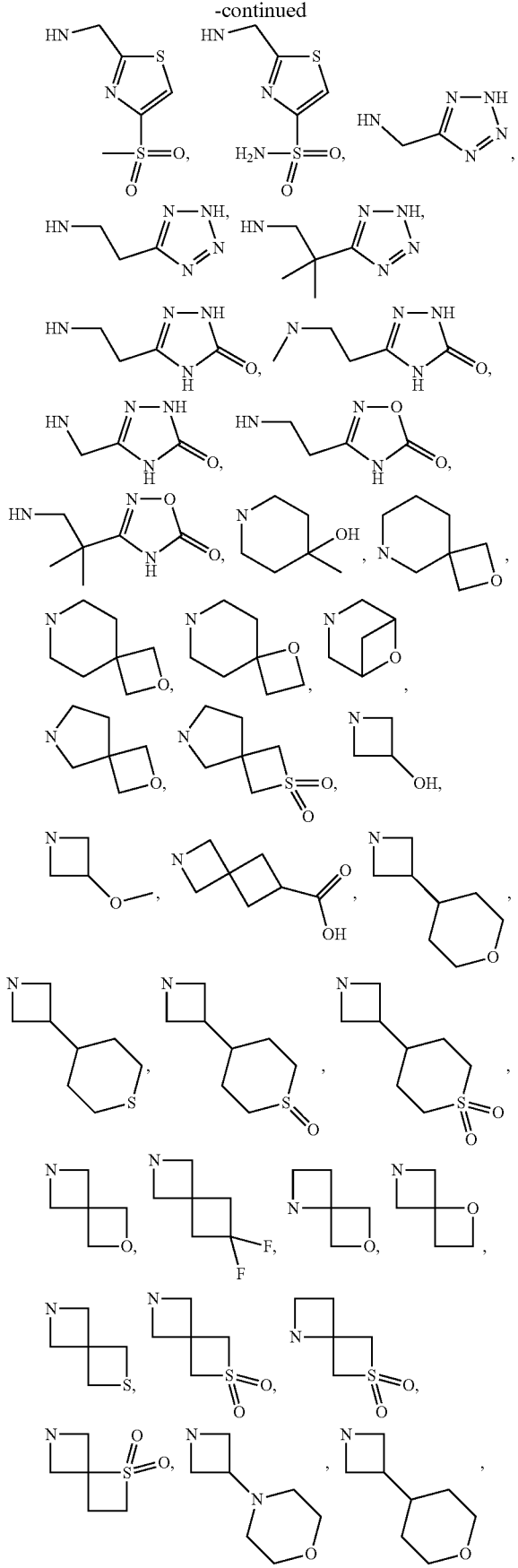
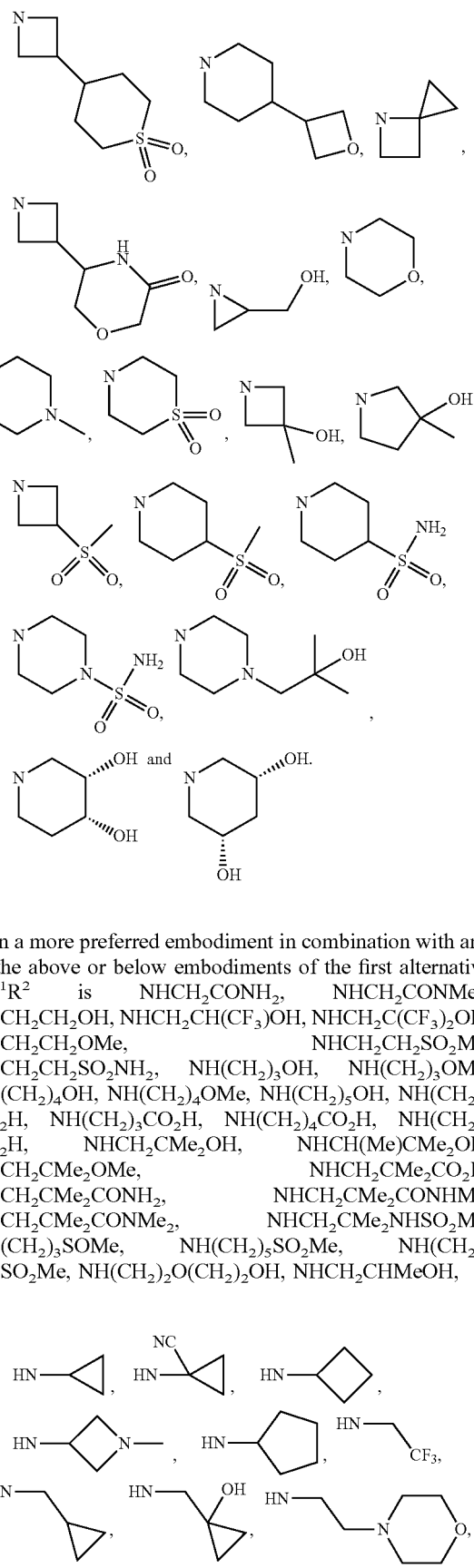

In a more preferred embodiment in combination with any of the above or below embodiments of the first alternative $NR^1R^2$ is $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_3NHSO_2Me$, $NH(CH_2)_2O(CH_2)_2OH$, $NHCH_2CHMeOH$,

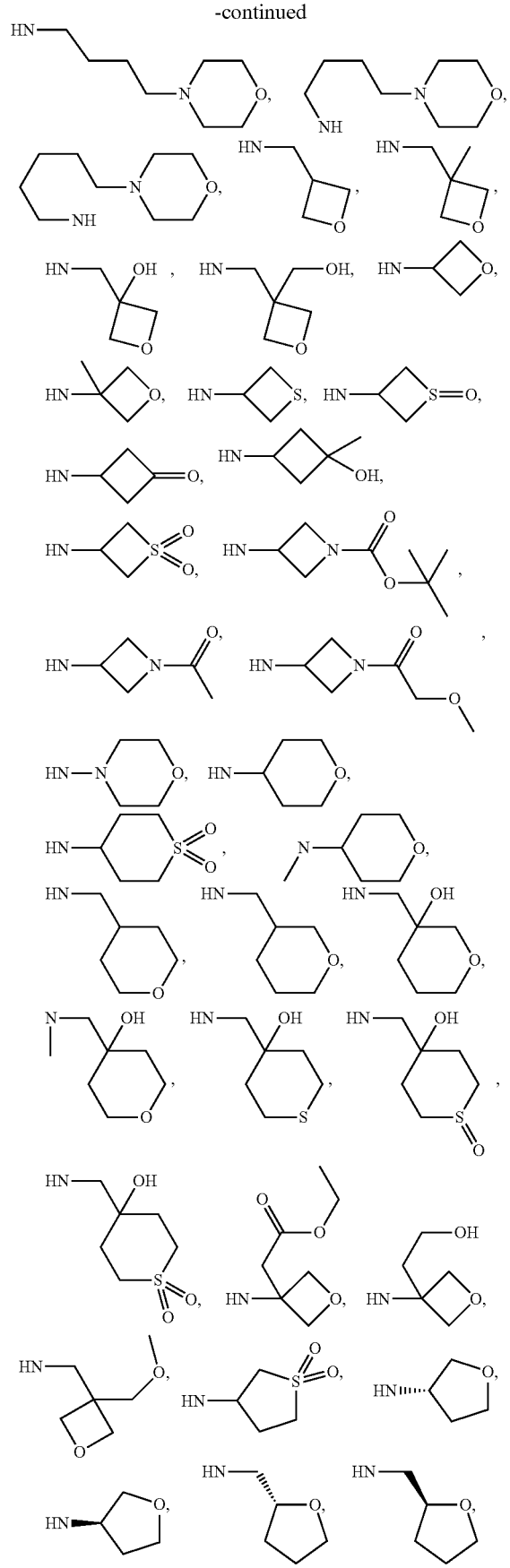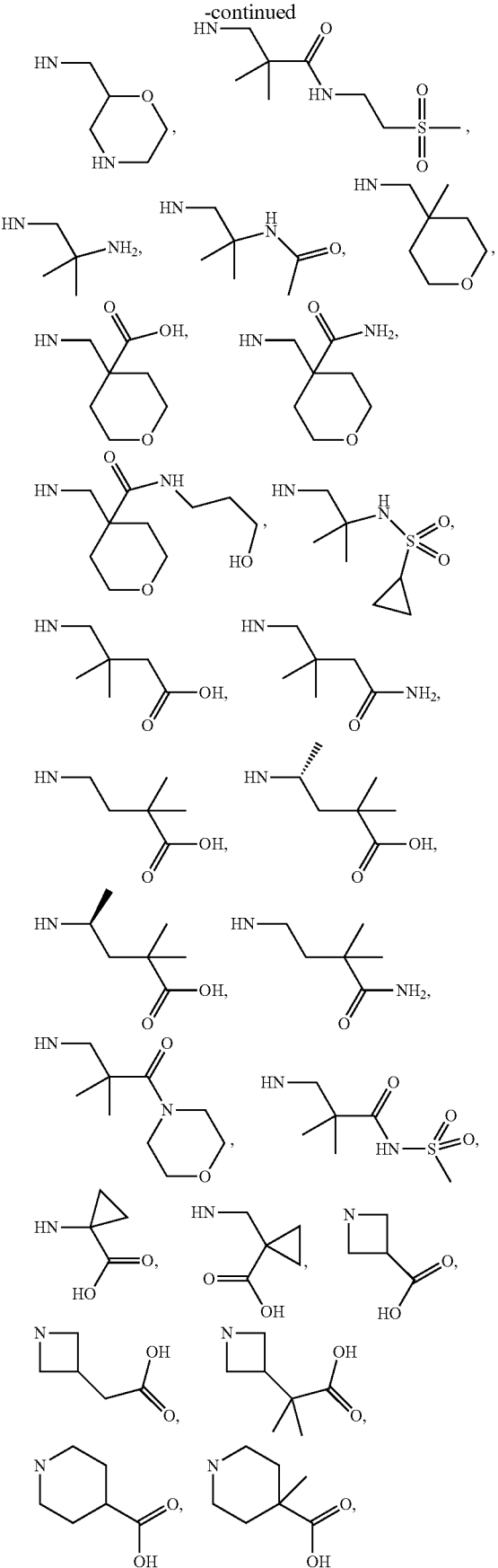

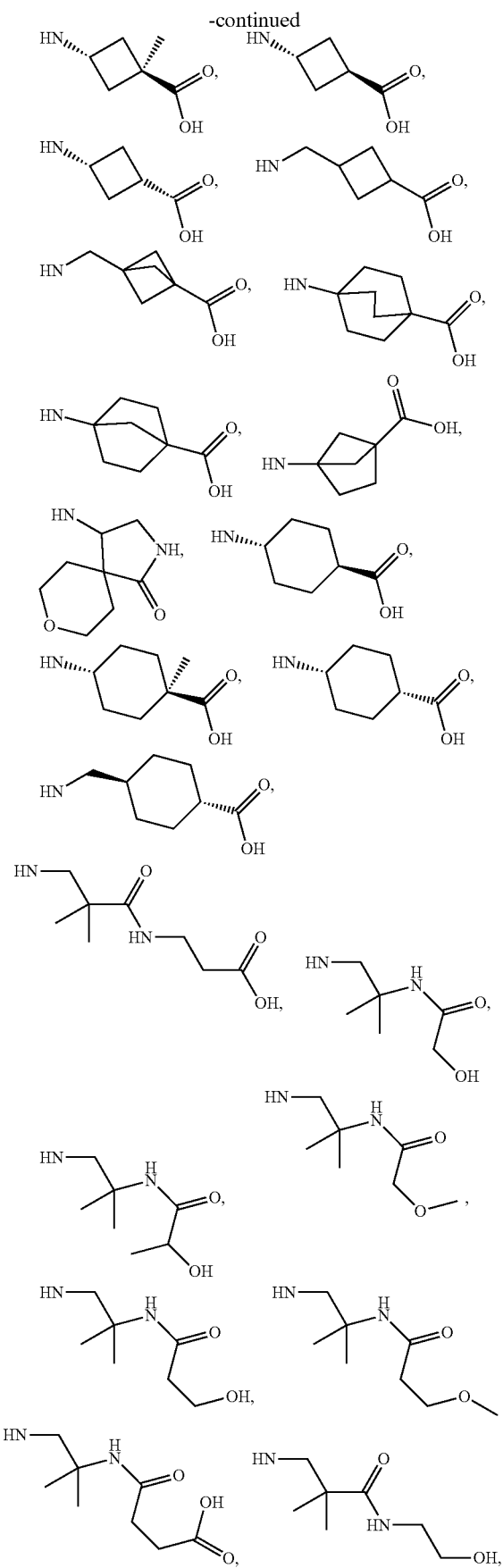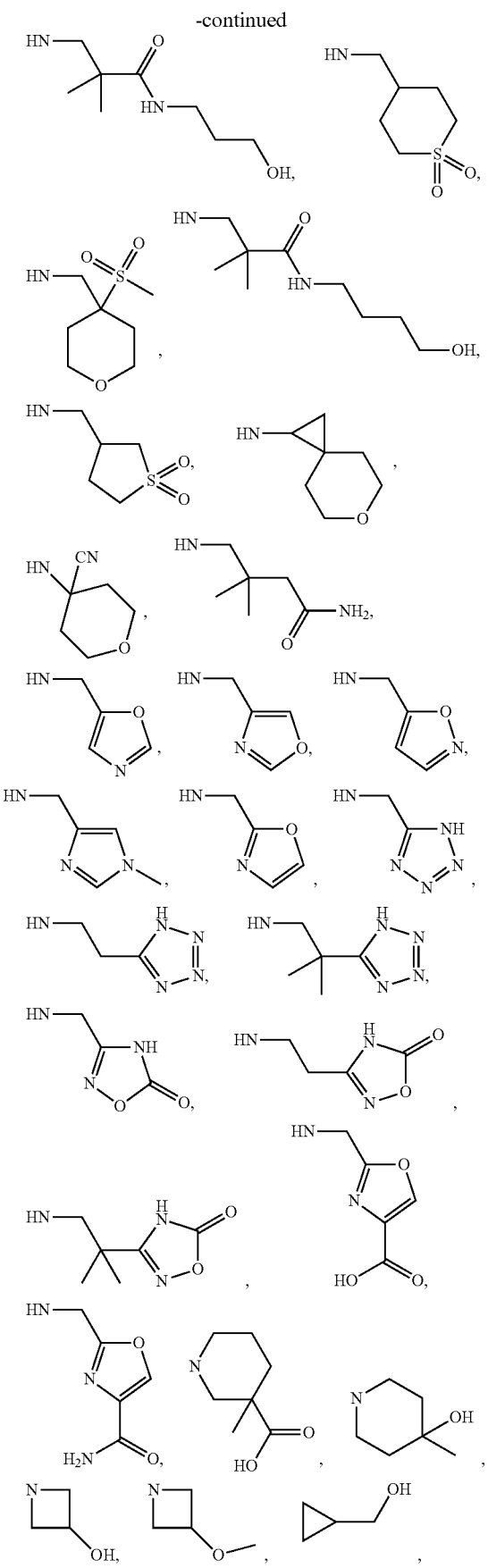

-continued

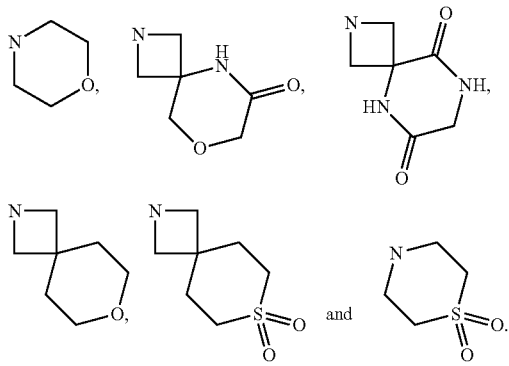

In an even more preferred embodiment in combination with any of the above or below embodiments of the first alternative $NR^1R^2$ is selected from NHEt, $NHCH_2CH_2OMe$, $NHCH_2CMe_2OH$, $NHCH_2CMe_2CO_2H$,

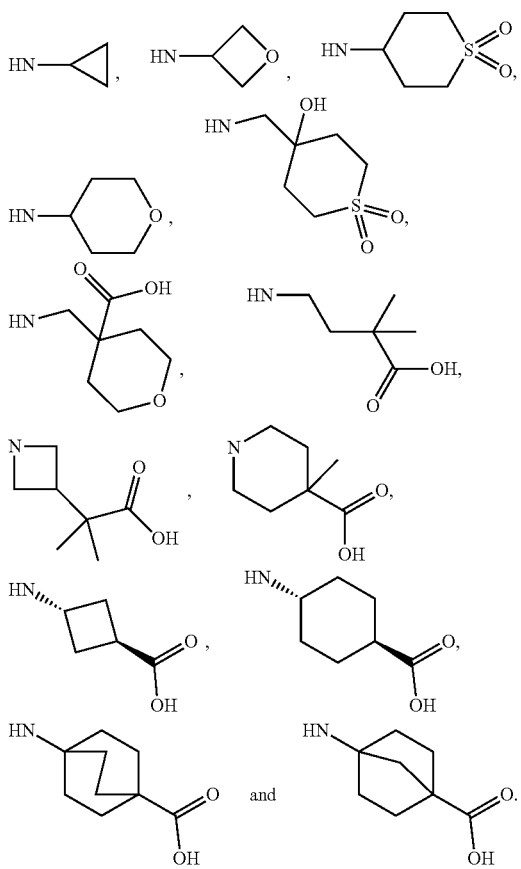

In a most preferred embodiment in combination with any of the above or below embodiments of the first alternative $NR^1R^2$ is selected from

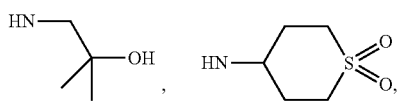

-continued

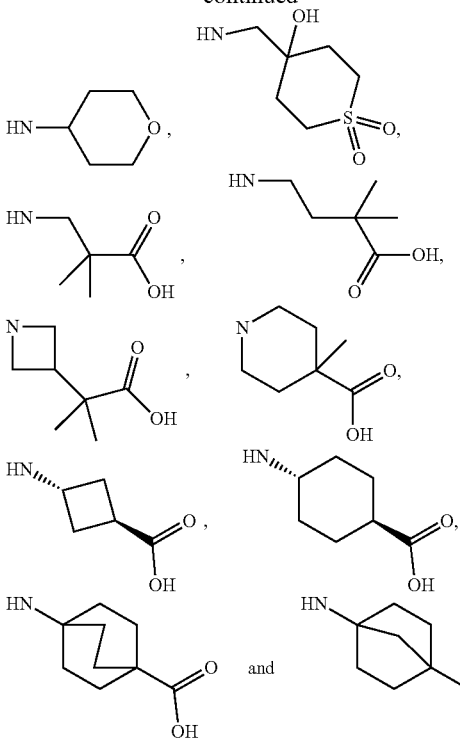

In another preferred embodiment in combination with any of the above or below embodiments of the first alternative $R^3$ is a 6-10 membered mono- or bicyclic aryl or a 5-10 membered mono- or bicyclic heteroaryl containing 1 to 4 heteroatoms independently selected from the group consisting of N, O and S wherein aryl and heteroaryl are unsubstituted or substituted with 1 to 5 substituents independently selected from halogen, CN, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_{2}$, $C_{0-6}$-alkylene-SO$_2$—N($R^{31}$)$_2$, $C_{0-6}$-alkylene-SO$_2$—$R^{31}$, $C_{0-6}$-alkylene-(5-membered heteroaryl), $C_{0-6}$-alkylene-(6-membered heteroaryl), wherein alkyl, alkylene, cycloalkyl, heterocycloalkyl and heteroaryl are unsubstituted or substituted by 1 to 3 substituents independently selected from the group consisting of halogen, OH, oxo, N($R^{31}$)$_2$, O—$C_{1-6}$-alkyl, COOH, CON($R^{31}$)$_2$, CN, $NR^{31}$—$COR^{31}$, $C_{3-10}$-cycloalkyl, $C_{3-10}$-heterocycloalkyl, 6-10-membered mono- or bicyclic aryl, 6-10-membered mono- or bicyclic heteroaryl, or wherein two adjacent substituents may complete a 3- to 8-membered saturated or partially unsaturated ring containing carbon atoms and optionally containing 1 to 3 heteroatoms selected from O, S, or $NR^{31}$, wherein the ring is unsubstituted or substituted with 1 to 4 substituents independently selected from halogen, oxo, OH, 0-$C_{1-6}$-alkyl, O-halo-$C_{1-6}$-alkyl, $C_{1-6}$-alkyl, $C_{3-6}$-cycloalkyl and halo-$C_{1-6}$-alkyl.

In an equally preferred embodiment in combination with any of the above or below embodiments of the first alternative $R^3$ is a 6-10 membered mono- or bicyclic aryl or a 5-10 membered mono- or bicyclic heteroaryl containing 1 to 4 heteroatoms independently selected from the group consisting of N, O and S wherein aryl and heteroaryl are unsubstituted or substituted with 1 to 5 substituents independently selected from the group consisting of halogen, CN, $C_{1-6}$-alkyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR$^{31}$, $C_{0-6}$-alkylene-C(O)R$^{31}$, $C_{0-6}$-alkylene-C(O)N(R$^{31}$)$_2$, $C_{0-6}$-alkylene-N(R$^{31}$)$_2$, $C_{0-6}$-alkylene-SO$_2$—N(R$^{31}$)$_2$, $C_{0-6}$-alkylene-SO$_2$—R$^{31}$, $C_{0-6}$-alkylene-(5-membered heteroaryl) and $C_{0-6}$-alkylene-(6-membered heteroaryl), wherein alkyl, alkylene, cycloalkyl, heterocycloalkyl and heteroaryl are unsubstituted or substituted by 1 to 3 substituents independently selected from the group consisting of halogen, OH, oxo, =N—OR$^{32}$, N(R$^{31}$)$_2$, O—$C_{1-6}$-alkyl, COOH, CON(R$^{31}$)$_2$, CN, NR$^{31}$—COR$^{31}$, $C_{3-10}$-cycloalkyl, $C_{3-10}$-heterocycloalkyl, 6-10-membered mono- or bicyclic aryl and 6-10-membered mono- or bicyclic heteroaryl, or wherein two adjacent substituents may complete a 4- to 8-membered saturated or partially unsaturated ring containing carbon atoms and optionally containing 1 to 3 members selected from the group consisting of O, S, SO, SO$_2$ and NR$^{31}$, wherein the ring is unsubstituted or substituted with 1 to 4 substituents independently selected from the group consisting of halogen, oxo, =N—OR$^{32}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

In a more preferred embodiment in combination with any of the above or below embodiments of the first alternative R$^3$ is a 6-membered aryl, a 10-membered bicyclic aryl, a 6-membered heteroaryl or 10-membered bicyclic heteroaryl containing 1 or 2 nitrogen atom.

In another preferred embodiment in combination with any of the above or below embodiments of the first alternative R$^3$ is selected from

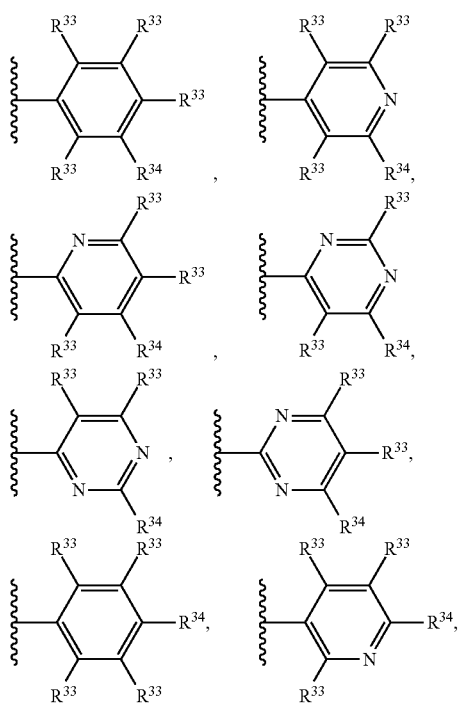

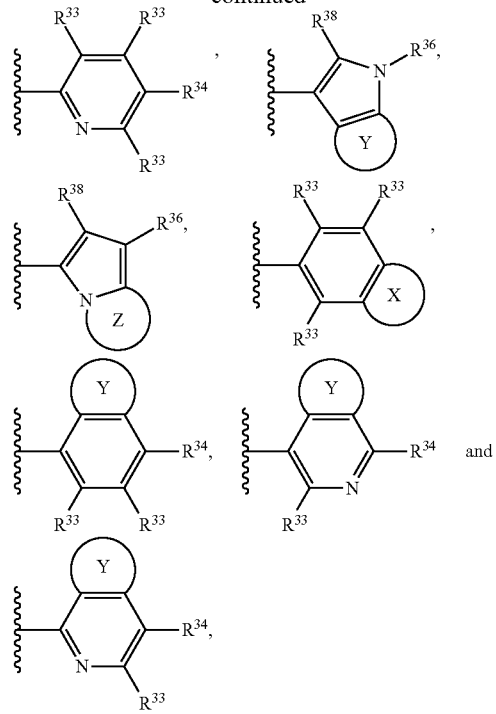

wherein

R$^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH-fluoro-$C_{1-6}$-alkyl, $C_{3-10}$-cycloalkyl, wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

R$^{34}$ are independently selected from H, halogen, CN, $C_{1-6}$-alkyl, fluoro-$C_{1-6}$alkyl, $C_{1-4}$-alkylene-OH, $C_{1-4}$-alkylene-O-fluoro-$C_{1-3}$-alkyl, OH, O—$C_{1-6}$-alkyl, O-fluoro-$C_{1-6}$-alkyl, NH-fluoro-$C_{1-6}$-alkyl, $C_{3-10}$-cycloalkyl, $C_{0-6}$-alkylene-$C_{3-10}$-heterocycloalkyl, 5-membered heteroaryl, 6-membered heteroaryl, C(O)N(R$^{37}$)$_2$ and SO$_2$N(R$^{37}$)$_2$, wherein alkylene is unsubstituted or substituted with 1 to 3 substituents selected from F and cycloalkyl, heterocycloalkyl and heteroaryl is unsubstituted or substituted with 1 to 3 substituents independently selected from F, fluoro-$C_{1-3}$-alkyl, OH, O—$C_{1-3}$-alkyl, fluoro-O—$C_{1-3}$-alkyl;

R$^{35}$ is selected from halogen, $C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl;

R$^{36}$ is selected from $C_{1-6}$-alkyl, fluoro-$C_{1-6}$-alkyl, C(O)N(R$^{37}$)$_2$, SO$_2$N(R$^{37}$)$_2$;

R$^{37}$ is independently selected from H, $C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with 1 to 4 substituents selected from halogen, OH, O—$C_{1-3}$-alkyl, CN, CONH$_2$; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;

$R^{38}$ is selected from H, $C_{1-3}$-alkyl and fluoro-$C_{1-3}$-alkyl;

X is an annelated saturated heterocycle selected from the group consisting of

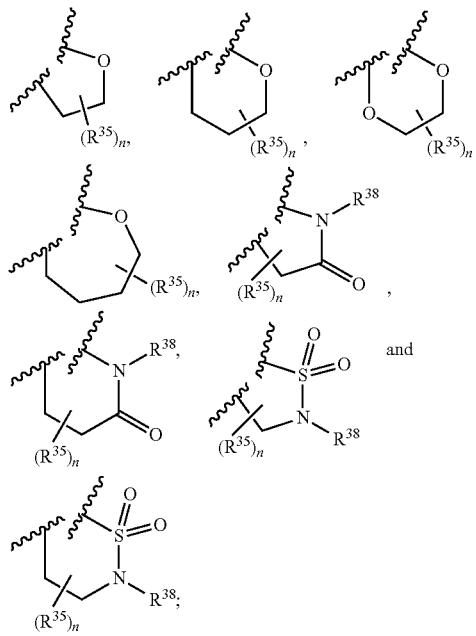

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from halogen, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl;

n is selected from 1 to 4.

In another equally preferred embodiment in combination with any of the above or below embodiments of the first alternative $R^3$ is

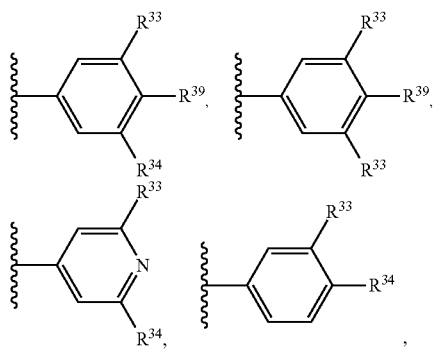

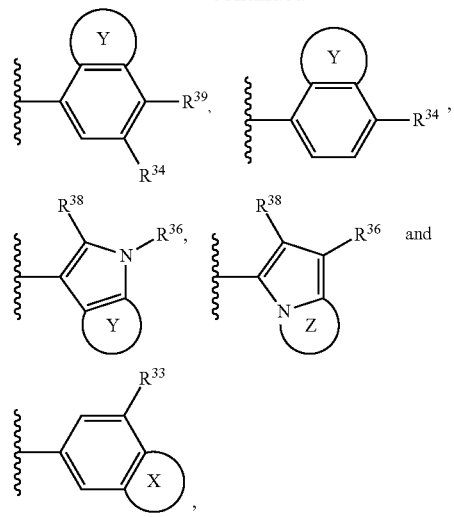

wherein $R^{33}$ is independently selected from halogen, $C_{1-6}$-alkyl, fluoro-$C_{1-6}$-alkyl, $C_{1-4}$-alkylene-OH, $C_{1-4}$-alkylene-CN, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl or $C(O)N(R^{37})_2$, wherein alkylene is unsubstituted or substituted with 1 to 3 F, and cycloalkyl is unsubstituted or substituted with 1 to 3 substituents independently selected from the group consisting of F, $C_{1-3}$-alkyl and fluoro-$C_{1-3}$-alkyl;

$R^{34}$ is $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{37})_2$ or $S(O_2)N(R^{37})_2$, wherein alkylene is unsubstituted or substituted with 1 to 3 substituents selected from F, and cycloalkyl is unsubstituted or substituted with 1 to 3 substituents independently selected from the group consisting of F, $C_{1-3}$-alkyl and fluoro-$C_{1-3}$-alkyl;

$R^{36}$ is $C_{1-6}$-alkyl, fluoro-$C_{1-6}$-alkyl, $C(O)N(R^{37})_2$ or $S(O_2)N(R^{37})_2$, $R^{37}$ is independently selected from the group consisting of H, $C_{1-6}$-alkyl, fluoro-$C_{1-6}$-alkyl, $C_{0-3}$-alkylene-$C_{3-6}$-cycloalkyl, $C_{1-6}$-alkylene-OH, $C_{1-6}$-alkylene-O—$C_{1-3}$-alkyl and $C_{1-6}$-alkylene-CN, wherein alkylene and cycloalkyl are unsubstituted or substituted with 1 to 3 substituents independently selected from the group consisting of F, $C_{1-3}$-alkyl and fluoro-$C_{1-3}$-alkyl, and wherein two $R^{37}$ when taken together with the nitrogen to which they are attached complete a 3- to 8-membered ring containing carbon atoms and optionally containing 1 or 2 heteroatoms independently selected from the group consisting of O, S and N, wherein the ring is unsubstituted or substituted with 1 to 4 substituents independently selected from the group consisting of F, oxo, $C_{1-4}$-alkyl and halo-$C_{1-4}$-alkyl;

$R^{38}$ is H, $C_{1-3}$-alkyl or fluoro-$C_{1-3}$-alkyl;

$R^{39}$ is H, F or OH;

X is an annelated saturated heterocycle selected from the group consisting of

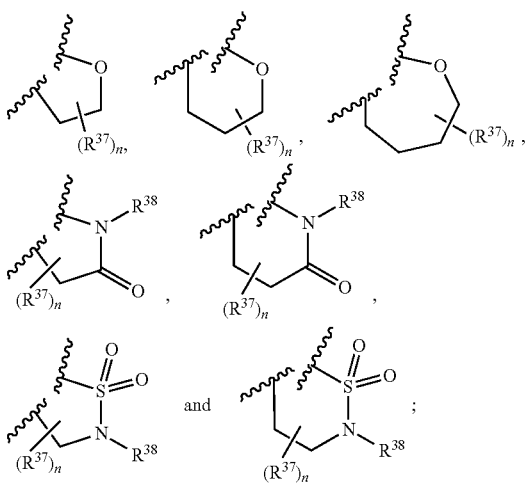

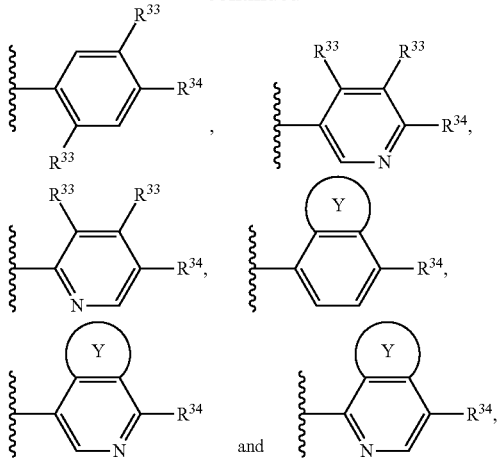

Y is an annelated 5- or 6-membered carbocycle, an annelated 5- or 6-membered heterocycle, an annelated 6-membered aryl or an annelated 5- or 6-membered heteroaryl containing 1 to 3 heteroatoms selected from the group consisting of O, S and N, wherein the carbocycle, heterocycle, aryl or heteroaryl are unsubstituted or substituted with 1 to 3 substituents selected from the group consisting of F, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents independently selected from the group consisting of F, $C_{1-3}$-alkyl and fluoro-$C_{1-3}$-alkyl;

n is selected from 1 to 4.

In a more preferred embodiment in combination with any of the above or below embodiments of the first alternative $R^3$ is selected from

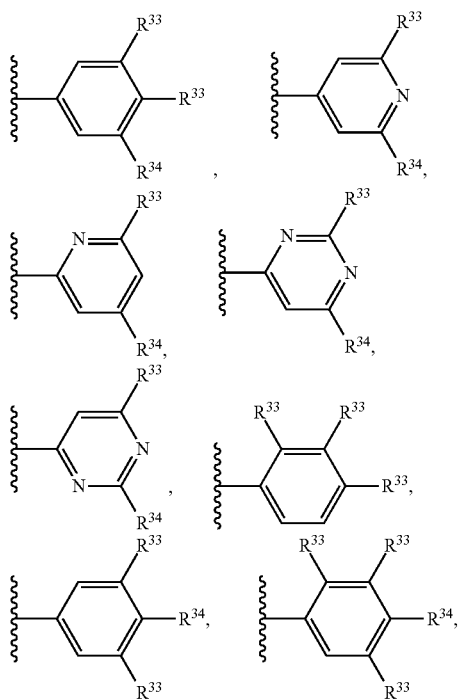

wherein
$R^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, OH, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, C(O)N($R^{37}$)$_2$,
   wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

$R^{34}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, C(O)N($R^{37}$)$_2$, SO$_2$N($R^{37}$)$_2$,
   wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

$R^{37}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl,
   wherein alkyl and alkylene is unsubstituted or substituted with 1 to 4 substituents selected from halogen, OH, O—$C_{1-3}$-alkyl, CN, CONH$_2$; and
   wherein cycloalkyl or heterocycloalkyl is unsubstituted or substituted with 1 to 3 substituents independently selected from F, CN, OH, oxo, O—$C_{1-3}$-alkyl, $C_{1-3}$-alkyl and fluoro-$C_{1-3}$-alkyl;
or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;

Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or CF$_3$.

In an even more preferred embodiment in combination with any of the above or below embodiments of the first alternative $R^3$ is selected from

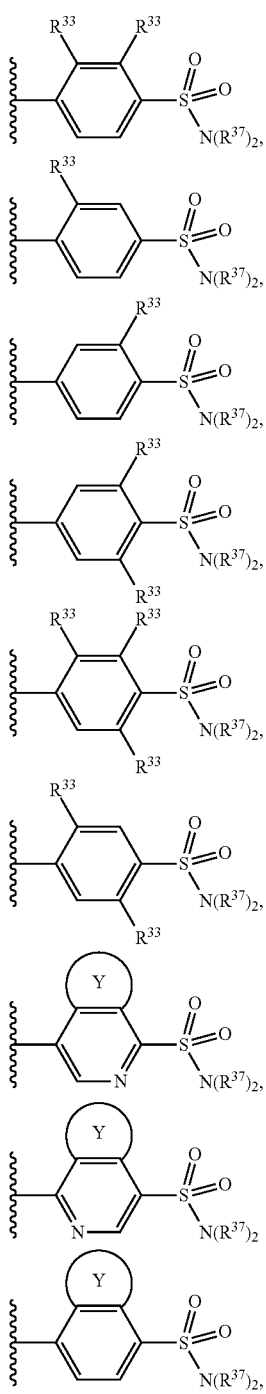

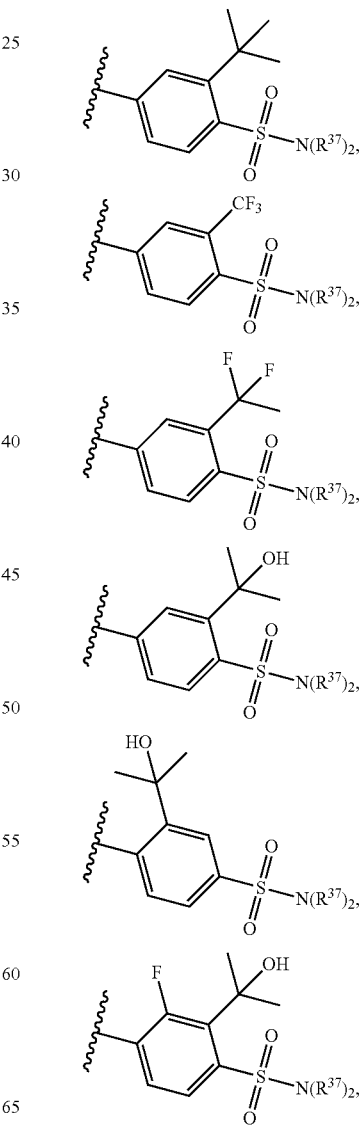

cloalkyl is unsubstituted or substituted with 1 to 3 substituents independently selected from F, CN, $CONH_2$, OH, oxo, $C_{1-3}$-alkyl and fluoro-$C_{1-3}$-alkyl, or wherein two $R^{37}$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;

Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In a most preferred embodiment in combination with any of the above or below embodiments of the first alternative $R^3$ is selected from wherein $R^{33}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{33}$ is independently selected from fluoro, chloro, $CF_3$, $CHF_2$, $OCF_3$, $OCHF_2$, methyl, $^t$butyl and $CMe_2OH$;

one $R^{37}$ is selected from H, $C_{1-6}$-alkyl, fluoro-$C_{1-6}$-alkyl and the other $R^{37}$ is selected from $C_{1-6}$-alkyl, fluoro-$C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with a substituent selected from halogen, OH, O—$C_{1-3}$-alkyl, CN, $CONH_2$; and cycloalkyl or heterocy- -continued
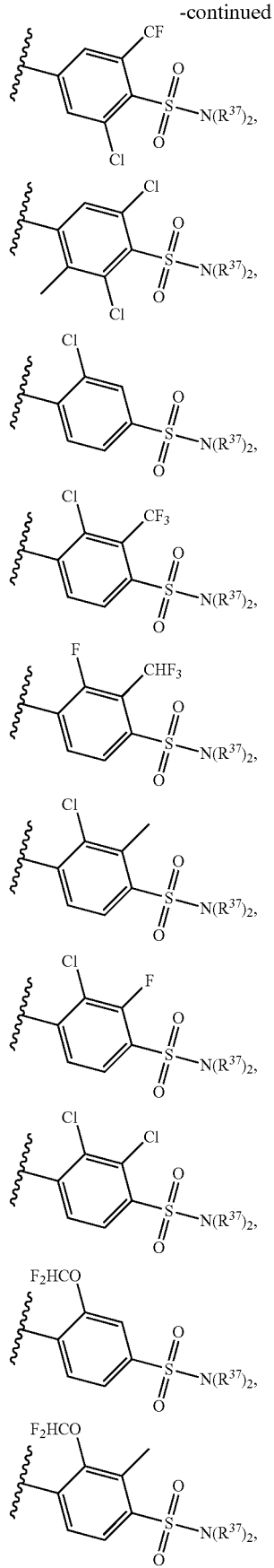
-continued
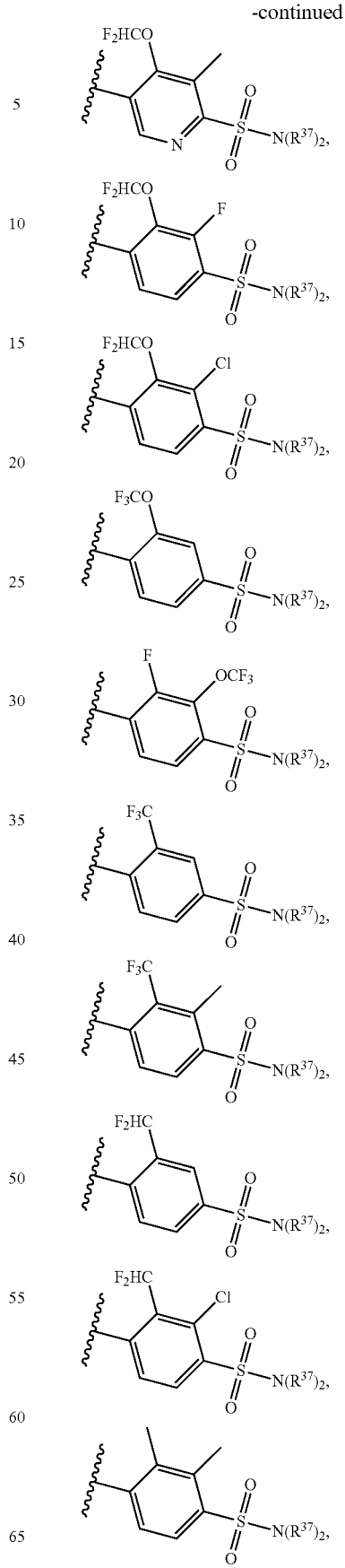

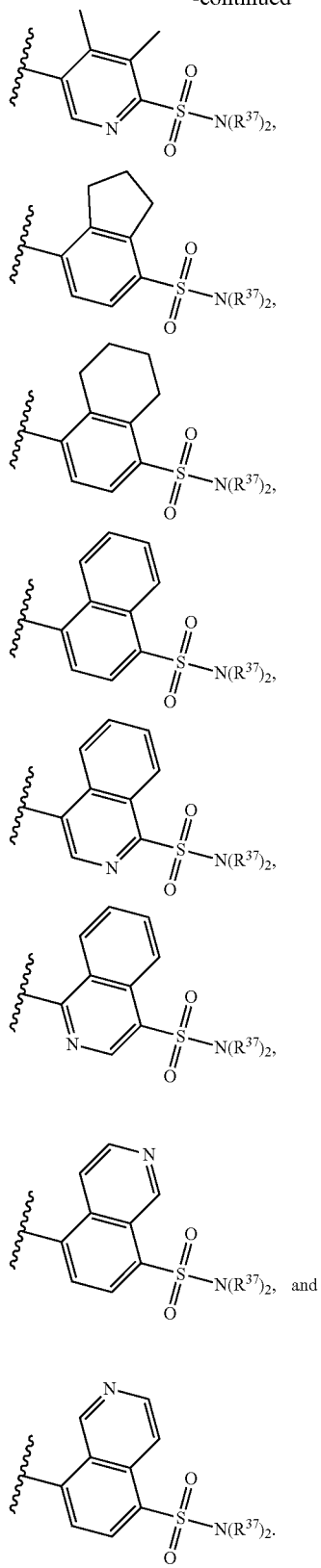
In another preferred embodiment in combination with any of the above or below embodiments of the first alternative N(R$^{37}$)$_2$ is selected from
In a more preferred embodiment in combination with any of the above or below embodiments of the first alternative N(R$^{37}$)$_2$ is selected from

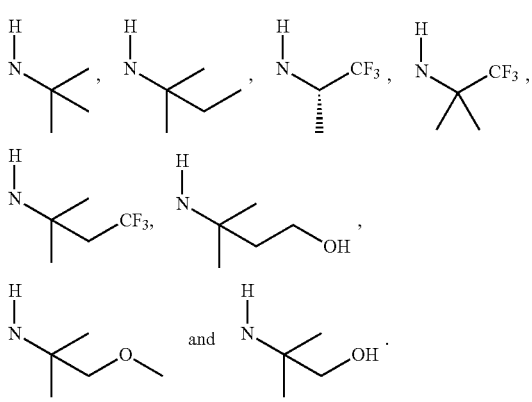
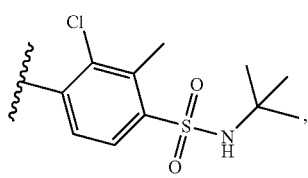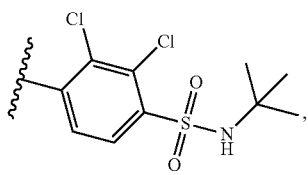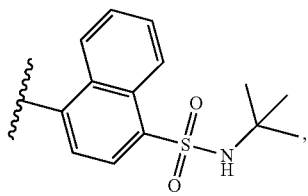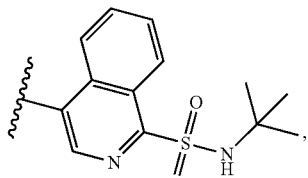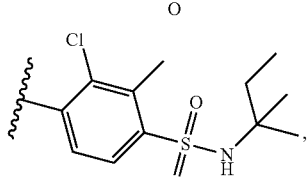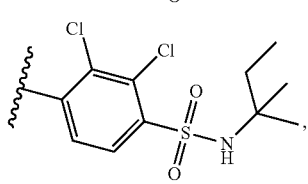
In another preferred embodiment in combination with any of the above or below embodiments of the first alternative R³ is selected from
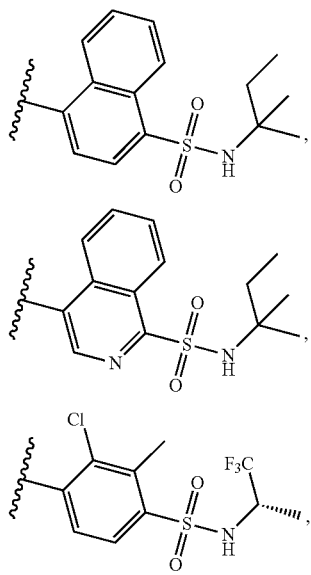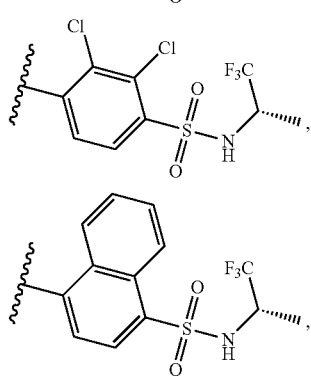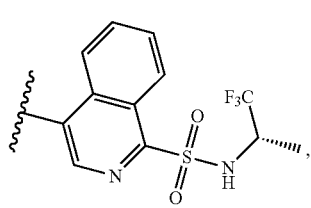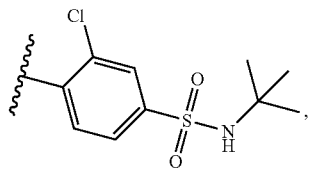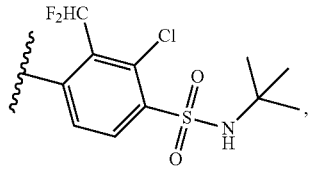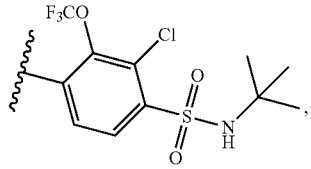

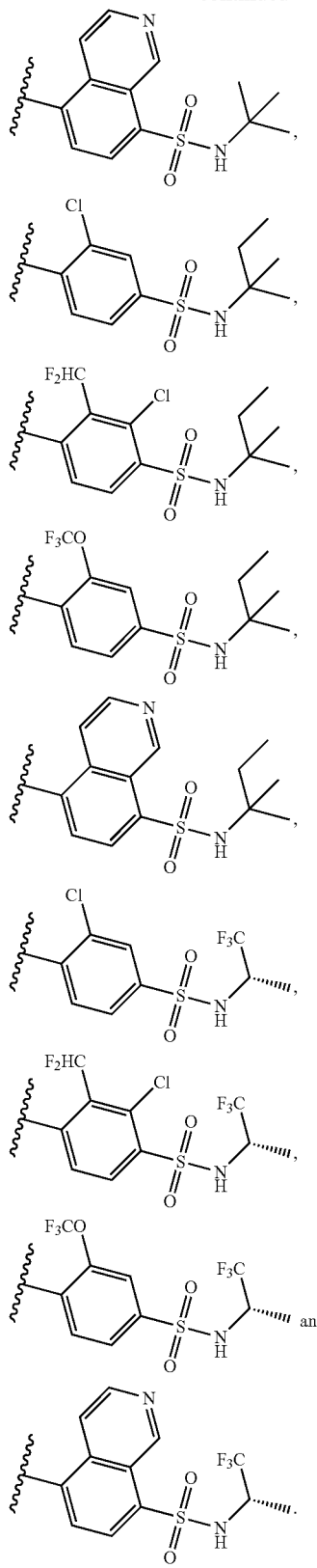

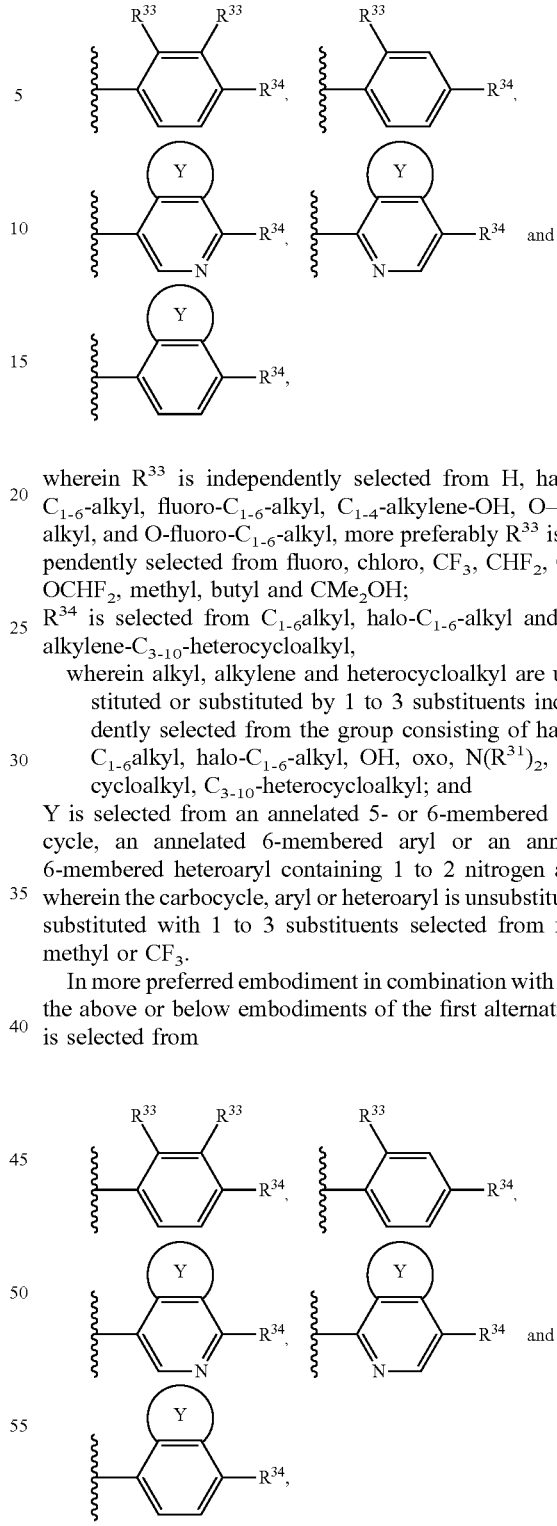

wherein $R^{33}$ is independently selected from H, halogen, $C_{1-6}$-alkyl, fluoro-$C_{1-6}$-alkyl, $C_{1-4}$-alkylene-OH, O—$C_{1-6}$-alkyl, and O-fluoro-$C_{1-6}$-alkyl, more preferably $R^{33}$ is independently selected from fluoro, chloro, $CF_3$, $CHF_2$, $OCF_3$, $OCHF_2$, methyl, butyl and $CMe_2OH$;

$R^{34}$ is selected from $C_{1-6}$alkyl, halo-$C_{1-6}$-alkyl and $C_{0-6}$-alkylene-$C_{3-10}$-heterocycloalkyl,
  wherein alkyl, alkylene and heterocycloalkyl are unsubstituted or substituted by 1 to 3 substituents independently selected from the group consisting of halogen, $C_{1-6}$alkyl, halo-$C_{1-6}$-alkyl, OH, oxo, $N(R^{31})_2$, $C_{3-10}$-cycloalkyl, $C_{3-10}$-heterocycloalkyl; and Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or $CF_3$.

In more preferred embodiment in combination with any of the above or below embodiments of the first alternative $R^3$ is selected from

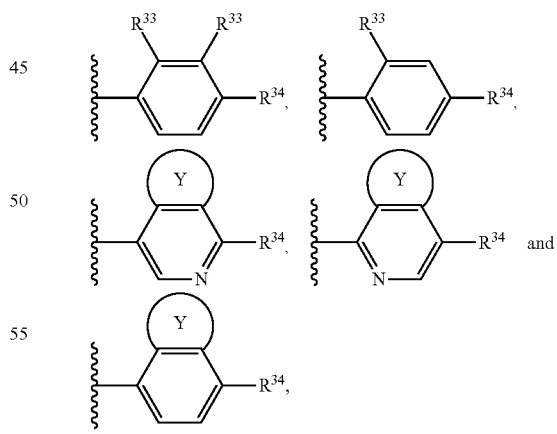

wherein $R^{33}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, and O-fluoro-$C_{1-6}$-alkyl, more preferably $R^{33}$ is independently selected from fluoro, chloro, $CF_3$, $CHF_2$, $OCF_3$, $OCHF_2$, methyl, butyl and $CMe_2OH$;

$R^{34}$ is selected from

In another preferred embodiment in combination with any of the above or below embodiments of the first alternative $R^3$ is selected from

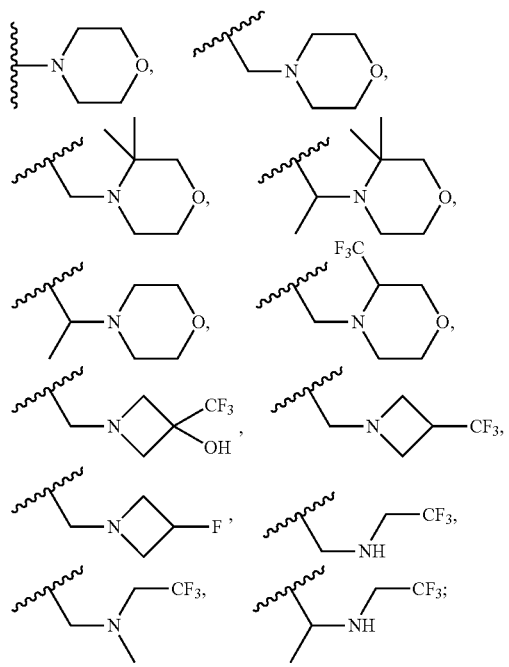

more preferably R³⁴ is

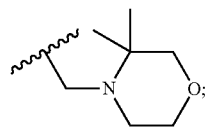 [SMILES: *CN1CCOCC1(C)C]

Y is selected from an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, methyl or CF₃.

In an alternative preferred embodiment in combination with any of the above or below embodiments of the first alternative R³ is selected from

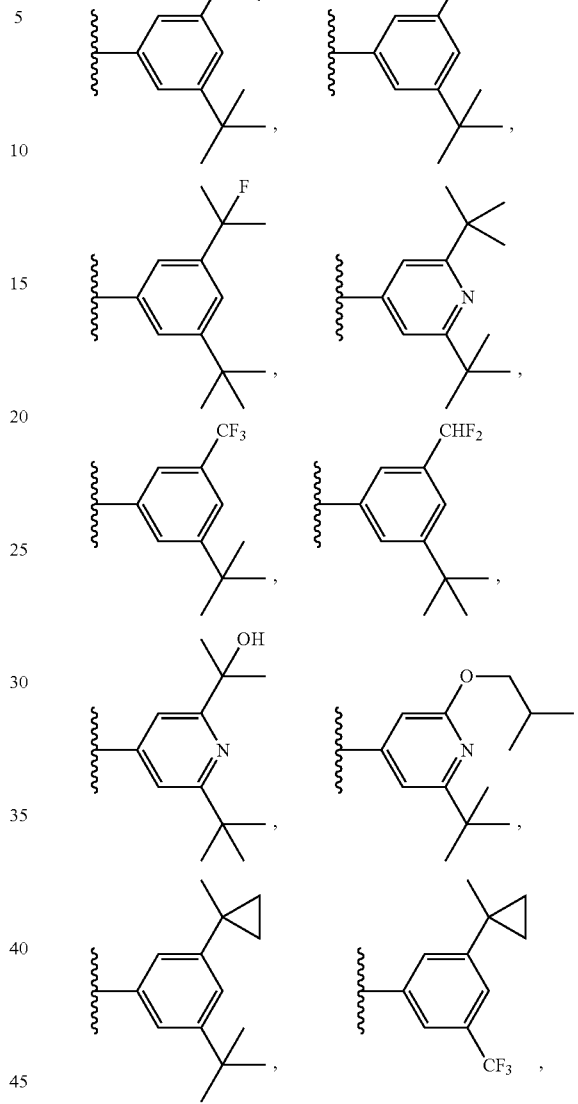

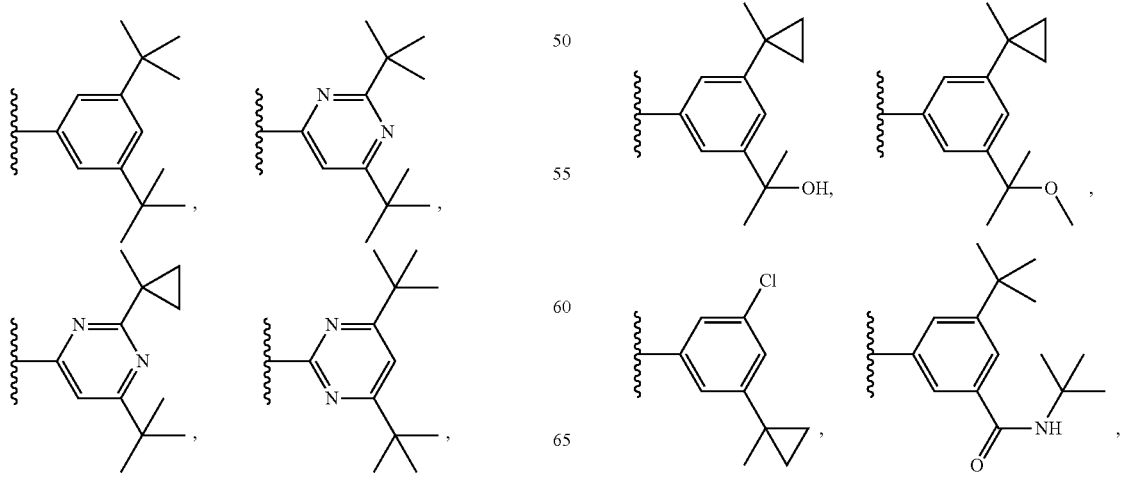

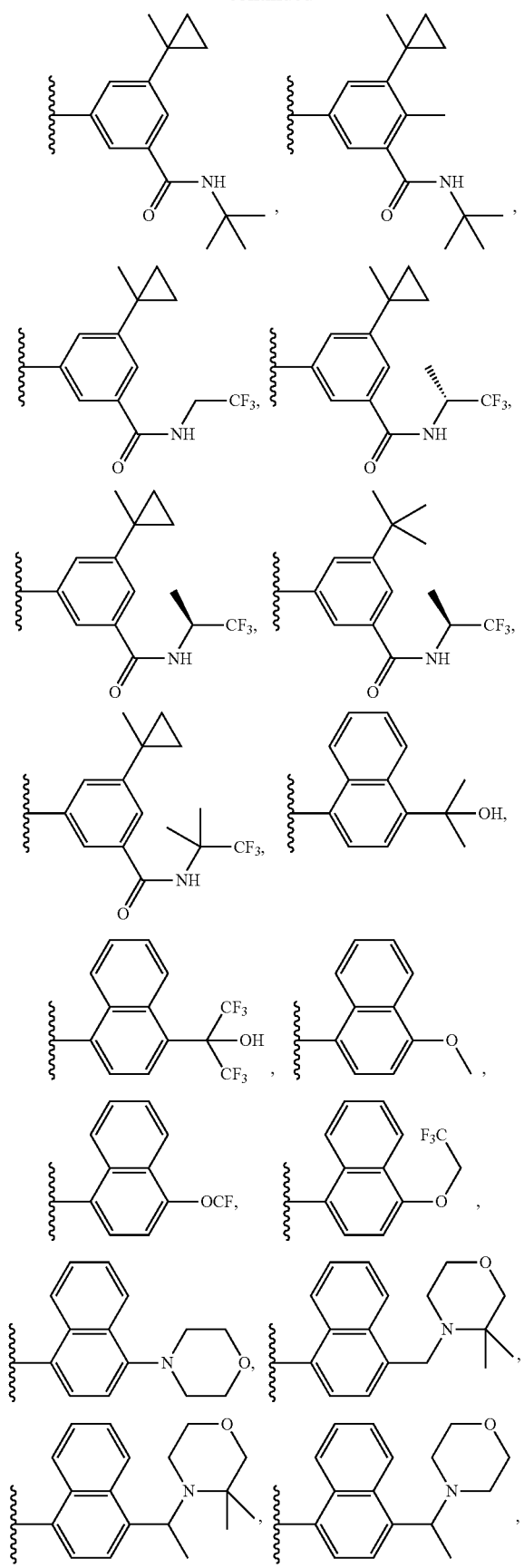
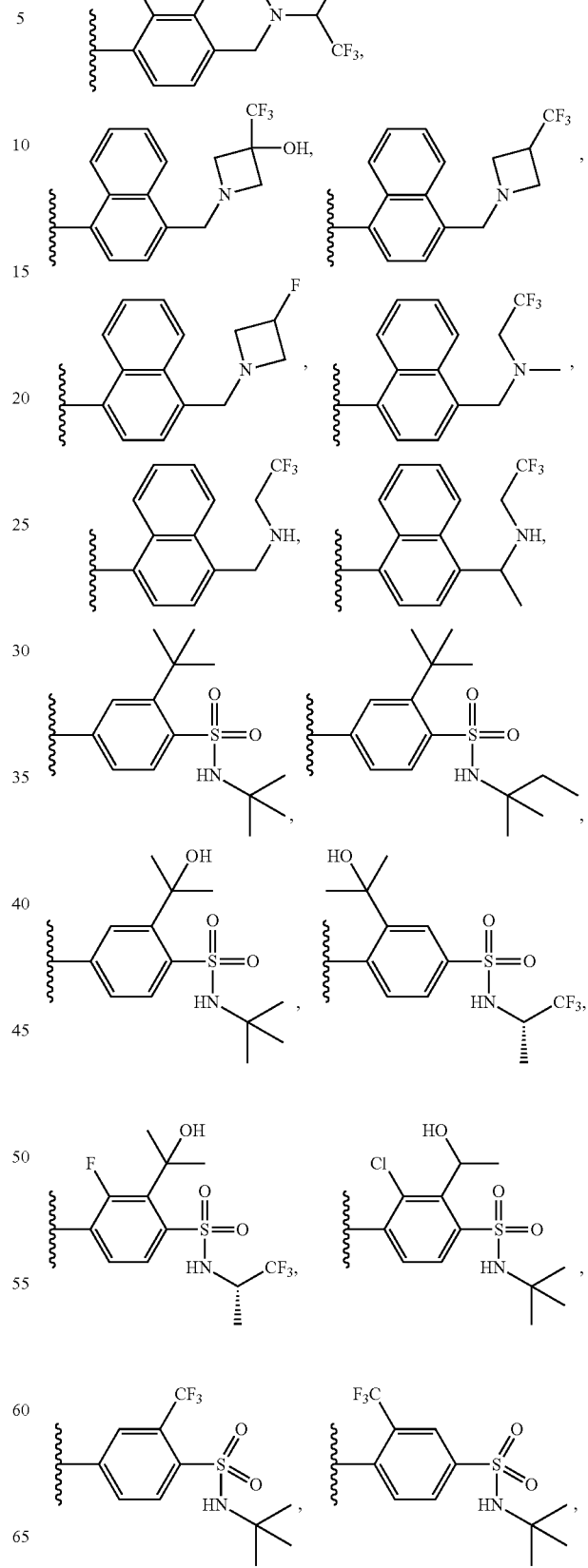

-continued
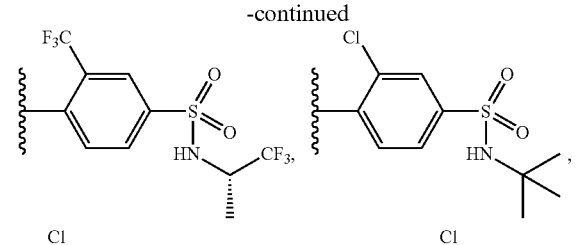
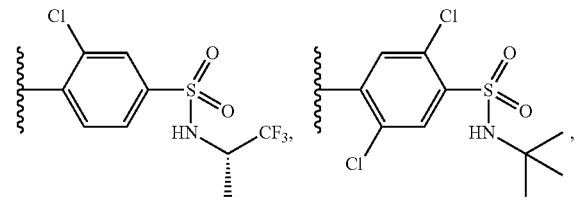
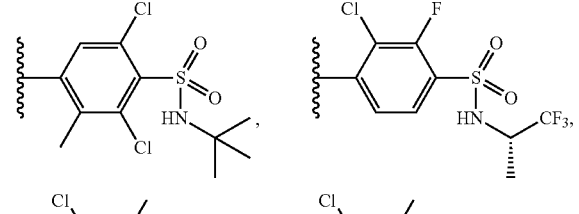
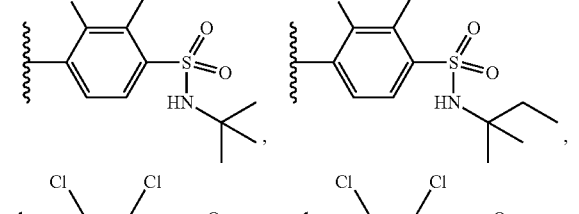
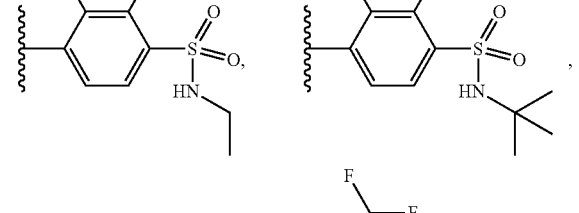
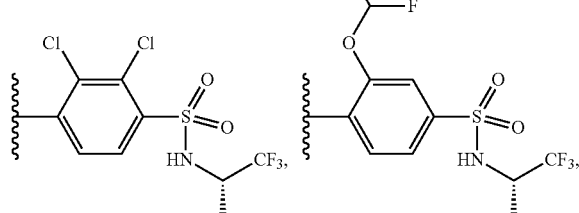
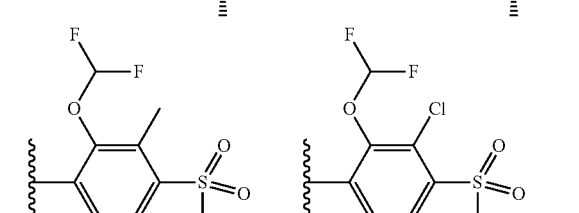
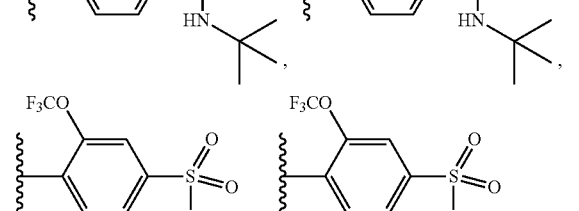
-continued
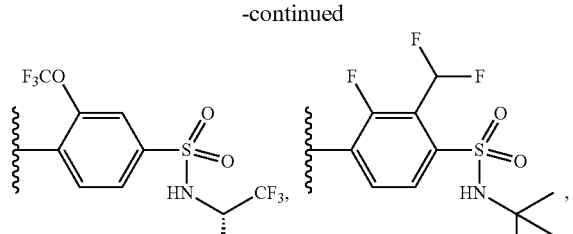
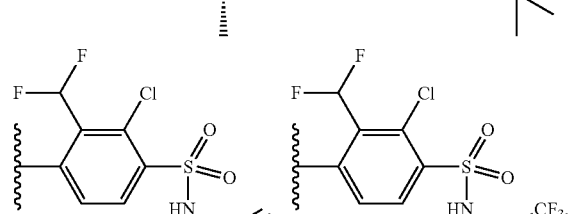
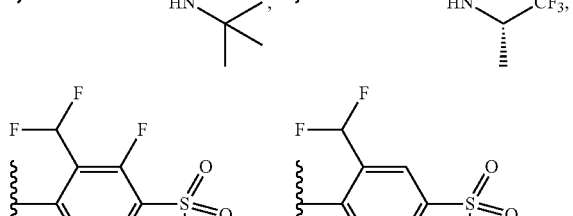
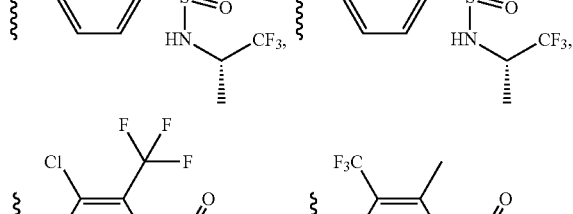

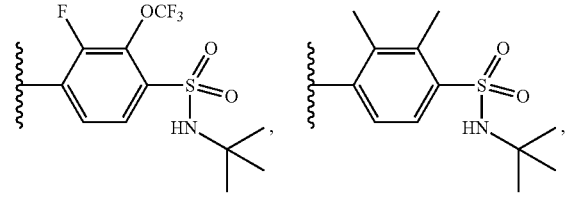
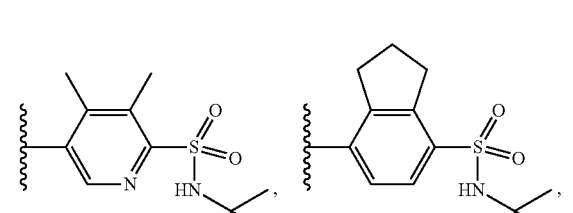
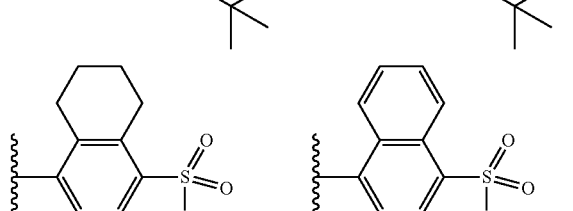

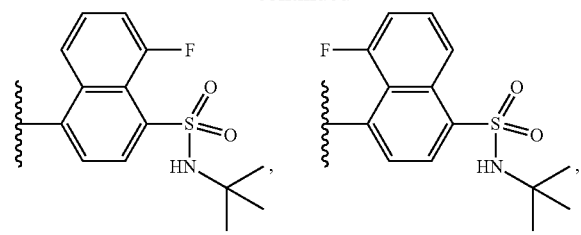
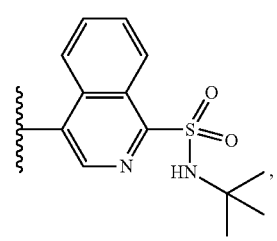
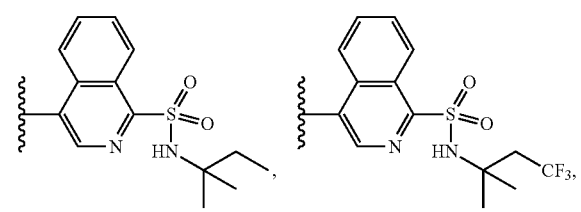
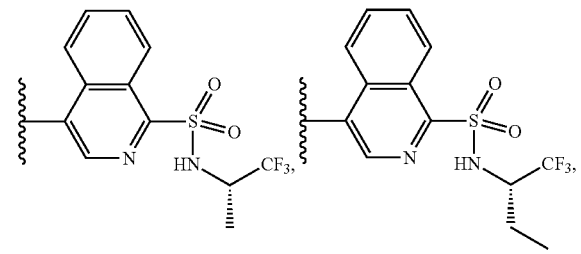
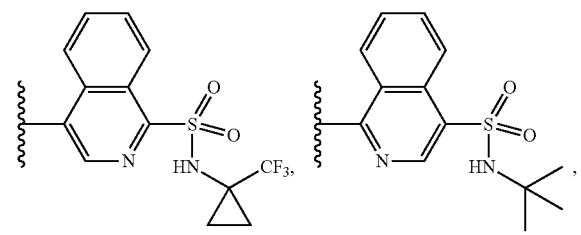
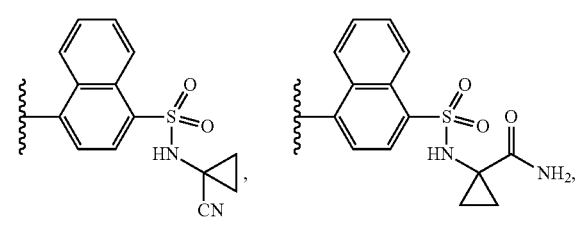
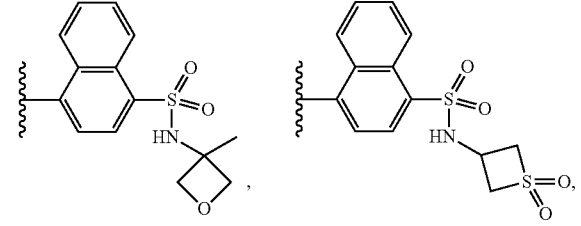
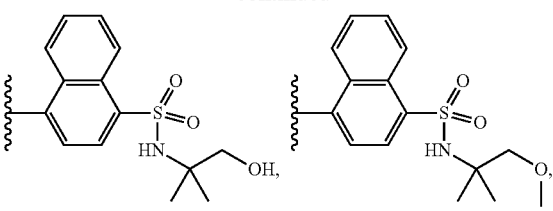
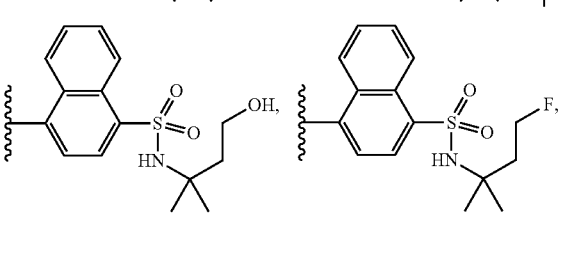
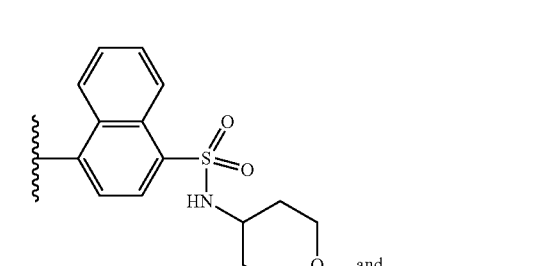
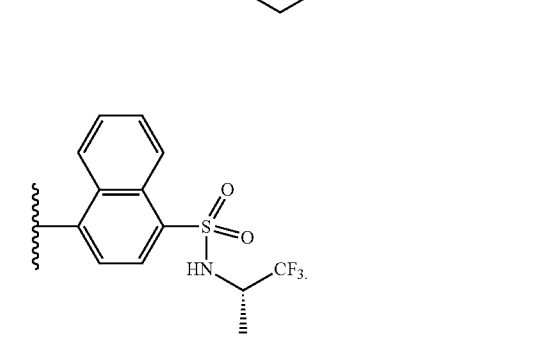
In an alternative preferred embodiment in combination with any of the above or below embodiments of the first alternative R³ is
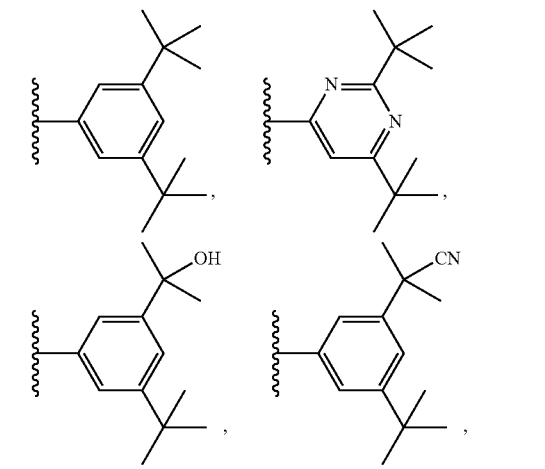

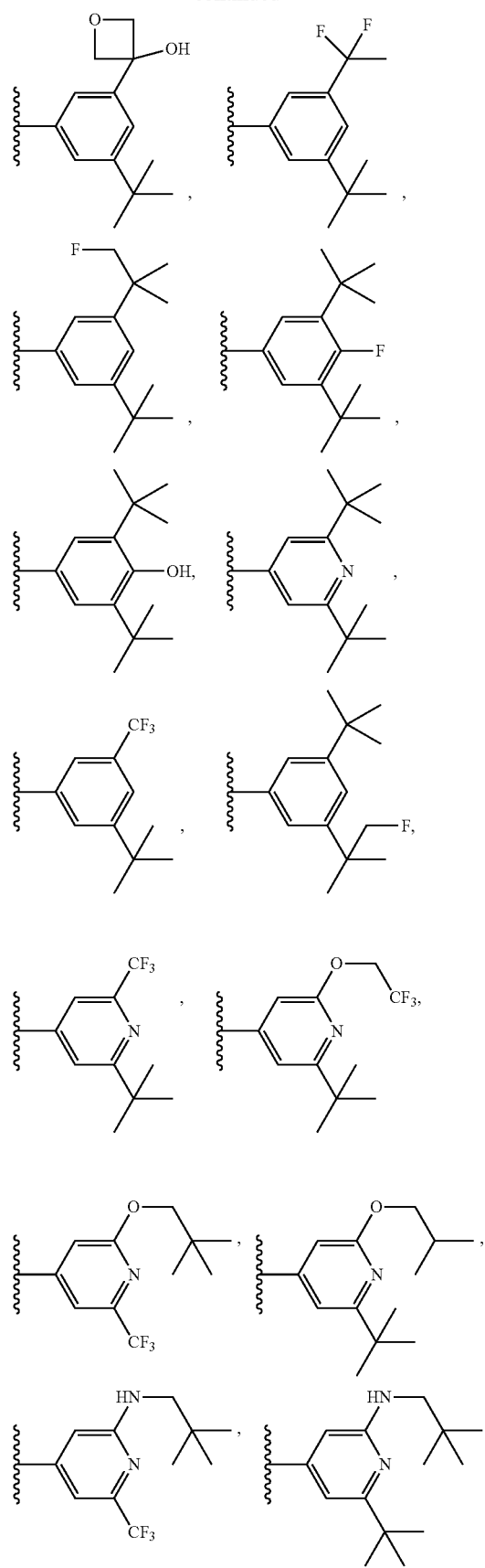
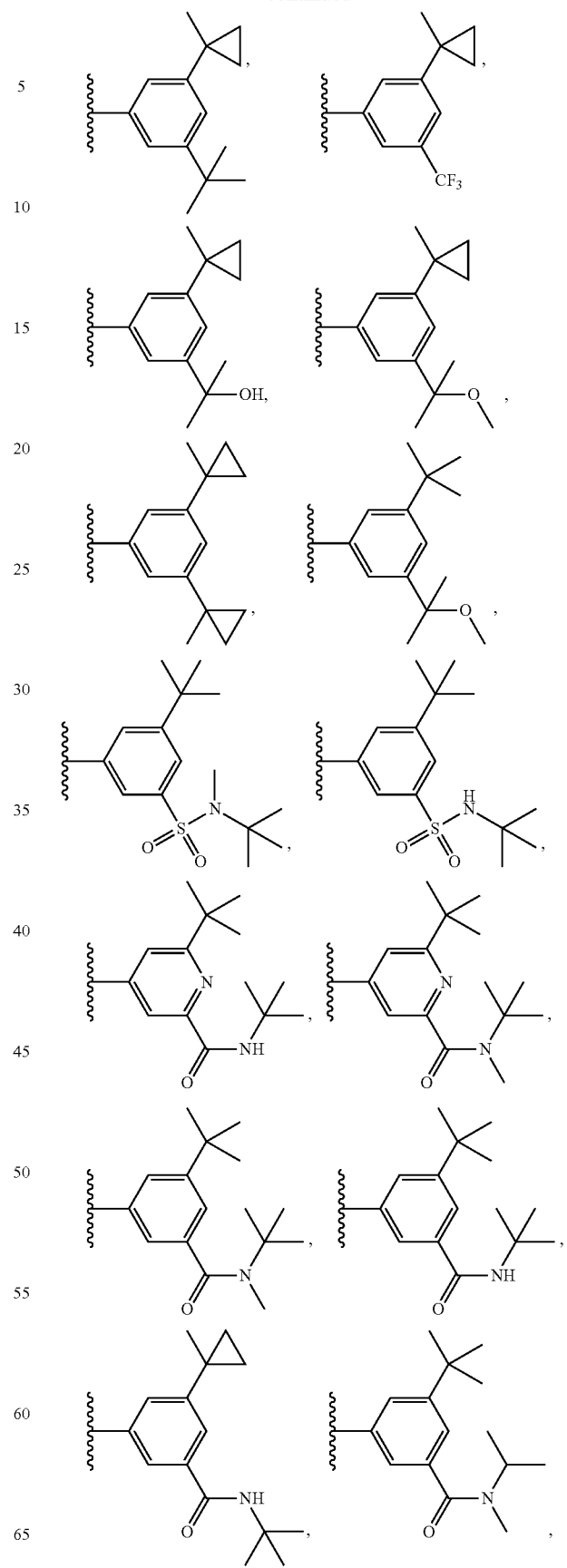

65
-continued
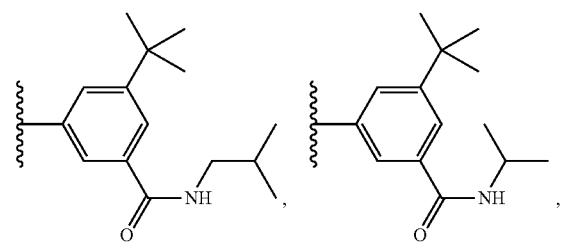
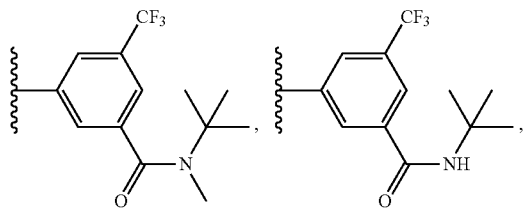
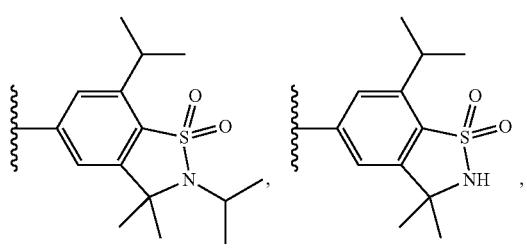
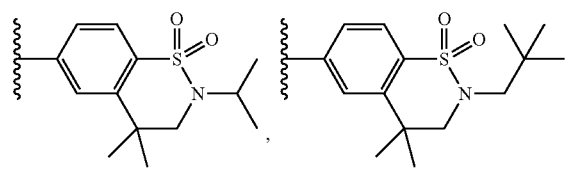
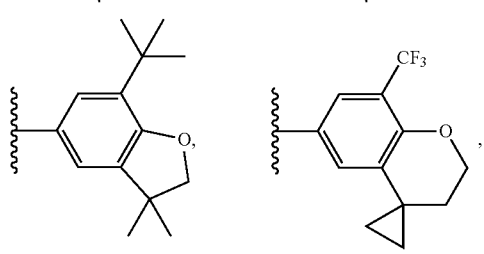
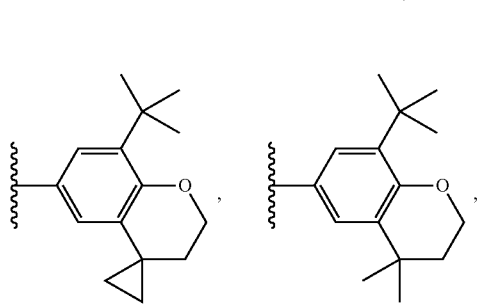
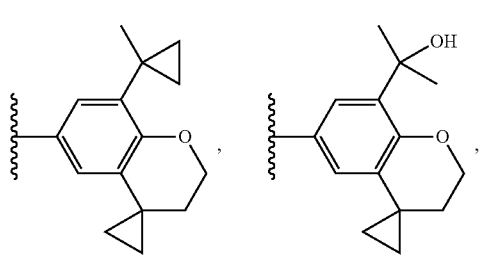
66
-continued
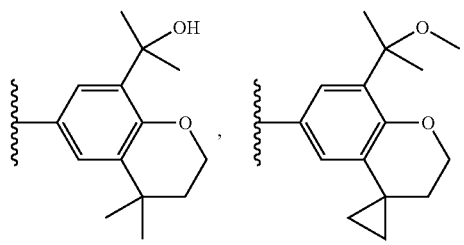
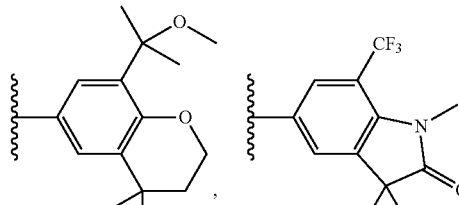
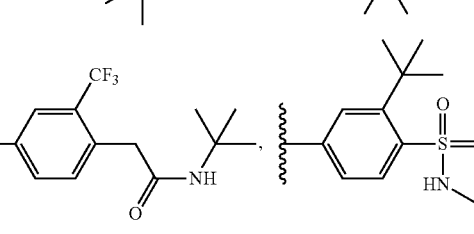
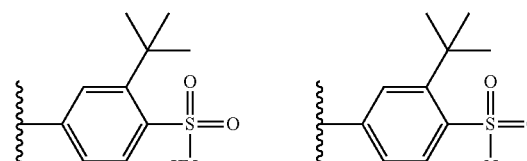
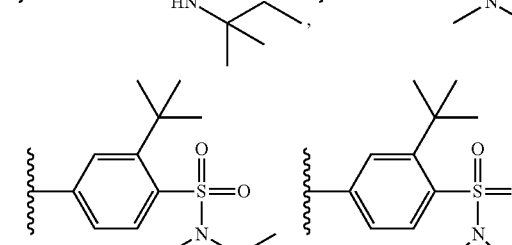
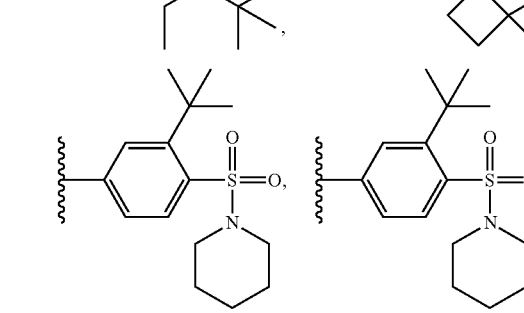
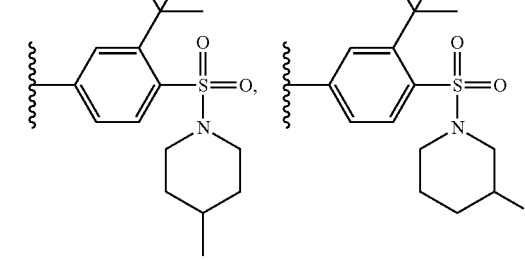

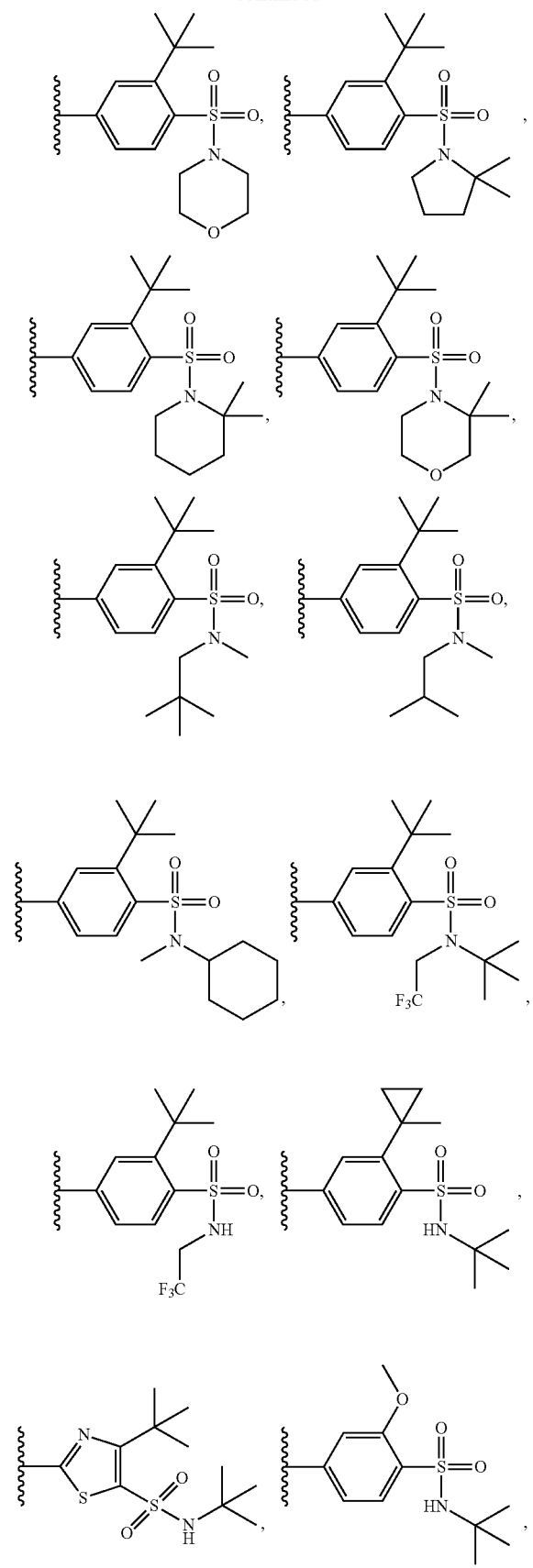
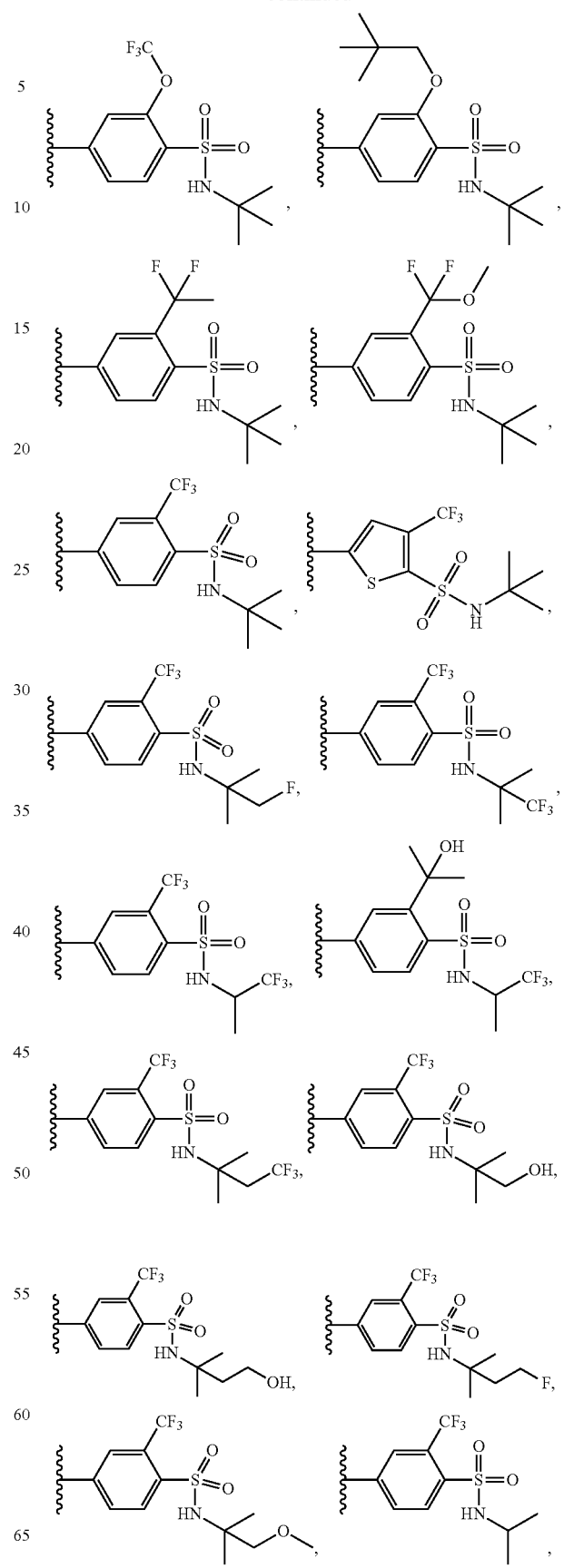

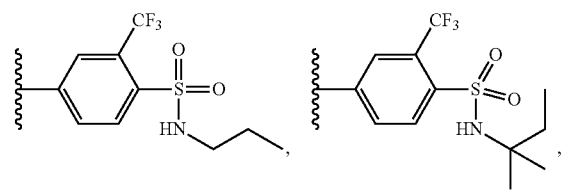
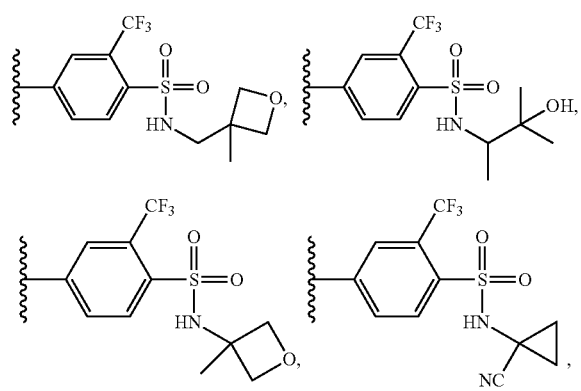
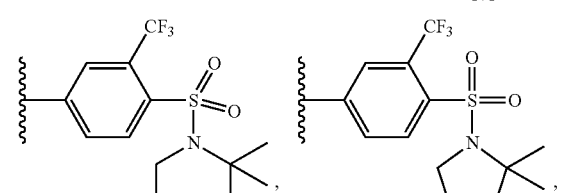
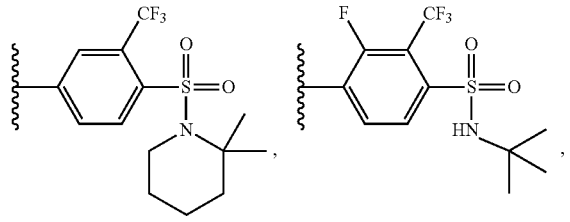
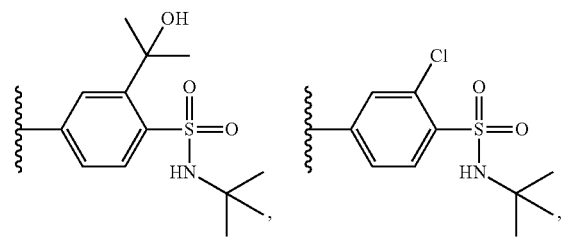
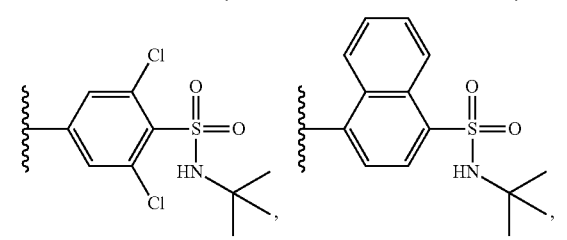
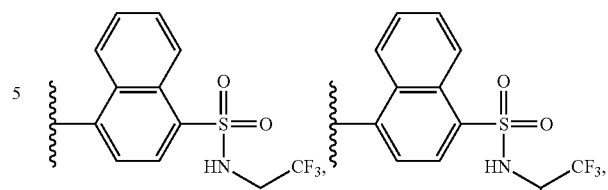
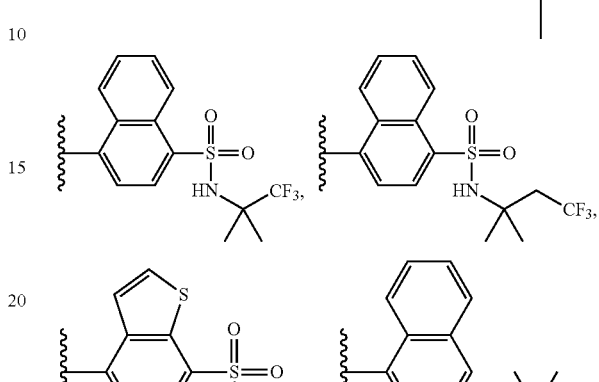
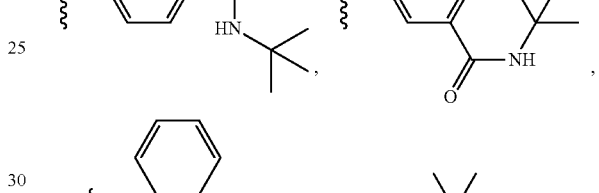

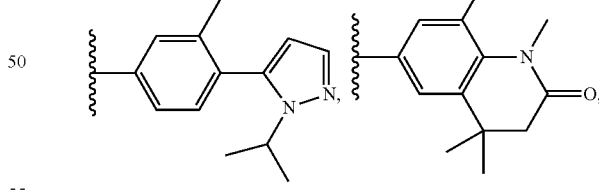
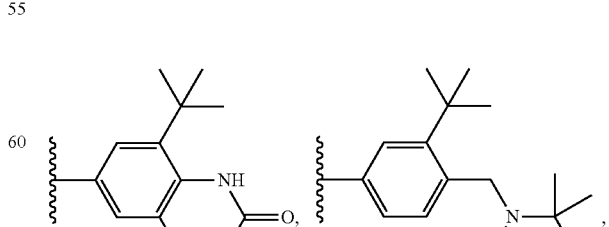

-continued

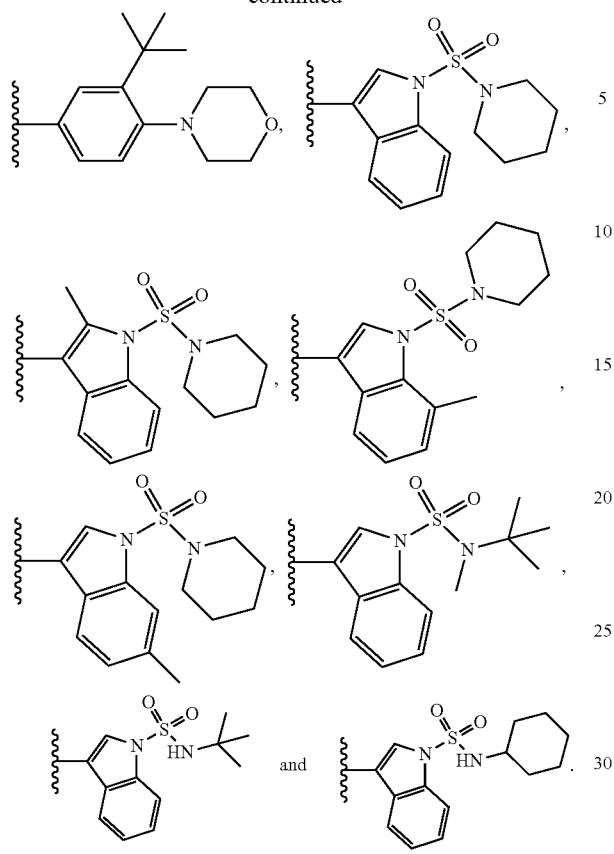

In a preferred embodiment in combination with any of the above or below embodiments of the first alternative R³ is selected from -continued

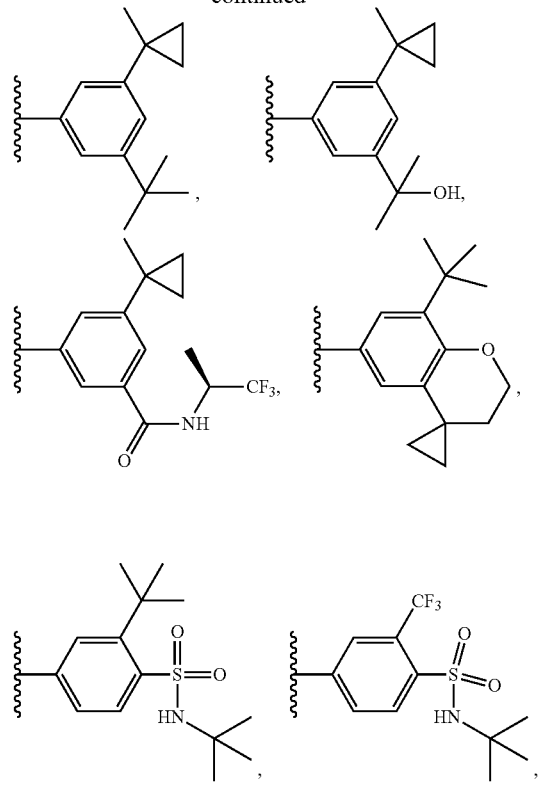

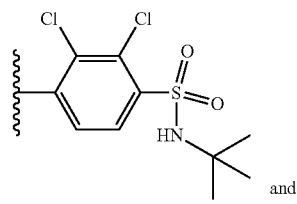

and

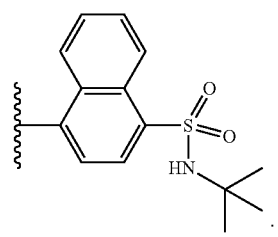

In another preferred embodiment in combination with any of the above or below embodiments of the first alternative the compound is represented by Formula (1) to Formula (3); more preferably by Formula (2).

In yet another preferred embodiment in combination with any of the above or below embodiments of the first alternative the compound is represented by Formula (4) and Formula (5); more preferably by Formula (4).

In another preferred embodiment in combination with any of the above or below embodiments of the first alternative, the compound of Formula (1) to Formula (3) is selected from the group consisting of

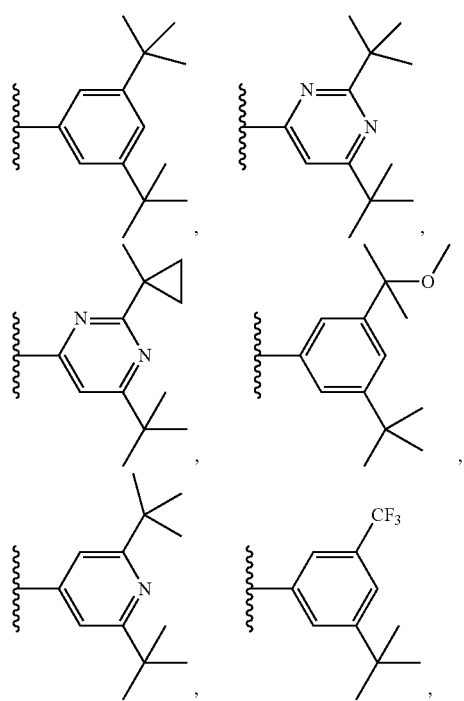

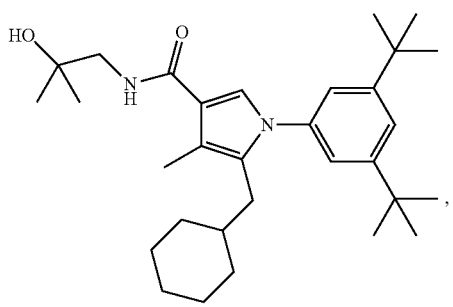
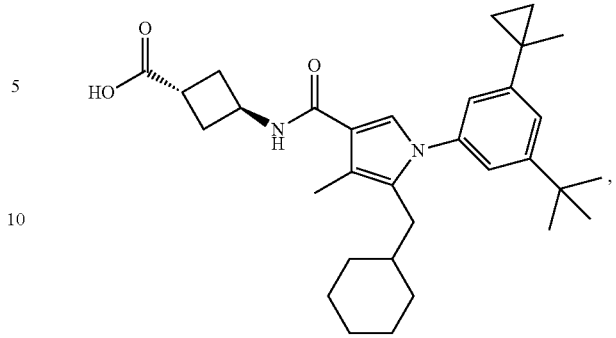
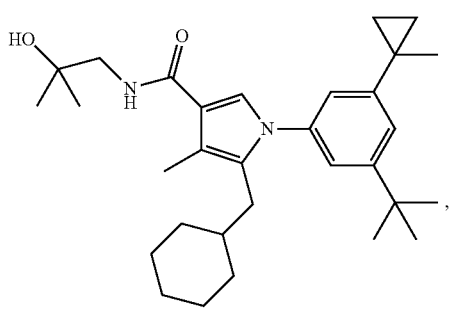
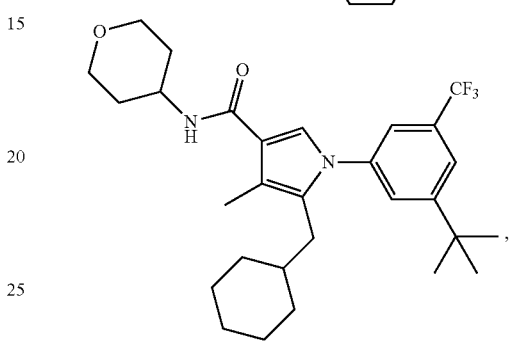
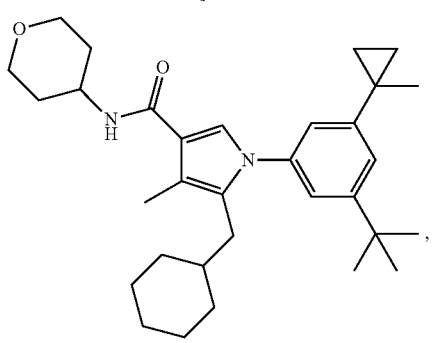
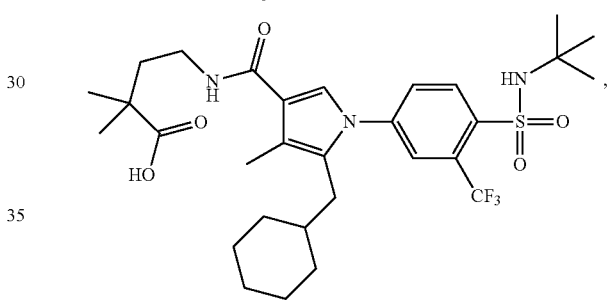
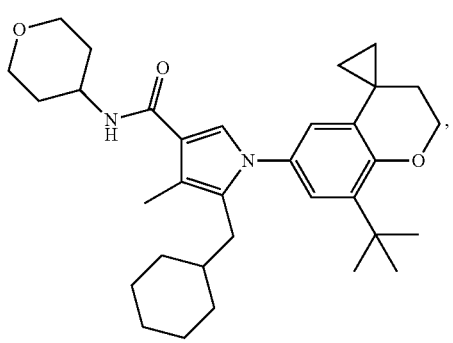
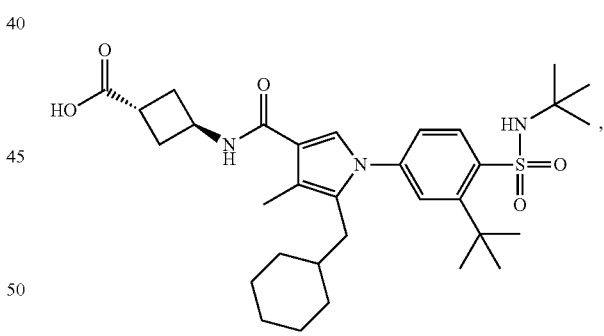
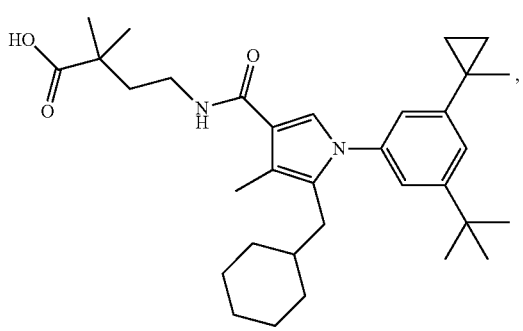
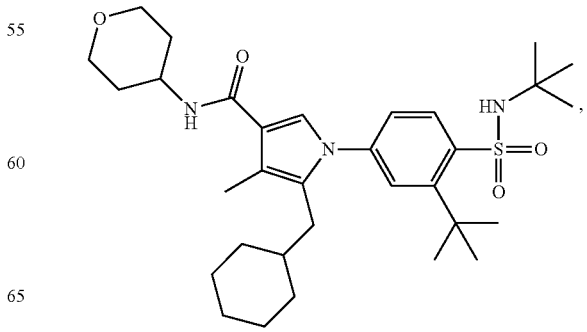

75
-continued
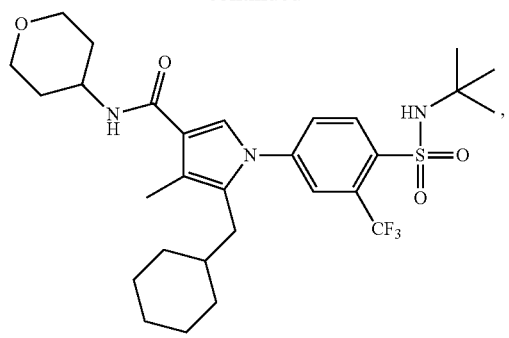
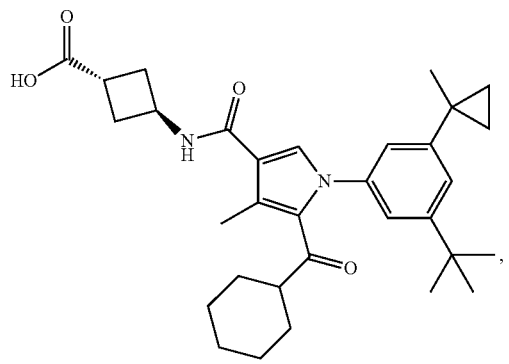
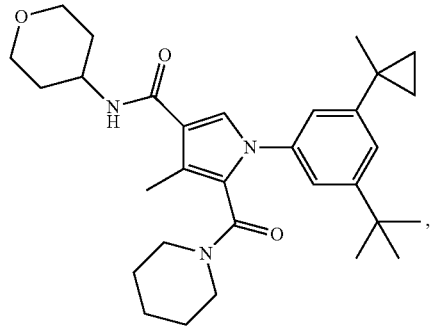
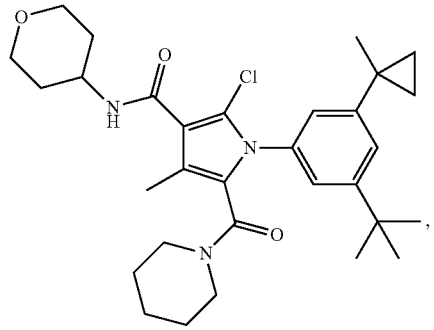
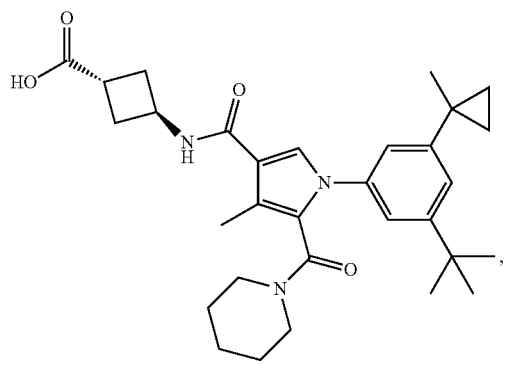
76
-continued
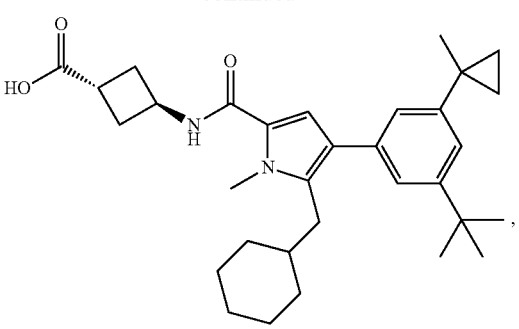
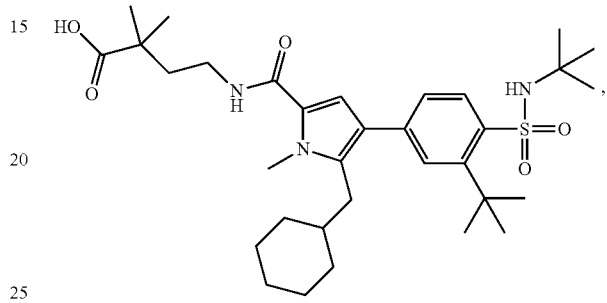
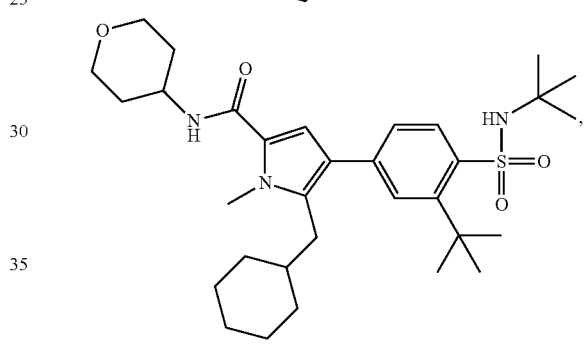
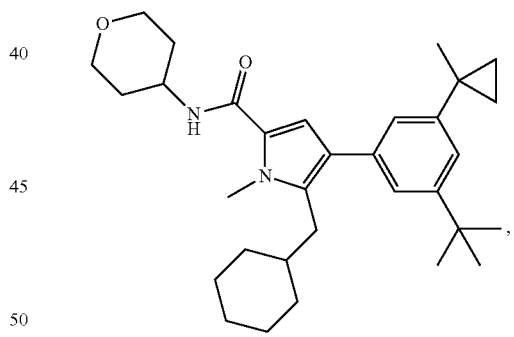
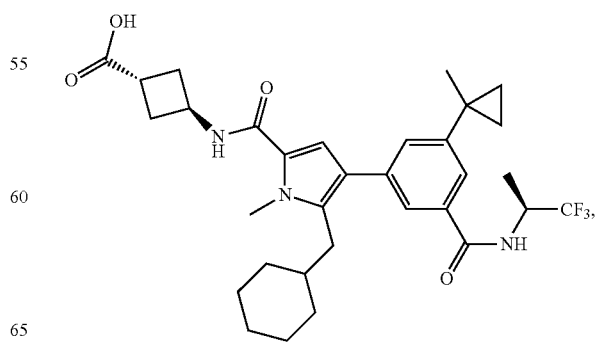

77
-continued
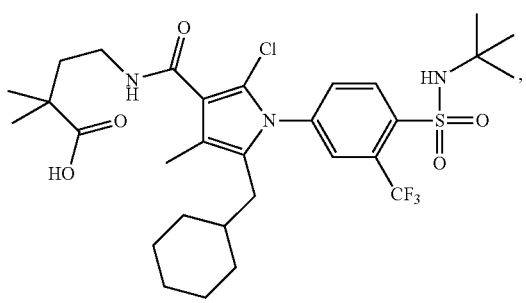
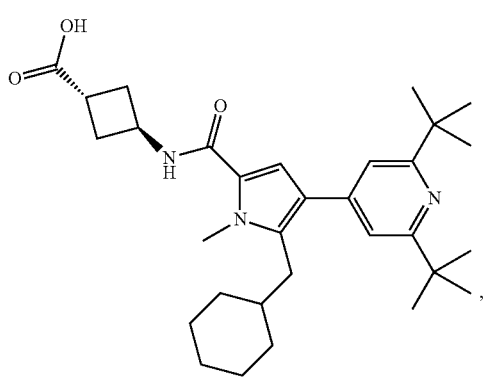
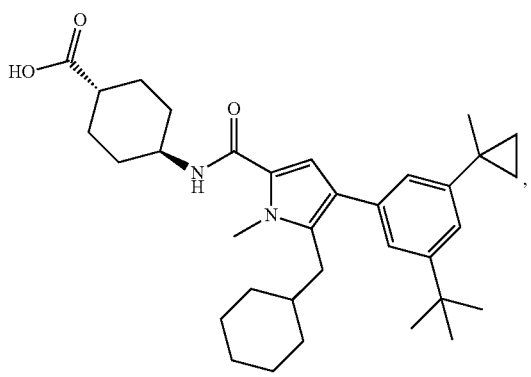
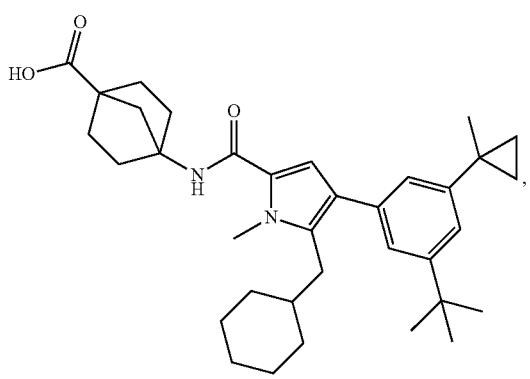
78
-continued
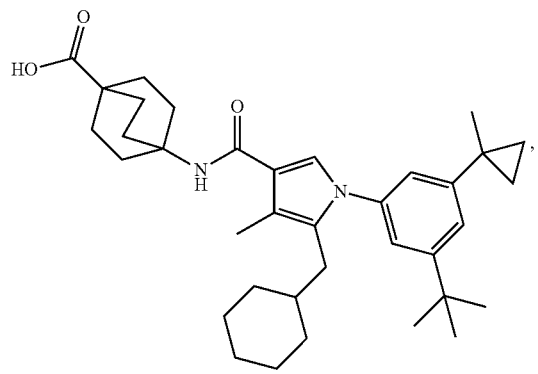
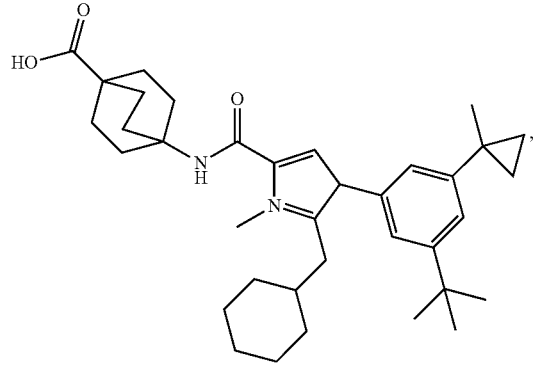
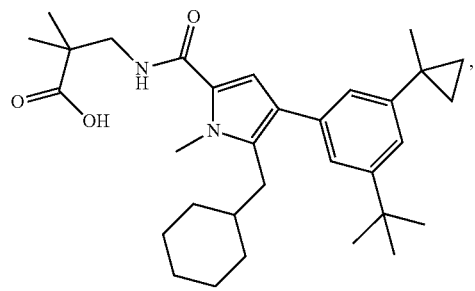
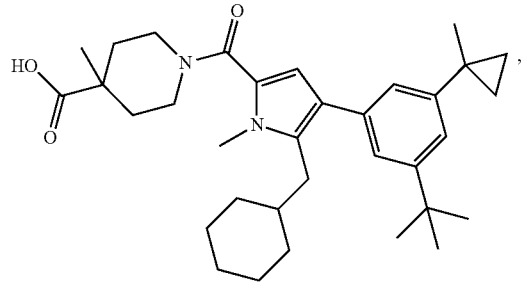
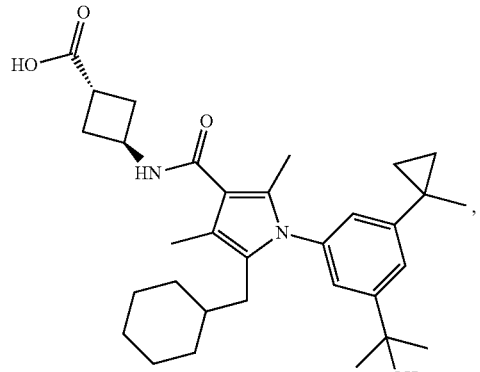

-continued

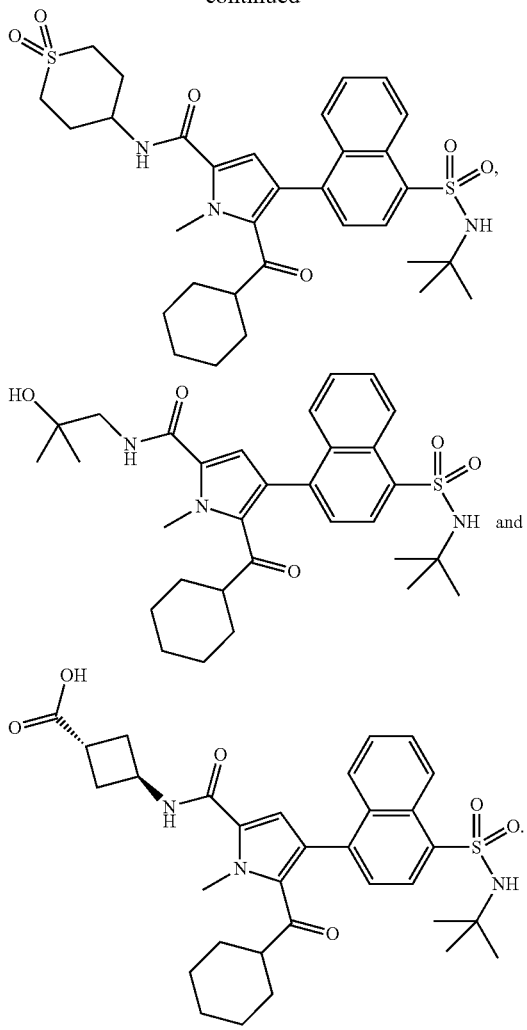

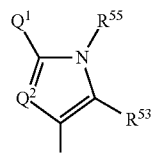

(6)

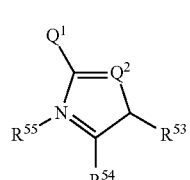

(7)

(8)

(9)

The invention also provides the compound of the first alternative of the invention for use as a medicament.

Also provided is the compound of the first alternative of the invention for use in the treatment or prophylaxis of a disease or disorder associated with the inhibition or activation of the RORγ receptor.

Also provided is the compound of the first alternative of the invention for use in treating RORγ mediated inflammatory and autoimmune diseases. Preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thromobotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

Also provided is a pharmaceutical composition comprising the compound of the first alternative of the invention and a pharmaceutically acceptable carrier.

In a second alternative the present invention provides a compound according to Formula (6) to Formula (9)

an enantiomer, diastereomer, tautomer, solvate, formulation and pharmaceutically acceptable salt thereof,
wherein
$Q^1$ is $CO-NR^{51}R^{52}$, $CO-R^{52}$, $CO_2R^{51}$, $SO_2-NR^{51}R^{52}$, $SO_2-R^{52}$, $NR^{52}CO-R^{51}$ or $NR^{52}SO_2-R^{51}$;
$Q^2$ and $Q^3$ are independently selected from N and $CR^{56}$;
$R^{51}$ and $R^{52}$ are independently selected from the group consisting of H, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene 5 to 10-membered heteroaryl and $C_{0-10}$-alkylene-aryl, wherein alkyl, alkenyl, alkynyl, alkylene, cycloalkyl, heterocycloalkyl, aryl and heteroaryl are unsubstituted or substituted with 1 to 7 substituents independently selected from the group consisting of oxo, CN, $OR^{61}$, $O-C_{2-6}$-alkylene-$OR^{61}$, $C_{1-6}$-alkyl, halo-$C_{1-6}$-alkyl, halogen, $CO_2R^{61}$, $CONR^{61}R^{62}$, $CONR^{61}SO_2R^{62}$, $COR^{61}$, $SO_xR^{61}$, $SO_3H$, $SO_2NR^{61}R^{62}$, $NR^{61}COR^{61}$, $NR^{61}SO_2R^{61}$, $NR^{61}-CO-NR^{61}R^{62}$, $NR^{61}-SO_2-NR^{61}R^{62}$, $C_{3-6}$-cycloalkyl, $O-C_{3-6}$-cycloalkyl, $C_{3-6}$-heterocycloalkyl, $O-C_{3-6}$-heterocycloalkyl and $NR^{61}R^{62}$;
or $R^{51}$ and $R^{52}$ when taken together with the nitrogen to which they are attached complete a 3- to 8-membered ring containing carbon atoms and optionally containing 1 or 2 heteroatoms independently selected from the group consisting of O, S and N, wherein the ring is unsubstituted or substituted with 1 to 4 substituents independently selected from the group consisting of halogen, oxo, CN, $OR^{61}$, $SO_xR^{61}$, $SO_3H$, $NR^{61}SO_2R^{61}$, $SO_2NR^{61}R^{62}$, $CO_2R^{61}$, $CONR^{61}R^{62}$, $CONR^{61}SO_2R^{62}$, $COR^{61}$, $NR^{61}-CO-R^{61}$, $NR_{61}-CO-NR^{61}R_{62}$, $NR_{61}-SO_2-NR^{61}R^{62}$, $NR^{61}R^{62}$, $C_{1-6}$-alkyl, halo-$C_{1-6}$-alkyl, hydroxy-$C_{1-6}$-alkyl, $C_{3-6}$-cycloalkyl, $O-C_{3-6}$-cycloalkyl, $C_{3-6}$-heterocycloalkyl and $O-C_{3-6}$-heterocycloalkyl;
$R^{53}$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl are unsubstituted or substituted with 1 to 5 substituents independently selected from the group consisting of halogen, CN, $C_{1-6}$-alkyl, $C_{2-6}$-alkenyl, $C_{2-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR$^{51}$, $C_{0-6}$-alkylene-C(I)R$^{81}$, $C_{0-6}$-alkylene-C(O)N(R$^{81}$)$_2$, $C_{0-6}$-alkylene-N(R$^{81}$)$_2$, $C_{0-6}$-alkylene-SO$_2$—N(R$^{81}$)$_2$, $C_{0-6}$-alkylene-SO$_2$—R$^{81}$, $C_{0-6}$-alkylene-(6-10-membered mono- or bicyclic aryl), and $C_{0-6}$-alkylene-(6-10-membered mono- or bicyclic heteroaryl), wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—OR$^{82}$, N(R$^{81}$)$_2$, O—$C_{1-6}$-alkyl, O-halo-$C_{1-6}$-alkyl, COOH, CON(R$^{81}$)$_2$, CN, NR$^{81}$—COR$^{81}$, $C_{3-10}$-cycloalkyl, $C_{3-10}$-heterocycloalkyl, 6-10-membered mono- or bicyclic aryl, and 6-10-membered mono- or bicyclic heteroaryl, or wherein two adjacent substituents may complete a 4- to 8-membered saturated or partially unsaturated ring containing carbon atoms and optionally containing 1 to 3 members selected from the group consisting of O, S, SO, SO$_2$ and NR$^{81}$, wherein the ring is unsubstituted or substituted with 1 to 4 substituents independently selected from the group consisting of halogen, oxo, =N—OR$^{82}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;

R$^{54}$ is $C_{0-6}$-alkylene-R$^{57}$, $C_3$-cycloalkyl-R$^{57}$, O—$C_{0-5}$-alkylene-R$^{57}$, NR$^{91}$—$C_{0-5}$-alkylene-R$^{57}$ and SO$_x$—$C_{0-5}$-alkylene-R$^{57}$, wherein alkylene is optionally substituted with 1 to 5 substituents independently selected from the group consisting of halogen, OH, oxo, =N—OR$^{82}$, N(R$^{81}$)$_2$, O—$C_{1-6}$-alkyl, COOH, CON(R$^{81}$)$_2$, CN, NR$^{81}$—COR$^{81}$, $C_{3-6}$-cycloalkyl and $C_{3-6}$-heterocycloalkyl;

R$^{55}$ is independently selected from H, $C_{1-6}$-alkyl and $C_{3-6}$-cycloalkyl, wherein alkyl and cycloalkyl is optionally substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

R$^{56}$ is independently selected from the group consisting of H, halogen, CN, $C_{1-6}$-alkyl, $C_{3-6}$-cycloalkyl, O—$C_{1-6}$-alkyl and CONHR$^{61}$R$^{62}$, wherein alkyl and cycloalkyl is unsubstituted or substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

R$^{57}$ is $C_{1-10}$-alkyl, $C_{3-10}$-cycloalkyl, $C_{3-10}$-heterocycloalkyl, 6-10-membered mono- or bicyclic aryl or 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-10}$-cycloalkyl and 5 to 10-membered heterocycloalkyl;

R$^{61}$ and R$^{81}$ are independently selected from the group consisting of H, $C_{1-6}$-alkyl, $C_{3-10}$-cycloalkyl, $C_{3-10}$-heterocycloalkyl, phenyl, 5-6-membered heteroaryl containing 1 to 4 heteroatoms independently selected from the group consisting of N, O and S wherein alkyl, cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 10-membered heteroaryl, halogen, NH$_2$, NH($C_{1-6}$-alkyl), N($C_{1-6}$-alkyl)$_2$, $C_{3-10}$-heterocloalkyl, $C_{3-10}$-cycloalkyl, SO$_2$—$C_{1-3}$-alkyl, oxo, and CN, wherein cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 6-membered heteroaryl, halogen, NH$_2$, NH($C_{1-6}$-alkyl), N($C_{1-6}$-alkyl)$_2$ and $C_{3-10}$-cycloalkyl, wherein phenyl and heteroaryl are unsubstituted or substituted with 1 to 3 substituents independently selected from the group consisting of OH, O—$C_{1-6}$-alkyl, O-halo-$C_{1-6}$-alkyl, halogen, $C_{1-6}$-alkyl, halo-$C_{1-6}$-alkyl, NH$_2$, NH($C_{1-6}$-alkyl), N($C_{1-6}$-alkyl)$_2$ and $C_{3-10}$-cycloalkyl;

R$^{62}$ and R$^{82}$ are independently selected from the group consisting of H, $C_{1-6}$-alkyl, halo-$C_{1-6}$-alkyl and $C_{3-10}$-cycloalkyl;

R$^{91}$ is H, $C_{1-6}$-alkyl, $C_{3-6}$-cycloalkyl or $C_{3-6}$-heterocycloalkyl, wherein alkyl, cycloalkyl and heterocycloalkyl are unsubstituted or substituted with 1 to 3 substituents independently selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

x is independently selected from 0, 1 and 2;

for use in the treatment or prophylaxis of a disease or disorder associated with the inhibition or activation of the RORγ receptor.

In a preferred embodiment of the second alternative, the present invention provides a compound wherein derivatives of Formula (8), wherein Q$^1$ is CO—NR$^{51}$R$^{52}$; Q$^2$ and Q$^3$ are CR$^{56}$;

R$^{54}$ is SO$_2$—(CR$^8$R$^8$)$_y$R$^7$, SO$_2$—NR$^{12}$R$^7$, (CR$^8$R$^8$)$_x$—R$^{10}$ or $C_{3-6}$-cycloalkyl, which is spirocyclic fused with $C_{3-10}$-cycloalkyl;

R$^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, cycloalkyl and heterocycloalkyl;

R$^8$ is independently selected from H, F, halo-$C_{1-3}$-alkyl or OH;

R$^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

R$^{12}$ is independently selected from H, $C_{1-6}$-alkyl and halo-$C_{1-6}$-alkyl;

x is selected from 1 and 2; and y is selected from 0, 1 and 2;

are excluded.

In another preferred embodiment of the second alternative, the present invention provides a compound wherein derivatives of Formula (6) to Formula (9), wherein $Q^1$ is $SO_2$—$NR^{51}R^{52}$; $Q^2$ and $Q^3$ are $CR^{56}$;
$R^{54}$ is $SO_2$—$(CR^8R^8)_y R^7$ or $(CR^8R^8)_x$—$R^{11}$;
$R^7$ is $C_{1-10}$-alkyl, $C_{3-10}$-cycloalkyl, $C_{3-10}$-heterocycloalkyl, 6-10 membered mono- or bicyclic aryl or 5-10 membered mono- or bicyclic heteroaryl
  wherein cycloalkyl, heterocycloalkyl, aryl and heteroaryl are unsubstituted or substituted with 1 to 3 substituents independently selected from the group consisting of halogen, OH, O—$C_{1-6}$-alkyl, O-halo-$C_{1-6}$-alkyl, $C_{1-6}$-alkyl, halo-$C_{1-6}$-alkyl and $NH_2$
  and wherein alkyl is unsubstituted or substituted with 1 to 3 substituents independently selected from the group consisting of halogen, OH, O—$C_{1-6}$-alkyl, O-halo-$C_{1-6}$-alkyl and $NH_2$;
$R^8$ is independently H, $C_{1-4}$-alkyl, O—$C_{1-4}$-alkyl, halo-$C_{1-4}$-alkyl or halogen;
$R^{11}$ is $C_{2-10}$-alkyl, $C_{3-10}$-cycloalkyl, $C_{3-10}$-heterocycloalkyl, 6-10 membered mono- or bicyclic aryl or 5-10 membered mono- or bicyclic heteroaryl
  wherein alkyl, cycloalkyl, heterocycloalkyl, aryl and heteroaryl is unsubstituted or substituted with 1 to 3 substituents independently selected from the group consisting of halogen, OH, oxo, O—$C_{1-6}$-alkyl, $C_{1-6}$-alkyl, halo-$C_{1-6}$-alkyl and $NH_2$;
x is selected from 1, 2 or 3; and y is selected from 0, 1 and 2;
are excluded.

In a preferred embodiment in combination with any of the above or below embodiments of the second alternative $Q^1$ is selected from CO—$NR^{51}R^{52}$; and $Q^2$ and $Q^3$ is nitrogen, more preferably the following structures:

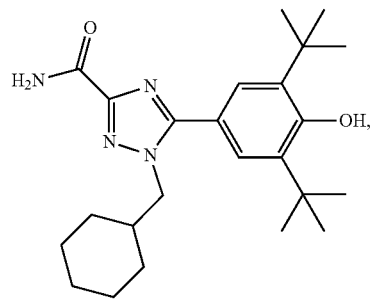

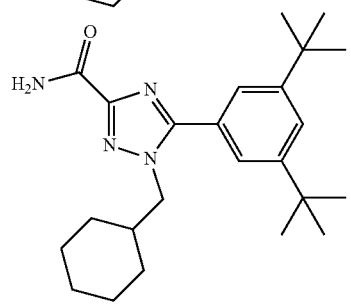

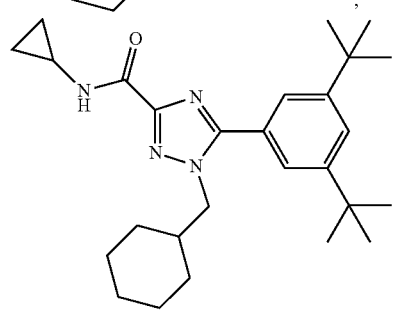

-continued

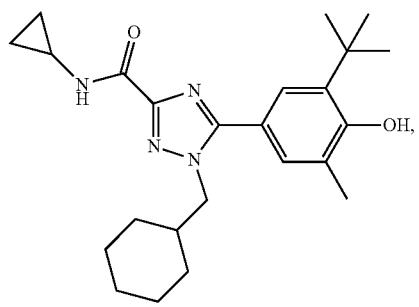

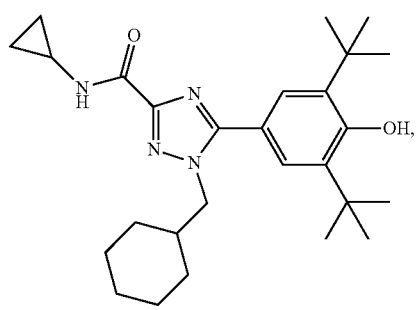

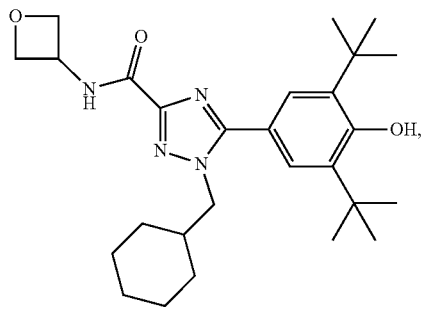

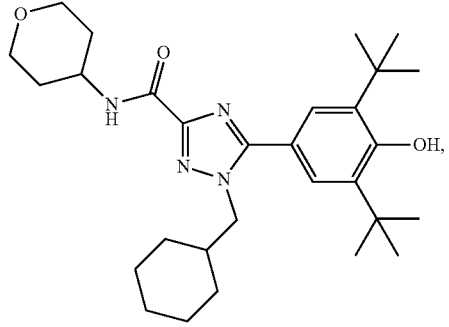

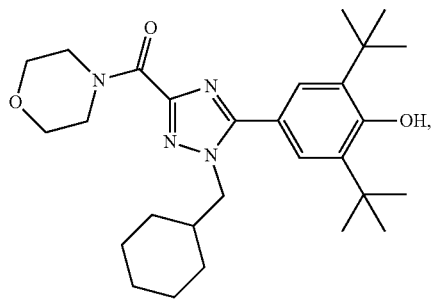

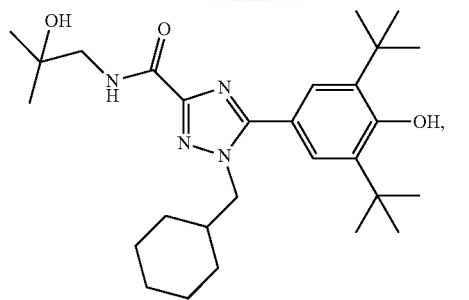

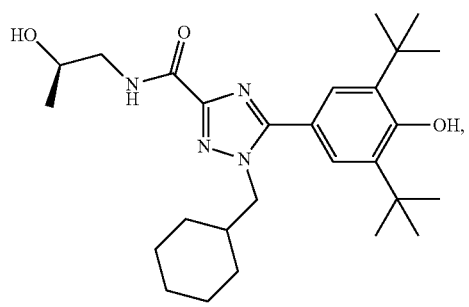

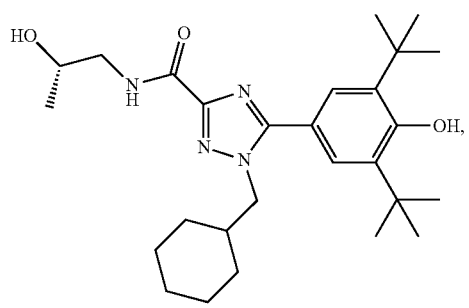

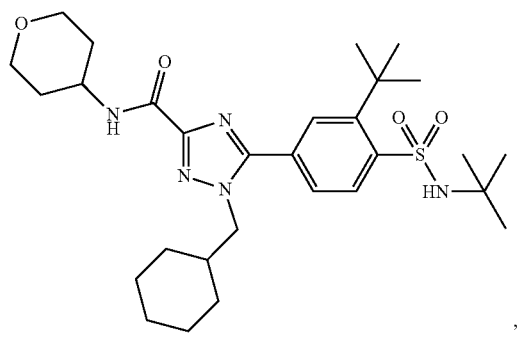

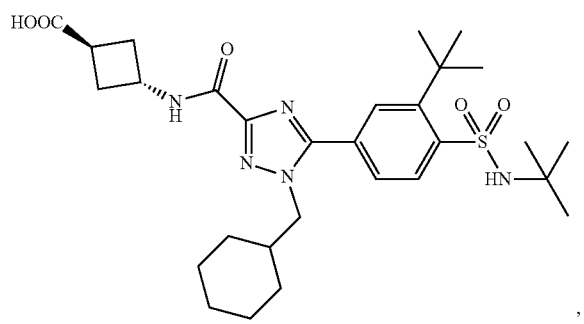

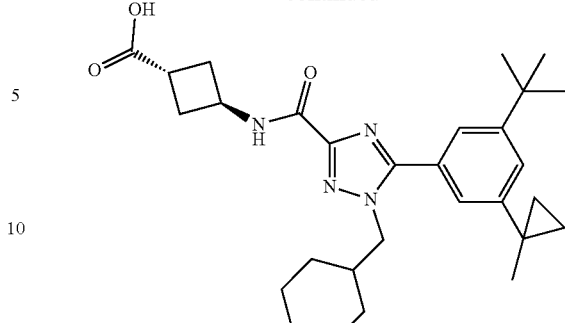

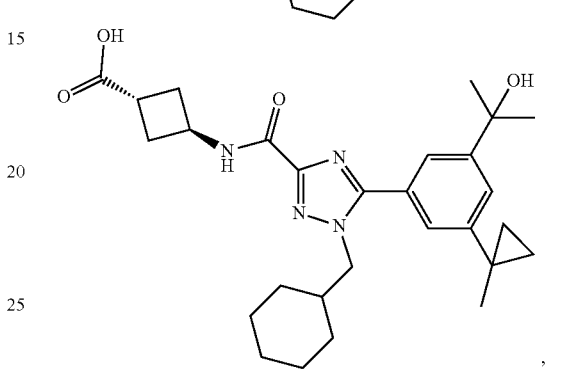

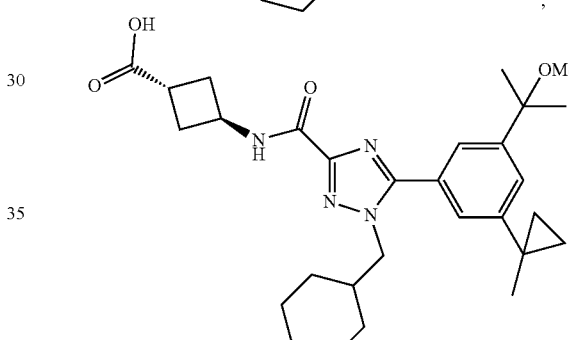

, and

In an equally preferred embodiment in combination with any of the above or below embodiments of the second alternative $Q^1$ is CO—NR$^{51}$R$^{52}$; and $Q^2$ and $Q^3$ is CR$^{66}$.

In a preferred embodiment in combination with any of the above or below embodiments of the second alternative R$^{51}$ is selected from the group consisting of H, $C_{1-10}$-alkyl, $C_{0-10}$-alkylene-$C_{3-10}$-cycloalkyl, $C_{0-10}$-alkylene-$C_{3-10}$-heterocycloalkyl, $C_{0-10}$-alkylene 5 to 10-membered heteroaryl and $C_{0-10}$-alkylene-aryl, wherein alkyl, alkenyl, alkynyl, alkylene, cycloalkyl, heterocycloalkyl, aryl and heteroaryl are unsubstituted or substituted with 1 to 7 substituents independently selected from the group consisting of oxo, CN, OR$^{61}$, O—$C_{2-6}$-alkylene-OR$^{61}$, $C_{1-6}$-alkyl, halo-$C_{1-6}$-alkyl, halogen, CO$_2$R$^{61}$R$^{62}$, CONR$^{61}$R$^{62}$, CONR$^{61}$SO$_2$R$^{62}$, COR$^{61}$, SO$_x$R$^{61}$, SO$_3$H, SO$_2$NR$^{61}$R$^{62}$, NR$^{61}$COR$^{61}$, NR$^{61}$SO$_2$R$^{61}$, NR$^{61}$—CO—NR$^{61}$R$^{62}$, NR$^{61}$—SO$_2$—NR$^{61}$R$^{62}$, $C_{3-6}$-cycloalkyl, O—$C_{3-6}$-cycloalkyl, $C_{3-6}$-heterocycloalkyl, O—$C_{3-6}$-heterocycloalkyl and NR$^{61}$R$^{62}$;

R$^{52}$ is selected from the group consisting of H, $C_{1-6}$ alkyl and halo-$C_{1-6}$ alkyl;

or R$^{51}$ and R$^{52}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{61}$, $SO_xR^{61}$, $SO_3H$, $NR^{61}SO_2R^{61}$, $SO_2NR^{61}R^{62}$, $CO_2R^{61}$, $CONR^{61}R^{62}$, $CONR^{61}SO_2R^{62}$, $COR^{61}$, $NR^{61}$—CO—$R^{61}$, $NR^{61}$—CO—$NR^{61}R^{62}$, $NR^{61}$—$SO_2$—$NR^{61}R^{62}$, $NR^{61}R^{62}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl.

In a more preferred embodiment in combination with any of the above or below embodiments of the second alternative $NR^1R^2$ is $NHCH_2CMe_2OH$, $NH(CH_2)_2CMe_2CO_2H$, $NHCH_2CMe_2CO_2H$,

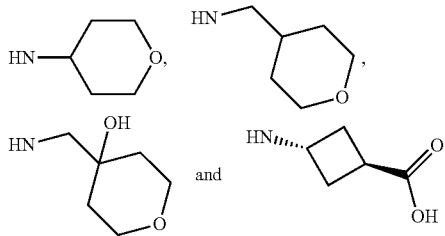

In a equally more preferred embodiment in combination with any of the above or below embodiments of the second alternative $NR^1R^2$ is

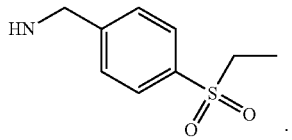

In a preferred embodiment in combination with any of the above or below embodiments of the second alternative $R^{53}$ is selected from

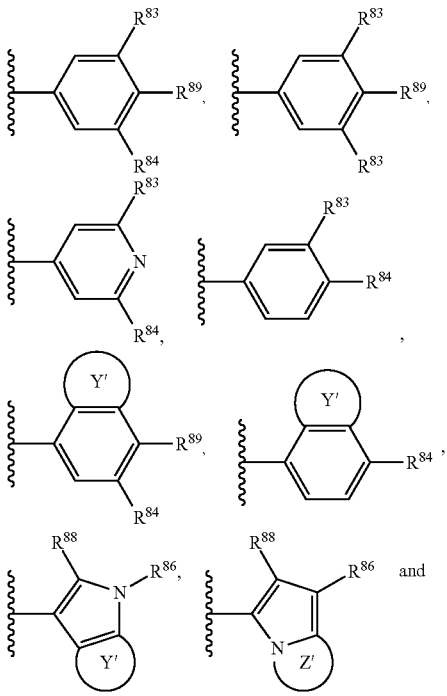

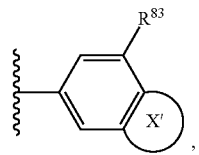

wherein $R^{83}$ is independently selected from halogen, $C_{1-6}$-alkyl, fluoro-$C_{1-6}$-alkyl, $C_{1-4}$-alkylene-OH, $C_{1-4}$-alkylene-CN, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, $C(O)N(R^{87})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{84}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{87})_2$, $S(O_2)N(R^{87})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{86}$ is selected from $C_{1-6}$-alkyl, fluoro-$C_{1-6}$-alkyl, $C(O)N(R^{87})_2$, $S(O_2)N(R^{87})_2$, $R^{87}$ is independently selected from H, $C_{1-6}$-alkyl, fluoro-$C_{1-6}$-alkyl, $C_{0-3}$-alkylene-$C_{1-6}$-cycloalkyl, $C_{1-6}$-alkylene-OH, $C_{1-6}$-alkylene-O—$C_{1-3}$-alkyl, $C_{1-6}$-alkylene-CN, wherein alkylene and cycloalkyl is unsubstituted or substituted with 1 to 3 substituents independently selected from F, $C_{1-3}$-alkyl and fluoro-$C_{1-3}$-alkyl, and wherein two $R^{87}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, oxo, $C_{1-4}$-alkyl and halo-$C_{1-4}$-alkyl;

$R^{88}$ is selected from H, $C_{1-3}$-alkyl and fluoro-$C_{1-3}$-alkyl;

$R^{89}$ is selected from H, F or OH;

X' is an annelated saturated heterocycle selected from the group consisting of

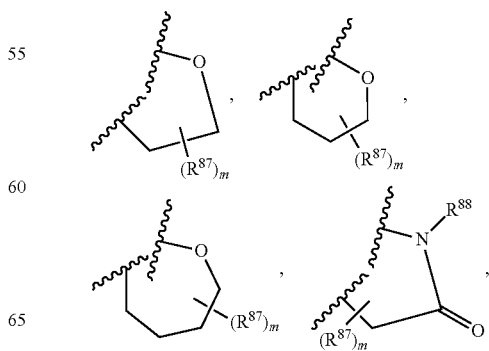

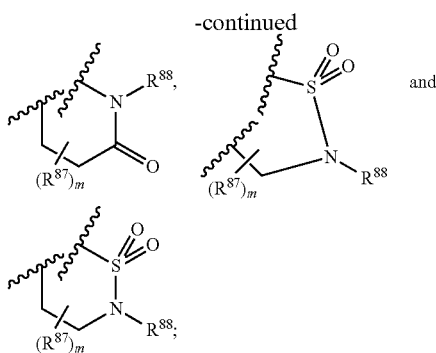

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;

Z' is an annelated 6-membered cycle forming a heteroaryl containing 1 to 3 heteroatoms selected from the group consisting of O, S and N, wherein the heteroaryl is unsubstituted or substituted with 1 to 3 substituents selected from fluoro, $C_{1-3}$-alkyl and fluoro-$C_{1-3}$-alkyl; and m is selected from 1 to 4.

In a more preferred embodiment in combination with any of the above or below embodiments of the second alternative $R^{53}$ is selected from

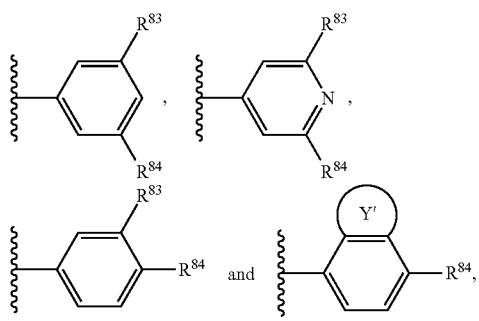

wherein $R^{83}$ is selected from halogen, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, O—$C_{1-6}$-alkyl, NH-fluoro-$C_{1-6}$-alkyl, NH—$C_{1-6}$-alkyl, O-fluoro-$C_{1-6}$-alkyl, $C_{3-10}$-cycloalkyl, $C(O)N(R^{87})_2$,
  wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{84}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{87})_2$, $S(O_2)N(R^{87})_2$,
  wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{87}$ is independently selected from H, $C_{1-6}$-alkyl, fluoro-$C_{1-6}$-alkyl, $C_{0-3}$-alkylene-$C_{1-6}$-cycloalkyl, $C_{1-6}$-alkylene-OH, $C_{1-6}$-alkylene-O—$C_{1-3}$-alkyl, $C_{1-6}$-alkylene-CN, wherein alkylene and cycloalkyl is unsubstituted or substituted with 1 to 3 substituents independently selected from F, $C_{1-3}$-alkyl and fluoro-$C_{1-3}$-alkyl, and wherein two $R^{87}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, oxo, $C_{1-4}$-alkyl and halo-$C_{1-4}$-alkyl;

Y' is an annelated 6-membered aryl or an annelated 5- to 6-membered heteroaryl containing 1 to 2 heteroatoms selected from the group consisting of S and N, wherein the carbocycle, aryl or heteroaryl is unsubstituted or substituted with 1 to 3 substituents selected from fluoro, $C_{1-3}$-alkyl and fluoro-$C_{1-3}$-alkyl.

In an more preferred embodiment in combination with any of the above or below embodiments of the second alternative $R^{53}$ is

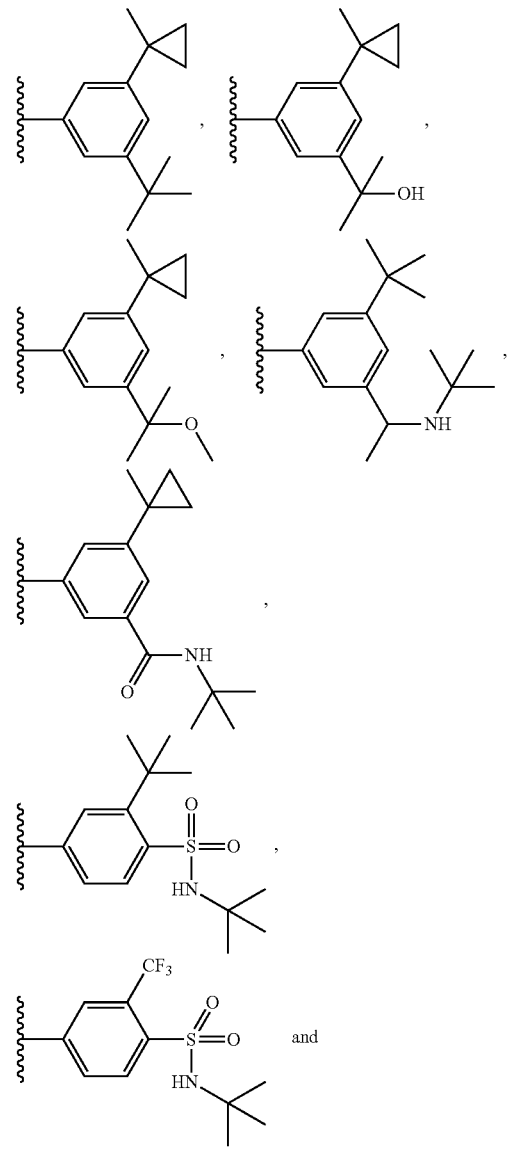

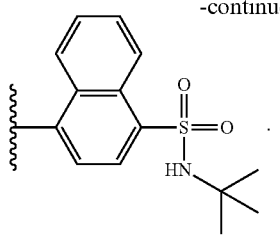

In an equally more preferred embodiment in combination with any of the above or below embodiments of the second alternative $R^{53}$ is

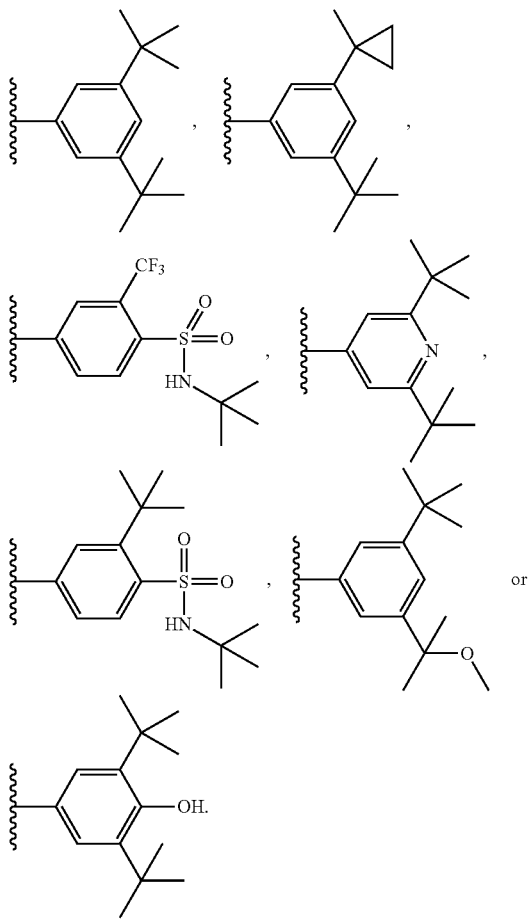

In a preferred embodiment in combination with any of the above or below embodiments of the second alternative $R^{54}$ is selected from $C_1$-alkylene-$R^{57}$ and $SO_2$—$R^{57}$,
wherein alkylene is optionally substituted once with OH, oxo, O—$C_{1-6}$-alkyl, CN and $C_{3-6}$-cycloalkyl, fluoro or twice with fluoro;
$R^{57}$ is selected from $C_{1-10}$-alkyl, $C_{3-10}$-cycloalkyl, $C_{3-10}$-heterocycloalkyl, 6-10-membered mono- or bicyclic aryl and 6-10-membered mono- or bicyclic heteroaryl,
wherein alkyl, cycloalkyl, heterocycloalkyl, aryl and heteroaryl are unsubstituted or substituted with 1 to 3 substituents independently selected from the group consisting of halogen, OH, oxo, O—$C_{1-3}$-alkyl, O-halo-$C_{1-3}$-alkyl, $C_{1-3}$-alkyl, halo-$C_{1-3}$-alkyl, cycloalkyl and heterocycloalkyl.

In a more preferred embodiment in combination with any of the above or below embodiments of the second alternative $R^{54}$ is $C_1$-alkylene-$R^{57}$, wherein alkylene is unsubstituted or substituted once with OH, oxo, O—$C_{1-6}$-alkyl, CN and $C_{3-6}$-cycloalkyl, fluoro or twice with fluoro and wherein $R^{57}$ is selected from $C_{1-10}$-alkyl, cyclohexyl, $C_{4-6}$-heterocycloalkyl containing one O as the heteroatom and phenyl.

In a preferred embodiment in combination with any of the above or below embodiments of the second alternative, the disease or disorder associated with the inhibition or activation of the RORγ receptor is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis.

In a more preferred embodiment in combination with any of the above or below embodiments of the second alternative, the disease or disorder associated with the inhibition or activation of the RORγ receptor is selected from the group consisting of rheumatoid arthritis, ankylosing spondylitis, lupus erythematosus, psoriasis, atopic eczema, inflammatory bowel diseases, Crohn's disease, ulcerative colitis, asthma, multiple sclerosis, type 1 diabetes, amyotrophic lateral sclerosis, Th17 mediated tissue inflammation, and a skin disease with associated symptoms such as pain, itching or excoriations.

Also provided is a pharmaceutical composition comprising a compound of the present invention and a pharmaceutically acceptable carrier or excipient.

In the context of the present invention "$C_{1-10}$-alkyl" means a saturated alkyl chain having 1 to 10 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl and decyl.

The term "halo-$C_{1-10}$-alkyl" means that one or more hydrogen atoms in the alkyl chain are replaced by a halogen. A preferred example thereof is $CF_3$.

"$C_{2-10}$-alkenyl" means an alkyl chain having 2 to 10 carbon atoms which may be straight chained or branched, containing at least one carbon to carbon double bond. Examples thereof include ethenyl, propenyl, decenyl, 2-methylenehexyl and (2E,4E)-hexa-2,4-dienyl.

"$C_{2-10}$-alkynyl" means an alkyl chain having 2 to 10 carbon atoms which may be straight chained or branched, containing at least one carbon to carbon triple bond. Examples thereof include ethynyl, propynyl and decynyl.

A "$C_{0-10}$-alkylene" means that the respective group is divalent and connects the attached residue with the remaining part of the molecule. Moreover, in the context of the present invention, "$C_0$-alkylene" is meant to represent a bond. The same applies to the divalent $C_3$-cycloalkylene.

A $C_{3-10}$-cycloalkyl group or $C_{3-10}$-carbocycle means a saturated or partially unsaturated mono-, bi- or multicyclic ring system comprising 3 to 10 carbon atoms. Examples include cyclopropyl, cyclobutyl, cyclopentyl, cyclohexyl, cyclohexenyl, bicyclo[2.2.2]octyl, bicyclo[2.2.1]heptyl, adamantyl and pentacyclo[4.2.0.0$^{2,5}$.0$^{3,8}$.0$^{4,7}$]octyl.

A $C_{3-10}$-heterocycloalkyl group means a saturated or partially unsaturated 3 to 10 membered carbon mono-, bi- or multicyclic ring wherein 1, 2 or 3 carbon atoms are replaced by 1, 2 or 3 heteroatoms, respectively, wherein the heteroatoms are independently selected from N, O, S, SO and SO₂. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected via a carbon or nitrogen atom with the remaining part of the molecule.

A 5-14-membered mono-, bi- or tricyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bi- or tricyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

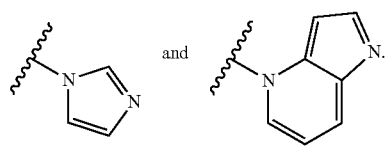 [SMILES: *n1ccnc1 ; "and" ; *n1cccc2nccc1-2]

Moreover, where not explicitely defined, heterocyclyl contains 1 to 3 heteroatoms and heteroaryl contains 1 to 4 heteroatoms independently selected from the group consisting of N, O and S, respectively.

A 6-10-membered mono- or bicyclic aromatic ring system (within the application also referred to as aryl) means an aromatic carbon cycle such as phenyl or naphthalenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

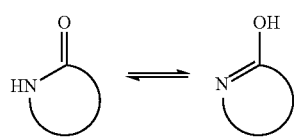

A $C_{3-10}$-cycloalkyl or $C_{3-10}$-heterocycloalkyl group can be connected straight or spirocyclic, e.g. when cyclohexane is substituted with the heterocycloalkyl group oxetane, the following structures are possible:

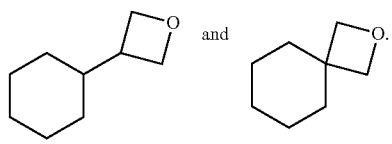 [SMILES: C1CCC(C2COC2)CC1 ; "and" ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group. The same applies to the number of possible substituents on a group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing RORγ-mediated conditions for which compounds of Formula (1) to (9) are indicated, generally satisfactory results are obtained when the compounds are administered at a daily dosage of from about 0.1 milligram to about 100 milligram per kilogram of mammal body weight, preferably given as a single daily dose or in divided doses two to six times a day, or in sustained release form. For most large mammals, the total daily dosage is from about 1.0 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The present invention describes modulators, in the following also referred to as ligands, which bind to the RORγ receptor. Surprisingly, it has been found that compounds of Formula (1 to (9) act as modulators of the RORγ receptor.

The term "modulator of the RORγ receptor" includes the inhibition or activation of the RORγ receptor, wherein the inhibition is preferred.

The RORγ receptor is considered to be involved in thymocyte development, thus the modulators described herein may be useful in the treatment of inflammatory skin diseases such as atopic eczema and psoriasis. It is further suggested that down-modulation of RORγ transcriptional activity with a ligand could result in a shift of the immune response towards a Th2 type response which could be beneficial in the treatment of certain allergic inflammatory conditions such as rheumatoid arthritis, systemic lupus erythomatosis, inflammatory bowel disease (Crohn's Disease) and multiple sclerosis (Tesmer et. al., *Immunol. Rev.* 2008, 223:97).

The compounds of Formula (1) to (9) show antagonistic activity, with respect to the dose dependent modulation of the constitutive interaction of the RORγ ligand binding domain with peptides derived from the co-activators such as SRC-1, TRAP 220 or TIF-2.

It has been surprisingly found that the interaction between RORγ ligand binding domain and the peptides can be determined by a homogenous FRET based ligand-sensing assays. Even more surprising was the identification of compounds of Formula (1) to (9) as ligands for RORγ.

The identification of high affinity ligands for RORγ with agonistic and antagonistic properties is the basis to enable experts knowledgeable in the field to establish assays for the identification of novel agonistic and antagonistic RORγ ligands from libraries of small molecules. The identification of ligands which bind to and modulate the activity of RORγ1 and RORγ2 is the first mandatory step to develop new small molecule based medicines with a potential to be developed for the treatment of diseases which are directly or indirectly controlled by the activity of RORγ1 or RORγ2. Such diseases include but are not restricted to inflammatory diseases, asthma, rheumatoid arthritis, autoimmune diseases or diseases with an autoimmune component such as systemic lupus erythomatosis, inflammatory bowel disease (Crohn's disease), ulcerative colitis, inflammatory skin diseases such as atopic eczema or psoriasis, multiple sclerosis or similar diseases.

Another aspect of the invention provides for combination therapy. Nitrogen containing heterocycles and related compounds (e.g. a compound of Formula (1) to (9)) or their pharmaceutically acceptable salts may be used in combination with additional therapeutic agents to treat medical disorders, such as medical disorders associated with inappropriate IL-17 pathway activity. Exemplary additional therapeutic agents include, for example, (1) a TNF-α inhibitor; (2) a non-selective COX-1/COX-2 inhibitor; (3) a selective COX-2 inhibitor, such as celecoxib and rofecoxib; (4) other agents for treating inflammatory disease and autoimmune disease including, for example, methotrexate, leflunomide, sulfasalazine, azathioprine, penicillamine, bucillamine, actarit, mizoribine, lobenzarit, hydroxychloroquine, d-penicillamine, aurothiomalate, auranofin, parenteral gold, oral gold, cyclophosphamide, Lymphostat-B, a BAFF/APRIL inhibitor, CTLA-4-Ig, or a mimetic of CTLA-4-Ig; (5) a leukotriene biosynthesis inhibitor, such as a 5-lipoxygenase (5-LO) inhibitor, or a 5-lipoxygenase activating protein (FLAP) antagonist; (6) a LTD4 receptor antagonist; (7) a phosphodiesterase type IV (PDE-IV) inhibitor, such as cilomilast (Ariflo) or roflumilast; (8) an antihistamine Hi receptor antagonist; (9) an α1- and α2-adrenoceptor agonist; (10) an anticholinergic agent; (11) a ρ-adrenoceptor agonist; (12) an insulin-like growth factor type I (IGF-1) mimetic; (13) a glucocorticoid; (14) a kinase inhibitor such as an inhibitor of a Janus Kinase (e.g., JAK1 and/or JAK2 and/or JAK3 and/or TYK2), p38 MAPK, Syk or IKK2; (15) a B-cell target biologic such as rituximab; (16) a selective co-stimulation modulator such as abatacept; (17) an interleukin inhibitor or interleukin receptor inhibitor, such as the IL-1 inhibitor anakinra, IL-6 inhibitor tocilizumab and IL12/IL-23 inhibitor ustekimumab; (18) an anti-IL17 antibody, anti-IL21 antibody, or anti-IL22 antibody (19) a S1P1 agonist, such as fingolimod; (20) an interferon, such as interferon beta 1; (21) an integrin inhibitor such as natalizumab; (22) a mTOR inhibitor such as rapamycin, cyclosporin and tacrolimus; (23) a non-steroidal antiinflammatory agent (NSAID), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and pyrazolones (apazone, bezpiperylon, feprazone, mofebutazone, oxyphenbutazone, phenylbutazone); (24) a NRF2 pathway activator, such as the fumaric acid derivative, BG-12; and (25) a chemokine or chemokine receptor inhibitor, such as a CCR9 antagonist.

The amount of the nitrogen containing heterocyclic and related compounds (e.g. a compound of Formula (1) to (9)) and additional therapeutic agent and the relative timing of administration may be selected in order to achieve a desired combined therapeutic effect. For example, when administering a combination therapy to a patient in need of such administration, the therapeutic agents in the combination or a pharmaceutical composition or compositions comprising the therapeutic agents, may be administered in any order such as, for example, sequentially, concurrently, together, simultaneously and the like. Further, for example, a nitrogen-containing 5-membered heterocycle or related compound may be administered during a time when the additional therapeutic agent(s) exerts its prophylactic or therapeutic effect, or vice versa.

DETAILED DESCRIPTION OF THE INVENTION

Abbreviations

Ac acetyl
ACN acetonitrile
aq. aqueous
$B_2Pin_2$ 4,4,4',4',5,5,5',5'-octamethyl-2,2'-bi-1,3,2-dioxaborolane
CC column chromatography on silica gel
COD cyclooctadiene
Cy cyclohexyl
DCM dichloromethane
DIPEA diisopropylethylamine
DMF N,N-dimethylformamide
DMAP dimethylaminopyridine
dppf 1,1'-bis(diphenylphosphino)ferrocene
dtbpy 4,4'-di-tert-butyl-2,2'-bipyridine
EA ethyl acetate
HATU 0-(7-azabenzotriazole-1-yl)-N,N,N,N'-tetramethyluronium hexafluorophosphate
MOM methoxymethyl
NBS N-bromosuccinimide
NCS N-chlorosuccinimide
Pin pinacolato ($OCMe_2CMe_2O$)
PE petroleum ether
PMB p-methoxybenzyl
prep. preparative
rt room temperature
SEM β-(trimethylsilyl)ethoxymethyl
TBAF tetrabutylammonium fluoride
Tf trifluoromethylsulfonyl
TFA trifluoroacetic acid
THF tetrahydrofuran
TLC thin layer chromatography

EXPERIMENTAL SECTION

Preparative Example P1

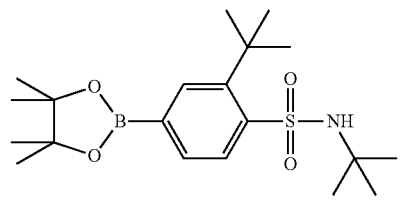

P1

Step 1: 4-Bromo-2-tert-butylaniline (P1a)

To a solution of NBS (218 mg, 1 mmol) in DMF was added a solution of 2-tert-butylaniline (149 mg, 1 mmol) in DMF at rt. The reaction mixture was stirred for 4 h at rt, then water (30 mL) was added and the mixture was extracted with EA (150 mL). The organic layer was washed with brine and dried over $Na_2SO_4$, concentrated and purified by CC (hexane/EA=3/1) to give compound P1a (180 mg, 79%).

Step 2: 4-Bromo-2-tert-butylbenzene-1-sulfonyl chloride (P1b)

4-Bromo-2-tert-butylaniline P1a (20 mmol) was added to a mixture of conc. HCl (11.2 mL) and AcOH (2.24 mL) at −10° C. To this mixture, a solution of $NaNO_2$ (1.52 g, 22 mmol) in minimum amount of water was added dropwise at −10° C. After stirring for 45 min at −10° C. the diazonium salt solution was obtained. $SO_2$ gas was bubbled into AcOH (22.4 mL) in a three-neck flask until saturation (30 min). Then CuCl (0.49 g, 0.49 mmol) was added and stirring was continued until the mixture turned green. The flask was placed in an ice bath and the diazonium salt solution was added dropwise at 5° C. After the addition was complete, the mixture was stirred overnight at rt and poured into ice water. The solid was collected by filtration to give the compound P1 b (45%).

Step 3: 4-Bromo-N,2-di-tert-butylbenzenesulfonamide (P1c)

Compound P1b (1.0 mmol) and $NEt_3$ (2.0 mmol) were added into a solution of 2-methylpropan-2-amine (88 mg, 1.2 mmol) in toluene (20 mL). The mixture was stirred for 4 h at reflux, evaporated, poured into water and extracted with EA. The combined organic layers were washed with brine, dried over $Na_2SO_4$, filtered and evaporated to give compound P1c as a solid (330 mg, 85%)

Step 4: N,2-Di-tert-butyl-4-(4,4,5,5-tetramethyl-1,3,2-dioxaborolan-2-yl)benzenesulfonamide (P1)

A flask charged with $Pd(dppf)Cl_2$ (30 μmol), KOAc (294 mg, 3.0 mmol) and compound P1c (279 mg, 1.0 mmol) was flushed with $N_2$, then 1,4-dioxane (6 mL) and $B_2Pin_2$ (1.2 mmol) were added. After being stirred at 80° C. for an appropriate period, the product was extracted with benzene, washed with water and dried over $MgSO_4$. Kugelrohr distillation in vacuo gave compound P1 (200 mg, 50%).

Preparative Example P1/1

Using similar procedures as those described in Preparative Example P1, the following compound was prepared:

| # | Structure |
|---|---|
| P1/1 | 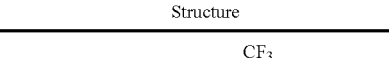 |

Preparative Example P2

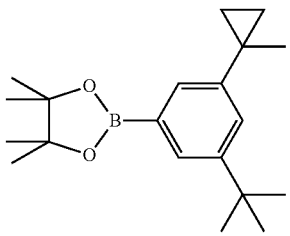

P2

Step 1: 1-Bromo-3-(tert-butyl)-5-(prop-1-en-2-yl)benzene (P2a)

To a solution of 1,3-dibromo-5-(tert-butyl)benzene (2.92 g, 10 mmol) in dioxane (20 mL) was added $Pd(PPh_3)_4$ (3.0 g, 2.6 mmol), prop-1-en-2-ylboronic acid (1.0 g, 12 mmol), $K_2CO_3$ (2.8 g, 20 mmol) and $H_2O$ (1 mL) under $N_2$. The resulting mixture was stirred at 90° C. overnight, concentrated and purified by CC (hexane) to give compound P2a (2.5 g, 100%; 80% by GC/MS) as a liquid.

Step 2: 1-Bromo-3-(tert-butyl)-5-(1-methylcyclopropyl)benzene (P2b)

To a solution of $Et_2Zn$ (20 mL of 1M solution in hexanes, 20 mmol) in dry DCM (20 mL) at 0° C. was added freshly distilled TFA (1.8 mL, 20 mmol) in DCM (20 mL) over a period of approx. 30 min. The gray mixture was stirred at 0° C. for 20 min at which time $CH_2I_2$ (2.0 mL, 20 mmol) dissolved in DCM (20 mL) was added to the reaction flask by cannulation. The resulting slurry was stirred for 20 min before the addition of compound P2a (2.5 g, 10 mmol) dissolved in DCM (15 mL). The slurry was allowed to warm to rt over 30 min, quenched with sat. $NH_4Cl$ (50 mL) and extracted with hexanes. The combined organic layers were dried over $MgSO_4$. Evaporation and purification by CC (hexane) afforded compound P2b (1.6 g, 60%) as a colorless oil.

Step 3: 2-(3-(tert-Butyl)-5-(1-methylcyclopropyl)phenyl)-4,4,5,5-tetramethyl-1,3,2-dioxaborolane (P2)

To a suspension of compound P2b (1.6 g, 70 mmol), $B_2Pin_2$ (3.0 g, 15 mmol), KOAc (2.32 g, 24 mmol) in dioxane (40 mL) was added $Pd(dppf)Cl_2$ (0.16 g) under $N_2$. The mixture was heated to 100° C. for 16 h, evaporated and purified by CC (PE/EA=4/1) to afford compound P2 (1.5 g, 68%) as a white solid.

Preparative Example P3

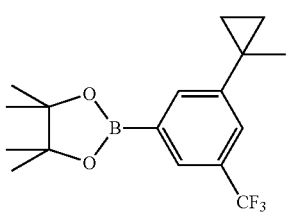

P3

Step 1: 1-Bromo-3-(prop-1-en-2-yl)-5-(trifluoromethyl)benzene (P3a)

To a solution of 1,3-dibromo-5-(trifluoromethyl)benzene (3.03 g, 10 mmol) in dioxane (20 mL) was added Pd(PPh$_3$)$_4$ (300 mg, 0.26 mmol), prop-1-en-2-ylboronic acid (1.0 g, 12 mmol), K$_2$CO$_3$ (2.8 g, 20 mmol) and water (1 mL) under N$_2$. The mixture was stirred at 90° C. overnight, concentrated and purified by CC (hexane) to afford compound P3a (1.9 g, 71%) as an oil.

Step 2: 1-Bromo-3-(1-methylcyclopropyl)-5-(trifluoromethyl)benzene (P3b)

To a solution of Et$_2$Zn (4 mL of 1.0 M solution in hexanes, 4 mmol) in dry DCM (4 mL) at 0° C. was added freshly distilled TFA (0.36 mL, 4 mmol) in DCM (4 mL) very slowly (ca. 30 min). The grey mixture was stirred at 0° C. for 20 min while adding CH$_2$I$_2$ (0.4 mL, 4 mmol) in DCM (4 mL), stirred for additional 20 min before compound P3a (0.53 g, 2 mmol) dissolved in DCM (3 mL) was added. The slurry was allowed to warm to rt over 30 min, quenched with sat. NH$_4$Cl (5 mL) and extracted with hexanes. The combined organic layers were dried (MgSO$_4$), evaporated and purified by CC (hexane) to afford P3b (300 mg, 46%) as a colorless oil.

Step 3: 4,4,5,5-Tetramethyl-2-(3-(1-methylcyclopropyl)-5-(trifluoromethyl)phenyl)-1,3,2-dioxaborolane (P3)

To a suspension of compound P3b (300 mg, 1.0 mmol), B$_2$Pin$_2$ (380 mg, 1.5 mmol), KOAc (290 mg, 3 mmol) in dioxane (5 mL) was added Pd(dppf)Cl$_2$ (20 mg) under N$_2$. The mixture was heated to 100° C. for 16 h, evaporated and purified by CC (PE/EA=4/1) to give compound P3 (200 mg, 68%) as a white solid.

Preparative Example P4

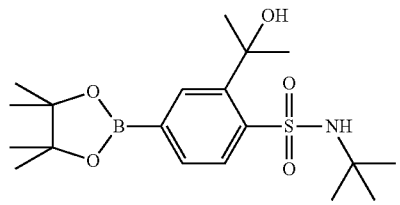

P4

Step 1: 2-Amino-5-bromobenzonitrile (P4a)

To a solution of 2-aminobenzonitrile (14.9 g, 100 mmol) was added a solution of NBS (17.8 g, 100 mmol) in DMF at rt. The mixture was stirred overnight at rt, then water (30 mL) was added and the mixture was extracted with Et$_2$O (3×250 mL). The organic layer was washed with brine, dried over Na$_2$SO$_4$, concentrated and purified by CC to give compound P4a (19 g, 83%).

Step 2: 4-Bromo-2-cyanobenzene-1-sulfonyl chloride (P4b)

Compound P4a (10 g, 51 mmol) was added to a mixture of conc. HCl (28 mL) and AcOH (5.6 mL) at −10° C. Then a solution of NaNO$_2$ (3.8 g, 55 mmol) in a minimum amount of water was added dropwise at −10° C. After stirring for 45 min at −10° C. a diazonium salt solution was obtained. SO$_2$ gas was bubbled into AcOH (56 mL) until saturation (60 min). Then CuCl$_2$ (3 g) was added and stirring was continued until the mixture turned green. The flask was placed in an ice bath and the diazonium salt solution was added dropwise at 5° C. After addition was complete, the mixture was stirred overnight at rt and poured into ice water. The solid was collected by filtration to give the crude compound P4b (9 g, 71%)

Step 3: 4-Bromo-N-(tert-butyl)-2-cyanobenzenesulfonamide (P4c)

To a solution of compound P4b (5.0 g, 18 mmol) in pyridine (20 mL) was added 2-methylpropan-2-amine (3.3 g, 45 mmol) and the reaction was purged with N$_2$, heated at 50° C. for 1 h, cooled and concentrated. The residue was purified by CC (DCM/MeOH=100/1) to give compound P4c (3.0 g, 53%) as a yellow solid.

Step 4: 2-Acetyl-4-bromo-N-(tert-butyl)benzenesulfonamide (P4d)

A suspension of compound P4c (2 g, 6.3 mmol) in THF (20 mL) was added slowly to MeMgBr (6.3 mL, 3M in Et$_2$O, 19 mmol) and the mixture was heated to reflux for 3 h, placed in an ice bath and 6N HCl (58 mL) was added slowly. The mixture was then heated to reflux, cooled, made alkaline by addition of solid Na$_2$CO$_3$ and extracted with EA. The combined organic phases were dried over Na$_2$SO$_4$, evaporated and purified by CC (n-heptan/EA=100/0 to 60/40) to give compound P4d (0.6 g, 34%).

Step 5: 4-Bromo-N-(tert-butyl)-2-(2-hydroxypropan-2-yl)benzenesulfonamide (P4e)

Compound P4d (200 mg, 0.60 mmol) was dissolved in THF (15 mL) at 0° C. A 3M solution of MeMgBr in Et$_2$O (1 mL, 3.0 mmol) was added slowly and the reaction mixture was stirred at rt for 3 h, then another portion of a MeMgBr in Et$_2$O (1 mL, 3.0 mmol) was added. The mixture was evaporated, diluted with water (20 mL) and extracted with Et$_2$O. The organic layer was dried over MgSO$_4$, filtered, evaporated and purified by HPLC (DCM/MeOH=100/0 to 70/30) to give compound P4e (100 mg, 39%; 47% purity).

Step 6: N-(tert-Butyl)-2-(2-hydroxypropan-2-yl)-4-(4,4,5,5-tetramethyl-1,3,2-dioxaborolan-2-yl)benzenesulfonamide (P4)

To a solution of compound P4e (200 mg, 0.57 mmol), B$_2$Pin$_2$ (290 mg, 1.14 mmol) and KOAc (160 mg, 1.7 mmol) in dioxane (10 mL) at rt under N$_2$ was added Pd(dppf)Cl$_2$ (42 mg, 0.05 mmol). The resulting mixture was stirred at rt for 1 h, then heated to 110° C. for 2 h, diluted with water (50 mL) and extracted with EA. The combined organic layers were concentrated and purified by CC(PE/EA=5/1) to give compound P4 (100 mg, 43%) as a colorless solid.

Preparative Example P5 and Preparative Example P6

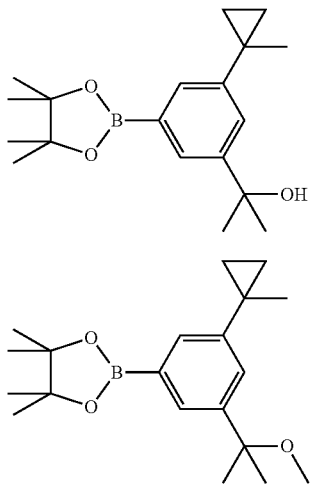

Step 1:
3,5-Dibromo-N-methoxy-N-methylbenzamide (P5a)

The solution of 3,5-dibromobenzoic acid (26 g, 93 mmol) in $SOCl_2$ (100 mL) was heated at reflux for 2 h, concentrated, diluted with dry DCM (300 mL) and added slowly to a stirred solution of N,O-dimethylhydroxylamine hydrochloride (9.75 g, 100 mmol) and $EtN_3$ (28 g, 277 mmol) in dry DCM (300 mL) at 0° C. The solution was stirred for 1 h at rt, poured into water and the organic layer was separated. The organic layer was washed with water and brine, dried over $Na_2SO_4$, filtered and concentrated to give crude compound P5a (28 g, 93%) as an oil.

Step 2: 1-(3,5-Dibromophenyl)ethanone (P5b)

To a solution of compound P5a (1.0 g, 3.1 mmol) in dry THF (10 mL) was added MeMgCl (3M in $Et_2O$, 1 mL, 3.0 mmol) dropwise at 0° C. and the solution was stirred for 4 h at rt, then quenched with aq. $NHCl_4$ and extracted with tert-butylmethylether. The organic layer was washed with water and brine consecutively, dried over $Na_2SO_4$, filtered and concentrated to give crude compound P5b (0.70 g, 66%) as a yellow oil.

Step 3: 1,3-Dibromo-5-(prop-1-en-2-yl)benzene (P5c)

To a stirred solution of $PPh_3CH_3Br$ (5.10 g, 14.4 mmol) in dry THF (50 mL) was added n-BuLi (2.5 M in n-hexane, 5.76 mL, 14.4 mmol) dropwise at −40° C. After stirring at this temperature for 0.5 h, a solution of compound P5b (2.0 g, 7.2 mmol) in dry THF (10 mL) was added dropwise. The resulting solution was allowed to warm to rt and stirred for 1 h, quenched with aq. $NHCl_4$ and extracted with $Et_2O$. The organic layer was concentrated and purified by CC (PE) to give compound P5c (1.6 g, 80%) as a light yellow oil.

Step 4:
1,3-Dibromo-5-(1-methylcyclopropyl)benzene (P5d)

To a solution of compound P5c (1.6 g, 5.8 mmol) and $Pd(OAc)_2$ (350 mg) in THF (20 mL) was added dropwise at 0° C. a solution of $CH_2N_2$ (487 mg, 11.6 mmol) in $Et_2O$ (20 mL) and the mixture was stirred for 1 h at rt. The suspension was filtered and the filtrate was concentrated and purified by CC (PE) to give compound P5d (1.4 g, 82%) as a colorless oil.

Step 5: 2-(3-Bromo-5-(1-methylcyclopropyl)phenyl)propan-2-ol (P5e)

To a stirred solution of compound P5d (0.5 g, 1.7 mmol) in dry THF (5 mL) was added dropwise n-BuLi (0.74 mL, 1.87 mmol) at −78° C. After 1 h at this temperature, dry acetone (118 mg, 2.04 mmol) was added dropwise. The solution was allowed to warm to rt and stirred overnight, then quenched with aq. $NHCl_4$ and extracted with EA. The combined organic layers were concentrated and purified by CC (PE/EA=20/1) to give compound P5e (250 mg, 52%) as a colorless oil.

Step 6: 1-Bromo-3-(2-methoxypropan-2-yl)-5-(1-methylcyclopropyl)benzene (P5f)

To a solution of compound P5e (1.5 g, 5.6 mmol) in dry THF (10 mL) was added NaH (450 mg, 11.2 mmol) under $N_2$ and the suspension was stirred for 1 h at rt. Then MeI (2.3 g, 16.8 mmol) was added and the solution was stirred at 70° C. in a sealed tube overnight, poured into water and extracted with $Et_2O$. The organic layer was washed with brine, dried over $Na_2SO_4$, filtered, concentrated and purified by CC (PE) to give compound P5f (1.6 g, 100%) as a colorless oil.

Step 7: 2-(3-(1-Methylcyclopropyl)-5-(4,4,5,5-tetramethyl-1,3,2-dioxaborolan-2-yl)phenyl)propan-2-ol (P5)

Compound P5 was prepared from compound P5e similar as described in Preparative Example 4, Step 6.

Step 8: 2-(3-(2-Methoxypropan-2-yl)-5-(1-methylcyclopropyl)phenyl)-4,4,5,5-tetramethyl-1,3,2-dioxaborolane (P6)

Compound P6 was prepared from compound P5f similar as described in Preparative Example 4, Step 6.

Preparative Example P7

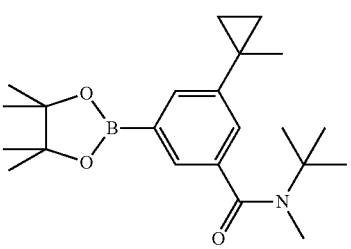

Step 1: Methyl 3-bromo-5-(prop-1-en-2-yl)benzoate (P7a)

To a solution of methyl 3-bromo-5-iodobenzoate (3.40 g, 10 mmol) in dioxane (20 mL) was added $Pd(PPh_3)_4$ (300 mg, 0.26 mmol), prop-1-en-2-yl boronic acid (1.0 g, 12 mmol), K₂CO₃ (2.8 g, 20 mmol) and H₂O (1 mL) under N₂ atmosphere. The mixture was stirred overnight at 90° C. Then the mixture was concentrated and purified by CC (PE/EA=6/1) to afford compound P7a (1.9 g, 71%) as a solid.

Step 2: Methyl 3-bromo-5-(1-methylcyclopropyl)benzoate (P7b)

To a solution of Et₂Zn (4 mL of 1.0M solution in hexanes, 4.0 mmol) in dry DCM (4 mL) at 0° C. was added freshly distilled TFA (0.36 mL, 4.0 mmol) in DCM (4 mL) very slowly (ca. 30 min). The grey mixture was stirred at 0° C. for 20 min at which time diodomethane (0.4 mL, 4.0 mmol) dissolved in DCM (4 mL) was introduced by cannulation. The resulting slurry was stirred for 20 min before the addition of compound P7a (0.53 g, 2.0 mmol) dissolved in DCM (3 mL). The slurry was allowed to warm to rt over 30 min. Progress of the reaction was monitored by TLC. When deemed complete, the reaction was quenched by the addition of sat. aq. NH₄Cl (5 mL) and the layers were separated. The aq. layer was extracted with hexane (2×) and dried over MgSO₄. Evaporation and purification by CC (PE/EA=7/1) afforded compound P7b (300 mg, 46%) as a clear colorless oil.

Step 3: 3-Bromo-5-(1-methylcyclopropyl)benzoic acid (P7c)

Compound P7b (270 mg, 1.0 mmol) and LiOH (50 mg, 2.0 mmol) were mixed in THF (3 mL) and H₂O (3 mL). The mixture was stirred for 10 h, then the pH was adjusted to pH 3 with aq. HCl and extracted with EA (3×10 mL). The organic layer was dried and concentrated to afford the crude product P7c (250 mg, 100%).

Step 4: 3-Bromo-N-(tertbutyl)-N-methyl-5-(1-methylcyclopropyl)benzamide (P7d)

To a solution of compound P7c (250 mg, 1.0 mmol) in DMF (5 mL) was added HATU (380 mg, 1.0 mmol) and Et₃N (202 mg, 2.0 mmol) and the mixture was stirred overnight. After removal of the solvents the crude product was purified with prep. HPLC to afford compound P7d (300 mg, 95%).

Step 5: N-(tert-Butyl)-N-methyl-3-(1-methylcyclopropyl)-5-(4,4,5,5-tetramethyl-1,3,2-dioxaborolan-2-yl)benzamide (P7)

To a suspension of compound P7d (323 mg, 1.0 mmol), B₂Pin₂ (380 mg, 1.5 mmol), KOAc (290 mg, 3.0 mmol) in dioxane (5 mL) was added Pd(dppf)Cl₂ (20 mg) under N₂ atmosphere. The mixture was heated to 100° C. for 16 h. The mixture was purified by CC (PE/EA=4/1) to afford compound P7 (200 mg, 68%) as a white solid.

Preparative Example P7/1 to P7/3

Using similar procedures as those described in Preparative Example P7, the following compounds were prepared:

| # | Structure |
|---|-----------|
| P7/1 | 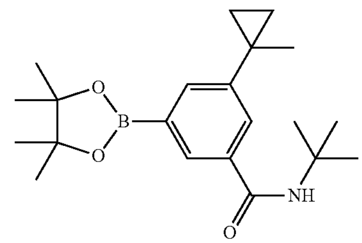 [SMILES: CC(C)(C)NC(=O)c1cc(B2OC(C)(C)C(C)(C)O2)cc(C2(C)CC2)c1] |
| P7/2 | 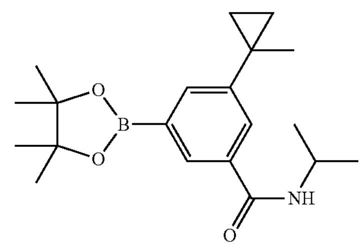 [SMILES: CC(C)NC(=O)c1cc(B2OC(C)(C)C(C)(C)O2)cc(C2(C)CC2)c1] |
| P7/3 | 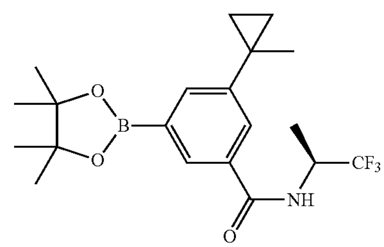 [SMILES: C[C@H](NC(=O)c1cc(B2OC(C)(C)C(C)(C)O2)cc(C2(C)CC2)c1)C(F)(F)F] |

Preparative Example P8

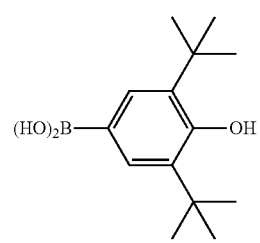

(3,5-Di-tert-butyl-4-hydroxyphenyl)boronic acid

To a -78° C. cooled solution of 4-bromo-2,6-di-tert-butylphenol (2.00 g, 7.0 mmol) in dry THF (30 mL) was added dropwise a 1.3M solution of tert-BuLi in hexane (18 mL, 20 mmol). The mixture was stirred for 1 h at rt and cooled to -78° C. prior to the addition of tri-isopropyl borate (5 mL, 21 mmol), stirred overnight at rt, diluted with sat. NH₄Cl solution, stirred at rt for 2 h and extracted with EA twice. The combined organic layers were washed with brine, dried over MgSO₄, filtered, evaporated and purified by recrystallization (30% EA in hexane) to give compound P8 (400 mg, 23%) as a white solid.

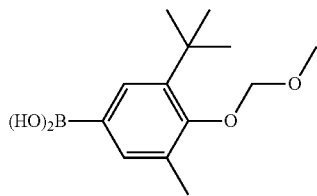

Preparative Example P9

Step 1: 4-Bromo-2-(tert-butyl)-6-methylphenol (P9a)

To a solution of 2-(tert-butyl)-6-methylphenol (20 g, 122 mmol) in dry DCM (500 mL) was added (nBu)$_4$NBr$_3$ (60.0 g, 122 mmol) at 0° C. and the solution was stirred for 25 min at 0° C., diluted with water (100 ml). The organic layer was separated, dried over Na$_2$SO$_4$, filtered, evaporated and purified by CC (PE) to give compound P9a (30 g, 58%) as an oil.

Step 2: 5-Bromo-1-(tert-butyl)-2-(methoxymethoxy)-3-methylbenzene (P9b)

To a solution of compound P9a (30 g, 183 mmol) in dry DCM (500 mL) was added NaH (10.0 g, 250 mmol) at 0° C. and the solution was stirred for 25 min at 0° C. Then MOMCl (15 g, 187 mmol) was added and the solution was stirred overnight at rt and quenched with water. The organic layer was dried over Na$_2$SO$_4$, filtered, evaporated and purified by CC (PE) to give compound P9b (8.5 g, 17%) as an oil.

Step 3: (3-(tert-Butyl)-4-(methoxymethoxy)-5-methylphenyl)boronic acid (P9)

To a 78° C. cooled solution of compound P9b (8.5 g, 30 mmol) in dry THF (150 mL) was added dropwise a 2M solution of tert-BuLi in hexane (15 mL, 30 mmol). The mixture was stirred for 2 h at rt and then cooled down to −78° C. prior to the addition of trimethyl borate (6.3 g, 60 mmol). The reaction was left overnight at rt prior to the addition of sat. NH$_4$Cl solution, stirred at rt for 2 h and extracted with EA twice. The combined organic layers were washed with brine, dried over MgSO$_4$, filtered, evaporated and purified by CC (PE/EA=5/1) to give compound P9 (2.0 g, 27%) as an oil.

Preparative Example P10

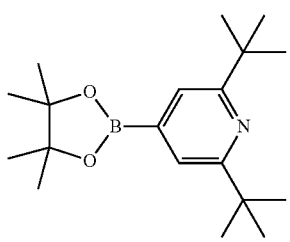

2,6-Di-tert-butyl-4-(4,4,5,5-tetramethyl-1,3,2-dioxaborolan-2-yl)pyridine (P10)

To a solution of 2,6-di-tert-butylpyridine (2.5 g, 13.0 mmol) in THF (30 mL) was added Ir(OMe)$_2$(COD)$_2$ (256 mg, 0.39 mmol), dtbpy (210 mg, 0.78 mmol) and (BPin)$_2$ (3.32 g, 13.0 mmol). The mixture was stirred overnight at 80° C. under nitrogen, concentrated and purified by CC (PE/EA=30/1) to give compound P10 (3.66 g, 88%) as an orange solid. $^1$H-NMR (400 MHz, CDCl$_3$) δ: 1.35 (30H, d, J=4.0 Hz), 7.43 (2H, s).

ADDITIONAL PREPARATIVE EXAMPLES

The synthesis of additional Preparative Examples (e.g. boronic esters) is described in WO2012/139775 and in PCT/EP2012/004977.

Example 1

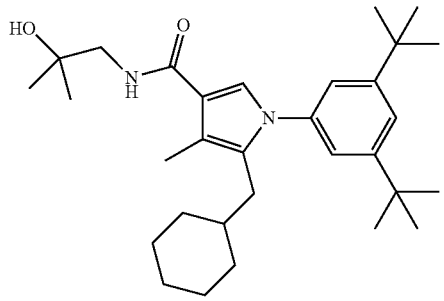

Step 1: Ethyl 1-(3,5-di-tert-butylphenyl)-4-methyl-1H-pyrrole-3-carboxylate (1a)

To a solution of 1-bromo-3,5-di-tert-butylbenzene (5.0 g, 18.5 mmol) in dry DMF (30 mL) was added Cs$_2$CO$_3$ (15.0 g, 46.2 mmol), ethyl 4-methyl-1H-pyrrole-3-carboxylate (3.0 g, 19 mmol), CuI (2.5 g, 13.1 mmol) and (1S,2R)-cycolohexane-1,2-diamine (1.3 g, 11.3 mmol) under N$_2$ and the mixture was heated at 90° C. overnight, cooled to rt, diluted with water and extracted with EA (3×). The combined organic layers were washed with brine, dried over Na$_2$SO$_4$, concentrated and purified by CC (PE/EA=10/1) to give compound 1a (2.8 g, 48%) as an oil.

Step 2: Ethyl 1-(3,5-di-tert-butylphenyl)-5-formyl-4-methyl-1H-pyrrole-3-carboxylate (1b)

To a solution of compound 1a (2.8 g, 8.2 mmol) in dry DMF (15 mL) was added POCl$_3$ (0.8 mL, 8.6 mmol) and the mixture was heated at 90° C. for 2 h, cooled to 0° C., poured into ice water and extracted with DCM (3×). The combined organic layers were washed with brine, dried over Na$_2$SO$_4$, concentrated and purified by CC (PE/EA=10/1) to give compound 1 b (2.7 g, 90%) as a yellow oil.

Step 3: Ethyl 5-(cyclohexyl(hydroxy)methyl)-1-(3,5-di-tert-butylphenyl)-4-methyl-1H-pyrrole-3-carboxylate (1c)

To the solution of compound 1b (1.0 g, 2.7 mmol) in dry THF (20 mL) was added cyclohexylMgBr (1M in THF, 14 mL) for 30 min at 0° C. under $N_2$ and the solution was stirred at rt overnight, quenched with aq. $NH_4Cl$ (40 mL) and extracted with DCM twice. The combined organic phases were dried over $Na_2SO_4$, filtered, concentrated and purified by CC (PE/EA=5/1) to give compound 1c (900 mg, 75%).

Step 4: Ethyl 5-(cyclohexylidenemethyl)-1-(3,5-di-tert-butylphenyl)-4-methyl-1H-pyrrole-3-carboxylate (1d)

To a solution of compound 1c (900 mg, 2.0 mmol) in dry toluene (10 mL) was added $TsOH.H_2O$ (46 mg, 0.24 mmol) in one portion and the mixture was heated at reflux for 2 h, concentrated and diluted with DCM. The organic layer was washed with water, concentrated under reduced pressure and purified by CC (PE/EA=1/20) to give compound 1d (670 mg, 81%) as a brown solid.

Step 5: Ethyl 5-(cyclohexylmethyl)-1-(3,5-di-tert-butylphenyl)-4-methyl-1H-pyrrole-3-carboxylate (1e)

A solution of compound 1d (670 mg, 1.6 mmol) and Pd/C (30 mg) in MeOH (20 mL) was stirred under $H_2$ (1 atm) at rt overnight, filtered and concentrated to give compound 1e (630 mg, 90%) as a solid.

Step 6: 5-(Cyclohexylmethyl)-1-(3,5-di-tert-butylphenyl)-4-methyl-1H-pyrrole-3-carboxylic acid (1f)

Compound 1e (630 mg, 1.44 mmol) was added to a solution of NaOH (69 mg, 1.7 mmol) in EtOH and $H_2O$ (2:1, 15 mL) and then the mixture was stirred overnight at reflux, diluted with $H_2O$, adjusted to pH 5 with 1N HCl and extracted with DCM (30 mL). The organic layer was washed with brine, dried over $Na_2SO_4$, filtered, concentrated and purified by CC (PE/EA=1/8) to give compound 1f (450 mg, 76%) as a brown solid.

Step 7: 5-(Cyclohexylmethyl)-1-(3,5-di-tert-butylphenyl)-N-(2-hydroxy-2-methylpropyl)-4-methyl-1H-pyrrole-3-carboxamide (1)

To a solution of compound 1f (200 mg, 0.49 mmol) in DMF (5 mL) was added HATU (280 mg, 0.73 mmol) and TEA (75 mg, 0.73 mmol) and the resulting solution was stirred at rt for 30 min, then 1-amino-2-methylpropan-2-ol (44 mg, 0.49 mmol) was added and stirred for additional 2 h, quenched with water (10 mL) and extracted with EA (3×20 mL). The organic layers were washed with brine, dried over $Na_2SO_4$, filtered, evaporated and purified by prep-HPLC to give compound 1 (50 mg, 21%) as a solid. $^1$H-NMR (400 MHz, DMSO-$d_6$) δ: 7.44 (t, 1H, J=1.2 Hz), 7.41-7.42 (m, 2H), 7.12 (d, 2H, J=1.2 Hz), 4.57 (s, 1H), 3.15 (d, 2H, J=5.2 Hz), 2.34 (d, 2H, J=6.0 Hz), 2.16 (s, 3H), 1.47-1.52 (m, 3H), 1.31-1.33 (m, 20H), 1.07 (s, 6H), 0.82-0.95 (m, 4H), 0.65-0.74 (m, 2H). MS 481.4 (M+1).

Example 1/1 to 1/6

The following Examples were prepared similar as in Example 1:

| # | Structure | Analytical data |
|---|-----------|-----------------|
| 1/1 | 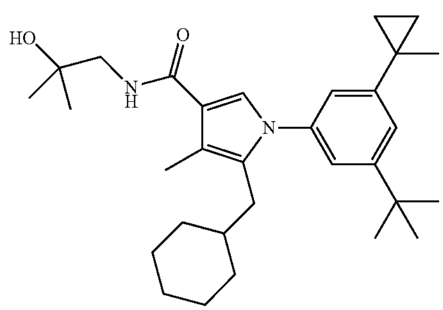 [SMILES: Cc1c(C(=O)NCC(C)(C)O)cn(-c2cc(C(C)(C)C)cc(C3(C)CC3)c2)c1CC1CCCCC1] | $^1$H-NMR (500 MHz, CDCl$_3$) δ: 7.30 (s, 1H), 7.19 (s, 1H), 7.06 (s, 1H), 6.94 (s, 1H), 6.19 (t, 1H, J = 5.5 Hz), 3.43 (d, 2H, J = 6.5 Hz), 3.02 (s, 1H), 2.36 (d, 2H, J = 7.0 Hz), 2.30 (s, 3H), 1.59-1.69 (m, 3H), 1.43-1.46 (m, 5H), 1.33 (s, 9H), 1.26-1.29 (m, 7H), 1.00-1.06 (m, 1H), 0.86-0.89 (m, 2H), 0.71-0.79 (m, 4H). MS 479.4 (M + 1) |
| 1/2 | 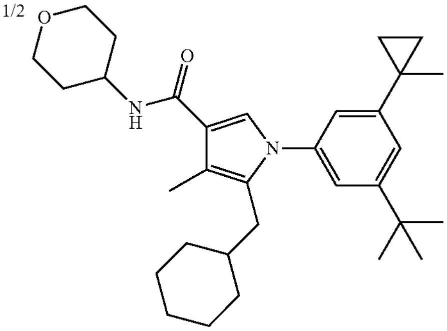 | $^1$H-NMR (500 MHz, CDCl$_3$) δ: 7.30 (d, 1H, J = 1.0 Hz), 7.14 (s, 1H), 7.06 (t, 1H, J = 1.8 Hz), 6.93 (t, 1H, J = 1.5 Hz), 5.64 (d, 1H, J = 7.5 Hz), 4.27 (br s, 1H), 3.99 (dd, 2H, J = 8.5, 3.0 Hz), 3.54 (dt, 2H, J = 12.0, 2.0 Hz), 2.35 (d, 2H, J = 7.0 Hz), 2.28 (s, 3H), 2.00-2.03 (m, 4H), 1.54-1.59 (m, 5H), 1.42-1.46 (s, 3H), 1.33 (s, 9H), 1.10-1.20 (m, 1H), 0.98-1.04 (m, 3H), 0.86-0.88 (m, 2H), 0.70-0.79 (m, 4H). MS 491.4 (M + 1) |

| # | Structure | Analytical data |
|---|---|---|
| 1/3 | 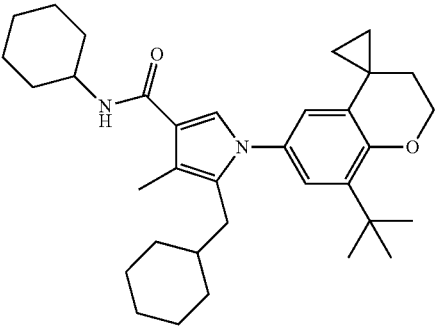 [SMILES: Cc1c(C(=O)NC2CCCCC2)cn(-c2cc(C(C)(C)C)c3c(c2)C2(CCO3)CC2)c1CC1CCCCC1] | ¹H-NMR (400 MHz, CDCl₃) δ: 7.06 (s, 1H), 6.91 (d, 1H, J = 2.0 Hz), 6.37 (d, 1H, J = 2.0 Hz), 5.59 (br s, 1H), 4.34-4.35 (m, 2H), 4.18-4.22 (m, 1H), 3.97-3.99 (m, 2H), 3.52-3.57 (m, 2H), 2.26-2.29 (m, 5H), 1.99-2.02 (m, 2H), 1.91 (t, 2H, J = 4.0 Hz), 1.47-1.64 (m, 10H), 1.38 (s, 9H), 1.05-1.08 (m, 3H), 0.97-0.99 (m, 2H), 0.85-0.89 (m, 2H), 0.76-0.81 (m, 2H). MS 519.4 (M + 1) |
| 1/4 | 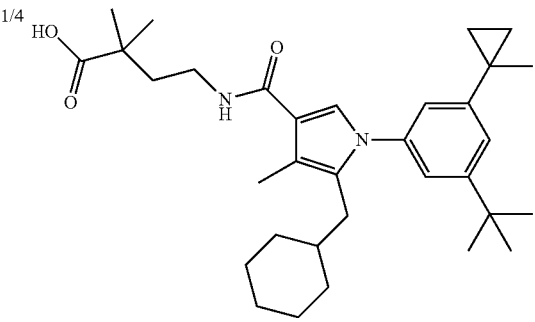 | ¹H-NMR (400 MHz, DMSO-d₆) δ: 12.15 (br s, 1H), 7.53 (t, 1H, J = 5.4 Hz), 7.27-7.29 (m, 2H), 7.09 (t, 1H, J = 1.6 Hz), 6.92 (t, 1H, J = 1.6 Hz), 3.12-3.17 (m, 2H), 2.34 (d, 2H, J = 6.8 Hz), 2.15 (s, 3H), 1.67-1.71 (m, 2H), 1.24-1.53 (m, 18H), 1.13 (s, 6H), 0.78-1.04 (m, 9H). MS 521.3 (M + 1) |
| 1/5 | 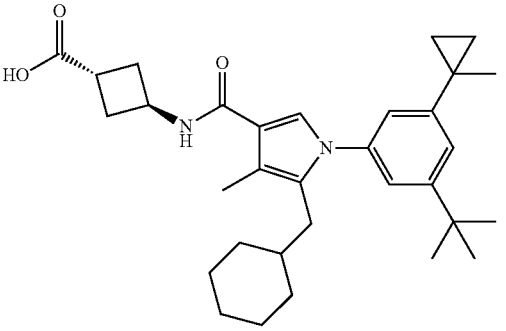 [SMILES: Cc1c(C(=O)N[C@H]2C[C@H](C(=O)O)C2)cn(-c2cc(C(C)(C)C)cc(C3(C)CC3)c2)c1CC1CCCCC1] | ¹H-NMR (400 MHz, DMSO-d₆): δ 12.15 (s, 1H), 7.79 (d, 1H, J = 7.6 Hz), 7.36 (s, 1H), 7.28 (t, 1H, J = 1.6 Hz), 7.10 (t, 1H, J = 1.6 Hz), 6.92 (t, 1H, J = 1.2 Hz), 4.47-4.50 (m, 1H), 2.90-2.92 (m, 1H), 2.15-2.42 (m, 9H), 1.49-1.52 (m, 3H), 1.41 (s, 3H), 1.04-1.35 (m, 12H), 0.74-0.98 (m, 9H). MS 505.3 (M + 1) |
| 1/6 | 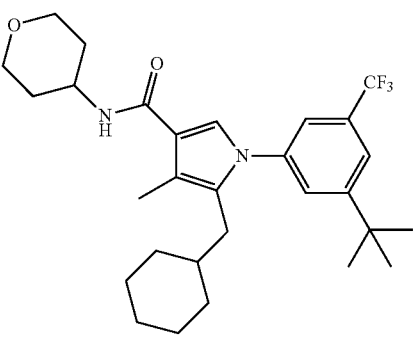 [SMILES: Cc1c(C(=O)NC2CCOCC2)cn(-c2cc(C(C)(C)C)cc(C(F)(F)F)c2)c1CC1CCCCC1] | ¹H-NMR (500 MHz, CDCl₃) δ: 7.66 (1H, s), 7.47 (1H, s), 7.35 (1H, s), 7.15 (1H, s), 5.65 (1H, d, J = 7.5 Hz), 4.20 (1H, m), 3.98-4.01 (2H, m), 3.55 (2H, dt, J = 2.0, 12.5 Hz), 2.37 (2H, d, J = 7.0 Hz), 2.28 (3H, s), 2.01-2.03 (2H, m), 1.55-1.60 (5H, m), 1.40-1.42 (2H, m), 1.39 (9H, s), 1.10-1.20 (4H, m), 0.94 (2H, br s), 0.70-0.80 (2H, m). MS 505.3 (M + 1) |

Example 2

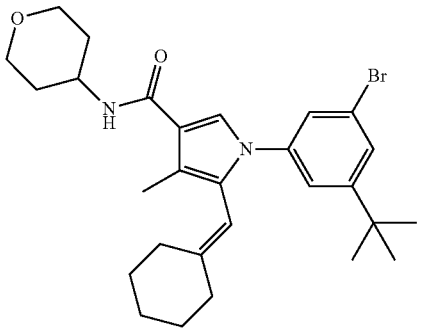

1-(3-Bromo-5-(tert-butyl)phenyl)-5-(cyclohexyliden-emethyl)-4-methyl-N-(tetrahydro-2H-pyran-4-yl)-1H-pyrrole-3-carboxamide (2)

Using appropriate building blocks and the procedure described in Example 1 without the hydrogenation Step 5 compound 2 was obtained. $^1$H-NMR (400 MHz, CDCl$_3$) δ: 7.46 (s, 1H, 7.25-7.30 (m, 3H), 5.71 (d, 1H, J=7.6 Hz), 5.65 (s, 1H), 4.20-4.24 (m, 1H), 3.98-4.02 (m, 2H), 3.52-3.58 (m, 2H), 2.01-2.22 (m, 9H), 1.34-1.60 (m, 8H), 1.32 (s, 9H). MS 513.1 (M+1).

Example 3 and Example 4

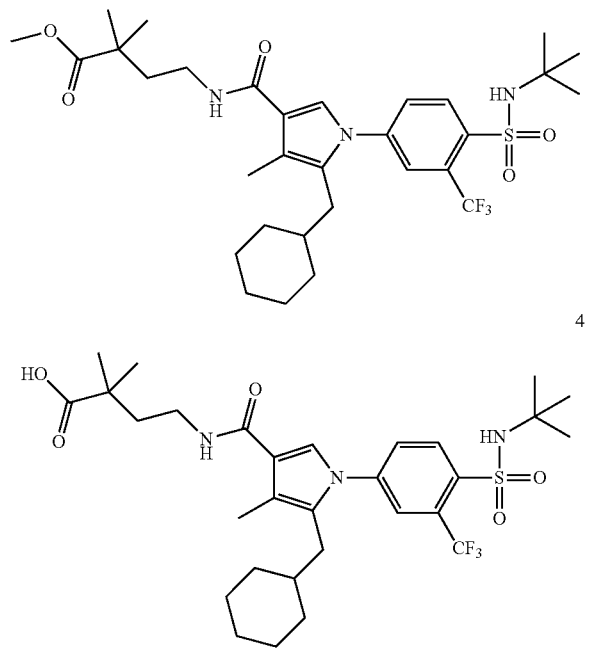

Step 1: Ethyl 5-formyl-4-methyl-1H-pyrrole-3-carboxylate (3a)

The Vilsmeier reagent was prepared by treatment of dry DMF (19.0 g, 261 mmol) with POCl$_3$ (40.0 g, 261 mol) at 0° C. and stirred for another hour at rt. In a flask, a solution of ethyl 4-methyl-1H-pyrrole-3-carboxylate (26.6 g, 174 mmol) in dry DMF (50 mL) was treated with the freshly prepared Vilsmeier reagent at 0° C. The resulting mixture was stirred for another hour at rt, then poured into ice, adjusted the pH to 7-8 with 10N NaOH, heated to 60° C. for 2 h and then cooled. The yellow precipitate was collected by filtration, redissolved in EA, washed with brine, dried over Na$_2$SO$_4$, filtered and concentrated to give compound 3a (25.3 g, 80%) as a yellow solid.

Step 2: Ethyl 5-formyl-1-(4-methoxybenzyl)-4-methyl-1H-pyrrole-3-carboxylate (3b)

To a mixture of compound 3a (9.0 g, 50 mmol) in dry DMF (80 mL) was added NaH (60%, 2.6 g, 65 mmol) in portions at 0° C. and the mixture was stirred at rt for 1 h. PMB-Cl (9.4 g, 60 mmol) was added dropwise and the solution was heated at 30° C. for 1 h, poured into sat. NH$_4$Cl and extracted with EA. The extract was washed with brine, dried over Na$_2$SO$_4$, filtered, concentrated and purified by CC (PE/EA=25/1) to give compound 3b (13.2 g, 88%) as a yellow oil.

Step 3: Ethyl 5-(cyclohexyl(hydroxy)methyl)-1-(4-methoxybenzyl)-4-methyl-1H-pyrrole-3-carboxylate (3c)

To a solution of compound 3b (13.2 g, 43.9 mmol) in THF (150 mL) was added cyclohexylMgBr (1M in THF, 51 mL, 51 mmol) dropwise at 0° C., then stirred at 25° C. for 1 h, diluted with sat. NH$_4$Cl (200 mL) and the resulting solution was extracted with DCM. The combined organic phases were washed with water and brine, dried over Na$_2$SO$_4$, filtered and concentrated to give compound 3c (16.7 g, 100%) as a yellow oil.

Step 4: Ethyl 5-(cyclohexylmethyl)-1-(4-methoxy-benzyl)-4-methyl-1H-pyrrole-3-carboxylate (3d)

To a stirred mixture of compound 3c (16.7 g, 42.4 mmol) in DCM (250 mL) was added TFA (9.7 g, 84.8 mmol) at 0° C. After 15 min Et$_3$SiH (49.5 g, 424 mmol) was added dropwise and the mixture was stirred at rt for 0.5 h, quenched with sat. NaHCO$_3$ and the resulting solution was extracted with DCM twice. The combined organic phases were washed with water and brine, dried over Na$_2$SO$_4$, filtered, concentrated and purified by CC (PE/EA=30/1) to give compound 3d (15.0 g, 93%) as a yellow oil.

Step 5: Ethyl 5-(cyclohexylmethyl)-4-methyl-1H-pyrrole-3-carboxylate (3e)

To a stirred solution of compound 3d (15.0 g, 40.6 mmol) in ACN (30 mL) at rt was added ceric ammonium nitrate (44.8 g, 81.2 mmol) followed by distilled water (100 mL) and the solution was stirred for 40 min, diluted with EA, washed with water, dried over MgSO$_4$, filtered, concentrated and purified by CC (PE/EA=15/1) to give compound 3e (4.1 g, 40%) as a yellow solid. $^1$H-NMR (300 MHz, CDCl$_3$) δ: 0.85-0.97 (m, 2H), 1.09-1.25 (m, 3H), 1.30-1.39 (m, 3H), 1.44-1.48 (m, 1H), 1.58-1.71 (m, 5H), 2.19 (s, 3H), 2.40 (d, J=7.2 Hz, 2H), 4.25 (q, J=7.2 Hz, 2H), 7.27-7.28 (m, 1H), 7.98 (br s, 1H).

Step 6: Ethyl 1-(4-(N-tert-butyl)sulfamoyl)-3-(trifluoromethyl)phenyl)-5-(cyclohexylmethyl)-4-methyl-1H-pyrrole-3-carboxylate (3f)

A mixture of compound 3e (1.0 g, 4.0 mmol), 4-bromo-N-(tert-butyl)-2-(trifluoromethyl)benzenesulfonamide (1.6 g, 4.4 mmol), CuI (762 mg, 4.0 mmol), $K_3PO_4$ (1.7 g, 8.0 mmol) and trans-N,N'-dimethylcyclohexane-1,2-diamine (565 mg, 4.0 mmol) in toluene (10 mL) was heated at reflux under $N_2$ overnight, cooled to rt and diluted with EA, washed with water and brine consecutively, dried over $Na_2SO_4$, filtered, concentrated and purified by CC (PE/EA=15/1) to give compound 3f (348 mg, 16%) as a purple oil.

Step 7: 1-(4-(N-(tert-Butyl)sulfamoyl)-3-(trifluoromethyl)phenyl)-5-(cyclohexylmethyl)-4-methyl-1H-pyrrole-3-carboxylic acid (3q)

A mixture of compound 3f (348 mg, 0.66 mmol) and t-BuOK (222 mg, 1.98 mmol) in a mixture of DMSO and $H_2O$ (10/1, 5 mL) was stirred at 90° C. for 1 h, cooled to rt, diluted with water, acidified with 1N HCl to pH=6 and extracted with EA (100 mL). The organic layer was washed with water and brine consecutively, dried over $Na_2SO_4$, filtered and concentrated to give compound 3g (330 mg, 100%) as a brown oil.

Step 8: Methyl 4-(1-(4-(N-(tert-butyl)sulfamoyl)-3-(trifluoromethyl)phenyl)-5-(cyclohexylmethyl)-4-methyl-1H-pyrrole-3-carboxamido)-2,2-dimethylbutanoate (3)

A mixture of compound 3g (200 mg, 0.40 mmol), methyl 4-amino-2,2-dimethylbutanoate hydrochloride (70 mg, 0.48 mmol), HATU (230 mg, 0.60 mmol) and DIPEA (160 mg, 1.2 mmol) in DMF (3 mL) was stirred at 30° C. for 1 h, diluted with water and extracted with EA twice. The combined organic layers were washed with water (3×) and brine consecutively, dried over $Na_2SO_4$, filtered, concentrated and purified by prep-TLC (PE/EA=3/2) to give compound 3 (240 mg, 96%) as a yellow oil.

Step 9: 4-(1-(4-(N-(tert-Butyl)sulfamoyl)-3-(trifluoromethyl)phenyl)-5-(cyclohexylmethyl)-4-methyl-1H-pyrrole-3-carboxamido)-2,2-dimethylbutanoic acid (4)

A mixture of compound 3 (240 mg, 0.38 mmol) and $LiOH·H_2O$ (160 mg, 3.8 mmol) in $MeOH/H_2O$ (10:1, 3.5 mL) was stirred at rt for 6 h, concentrated and diluted with water (10 mL), acidified with 4N HCl to pH<2, extracted with EA (50 mL) and washed with brine, dried over $Na_2SO_4$, concentrated and purified by prep-HPLC to give compound 4 (23 mg, 10%) as a white solid. $^1$H-NMR ($CD_3OD$, 400 MHz) δ: 0.72-0.78 (m, 2H), 0.92-1.07 (m, 4H), 1.24 (s, 6H), 1.25 (s, 9H), 1.37-1.41 (m, 2H), 1.54-1.58 (m, 3H), 1.83-1.87 (m, 2H), 2.22 (s, 3H), 2.53 (d, J=7.2 Hz, 2H), 3.34-3.38 (m, 2H), 7.31 (s, 1H), 7.79 (d, J=8.4 Hz, 1H), 7.87 (s, 1H), 8.40 (d, J=8.4 Hz, 1H). MS 614.3 (M+1)$^+$.

Example 4/1 to 4/3

The following Examples were prepared similar as in Example 3 and optionally 4:

| # | Structure | Analytical data |
|---|---|---|
| 4/1 | 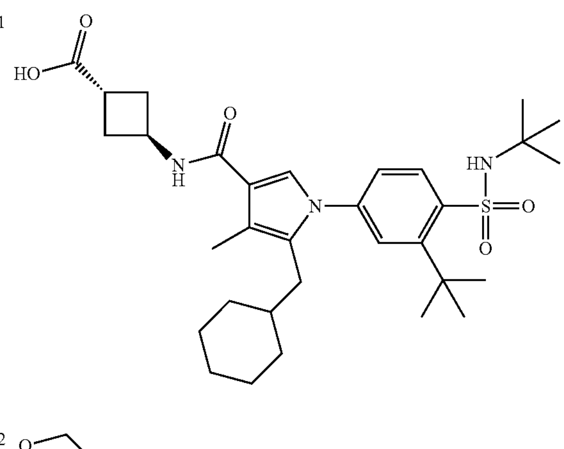 | $^1$H-NMR ($CD_3OD$, 400 MHz) δ: 0.70-0.75 (m, 2H), 0.92-1.00 (m, 3H), 1.28 (s, 9H), 1.34-1.39 (m, 3H), 1.52-1.57 (m, 3H), 1.62 (s, 9H), 2.21 (s, 3H), 2.33-2.39 (m, 2H), 2.49 (d, J = 7.2 Hz, 2H), 2.61-2.65 (m, 2H), 3.00-3.06 (m, 1H), 4.62-4.69 (m, 1H), 7.34-7.36 (m, 2H) 7.57 (d, J = 1.6 Hz, 1H), 8.29 (d, J = 8.4 Hz, 1H). MS 586.3 (M + 1)$^+$ |
| 4/2 | 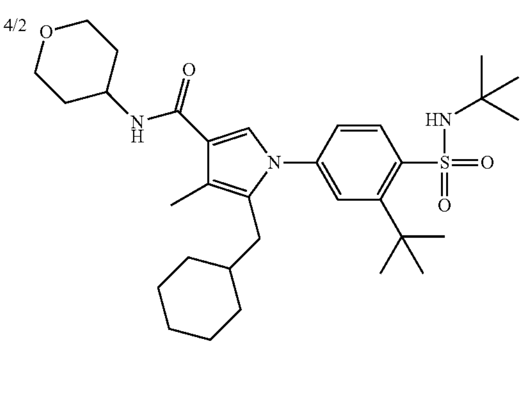 | $^1$H-NMR ($CDCl_3$, 400 MHz) δ: 0.67-0.73 (m, 2H), 0.94-1.04 (m, 3H), 1.31 (s, 9H), 1.38-1.41 (m, 2H), 1.51-1.56 (m, 6H), 1.61 (s, 9H), 2.00 (d, J = 10.4 Hz, 2H), 2.26 (s, 3H), 2.41 (d, J = 7.2 Hz, 2H), 3.53 (t, J = 10.4 Hz, 2H), 3.98 (d, J = 12.0 Hz, 2H), 4.12-4.24 (m, 1H), 4.50 (s, 1H), 5.60 (d, J = 8.0 Hz, 1H), 7.13 (s, 1H), 7.19 (dd, J = 2.0, 8.4 Hz, 1H), 7.51 (d, J = 2.0 Hz, 1H), 8.26 (d, J = 8.4 Hz, 1H). MS 572.3 (M + 1)$^+$ |

| # | Structure | Analytical data |
|---|---|---|
| 4/3 | 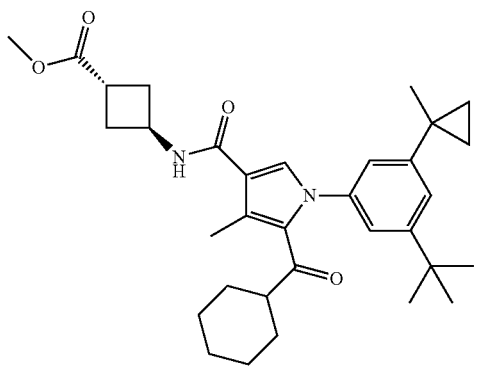 | $^1$H-NMR (CD$_3$OD, 400 MHz) δ: 0.71-0.77 (m, 2H), 0.88-1.04 (m, 3H), 1.25 (s, 9H), 1.29-1.41 (m, 3H), 1.52-1.64 (m, 5H), 1.86-1.89 (m, 2H), 2.23 (s, 3H), 2.54 (d, J = 7.2 Hz, 2H), 3.52 (t, J = 11.2 Hz, 2H), 3.95-4.06 (m, 3H), 7.38 (s, 1H), 7.80 (d, J = 8.4 Hz, 1H), 7.87 (s, 1H), 8.40 (d, J = 8.4 Hz, 1H). MS 584.2 (M + 1)$^+$ |

Example 5 and Example 6

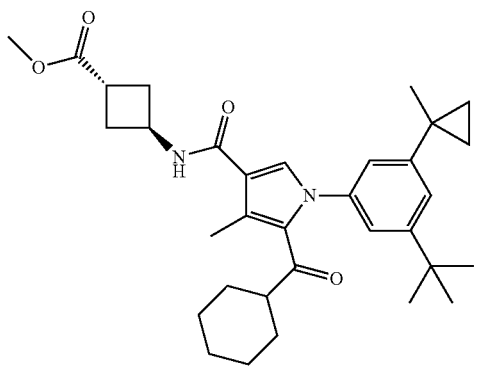

5

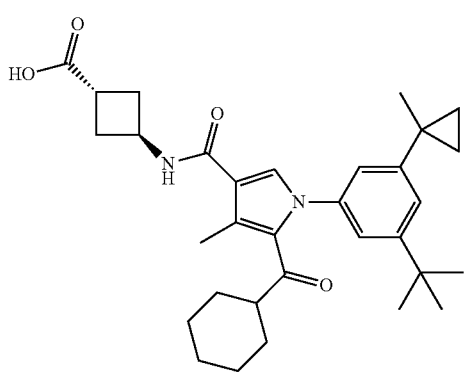

6

Step 1: Ethyl 5-formyl-4-methyl-1H-pyrrole-3-carboxylate (5a)

The Vilsmeier reagent was prepared by treatment of dry DMF (19.0 g, 261 mmol) with POCl$_3$ (40.0 g, 261 mmol) at 0° C. and stirred for another hour at rt. In a flask, a solution of ethyl 4-methyl-1H-pyrrole-3-carboxylate (26.6 g, 174 mmol) in DMF (50 mL) was treated with the freshly prepared Vilsmeier reagent at 0° C. The resulting solution was stirred for another hour at rt, poured into ice, adjusted the pH to 7-8 with 10N NaOH, heated to 60° C. for 2 h and cooled. The precipitated yellow solid was collected by filtration, dissolved in EA, washed with brine, dried over Na$_2$SO$_4$, filtered and concentrated to give compound 5a (25.3 g, 80%) as a yellow solid.

Step 2: Ethyl 1-(3-(tert-butyl)-5-(1-methylcyclopropyl)phenyl)-5-formyl-4-methyl-1H-pyrrole-3-carboxylate (5b)

A suspension of compound 5a (2.0 g, 11.0 mmol), compound P2a (3.95 g, 14.8 mmol), (1R,2R)-1N,2N-dimethylcyclohexane-1,2-diamine (1.90 g, 13.4 mmol), CuI (2.55 g, 13.4 mmol) and K$_3$PO$_4$ (5.68 g, 26.8 mmol) in toluene (50 mL) was refluxed overnight under N$_2$, filtered and the cake was washed with EA. The combined filtrates were washed by water and brine consecutively, dried by Na$_2$SO$_4$, filtered, concentrated and purified by CC (PE/EA=100/1 to 30/1) to give compound 5b (3.1 g, 77%) as a white solid.

Step 3: Ethyl 1-(3-(tert-butyl)-5-(1-methylcyclopropyl)phenyl)-5-(cyclohexyl(hydroxy)methyl)-4-methyl-1H-pyrrole-3-carboxylate (5c)

To a solution of compound 5b (1.0 g, 2.72 mmol) in THF (30 mL) was added cyclohexylMgBr (1M solution in THF, 3.57 mL, 3.57 mmol) at 0° C. and the solution was stirred at rt for 2 h, quenched by sat. NH$_4$Cl and extracted with EA. The organic layer was washed with water and brine consecutively, dried by Na$_2$SO$_4$, filtered, concentrated and purified by CC (PE/EA=100/1 to 30/1) to give compound 5c (872 mg, 71%) as a yellow oil.

Step 4: Ethyl 1-(3-(tert-butyl)-5-(1-methylcyclopropyl)phenyl)-5-(cyclohexanecarbonyl)-4-methyl-1H-pyrrole-3-carboxylate (5d)

To a solution of compound 5c (860 mg, 1.90 mmol) in DCM (25 mL) was added Dess-Martin periodinane (2.02 g, 4.76 mmol) and the solution was stirred at rt for 2 h, quenched with sat. NaHCO$_3$ and extracted with DCM. The organic layer was washed by water then brine consecutively, dried by Na$_2$SO$_4$, filtered, concentrated and purified by CC (PE/EA=50/1) to give compound 5d (850 mg, 99%) as a yellow solid.

Step 5: 1-(3-(tert-Butyl)-5-(1-methylcyclopropyl)phenyl)-5-(cyclohexanecarbonyl)-4-methyl-1H-pyrrole-3-carboxylic acid (5e)

A solution of compound 5d (850 mg, 1.89 mmol) and t-BuOK (1.27 g, 11.3 mmol) in a mixture of DMSO (3.5 mL)

and H₂O (0.5 mL) was stirred at 90° C. overnight, cooled to 0° C., diluted with water, adjusted to pH=5 with conc. HCl and extracted by EA (3×). The combined organic layers were washed by water (3×) and brine consecutively, dried over Na₂SO₄, filtered, concentrated and purified by CC (PE/EA=5/1) to give compound 5e (200 mg, 25%) as a yellow solid

Step 6: (trans)-Methyl 3-(1-(3-(tert-butyl)-5-(1-methylcyclopropyl)phenyl)-5-(cyclohexanecarbonyl)-4-methyl-1H-pyrrole-3-carboxamido)cyclobutanecarboxylate (5)

A solution of compound 5e (200 mg, 0.47 mmol), trans methyl 3-aminocyclobutane carboxylate HCl salt (86 mg, 0.52 mmol), HATU (271 mg, 0.71 mmol) and DIPEA (184 mg, 1.42 mmol) in DMF (5 mL) was stirred at rt overnight, quenched by water and extracted by EA twice. The combined organic layers were washed by water (3×) and brine consecutively, dried over Na₂SO₄, filtered and concentrated to give compound 5 (271 mg, quant.) as a yellow solid.

Step 7: (trans)-3-(1-(3-(tert-Butyl)-5-(1-methylcyclopropyl)phenyl)-5-(cyclohexanecarbonyl)-4-methyl-1H-pyrrole-3-carboxamido)cyclobutanecarboxylic acid (6)

A solution of compound 5 (270 mg, 0.51 mmol) and LiOH.H₂O (213 mg, 5.07 mmol) in a mixture of MeOH (4.5 mL) and H₂O (0.5 mL) was stirred at rt for 2 h, concentrated, diluted with water, adjusted to pH=5 with conc. HCl and extracted with EA. The organic layer was washed with water and brine consecutively, dried by Na₂SO₄, filtered, concentrated, purified by CC (PE/EA=2/1 to DCM/MeOH=20/1) and then being washed with Et₂O to give compound 6 (50 mg, 19%) as a white solid. $^1$H-NMR (400 MHz, CDCl₃) δ: 0.75-0.77 (m, 2H), 0.84-0.89 (m, 4H), 1.03-1.31 (m, 3H) 1.31 (s, 9H), 1.40 (s, 3H), 1.47-1.65 (m, 5H), 2.11-2.19 (m, 1H), 2.28-2.36 (m, 2H), 2.49 (s, 3H), 2.77-2.84 (m, 2H), 3.08-3.17 (m, 1H), 4.75-4.85 (m, 1H), 5.96 (d, J=6.8 Hz, 2H), 6.94 (t, J=1.6 Hz, 1H), 7.03 (t, J=2.0 Hz, 1H), 7.28 (s, 1H), 7.31 (d, J=1.6 Hz, 2H). MS 519.3 (M+1)⁺.

Example 7 and Example 8

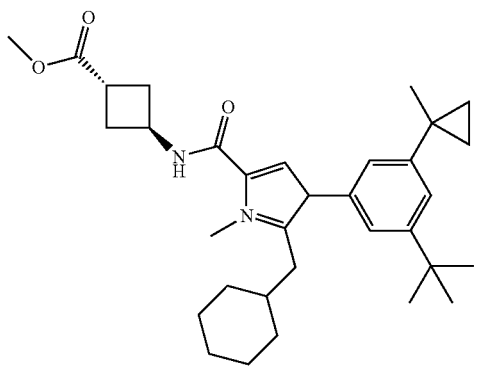

7

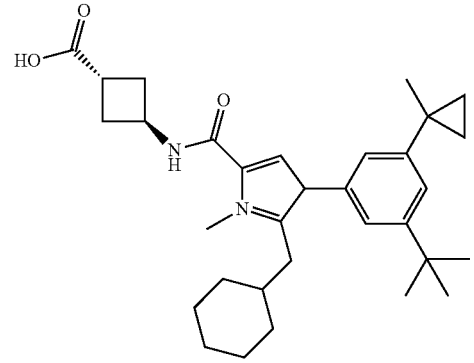

8

Step 1: Methyl 5-formyl-1-methyl-1H-pyrrole-2-carboxylate (7a)

The Vilsmeier reagent was prepared by treatment of dry DMF (440 mL) with POCl₃ (220 g, 1.44 mol) at 0° C. and stirred for another hour at rt. A solution of methyl 1-methyl-1H-pyrrole-2-carboxylate (40 g, 288 mmol) in 1,2-dichloroethane (800 mL) was treated with the freshly prepared Vilsmeier reagent at 0° C., stirred for 8 h at 80° C., cooled to rt, poured into ice, adjusted to pH=7-8 with sat. NaHCO₃, stirred at rt for 0.5 h and extracted with EA twice. The combined organic layers were washed with water (3×) and brine consecutively, dried over Na₂SO₄, filtered, concentrated and purified by CC (PE/EA=5/1) to give compound 7a (21 g, 44%) as a yellow solid.

Step 2: Methyl 5-(cyclohexyl(hydroxy)methyl)-1-methyl-1H-pyrrole-2-carboxylate (7b)

To a solution of compound 7a (21 g, 126 mmol) in Et₂O (200 mL) was added cyclohexylMgBr (1M in THF, 150 mL, 150 mmol) at 0° C. and the solution was stirred at rt for 3 h, poured into sat. NH₄Cl and extracted with EA. The organic layer was washed with brine, dried over Na₂SO₄, filtered, concentrated and purified by CC (PE/EA=3/1) to give compound 7b (16 g, 51%) as a white solid.

Step 3: Methyl 5-(cyclohexylmethyl)-1-methyl-1H-pyrrole-2-carboxylate (7c)

To a solution of compound 7b (16 g, 63.7 mmol) in dry DCM (250 mL) was added Et₃SiH (51.2 mL, 318 mmol) at 0° C., followed by TFA (200 mL) and the solution was stirred overnight at 50° C., diluted with water and extracted with DCM. The organic layer was washed with sat. NaHCO₃, water and brine consecutively, dried by Na₂SO₄, filtered, concentrated and purified by CC (PE/EA=10/1) to give compound 7c (9.6 g, 64%) as a yellow solid.

Step 4: Methyl 4-bromo-5-(cyclohexylmethyl)-1-methyl-1H-pyrrole-2-carboxylate (7d)

To a solution of compound 7c (3.20 g, 13.6 mmol) in THF (50 mL) was added NBS (2.21 g, 12.5 mmol) at 78° C. and the solution was stirred at this temperature for 20 min, diluted with sat. NaHCO₃ and extracted with DCM. The organic layer was washed with water and brine consecutively, dried by Na₂SO₄, filtered, concentrated and purified by CC (PE/EA=10/1) to give compound 7d (3.2 g, 75%) as a pale yellow solid.

Step 5: Methyl 4-(3-(tert-butyl)-5-(1-methylcyclopropyl)phenyl)-5-(cyclohexylmethyl)-1-methyl-1H-pyrrole-2-carboxylate (7e)

A solution of compound 7d (800 mg, 2.56 mmol), compound P2 (728 mg, 2.32 mmol), Pd(dppf)Cl₂ (163 mg) and K₂CO₃ (962 mg, 6.97 mmol) in DMF (10 mL) was stirred overnight at 80° C. under N₂, cooled to rt, diluted with water and extracted with EA (3×). The combined organic layers were washed by water (3×) and brine consecutively, dried by Na₂SO₄, filtered, concentrated and purified by CC (PE/EA=5/1) to give compound 7e (700 mg, 65%) as a white solid.

Step 6: 4-(3-(tert-Butyl)-5-(1-methylcyclopropyl)phenyl)-5-(cyclohexylmethyl)-1-methyl-1H-pyrrole-2-carboxylic acid (7f)

A solution of compound 7e (700 mg, 1.66 mmol) and KOH (560 mg, 10 mmol) in a mixture of EtOH (10 mL) and H₂O (2 mL) was stirred overnight at 70° C., concentrated, diluted with water, adjusted to pH=5 with conc. HCl and extracted with DCM. The organic layer was dried by Na₂SO₄, filtered, concentrated and purified by CC (PE/EA=1/1) to give compound 7f (400 mg, 59%) as a white solid.

Step 7: (trans)-Methyl 3-(4-(3-(tert-butyl)-5-(1-methylcyclopropyl)phenyl)-5-(cyclohexylmethyl)-1-methyl-1H-pyrrole-2-carboxamido)cyclobutanecarboxylate (7)

A solution of compound 7f (260 mg, 0.64 mmol), trans methyl 3-aminocyclobutane carboxylate HCl salt (166 mg, 1.00 mmol), HATU (285 mg, 0.75 mmol) and DIPEA (387 mg, 3.00 mmol) in DMF (6 mL) was stirred at rt for 30 min, diluted with water and extracted with EA (3×). The combined organic layers were washed by water (3×) and brine consecutively, dried over Na₂SO₄, filtered, concentrated and purified by CC (PE/EA=3/1) to give compound 7 (150 mg, 45%) as a white solid.

Step 8: (trans)-3-(4-(3-(tert-BUTYL)-5-(1-methylcyclopropyl)phenyl)-5-(cyclohexylmethyl)-1-methyl-1H-pyrrole-2-carboxamido)cyclobutanecarboxylic acid (8)

A solution of compound 7 (150 mg, 0.29 mmol) and LiOH.H₂O (120 mg, 2.86 mmol) in a mixture of MeOH (5 mL) and H₂O (1 mL) was stirred overnight at rt, concentrated, diluted with water, adjusted to pH=5 with conc. HCl and extracted with EA. The organic layer was dried by Na₂SO₄, filtered, concentrated and purified by prep-HPLC to give compound 8 (40 mg, 27%) as a white solid. $^1$H-NMR (CDCl₃, 300 MHz) δ: 0.72-0.74 (m, 2H), 0.83-0.90 (m, 4H), 1.08-1.13 (m, 3H), 1.34 (s, 9H), 1.43 (s, 3H), 1.50-1.59 (m, 5H), 2.29-2.37 (m, 2H), 2.61 (d, J=7.6 Hz, 2H), 2.76-2.82 (m, 2H), 3.09-3.12 (m, 1H), 3.88 (s, 3H), 4.73-4.78 (m, 1H), 6.08 (d, J=7.2 Hz, 1H), 6.60 (s, 1H), 7.02 (s, 1H), 7.16-7.18 (m, 2H). MS 505.3 (M+1)⁺.

Example 8/1 to 8/19

The following Examples were prepared similar as in Example 7 and optionally 8:

| # | Structure | Analytical data |
|---|-----------|-----------------|
| 8/1 | 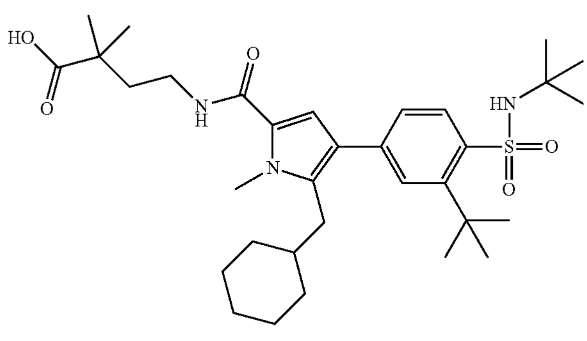 [SMILES: Cn1c(C(=O)NCCC(C)(C)C(=O)O)cc(-c2ccc(S(=O)(=O)NC(C)(C)C)c(C(C)(C)C)c2)c1CC1CCCCC1] | $^1$H-NMR (CDCl₃, 300 MHz) δ: 0.76-0.79 (m, 2H), 1.04-1.09 (m, 3H), 1.25 (s, 8H), 1.29 (s, 9H), 1.42-1.59 (m, 6H), 1.62 (s, 9H), 1.85 (t, J = 7.2 Hz, 2H), 2.65 (d, J = 7.2 Hz, 2H), 3.40-3.46 (m, 2H), 3.89 (s, 3H), 4.62 (s, 1H), 6.14 (t, J = 5.6 Hz, 1H), 6.60 (s, 1H), 7.24 (d, J = 1.2 Hz, 1H), 7.61 (d, J = 2.0 Hz, 1H), 8.12 (d, J = 8.4 Hz, 1H). MS 602.4 (M + 1)⁺ |
| 8/2 | 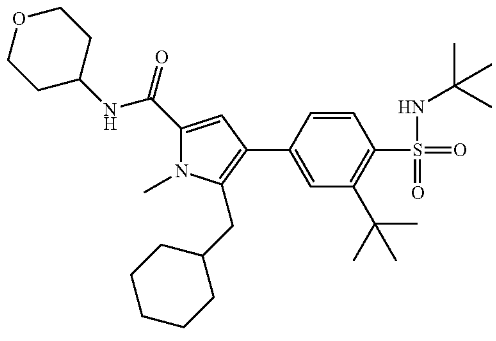 [SMILES: Cn1c(C(=O)NC2CCOCC2)cc(-c2ccc(S(=O)(=O)NC(C)(C)C)c(C(C)(C)C)c2)c1CC1CCCCC1] | $^1$H-NMR (CDCl₃, 300 MHz) δ: 0.76-0.82 (m, 2H), 1.05-1.10 (m, 3H), 1.24-1.30 (m, 11H), 1.44-1.60 (m, 6H), 1.62 (s, 9H), 1.96-2.00 (m, 2H), 2.65 (d, J = 6.8 Hz, 2H), 3.53 (td, J = 12.0 Hz, 2.0 Hz, 2H), 3.90 (s, 3H), 3.98-4.01 (m, 2H), 4.11-4.14 (m, 1H), 4.45 (s, 1H), 5.76 (d, J = 7.6 Hz, 1H), 6.60 (s, 1H), 7.24 (d, J = 2.0 Hz, 1H), 7.60 (d, J = 1.2 Hz, 1H), 8.15 (d, J = 8.4 Hz, 1H). MS 572.3 (M + 1)⁺ |

| # | Structure | Analytical data |
|---|---|---|
| 8/3 | 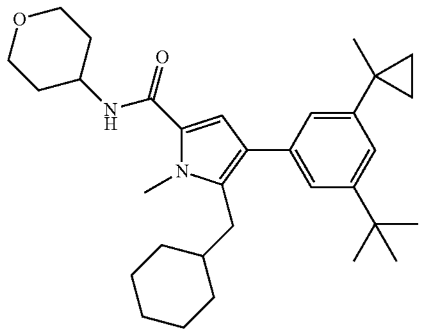 [SMILES: Cn1c(C(=O)NC2CCOCC2)cc(-c2cc(C(C)(C)C)cc(C3(C)CC3)c2)c1CC1CCCCC1] | ¹H-NMR (CDCl₃, 300 MHz) δ: 0.72-0.74 (m, 2H), 0.83-0.90 (m, 4H), 1.07-1.12 (m, 3H), 1.34 (s, 9H), 1.43 (s, 3H), 1.50-1.60 (m, 5H), 1.98 (dd, J = 12.4 Hz, 2.0 Hz, 2H), 2.61 (d, J = 7.2 Hz, 2H), 3.52 (td, J = 11.2 Hz, 2.0 Hz, 2H), 3.89 (s, 3H), 3.99 (d, J = 11.2 Hz, 2H), 4.10-4.16 (m, 1H), 5.74 (d, J = 7.6 Hz, 1H), 6.56 (s, 1H), 7.02 (s, 1H), 7.16 (d, J = 9.6 Hz, 2H). MS 491.3 (M + 1)⁺ |
| 8/4 | 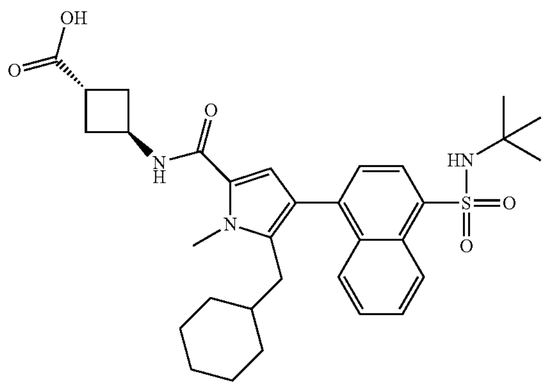 [SMILES: Cn1c(C(=O)N[C@H]2C[C@H](C(=O)O)C2)cc(-c2ccc(S(=O)(=O)NC(C)(C)C)c3ccccc23)c1CC1CCCCC1] | ¹H-NMR (CDCl₃, 300 MHz) δ: 0.47-0.50 (m, 2H), 0.88-0.97 (m, 3H), 1.16 (s, 9H), 1.20-1.25 (m, 2H), 1.37-1.46 (m, 4H), 2.27-2.37 (m, 4H), 2.75-2.83 (m, 2H), 3.05-3.15 (m, 1H), 3.72 (s, 3H), 4.69 (s, 1H), 4.74-4.82 (m, 1H), 6.13 (d, J = 7.5 Hz, 1H), 6.64 (s, 1H), 7.37 (d, J = 7.5 Hz, 1 H), 7.49-7.54 (m, 1H), 7.62-7.67 (m, 1H), 7.94 (d, J = 8.4 Hz, 1H), 8.30 (d, J = 7.5 Hz, 1H), 8.63 (d, J = 8.4 Hz, 1H). MS 580.3 (M + 1)⁺ |
| 8/5 | 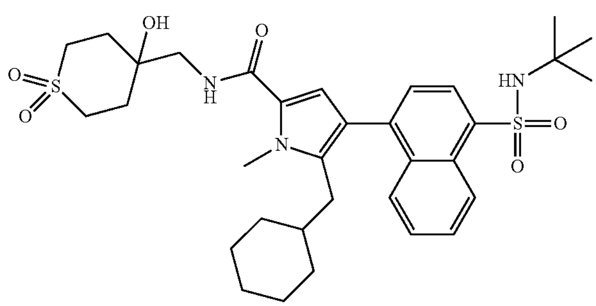 [SMILES: Cn1c(C(=O)NCC2(O)CCS(=O)(=O)CC2)cc(-c2ccc(S(=O)(=O)NC(C)(C)C)c3ccccc23)c1CC1CCCCC1] | ¹H-NMR (CDCl₃, 300 MHz) δ: 0.43-0.54 (m, 2H), 0.78-0.99 (m, 3H), 1.15 (s, 9H), 1.20-1.25 (m, 3H), 1.30-1.50 (m, 5H), 2.01-2.15 (m, 4H), 2.87 (d, J = 12.3 Hz, 2H), 3.42-3.52 (m, 4H), 3.94 (s, 3H), 4.61 (s, 1H), 6.45-6.49 (m, 1H), 6.73 (s, 1H), 7.33 (d, J = 7.8 Hz, 1H), 7.48-7.53 (m, 1H), 7.61-7.66 (m, 1H), 7.89 (d, J = 8.1 Hz, 1H), 8.27 (d, J = 7.5 Hz, 1H), 8.61 (d, J = 8.4 Hz, 1H). MS 644.3 (M + 1)⁺ |
| 8/6 | 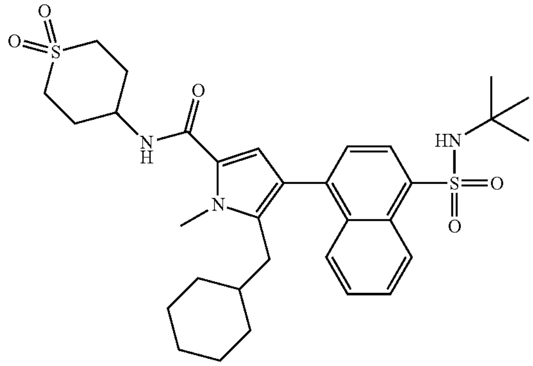 [SMILES: Cn1c(C(=O)NC2CCS(=O)(=O)CC2)cc(-c2ccc(S(=O)(=O)NC(C)(C)C)c3ccccc23)c1CC1CCCCC1] | ¹H-NMR (CDCl₃, 300 MHz) δ: 0.45-0.52 (m, 2H), 0.87-0.96 (m, 3H), 1.15 (s, 9H), 1.20-1.55 (m, 9H), 2.16-2.27 (m, 2H), 2.38-2.43 (m, 2H), 3.15-3.18 (m, 4H), 3.96 (s, 3H), 4.24-4.28 (m, 1H), 4.79 (s, 1H) 5.99 (d, J = 8.4 Hz, 1H) 6.67 (s, 1H), 7.36 (d, J = 8.1 Hz, 1H), 7.48-7.53 (m, 1H), 7.62-7.67 (m, 1H), 7.89 (d, J = 8.7 Hz, 1H), 8.27 (d, J = 7.5 Hz, 1H), 8.61 (d, J = 8.4 Hz, 1H). MS 614.3 (M + 1)⁺ |

| # | Structure | Analytical data |
|---|---|---|
| 8/7 | 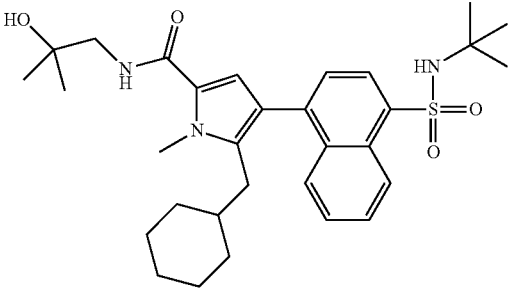 [SMILES: Cn1c(C(=O)NCC(C)(C)O)cc(-c2ccc(S(=O)(=O)NC(C)(C)C)c3ccccc23)c1CC1CCCCC1] | $^1$H-NMR (CDCl$_3$, 300 MHz) δ: 0.45-0.52 (m, 2H), 0.84-1.10 (m, 3H), 1.17 (s, 9H), 1.25 (s, 6H), 1.28-1.65 (m, 6H), 2.31-2.47 (m, 2H), 3.40 (d, J = 6.0 Hz, 2H), 3.96 (s, 3H), 4.59 (s, 1H), 6.30 (t, J = 6.0 Hz, 1H), 6.65 (s, 1H), 7.39 (d, J = 8.1 Hz, 1H), 7.49-7.54 (m, 1H), 7.63-7.68 (m, 1H), 7.94 (d, J = 8.4 Hz, 1H), 8.30 (d, J = 8.1 Hz, 1H), 8.62 (d, J = 8.4 Hz, 1H). MS 554.3 (M + 1)$^+$ |
| 8/8 | 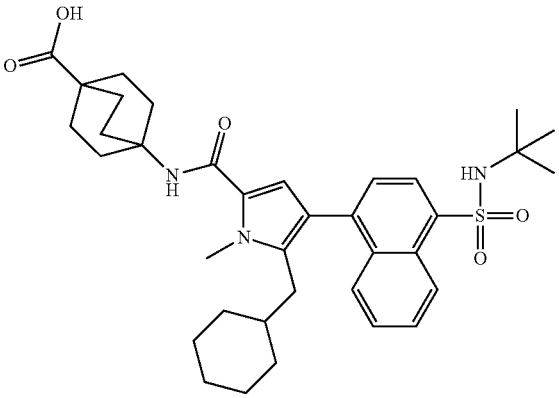 [SMILES: Cn1c(C(=O)NC23CCC(C(=O)O)(CC2)CC3)cc(-c2ccc(S(=O)(=O)NC(C)(C)C)c3ccccc23)c1CC1CCCCC1] | $^1$H-NMR (CDCl$_3$, 300 MHz) δ: 0.45-0.52 (m, 2H), 0.88-0.92 (m, 3H), 1.16 (s, 9H), 1.32-1.45 (m, 6H), 1.95-2.04 (m, 14H), 3.91 (s, 3H), 4.63 (s, 1H), 5.59 (s, 1H), 6.51 (s, 1H), 7.37 (d, J = 7.2 Hz, 1H), 7.51-7.54 (m, 1H), 7.63-7.68 (m, 1H), 7.93 (d, J = 8.4 Hz, 1H), 8.29 (d, J = 7.5 Hz, 1H), 8.62 (d, J = 8.4 Hz, 1H). MS 634.3 (M + 1)$^+$ |
| 8/9 | 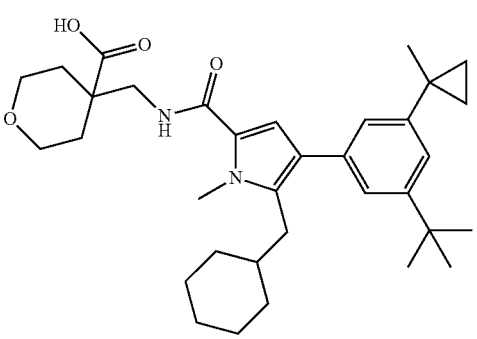 | $^1$H-NMR (CDCl$_3$, 300 MHz) δ: 0.70-0.74 (m, 2H), 0.79-0.89 (m, 4H), 1.07-1.14 (m, 3H), 1.33 (s, 9H), 1.42 (s, 3H), 1.50-1.65 (m, 7H), 2.08-2.13 (m, 2H), 2.58 (d, J = 7.2 Hz, 2H), 3.51-3.64 (m, 4H), 3.80-3.85 (m, 5H), 6.30-6.32 (m, 1H), 6.60 (s, 1H), 7.00 (s, 1H), 7.14 (s, 1H), 7.17 (s, 1H). MS 533.4 (M + 1)$^+$ |
| 8/10 | 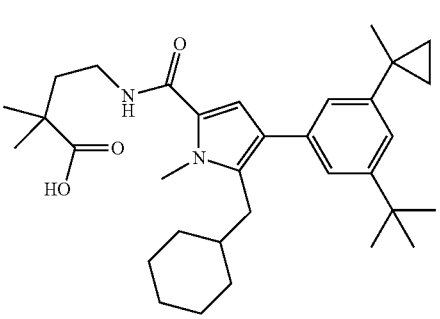 [SMILES: Cn1c(C(=O)NCCC(C)(C)C(=O)O)cc(-c2cc(C(C)(C)C)cc(C3(C)CC3)c2)c1CC1CCCCC1] | $^1$H-NMR (CDCl$_3$, 300 MHz) δ: 0.70-0.74 (m, 2H), 0.79-0.89 (m, 4H), 1.07-1.14 (m, 3H), 1.27 (s, 6H), 1.33 (s, 9H), 1.42 (s, 3H), 1.50-1.65 (m, 7H), 1.85-1.90 (m, 2H), 2.60 (d, J = 7.2 Hz, 2H), 3.40-3.47 (m, 2H), 3.88 (s, 3H), 5.97-5.99 (m, 1H), 6.55 (s, 1H), 7.02 (d, J = 1.8 Hz, 1H), 7.16-7.17 (m, 2H). MS 521.4 (M + 1)$^+$ |

-continued

| # | Structure | Analytical data |
|---|---|---|
| 8/11 | 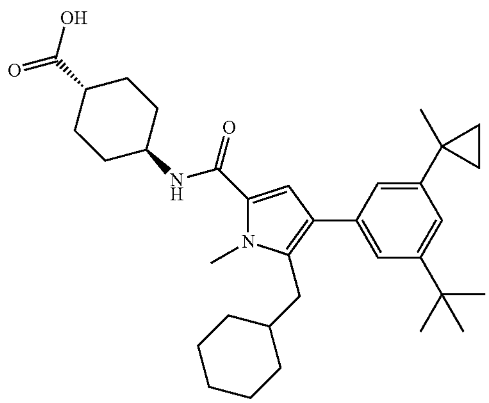 [SMILES: Cn1c(C(=O)N[C@H]2CC[C@H](C(=O)O)CC2)cc(-c2cc(C(C)(C)C)cc(C3(C)CC3)c2)c1CC1CCCCC1] | ¹H-NMR (DMSO-d₆, 300 MHz) δ: 0.70-0.74 (m, 2H), 0.79-0.89 (m, 4H), 1.07-1.14 (m, 3H), 1.13-1.22 (m, 2H), 1.28 (s, 9H), 1.32-1.40 (m, 2H), 1.42 (s, 3H), 1.46-1.53 (m, 5H), 1.82-1.96 (m, 4H), 2.10-2.23 (m, 1H), 2.60 (d, J = 6.6 Hz, 2H), 3.55-3.65 (m, 1H), 3.77 (s, 3H), 6.85 (s, 1H), 6.98 (s, 1H), 7.07 (s, 1H), 7.14 (s, 1H), 7.68 (d, J = 8.7 Hz, 1H), 12.02 (br s, 1H). MS 533.4 (M + 1)⁺ |
| 8/12 | 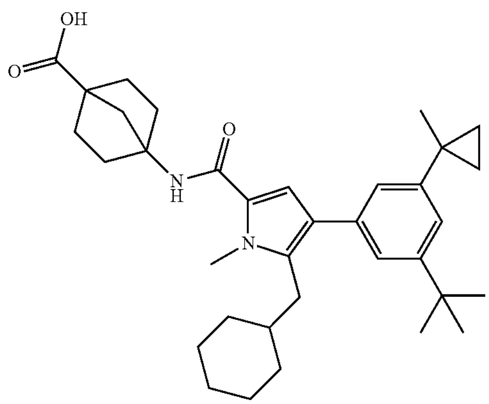 [SMILES: Cn1c(C(=O)NC23CCC(C(=O)O)(CC2)C3)cc(-c2cc(C(C)(C)C)cc(C3(C)CC3)c2)c1CC1CCCCC1] | ¹H-NMR (CDCl₃, 300 MHz) δ: 0.71-0.74 (m, 2H), 0.81-0.90 (m, 4H), 1.07-1.12 (m, 3H), 1.33 (s, 9H), 1.43 (s, 3H), 1.57-1.60 (m, 6H), 1.74-2.18 (m, 10H), 2.60 (d, J = 7.5 Hz, 2H), 3.88 (s, 3H), 6.08 (s, 1H), 6.54 (s, 1H), 7.01 (t, J = 1.5 Hz, 1H), 7.15-7.17 (m, 2H). MS 545.4 (M + 1)⁺ |
| 8/13 | 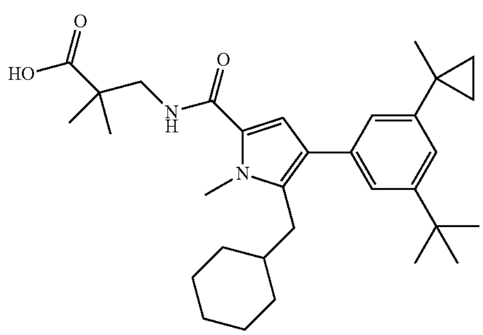 [SMILES: Cn1c(C(=O)NCC(C)(C)C(=O)O)cc(-c2cc(C(C)(C)C)cc(C3(C)CC3)c2)c1CC1CCCCC1] | ¹H-NMR (CDCl₃, 300 MHz) δ: 0.70-0.73 (m, 2H), 0.80-0.89 (m, 4H), 1.07-1.10 (m, 3H), 1.26 (s, 6H), 1.29 (s, 9H), 1.42 (s, 3H), 1.51-1.63 (m, 6H), 2.59 (d, J = 7.2 Hz, 2H), 3.52 (d, J = 6.6 Hz, 2H), 3.88 (s, 3H), 6.44-6.46 (m, 1H), 6.58 (s, 1H), 7.02 (s, 1H), 7.15 (d, J = 1.5 Hz, 1H), 7.17 (d, J = 1.5 Hz, 1H). MS 507.3 (M + 1)⁺ |
| 8/14 | 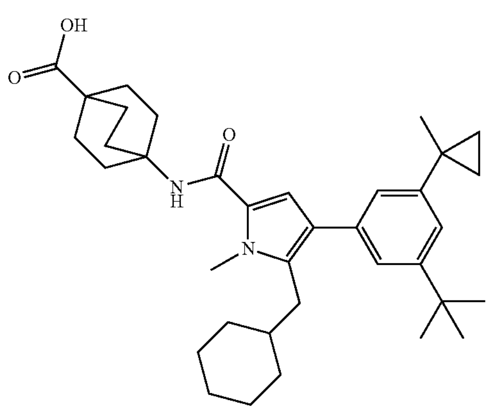 [SMILES: Cn1c(C(=O)NC23CCC(C(=O)O)(CC2)CC3)cc(-c2cc(C(C)(C)C)cc(C3(C)CC3)c2)c1CC1CCCCC1] | ¹H-NMR (CDCl₃, 300 MHz) δ: 0.72-0.74 (m, 2H), 0.86-0.88 (m, 4H), 1.07-1.09 (m, 3H), 1.33 (s, 9H), 1.42 (s, 3H), 1.54-1.59 (m, 6H), 1.92-2.04 (m, 13H), 2.58 (d, J = 7.5 Hz, 2H), 3.85 (s, 3H), 5.58 (s, 1H), 6.47 (s, 1H), 7.00 (s, 1H), 7.14 (s, 1H), 7.17 (s, 1H). MS 559.4 (M + 1)⁺ |

| # | Structure | Analytical data |
|---|---|---|
| 8/15 | 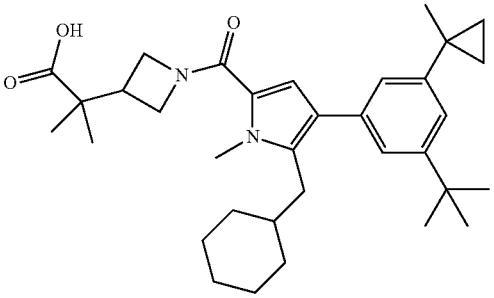 [SMILES: Cn1c(C(=O)N2CC(C(C)(C)C(=O)O)C2)cc(-c2cc(C(C)(C)C)cc(C3(C)CC3)c2)c1CC1CCCCC1] | ¹H-NMR (CDCl₃, 300 MHz) δ: 0.71-0.73 (m, 2H), 0.74-0.90 (m, 4H), 1.06-1.12 (m, 3H), 1.21 (s, 6H), 1.33 (s, 9H), 1.43 (s, 3H), 1.47-1.58 (m, 6H), 2.57-2.59 (m, 2H), 2.93-2.96 (m, 1H), 3.88 (s, 3H), 4.09-4.13 (m, 4H), 6.51 (s, 1H), 7.00 (s, 1H), 7.14 (s, 1H), 7.18 (s, 1H). MS 533.4 (M + 1)⁺ |
| 8/16 | 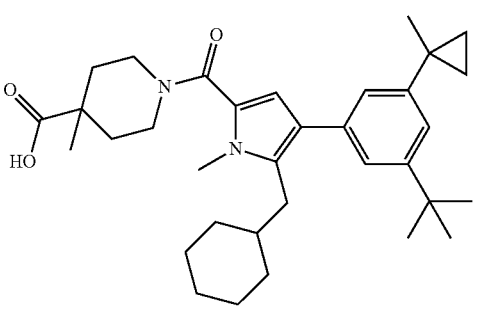 [SMILES: Cn1c(C(=O)N2CCC(C)(C(=O)O)CC2)cc(-c2cc(C(C)(C)C)cc(C3(C)CC3)c2)c1CC1CCCCC1] | ¹H-NMR (CDCl₃, 300 MHz) δ: 0.70-0.74 (m, 2H), 0.81-0.90 (m, 4H), 1.08-1.14 (m, 3H), 1.33 (s, 3H), 1.35 (s, 9H), 1.42 (s, 3H), 1.44-1.60 (m, 3H), 1.61-1.62 (m, 6H), 2.17 (d, J = 13.5 Hz, 2H), 2.60 (d, J = 6.9 Hz, 2H), 3.31-3.35 (m, 2H), 3.69 (s, 3H), 4.18-4.24 (m, 2H), 6.38 (s, 1H), 7.03 (t, J = 1.5 Hz, 1H), 7.16 (s, 1H), 7.17 (s, 1H). MS 533.4 (M + 1)⁺ |
| 8/17 | 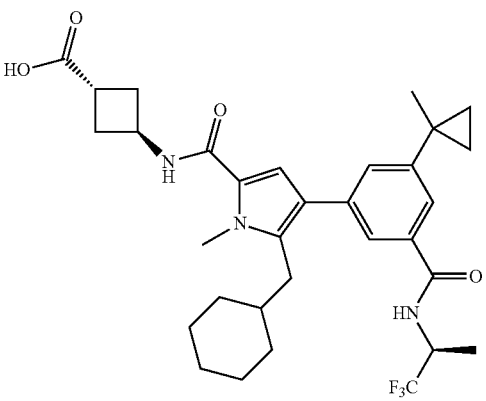 [SMILES: C[C@H](NC(=O)c1cc(-c2cc(C(=O)N[C@H]3C[C@H](C(=O)O)C3)n(C)c2CC2CCCCC2)cc(C2(C)CC2)c1)C(F)(F)F] | ¹H-NMR (300 MHz, CD₃OD) δ: 0.79-0.87 (m, 4H), 0.91-0.95 (m, 2H), 1.08-1.19 (m, 3H), 1.43 (d, J = 6.9 Hz, 3H), 1.46 (s, 3H), 1.56-1.59 (m, 6H), 2.37-2.40 (m, 2H), 2.55-2.65 (m, 2H), 2.70 (d, J = 7.2 Hz, 2H), 3.00-3.10 (m, 1H), 3.83 (s, 3H), 4.60-4.68 (m, 1H), 4.83-4.88 (m, 1H), 6.92 (s, 1H), 7.47 (t, J = 1.8 Hz, 1H), 7.61 (t, J = 1.8 Hz, 1H), 7.66 (t, J = 1.8 Hz, 1H), 8.21 (d, J = 8.8 Hz, 1H). MS 588.3 [M + 1]⁺ |
| 8/18 | 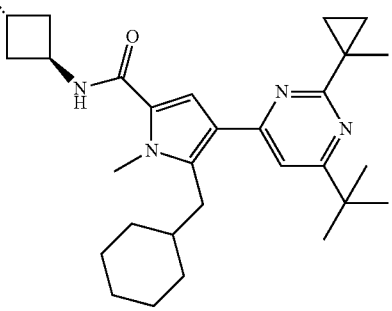 | ¹H-NMR (400 MHz, CDCl₃) δ: 7.09 (s, 1H), 6.95 (s, 1H), 6.12-6.10 (m, 1H), 4.75 (m, 1H), 3.87 (s, 3H), 3.18-3.13 (m, 3H), 2.86 (m, 2H), 2.42-2.34 (m, 2H), 1.65-1.57 (m, 9H), 1.41-1.31 (m, 11H), 1.13-1.00 (m, 5H), 0.85-0.82 (m, 2H). MS 507.4 (M + 1)⁺. |

| # | Structure | Analytical data |
|---|---|---|
| 8/19 | 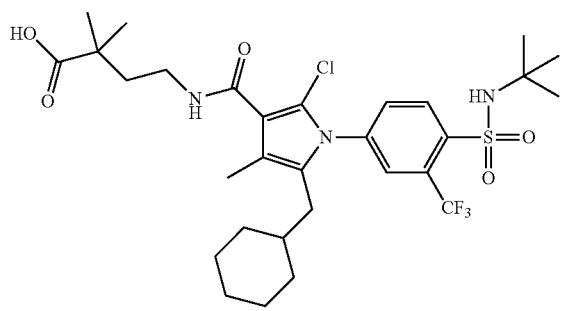 | $^1$H-NMR (400 MHz, CDCl$_3$) δ: 7.17 (s, 1H), 7.02 (s, 1H), 4.78-4.75 (m, 1H), 3.87 (s, 3H), 3.20-3.11 (m, 3H), 2.79 (m, 2H), 2.43-2.35 (m, 2H), 1.65-1.59 (m, 6H), 1.43 (s, 9H), 1.40 (s, 9H), 1.14-0.97 (m, 5H). MS 509.4(M + 1)$^+$ |

Example 9

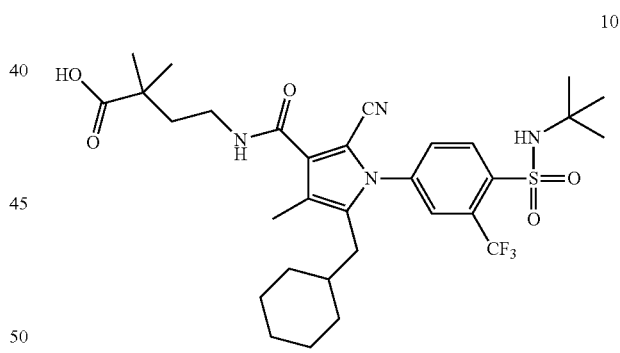

Step 1: Ethyl 1-(44N-(tert-butyl)sulfamoyl)-3-(trifluoromethyl)phenyl)-2-chloro-5-(cyclohexylmethyl)-4-methyl-1H-pyrrole-3-carboxylate (9a)

To a solution of ethyl 1-(4-(N-(tert-butyl)sulfamoyl)-3-(trifluoromethyl)phenyl)-5-(cyclohexylmethyl)-4-methyl-1H-pyrrole-3-carboxylate (100 mg, 0.19 mmol) in dry THF (2 mL) was added a solution of NCS (26 mg, 0.20 mmol) in dry THF (1 mL) at −78° C. and the solution was stirred at −78° C. for 1 h, then for another 1 h at rt, then quenched with water and extracted with EA. The organic layer was washed with brine, dried over Na$_2$SO$_4$, filtered, concentrated and purified by CC (PE/EA=30/1) to give compound 9a (90 mg, 84%) as a brown oil.

Step 2: 1-(4-(N-(tert-Butyl)sulfamoyl)-3-(trifluoromethyl)phenyl)-2-chloro-5-(cyclohexylmethyl)-4-methyl-1H-pyrrole-3-carboxylic acid (9b)

A mixture of compound 9a (90 mg, 0.16 mmol) and t-BuOK (54 mg, 0.48 mmol) in a mixture of DMSO and H$_2$O (10/1, 1.5 mL) was stirred at 90° C. for 1 h, cooled, diluted with water, acidified with 1N HCl to pH=2 and extracted with EA. The organic layer was washed with water and brine consecutively, dried over Na$_2$SO$_4$, filtered and concentrated to give crude compound 9b (90 mg, 100%) as a brown oil.

Step 3: 4-(1-(4-(N-(tert-Butyl)sulfamoyl)-3-(trifluoromethyl)phenyl)-2-chloro-5-(cyclohexylmethyl)-4-methyl-1H-pyrrole-3-carboxamido)-2,2-dimethylbutanoic acid (9)

Compound 9b was coupled with methyl 4-amino-2,2-dimethyl butanoate hydrochloride and saponified with KOH in aq. EtOH as described above to give compound 9 as white solid. $^1$H-NMR (CDCl$_3$, 400 MHz) δ: 0.65-0.73 (m, 2H), 0.94-1.01 (m, 4H), 1.27-1.28 (m, 15H), 1.36-1.58 (m, 5H), 2.23-2.26 (m, 5H), 3.45-3.51 (m, 2H), 4.80 (s, 1H), 6.20 (br t, 1H), 7.54 (dd, J=2.0, J=8.4 Hz, 1H), 7.68 (d, J=2.0 Hz, 1H), 8.45 (d, J=8.4 Hz, 1H). MS 648.3 (M+1)$^+$.

Example 10

Step 1: Ethyl 1-(4-(N-(tert-butyl)sulfamoyl)-3-(trifluoromethyl)phenyl)-2-cyano-5-(cyclohexylmethyl)-4-methyl-1H-pyrrole-3-carboxylate (10a)

The solution of ethyl 1-(4-(N-(tert-butyl)sulfamoyl)-3-(trifluoromethyl)phenyl)-2-bromo-5-(cyclohexylmethyl)-4-methyl-1H-pyrrole-3-carboxylate (1.0 g, 1.65 mmol), CuCN (295 mg, 3.29 mmol) and KI (20 mg, cat.) in DMF (10 mL) was stirred at 120° C. overnight under N$_2$, cooled to rt and diluted with 27% aq. NH$_4$OH (5 mL). The resulting solution was filtered and the filtrate was extracted with EA. The organic layer was washed with brine, dried over Na$_2$SO$_4$, filtered and purified by CC (PE/EA=5/1) to give compound 10a (810 mg, 89%) as a purple oil.

Step 2: 4-(1-(4-(N-(tert-Butyl)sulfamoyl)-3-(trifluoromethyl)phenyl)-2-cyano-5-(cyclohexylmethyl)-4-methyl-1H-pyrrole-3-carboxamido)-2,2-dimethylbutanoic acid (10)

Compound 10a was saponified and coupled with methyl 4-amino-2,2-dimethyl butanoate hydrochloride and again saponified with KOH in MeOH similar as described above to give compound 10 as white solid. $^1$H-NMR (CDCl$_3$, 400 MHz) δ: 0.65-0.75 (m, 2H), 1.02-1.24 (m, 4H), 1.22-1.24 (m, 15H), 1.37-1.59 (m, 5H), 1.88-1.92 (m, 2H), 2.25 (s, 3H), 2.37 (d, J=7.2 Hz, 2H), 3.49-3.54 (m, 2H), 4.83 (s, 1H), 6.22 (t, J=5.4 Hz, 1H), 7.64 (dd, J=1.8, J=8.6 Hz, 1H), 7.45 (d, J=1.6 Hz, 1H), 8.49 (d, J=8.4 Hz, 1H). MS 639.3 (M+1)$^+$.

Example 11

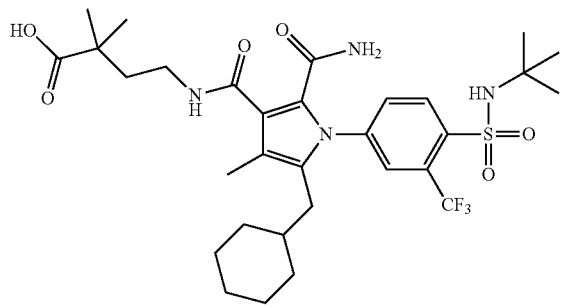

11

4-(1-(4-(N-(tert-Butyl)sulfamoyl)-3-(trifluoromethyl)phenyl)-2-carbamoyl-5-(cyclohexylmethyl)-4-methyl-1H-pyrrole-3-carboxamido)-2,2-dimethylbutanoic acid (11)

To a solution of the methyl ester of compound 10 (75 mg, 0.118 mmol) and K$_2$CO$_3$ (49 mg, 0.353 mmol) in DMSO (5 mL) was added 37% aq. H$_2$O$_2$ (0.4 mL) and the solution was stirred for 2 h at 50° C. under N$_2$, cooled to rt, diluted with water and extracted with EA twice. The combined organic layers were washed with water (3×) and brine consecutively, dried over Na$_2$SO$_4$, filtered, concentrated and purified by prep-HPLC to give compound 11 (18 mg, 23%) as a white solid. $^1$H-NMR (CD$_3$OD, 400 MHz) δ: 0.65-0.98 (m, 5H), 1.11-1.31 (m, 15H), 1.47-1.64 (m, 7H), 1.80-1.83 (m, 2H), 1.91-1.96 (m, 1H), 2.09 (s, 3H), 2.41 (d, J=7.2 Hz, 2H), 3.10-3.15 (q, 1H), 4.38-3.42 (m, 2H), 5.24-5.26 (m, 1H), 7.89 (dd, J=2.0, 8.8 Hz, 1H), 8.10 (d, J=8.8 Hz, 1H), 8.22 (d, J=2.0 Hz, 1H). MS 657.3 (M+1)$^+$.

Example 12

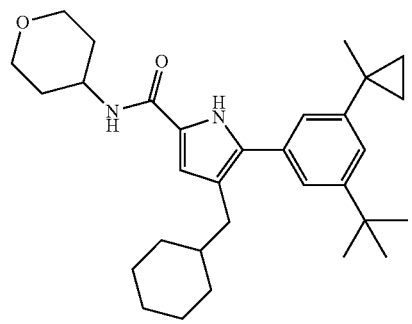

12

Step 1: Methyl 4-(cyclohexyl(hydroxy)methyl)-1H-pyrrole-2-carboxylate (12a)

Cyclohexylmagnesiumchloride (1M in THF, 88.0 mL, 88.0 mmol) was added to a solution of methyl 4-formyl-1H-pyrrole-2-carboxylate (3.06 g, 20.0 mmol) in THF (80 mL) at −78° C. The mixture was stirred at −78° C. to rt for 3 h, quenched with aq. NH$_4$Cl (aq.) and extracted with EA. The organic layer was washed with water then brine, dried by Na$_2$SO$_4$, filtered and concentrated to give crude compound 12a (8.0 g, quant.) as a yellow solid. $^1$H-NMR (400 MHz, CDCl$_3$) δ: 0.76-1.21 (m, 10H), 1.84-1.87 (m, 1H), 3.78-3.85 (m, 1H), 6.74-6.77 (m, 2H), 9.04 (d, J=1.6 Hz, 1H).

Step 2: Methyl 4-(cyclohexylmethyl)-1H-pyrrole-2-carboxylate (12b)

To a solution of compound 12a (1.52 g, 6.4 mmol) in DCM (20 mL) at 0° C. was added Et$_3$SiH (3.75 g, 32.0 mmol) and TFA (15 mL). The mixture was stirred at 0° C. to rt for 2 h, concentrated, diluted with aq. NaHCO$_3$ to adjust pH=6-7 and extracted with EA. The organic layer was washed with water followed by brine, dried by Na$_2$SO$_4$, filtered, concentrated and purified by CC (PE/EA=10/1) to give compound 12b (1.1 g, 70%) as a white solid. $^1$H-NMR (400 MHz, CDCl$_3$) δ: 0.86-0.94 (m, 2H), 1.12-1.26 (m, 3H), 1.36-1.45 (m, 1H), 1.67-1.72 (m, 5H), 2.32 (d, J=7.2 Hz, 2H), 3.83 (s, 3H), 6.70-6.72 (m, 2H), 8.91 (br s, 1H).

Step 3: Methyl 5-bromo-4-(cyclohexylmethyl)-1H-pyrrole-2-carboxylate (12c)

To a solution of compound 12b (884 mg, 4.0 mmol) in THF (20 mL) at 0° C. was added NBS (708 mg, 4.0 mmol). The mixture was stirred at 0° C. for 2 h under N₂, diluted with aq. NaHCO₃, extracted with EA, dried by Na₂SO₄, filtered, concentrated, purified by CC (PE/EA=10/1) to afford compound 12c (1.13 g, 94%) as a white solid. $^1$H-NMR (400 MHz, CDCl₃) δ: 0.89-0.97 (m, 2H), 1.11-1.21 (m, 3H), 1.43-1.49 (m, 1H), 1.67-1.70 (m, 5H), 2.27 (d, J=7.2 Hz, 2H), 3.83 (s, 3H), 6.69 (s, 1H), 8.97 (br s, 1H).

Step 4: Methyl 5-(3-(tert-butyl)-5-(1-methylcyclopropyl)phenyl)-4-(cyclohexylmethyl)-1H-pyrrole-2-carboxylate (12d)

To a mixture of compound 12c (100 mg, 0.33 mmol), 2-(3-(tert-butyl)-5-(1-methylcyclopropyl)phenyl)-4,4,5,5-tetramethyl-1,3,2-dioxaborolane (126 mg, 0.4 mmol), K₂CO₃ (138 mg, 1.0 mmol), Pd(dppf)Cl₂ (27 mg, 0.03 mmol) and TBAB (16 mg, 0.05 mmol) was added 1,4-dioxane:H₂O (2 mL:1 mL). The mixture was heated under MW at 100° C. for 2 h, diluted with water, extracted with EA, dried by Na₂SO₄, filtered, concentrated and purified by CC (PE/EA=9/1) to give compound 12d (128 mg, 94%) as a yellow solid. $^1$H-NMR (400 MHz, CDCl₃) δ: 0.75-0.77 (m, 2H), 0.88-0.97 (m, 4H), 1.12-1.23 (m, 3H), 1.35 (s, 9H), 1.44 (s, 3H), 1.50-1.54 (m, 1H), 1.63-1.70 (m, 3H), 1.76-1.80 (m, 2H), 2.44 (d, J=7.2 Hz, 2H), 3.86 (s, 3H), 6.81 (d, J=2.8 Hz, 1H), 7.14 (t, J=1.6 Hz, 1H), 7.26 (s, 2H), 8.89 (br s, 1H).

Step 5: 5-(3-(tert-Butyl)-5-(1-methylcyclopropyl)phenyl)-4-(cyclohexylmethyl)-1H-pyrrole-2-carboxylic acid (12e)

To a solution of compound 12d (300 mg, 0.7 mmol) in THF:MeOH:water (3:3:1.5 mL) was added LiOH (308 mg, 7.4 mmol). The mixture was stirred at 65° C. for 6 h, adjusted to pH=6 to 7 with 1N HCl, extracted with EA, dried by Na₂SO₄, filtered, concentrated and purified by CC (PE/EA=4/1) to give compound 12e (300 mg, 97%) as a red solid. $^1$H-NMR (400 MHz, CDCl₃) δ: 0.77-0.80 (m, 2H), 0.92-1.00 (m, 4H), 1.21-1.25 (m, 4H), 1.37 (s, 9H), 1.46 (s, 3H), 1.54-1.58 (m, 1H), 1.63-1.82 (m, 5H), 2.47 (d, J=7.2 Hz, 2H), 6.97 (d, J=3.2 Hz, 1H), 7.18 (s, 1H), 7.30 (s, 2H), 9.07 (br s, 1H).

Step 6: 5-(3-(tert-Butyl)-5-(1-methylcyclopropyl)phenyl)-4-(cyclohexylmethyl)-N-(tetrahydro-2H-pyran-4-yl)-1H-pyrrole-2-carboxamide (12)

A solution of compound 12e (60 mg, 0.15 mmol), tetrahydro-2H-pyran-4-amine (40 mg, 0.36 mmol), HOAT (82 mg, 0.6 mmol), DIPEA (116 mg, 0.9 mmol) in DCM (3 mL) was stirred at rt for 15 min. HATU (114 mg, 0.3 mmol) was added at rt and then stirred overnight. The mixture was diluted with water, extracted with DCM, dried by Na₂SO₄, filtered, concentrated and purified by prep-TLC (PE/EA=2/1) to furnish compound 12 (59 mg, 83%) as a white solid. $^1$H-NMR (300 MHz, CDCl₃) δ: 0.77-0.79 (m, 2H), 0.90-1.01 (m, 4H), 1.15-1.27 (m, 4H), 1.36 (s, 9H), 1.45 (s, 3H), 1.49-1.73 (m, 5H), 1.80 (d, J=13.2 Hz, 2H), 2.01 (d, J=13.2 Hz, 2H), 2.46 (d, J=7.2 Hz, 2H), 3.55 (t, J=11.4 Hz, 2H), 4.02 (d, J=12.6 Hz, 2H), 4.16-4.21 (m, 1H), 5.70 (d, J=8.4 Hz, 1H), 6.46 (d, J=2.1 Hz, 1H), 7.16 (s, 1H), 7.25 (s, 1H), 9.18 (br s, 1H). MS 477.3 (M+1)⁺.

Example 12/1

The following Example was prepared similar as in Example 12.

| # | Structure | Analytical data |
|---|-----------|-----------------|
| 12/1 | 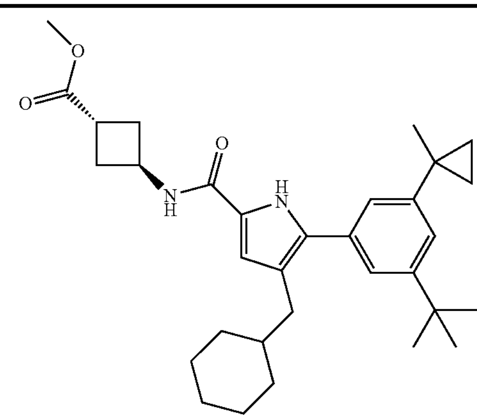 | $^1$H-NMR (400 MHz, CDCl₃) δ: 0.74-0.75 (m, 2H), 0.87-.95 (m, 5H), 1.20-1.29 (m, 4H), 1.34 (s, 9H), 1.43 (s, 3H), 1.67-1.72 (m, 3H), 1.77-1.80 (m, 2H), 2.30-2.33 (m, 2H), 2.45 (d, J = 7.2 Hz, 2H), 2.72-2.83 (m, 2H), 3.09-3.13 (m, 1H), 3.74 (s, 3H), 4.70-4.76 (m, 1H), 5.95 (d, J = 7.6 Hz, 1H), 6.44 (d, J = 2.4 Hz, 1H), 7.13 (t, J = 1.6 Hz, 1H), 7.23-7.26 (m, 2H), 9.15 (s, 1H) |

Example 12/2

The following Example was prepared by saponification of the corresponding ester as described above.

| # | Structure | Analytical data |
|---|---|---|
| 12/2 | 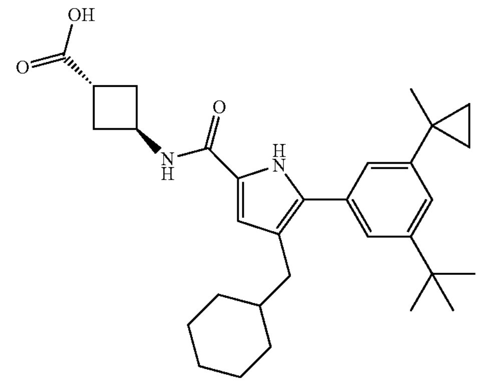 [SMILES: CC(C)(C)c1cc(-c2[nH]c(C(=O)N[C@H]3C[C@H](C(=O)O)C3)cc2CC2CCCCC2)cc(C2(C)CC2)c1] | ¹H-NMR (400 MHz, CDCl₃) δ: 0.74 (t, J = 4.8 Hz, 2H), 0.90-0.98 (m, 4H), 1.13-1.25 (m, 3H), 1.34 (s, 9H), 1.43 (s, 3H), 1.53 (br s, 1H), 1.68-1.80 (m, 5H), 2.35 (q, J = 10.0 Hz, 2H), 2.47 (d, J = 6.8 Hz, 2H), 2.81 (t, J = 9.6 Hz, 2H), 3.08 (br s, 1H), 4.87-4.93 (m, 1H), 6.09 (d, J = 6.0 Hz, 1H), 6.48 (s, 1H), 7.17 (s, 1H), 7.23 (s, 1H), 7.30 (s, 1H), 9.96 (s, 1H). MS 491.3 (M + 1)⁺ |

Example 13

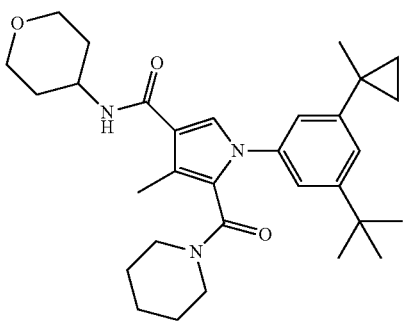

13

Step 1: 1-(3-(tert-Butyl)-5-(1-methylcyclopropyl)phenyl)-4-(ethoxycarbonyl)-3-methyl-1H-pyrrole-2-carboxylic acid (13a)

To a solution of compound 5b (918 mg, 2.5 mmol) in a mixture of THF (50 mL) and water (10 mL) was added sulfamic acid (1.39 g, 14.8 mmol) at 0° C., followed by a solution of NaClO₂ (434 mg, 4.83 mmol) and KH₂PO₄ (4.02 g, 29.6 mmol) in water (40 mL) and the solution was stirred for 1 h at rt, concentrated and the formed solid was collected by filtration and dried in vacuum to give compound 13a (570 mg, 59%) as a yellow solid. ¹H-NMR (CDCl₃, 400 MHz) δ: 0.63-0.75 (m, 2H), 0.87-0.95 (m, 2H), 1.28 (s, 9H), 1.30-1.36 (m, 3H), 1.41 (s, 3H), 2.67 (s, 3H), 4.29 (q, J=7.2 Hz, 2H), 6.92-6.93 (m, 1H), 7.03-7.04 (m, 1H), 7.27 (s, 1H), 7.49 (s, 1H).

Step 2: Ethyl 1-(3-(tert-butyl)-5-(1-methylcyclopropyl)phenyl)-4-methyl-5-(piperidine-1-carbonyl)-1H-pyrrole-3-carboxylate (13b)

A solution of compound 13a (77 mg, 0.2 mmol), piperidine (175 mg, 2.0 mmol) and HATU (92 mg, 0.24 mmol) in DMF (1 mL) was stirred at 50° C. for 2 h, diluted with water and extracted with EA twice. The combined organic layers were washed with water twice and brine consecutively, dried over Na₂SO₄, filtered, concentrated and purified by CC (PE/EA=4/1) to give compound 13b (60 mg, 67%) as a colorless oil. ¹H-NMR (CDCl₃, 400 MHz) δ: 0.75-0.79 (m, 2H), 0.97-0.96 (m, 2H), 1.31 (s, 9H), 1.35-1.37 (m, 3H), 1.44 (s, 3H), 1.49-1.58 (m, 6H), 2.32 (s, 3H), 3.04-3.12 (m, 2H), 3.45-3.47 (m, 1H), 3.60-3.63 (m, 1H), 4.31 (q, J=7.2 Hz, 2H), 7.00-7.01 (m, 1H), 7.11-7.12 (m, 1H), 7.23 (s, 1H), 7.48 (s, 1H).

Step 3: 1-(3-(tert-Butyl)-5-(1-methylcyclopropyl)phenyl)-4-methyl-5-(piperidine-1-carbonyl)-N-(tetrahydro-2H-pyran-4-yl)-1H-pyrrole-3-carboxamide (13)

Compound 13b was treated similar as described in Example 1, Step 6 and 7 to furnish compound 13. ¹H-NMR (CDCl₃, 400 MHz) δ: 0.74-0.88 (m, 4H), 1.26-1.30 (m, 12H), 1.30 (s, 3H), 1.40-1.58 (m, 5H), 2.01 (d, J=12.4 Hz, 2H), 2.31 (s, 3H), 2.95-3.09 (m, 2H), 3.43-3.56 (m, 4H), 3.97-3.99 (m, 2H), 4.17-4.21 (m, 1H), 5.61 (d, J=8.0 Hz, 1H), 7.00 (s, 1H), 7.12 (d, J=1.2 Hz, 1H), 7.23 (s, 1H), 7.30 (s, 1H). MS 506.3 (M+1)⁺.

Example 13/1

The following Example was prepared similar as in Example 13:

| # | Structure | Analytical data |
|---|---|---|
| 13/1 | 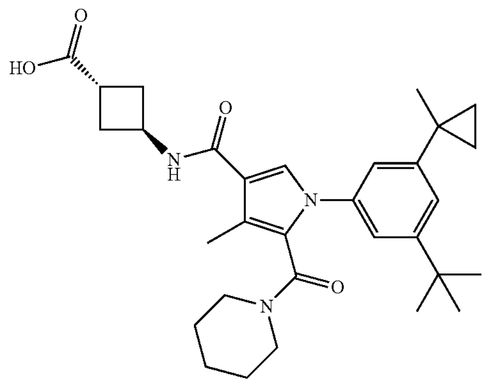 [SMILES: Cc1c(C(=O)N[C@H]2C[C@H](C(=O)O)C2)cn(-c2cc(C(C)(C)C)cc(C3(C)CC3)c2)c1C(=O)N1CCCCC1] | $^1$H-NMR (CDCl$_3$, 400 MHz) δ: 0.74-0.90 (m, 4H), 1.26-1.30 (m, 12H), 1.40 (s, 3H), 1.46-1.52 (m, 2H), 2.29-2.32 (m, 5H), 2.73-3.08 (m, 5H), 3.46-3.58 (m, 2H), 4.71-4.79 (m, 1H), 6.08 (d, J = 7.2 Hz, 1H), 7.00 (t, J = 1.4 Hz, 1H), 7.12 (t, J = 1.8 Hz, 1H), 7.23 (t, J = 1.4 Hz, 1H), 7.35 (s, 1H). MS 520.3 (M + 1)$^+$ |

Example 14

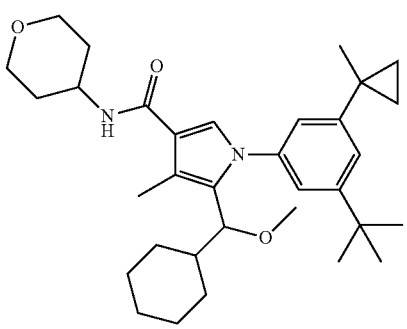

14

Step 1: Ethyl 1-(3-(tert-butyl)-5-(1-methylcyclopropyl)phenyl)-5-(cyclohexyl(methoxy)methyl)-4-methyl-1H-pyrrole-3-carboxylate (14a)

To a solution of compound 5c (700 mg, 1.55 mmol) in dry THF (8 mL) was added NaH (95 mg, 2.33 mmol) and the solution was stirred for 10 min at rt under N$_2$, then MeI (500 mg, 2.33 mmol) was added and the solution was stirred for another 2 h at rt, quenched with water and extracted with EA. The organic layer was washed with water and brine consecutively, dried over Na$_2$SO$_4$, filtered, concentrated and purified by CC (PE/EA=10/1) to give compound 14a (430 mg, 60%) as a white solid.

Step 2: 1-(3-(tert-Butyl)-5-(1-methylcyclopropyl)phenyl)-5-(cyclohexyl(methoxy)methyl)-4-methyl-1H-pyrrole-3-carboxylic acid (14b)

A solution of compound 14a (430 mg, 0.92 mmol) and t-BuOK (360 mg, 3.2 mmol) in a mixture of DMSO and H$_2$O (10/1, 6 mL) was stirred at 90° C. for 1.5 h, cooled to rt, diluted with water, acidified pH to 2 with 1N HCl and extracted with EA. The organic layer was washed with water and brine, dried over Na$_2$SO$_4$, filtered and concentrated to give compound 14b (360 mg, 90%) as a white solid. $^1$H-NMR (CDCl$_3$, 300 MHz) δ: 0.68-0.71 (m, 2H), 0.94-1.04 (m, 3H), 1.34 (s, 11H), 1.39 (s, 5H), 2.00 (d, J=3.6 Hz, 2H), 2.38 (s, 3H), 3.21 (s, 3H), 3.79 (d, J=0.6 Hz, 1H), 6.96 (t, J=3.0 Hz, 1H), 7.10 (t, J=3.6 Hz, 1H), 7.20 (t, J=3.6 Hz, 1H), 7.41 (s, 1H).

Step 3: 1-(3-(tert-Butyl)-5-(1-methylcyclopropyl)phenyl)-5-(cyclohexyl(methoxy)methyl)-4-methyl-N-(tetrahydro-2H-pyran-4-yl)-1H-pyrrole-3-carboxamide (14)

A solution of compound 14b (80 mg, 0.16 mmol), 2H-3,4,5,6-tetrahydropyran-4-yl amine (50 mg, 0.5 mmol), HATU (120 mg, 0.32 mmol) in DMF (6 mL) was stirred for 1 h at 40° C., cooled to rt, diluted with water and extracted with EA (3×). The combined organic layers were washed with water (3×) and brine consecutively, dried over Na$_2$SO$_4$, filtered, concentrated and purified by CC (PE/EA=3/1) to give compound 14 (36 mg, 38%) as a yellow solid. $^1$H-NMR (CDCl$_3$, 400 MHz) δ: 0.60-0.66 (m, 1H), 0.76-0.78 (m, 3H), 0.85-0.90 (m, 3H), 0.98-1.03 (m, 3H), 1.18-1.28 (4, 4H), 1.31 (s, 9H), 1.41 (s, 3H), 1.48-1.62 (m, 4H), 2.00 (d, J=9.2 Hz, 3H), 2.37 (s, 3H), 3.19 (s, 3H), 3.51-3.57 (m, 2H), 3.75 (d, J=9.2 Hz, 1H), 3.97 (dd, J=8.8 Hz, 2.4 Hz, 2H), 4.17-4.21 (m, 1H), 5.60 (d, J=8.0 Hz, 1H), 6.92 (t, J=1.6 Hz, 1H), 7.07 (t, J=1.2 Hz, 1H), 7.11 (s, 1H), 7.29 (t, J=1.6 Hz, 1H). MS 521.3 (M+1)$^+$.

Example 14/1

The following Example was prepared similar as in Example 14:

| # | Structure | Analytical data |
|---|---|---|
| 14/1 | 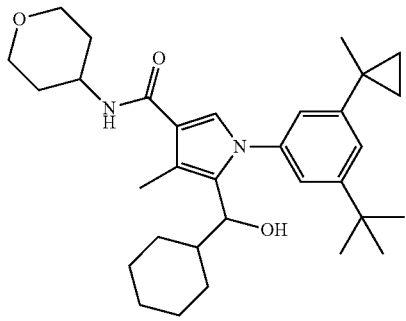 | $^1$H-NMR (CDCl$_3$, 400 MHz) δ: 0.61-0.64 (m, 1H), 0.75-0.87 (m, 5H), 0.98-1.03 (m, 3H), 1.16-1.20 (m, 1H), 1.31 (s, 9H), 1.41 (s, 3H), 1.46-1.62 (m, 4H), 2.00 (d, J = 12.8 Hz, 1H), 2.27-2.34 (m, 2H), 3.37 (s, 3H), 2.77-2.84 (m, 2H), 3.06-3.13 (m, 1H), 3.19 (s, 3H), 3.75 (d, J = 9.6 Hz, 1H), 4.76-4.82 (m, 1H), 5.94 (d, J = 6.8 Hz, 1H), 6.92 (s, 1H), 7.06 (s, 1H), 7.14 (s, 1H), 7.29 (s, 1H). MS 535.3 (M + 1)$^+$ |

Example 15

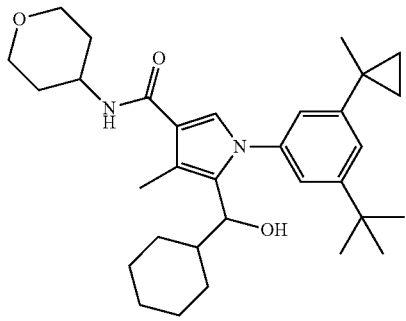

1-(3-(tert-Butyl)-5-(1-methylcyclopropyl)phenyl)-5-(cyclohexyl(hydroxy)methyl)-4-methyl-N-(tetrahydro-2H-pyran-4-yl)-1H-pyrrole-3-carboxamide (15)

Compound 5c was saponified and coupled to 2H-3,4,5,6-tetrahydropyran-4-yl amine as described in Example 14, Step 2 and 3 to obtain compound 15 as a white solid. $^1$H-NMR (CDCl$_3$, 400 MHz) δ: 0.60-0.64 (m, 1H), 0.76-0.79 (m, 3H), 0.82-0.90 (m, 3H), 1.03-1.08 (m, 3H), 1.22-1.32 (s, 15H), 1.42 (s, 3H), 1.48-1.61 (m, 4H), 1.97-2.04 (m, 3H), 2.41 (s, 3H), 3.50-3.56 (m, 2H), 3.97 (dd, J=8.8 Hz, 5.2 Hz, 2H), 4.17-4.19 (m, 1H), 4.23-4.26 (m, 1H), 5.57 (d, J=8.0 Hz, 1H), 6.98 (t, J=1.6 Hz, 1H), 7.07 (s, 1H), 7.12 (t, J=1.6 Hz, 1H), 7.30 (t, J=1.6 Hz, 1H). MS 507.3 (M+1)$^+$.

Example 16

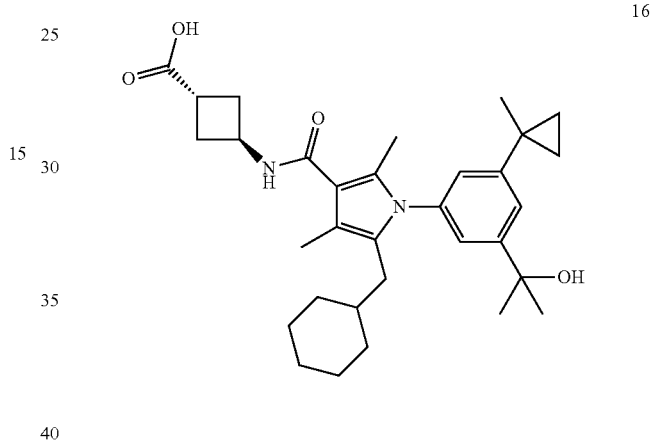

Step 1: 1-(2-(Benzyloxy)propan-2-yl)-3-bromo-5-(1-methylcyclopropyl)benzene (16a)

To a solution of 2-(3-bromo-5-(1-methylcyclopropyl)phenyl)propan-2-ol (1.6 g, 6.0 mmol) and BnBr (2.05 g, 12.0 mmol) in dry DMF (20 mL) was added NaH (60%, 480 mg, 12.0 mmol) in portions at rt and the solution was stirred at rt for 4 h, diluted with EA, washed with water and brine, dried over Na$_2$SO$_4$, concentrated and purified by CC (PE/EA=50/1) to give compound 16a (2.0 g, 93%) as a colorless oil.

Step 2: 1-(2-(Benzyloxy)propan-2-yl)-3-bromo-5-(1-methylcyclopropyl)benzene (16b)

A suspension of compound 16a (1.80 g, 5.0 mmol), ethyl 5-formyl-2,4-dimethyl-1H-pyrrole-3-carboxylate (975 mg, 5.0 mmol), (1R,2R)-1-N,2-N-dimethylcyclohexane-1,2-diamine (2.12 mg, 10.0 mmol), CuI (955 mg, 5.0 mmol) and K$_3$PO$_4$ (1.42 g, 10.0 mmol) in toluene (20 mL) was stirred overnight at reflux under N$_2$, cooled to rt and filtered. The filtrate was concentrated and dissolved in DCM, washed with water and brine, dried over Na$_2$SO$_4$, filtered, concentrated and purified by CC (PE/EA=50/1 to 25/1) to give compound 16b (300 mg, 13%) as a yellow oil.

Step 3: Ethyl 1-(3-(2-(benzyloxy)propan-2-yl)-5-(1-methylcyclopropyl)phenyl)-5-(cyclohexyl(hydroxy)methyl)-2,4-dimethyl-1H-pyrrole-3-carboxylate (16c)

To a solution of compound 16b (260 mg, 0.55 mmol) in dry THF (3 mL) was added cyclohexylmagnesium bromide (1M in THF, 1.4 mL, 1.4 mmol) dropwise at 0° C. under $N_2$ and the solution was stirred at rt for 2 h, diluted with sat. $NH_4Cl$ and extracted with EA (3×).

The combined organic layers were washed with water and brine, dried over $Na_2SO_4$, filtered and concentrated to give compound 16c (280 mg, 91%) as a yellow oil.

Step 4: Ethyl 1-(3-(2-(benzyloxy)propan-2-yl)-5-(1-methylcyclopropyl)phenyl)-5-(cyclohexylmethyl)-2,4-dimethyl-1H-pyrrole-3-carboxylate (16d)

To a solution of compound 16c (280 mg, 0.5 mmol) in DCM (4 mL) was added TFA (114 mg, 1.0 mmol) at 0° C. and the solution was stirred for 10 min. $Et_3SiH$ (580 mg, 5.0 mmol) was added and the solution was stirred at 0° C. for 30 min, diluted with DCM, washed with water and brine, dried, concentrated and purified with prep-TLC (PE/EA=10/1) to give compound 16d (134 mg, 50%) as a yellow oil.

Step 5: Ethyl 5-(cyclohexylmethyl)-1-(3-(2-hydroxypropan-2-yl)-5-(1-methylcyclopropyl)phenyl)-2,4-dimethyl-1H-pyrrole-3-carboxylate (16e)

A suspension of compound 16d (150 mg, 0.28 mmol) and 10% Pd/C (wet, 100 mg) in MeOH (3 mL) was stirred overnight at rt under $H_2$, filtered, and the filtrate was concentrated to give compound 16e (124 mg, 99%) as a yellow oil.

Step 6: trans-3-(5-(Cyclohexylmethyl)-1-(3-(2-hydroxypropan-2-yl)-5-(1-methylcyclopropyl)phenyl)-2,4-dimethyl-1H-pyrrole-3-carboxamido)cyclobutanecarboxylic acid (16)

Compound 16e was saponified, then coupled with trans 3-amino-cyclobutanecarboxylic acid methyl ester hydrochloride and finally again saponified as described in Example 7 and 8, step 6 to 8 to give compound 16 as a white solid. $^1$H-NMR (300 MHz, $CD_3OD$) δ: 0.67-1.07 (m, 12H), 1.29-1.39 (m, 2H), 1.43 (s, 3H) 1.52-1.60 (m, 7H), 2.07 (s, 3H), 2.11 (s, 3H), 2.23 (d, J=7.5 Hz, 2H), 2.32-2.41 (m, 2H), 2.61-2.69 (m, 2H), 3.03-3.09 (m, 1H), 4.61-4.70 (m, 1H), 6.89 (t, J=1.5 Hz, 1H), 7.05 (t, J=1.5 Hz, 1H), 7.52 (t, J=1.5 Hz, 1H), 7.81 (d, J=7.8 Hz, 1H). MS 521.3 (M+1)$^+$.

Example 17

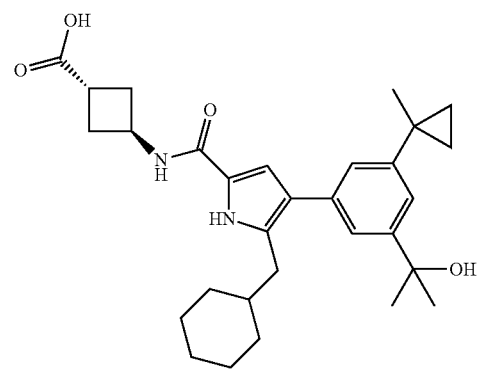

trans-3-(5-(Cyclohexylmethyl)-4-(3-(2-hydroxypropan-2-yl)-5-(1-methylcyclopropyl)phenyl)-1H-pyrrole-2-carboxamido)cyclobutanecarboxylic acid (17)

Compound 17 was prepared from methyl 5-formyl-1H-pyrrole-2-carboxylate similar as described in Example 7 to 8, Step 2 to 8. $^1$H-NMR (400 MHz, $CD_3OD$) δ: 0.63-0.65 (m, 2H), 0.72-0.81 (m, 4H), 0.88-0.90 (m, 3H), 1.33 (s, 3H), 1.48-1.56 (m, 12H), 2.25-2.32 (m, 2H), 2.51-2.56 (m, 4H), 2.95-2.98 (m, 1H), 4.56-4.60 (m, 1H), 6.87 (s, 1H), 7.06 (s, 1H), 7.19 (s, 1H), 7.20 (s, 1H). MS 493.3 (M+1)$^+$.

Example 17/1

The following Example was prepared similar as in Example 17:

| # | Structure | Analytical data |
|---|---|---|
| 17/1 | 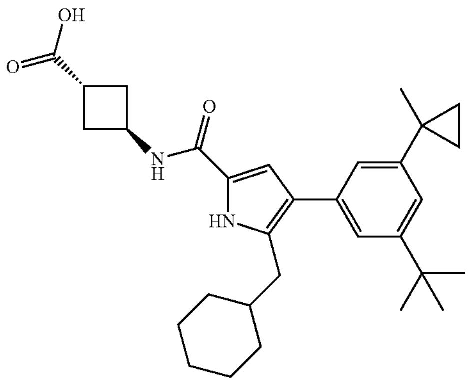 [SMILES: CC(C)(C)c1cc(-c2cc(C(=O)N[C@H]3C[C@H](C(=O)O)C3)[nH]c2CC2CCCCC2)cc(C2(C)CC2)c1] | $^1$H NMR (400 MHz, CD$_3$OD) δ: 0.61-0.64 (m, 2H), 0.75-0.85 (m, 4H), 1.04-1.08 (m, 3H), 1.19-1.24 (m, 10H), 1.32 (s, 3H), 1.53-1.56 (m, 4H), 2.26-2.34 (m, 2H), 2.53-2.54 (m, 4H), 2.93-2.96 (m, 1H), 4.57-4.61 (m, 1H), 6.87 (s, 1H), 7.01 (s, 1H), 7.06 (s, 1H), 7.13 (s, 1H). MS 491.3 (M + 1)$^+$ |

Example 18

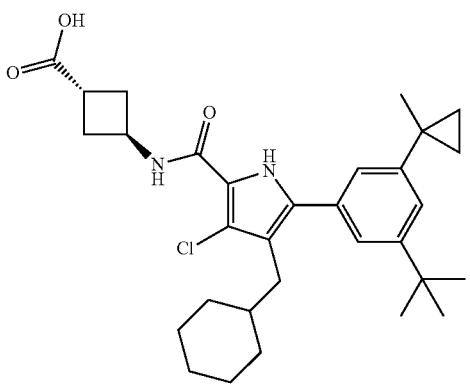

Step 1: (trans)-Methyl 3-(5-(3-(tert-butyl)-5-(1-methylcyclopropyl)phenyl)-3-chloro-4-(cyclohexylmethyl)-1H-pyrrole-2-carboxamido)cyclobutanecarboxylate (18a)

To a solution of compound 12/1 (90 mg, 0.18 mmol) in ACN (5 mL) at rt was added NCS (29 mg, 0.21 mmol). The mixture was stirred overnight, diluted with water, extracted with EA, dried by Na$_2$SO$_4$, filtered, concentrated and purified by prep-TLC (PE/DCM=2/1) to get compound 18a (50 mg, 51%) as a white solid. $^1$H-NMR (400 MHz, CDCl$_3$) δ: 0.76-0.77 (m, 2H), 0.86-0.92 (m, 5H), 1.12-1.14 (m, 3H), 1.24-1.25 (m, 1H), 1.33 (s, 9H), 1.42 (s, 3H), 1.63-1.69 (m, 4H), 2.32-2.39 (m, 2H), 2.50 (d, J=7.2 Hz), 2.74-2.80 (m, 2H), 3.14-3.18 (m, 1H), 3.74 (s, 3H), 4.72-4.78 (m, 1H), 6.99 (d, J=6.8 Hz, 1H), 7.14 (t, J=2.0 Hz, 1H), 7.26 (s, 1H), 9.24 (d, J=6.6 Hz, 1H). MS 425 (M+1)$^+$.

Step 2: trans-3-(5-(3-(tert-Butyl)-5-(1-methylcyclopropyl)phenyl)-3-chloro-4-(cyclohexylmethyl)-1H-pyrrole-2-carboxamido)cyclobutanecarboxylic acid (18)

To a solution of 18a (90 mg, 0.17 mmol) in THF:MeOH: water (2:2:1, 5 mL) at rt was added LiOH (11 mg, 0.25 mmol). The mixture was stirred for 2 h, adjusted to pH=6-7 with 1N HCl, diluted with water, extracted with EA, dried by Na$_2$SO$_4$, filtered, concentrated and purified by prep-HPLC to afford compound 18 (31 mg, 35%) as a white solid. $^1$H-NMR (300 MHz, CDCl$_3$) δ: 0.72-0.76 (m, 2H), 0.89-0.95 (m, 4H), 1.13 (br s, 1H), 1.26 (br s, 1H), 1.34 (s, 9H), 1.49 (s, 3H), 1.65 (br s, 5H), 2.32-2.40 (m, 2H), 2.51 (d, J=6.9 Hz, 2H), 2.80-2.85 (m, 2H), 3.09 (br s, 1H), 4.92-4.94 (m, 1H), 7.14 (d, J=7.2 Hz, 1H), 7.19 (s, 1H), 7.32 (s, 1H), 10.15 (d, J=8.4 Hz, 1H). MS 525.3 (M+1)$^+$.

Example 18/1

The following Example was prepared similar as in Example 18:

| # | Structure | Analytical data |
|---|-----------|-----------------|
| 18/1 | 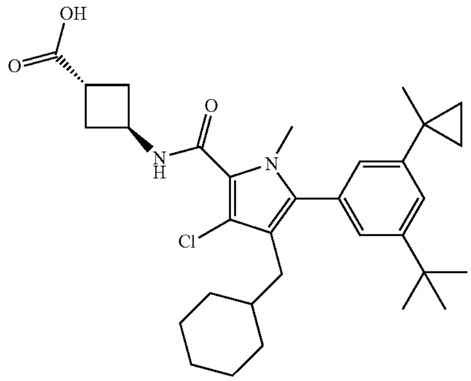 [SMILES: Cn1c(C(=O)N[C@H]2C[C@H](C(=O)O)C2)c(Cl)c(CC2CCCCC2)c1-c1cc(C(C)(C)C)cc(C2(C)CC2)c1] | $^1$H-NMR (300 MHz, CDCl$_3$) δ: 0.72-1.06 (m, 8H), 1.25 (br s, 1H), 1.32 (s, 9H), 1.41 (s, 3H), 1.56 (br s, 5H), 2.21 (d, J = 7.5 Hz, 2H), 2.35-2.37 (m, 3H), 2.80-2.83 (m, 2H), 3.14-3.16 (m, 1H), 3.63 (s, 3H), 4.78-4.81 (m, 1H), 6.91 (s, 1H), 6.98 (d, J = 6.3 Hz, 1H), 7.04 (s, 1H), 7.28 (s, 1H). MS 539.3 (M + 1)$^+$ |

Example 19/1 to 19/2

The following Examples were prepared similar as described above:

| # | Structure | Analytical data |
|---|-----------|-----------------|
| 19/1 | 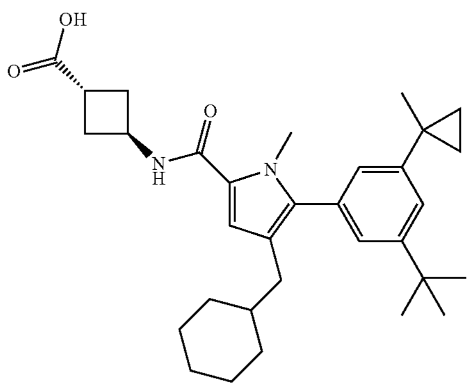 [SMILES: Cn1c(C(=O)N[C@H]2C[C@H](C(=O)O)C2)cc(CC2CCCCC2)c1-c1cc(C(C)(C)C)cc(C2(C)CC2)c1] | $^1$H-NMR (300 MHz, CDCl$_3$) δ: 0.76-0.87 (m, 7H), 1.12 (br s, 2H), 1.32 (s, 9H), 1.42 (s, 3H), 1.63 (br s, 2H), 2.18 (d, J = 5.2 Hz, 2H), 2.29-2.39 (m, 3H), 2.77-2.83 (m, 2H), 3.07-3.12 (m, 1H), 3.69 (s, 3H), 4.75-4.78 (m, 1H), 6.07 (d, J = 7.2 Hz, 1H), 6.46 (s, 1H), 6.93 (s, 1H), 7.06 (s, 1H). MS 505.4 (M + 1)$^+$ |
| 19/2 | 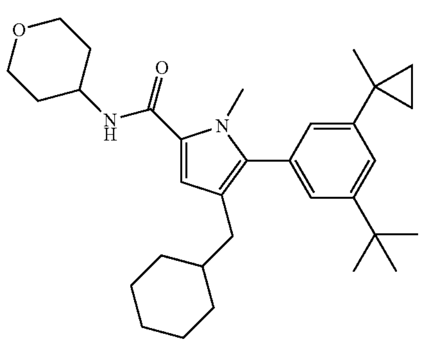 [SMILES: Cn1c(C(=O)NC2CCOCC2)cc(CC2CCCCC2)c1-c1cc(C(C)(C)C)cc(C2(C)CC2)c1] | $^1$H-NMR (400 MHz, CDCl$_3$) δ: 0.74-0.89 (m, 5H), 1.11-1.36 (m, 4H), 1.37 (s, 9H), 1.42 (s, 3H), 1.54-1.66 (m, 9H), 1.97-2.00 (m, 2H), 2.19 (d, J = 7.2 Hz, 2H), 3.49-3.56 (m, 2H), 3.70 (s, 3H), 3.96-4.01 (m, 2H), 4.13-4.15 (m, 1H), 5.75 (d, J = 8.0 Hz, 1H), 6.44 (s, 1H), 6.94 (d, J = 1.6 Hz, 1H), 7.07 (t, J = 1.6 Hz, 1H), 7.27 (d, J = 1.6 Hz, 1H). MS 491.3 (M + 1)$^+$ |

Example 20

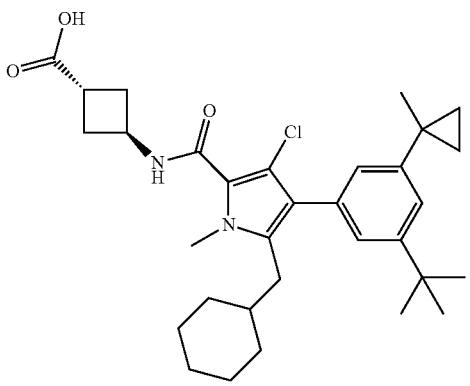

Step 1: Methyl 4-(3-(tert-butyl)-5-(1-methylcyclopropyl)phenyl)-3-chloro-5-(cyclohexylmethyl)-1-methyl-1H-pyrrole-2-carboxylate (20a)

To a solution of methyl 4-(3-(tert-butyl)-5-(1-methylcyclopropyl)phenyl)-5-(cyclohexylmethyl)-1-methyl-1H-pyrrole-2-carboxylate (200 mg, 0.48 mmol) in ACN (5 mL) was added a solution of NCS (63 mg, 0.48 mmol) in ACN (3 mL) at −78° C. and the solution was stirred at 0° C. for 16 h, quenched with water and extracted with EA. The organic layer was washed with brine, dried over Na$_2$SO$_4$, filtered, concentrated and purified by CC (PE/EA=20/1) to give compound 20a (160 mg, 76%) as a white solid.

Step 2: trans-3-(4-(3-(tert-Butyl)-5-(1-methylcyclopropyl)phenyl)-3-chloro-5-(cyclohexylmethyl)-1-methyl-1H-pyrrole-2-carboxamido)cyclobutanecarboxylic acid (20)

Compound 20a was saponified, then coupled with trans 3-amino-cyclobutanecarboxylic acid methyl ester hydrochloride and finally again saponified as described in Example 7 and 8, Step 6 to 8 to give compound 20 as a white solid. $^1$H-NMR (300 MHz, CDCl$_3$) δ: 0.72-0.76 (m, 4H), 0.85-0.91 (m, 2H), 1.02-1.08 (m, 3H), 1.33 (s, 9H), 1.43 (s, 3H), 1.50-1.54 (m, 6H), 2.29-2.40 (m, 2H), 2.47 (d, J=7.2 Hz, 2H), 2.76-2.86 (m, 2H), 3.11-3.19 (m, 1H), 3.87 (s, 3H), 4.75-4.83 (m, 1H), 6.93 (t, J=1.5 Hz, 1H), 7.02 (d, J=8.4 Hz, 1H), 7.07 (t, J=1.5 Hz, 1H), 7.23 (t, J=1.5 Hz, 1H). MS 539.3 (M+1)$^+$.

Example 21 to Example 23

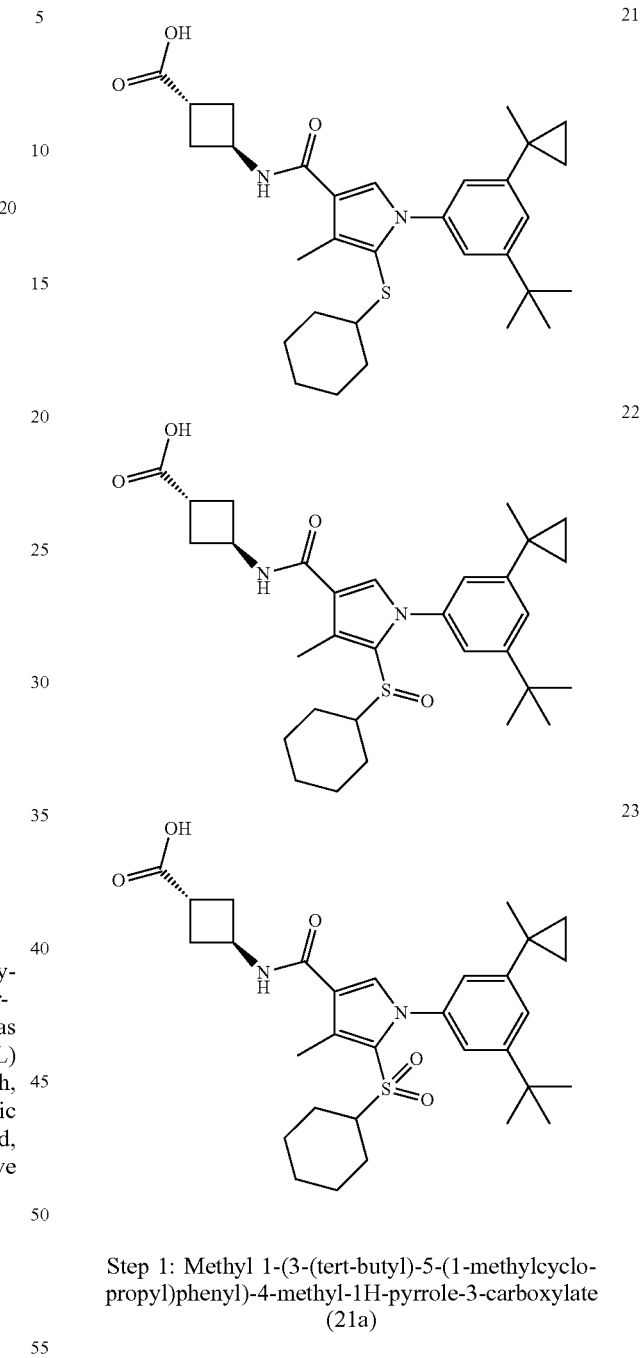

Step 1: Methyl 1-(3-(tert-butyl)-5-(1-methylcyclopropyl)phenyl)-4-methyl-1H-pyrrole-3-carboxylate (21a)

The suspension of methyl 4-methyl-1H-pyrrole-3-carboxylate (6.92 g, 45.2 mmol), 1-bromo-3-(tert-butyl)-5-(1-methylcyclopropyl)benzene (6.00 g, 22.6 mmol), (1R,2R)-1-N,2-N-dimethylcyclohexane-1,2-diamine (3.85 g, 27.1 mmol), CuI (5.15 g, 27.1 mmol) and anhydrous K$_3$PO$_4$ (11.5 g, 54.2 mmol) in toluene (60 mL) was refluxed under N$_2$ overnight, cooled to rt, filtered and the filtrate was washed with conc. NH$_4$OH two times. The aq. layer was extracted with EA (3×). The combined organic layers were washed with brine, dried over Na$_2$SO$_4$, filtered, concentrated and purified by CCl (PE/EA=80/1) to give compound 21a (6.02 g, 78%) as a colorless oil.

Step 2: Methyl 5-bromo-1-(3-(tert-butyl)-5-(1-methylcyclopropyl)phenyl)-4-methyl-1H-pyrrole-3-carboxylate (21b)

To a solution of compound 21a (6.00 g, 17.7 mmol) in THF (300 mL) was added a solution of NBS (3.78 g, 21.2 mmol) in THF (50 mL) at −78° C. and the solution was stirred at −78° C. for 15 min. Then pyridine (0.5 mL) was added and the solution was stirred at 0° C. for 1 h, heated at 50° C. for 20 h, concentrated and purified by CC (PE/EA=80/1) to give compound 21b (6.50 g, 88%) as a pale yellow oil.

Step 3: Methyl 1-(3-(tert-butyl)-5-(1-methylcyclopropyl)phenyl)-5-(cyclohexylthio)-4-methyl-1H-pyrrole-3-carboxylate (21c)

To a solution of compound 21b (4.80 g, 11.5 mmol) in THF (150 mL) was added n-BuLi (6.0 mL, 15.0 mmol) at −78° C. under $N_2$ and the solution was stirred at this temperature for 2 h. Then a solution of dicyclohexyl disulfide (3.97 g, 17.3 mmol) in THF (5 mL) was added at −78° C. and the solution was stirred at −78° C. for 2.5 h, quenched by sat. $NH_4Cl$ at −70° C. and extracted with EA. The organic layer was washed with brine, dried over $Na_2SO_4$, filtered, concentrated and purified by CC (PE/EA=30/1) and then prep-HPLC to give compound 21c (450 mg, 8%) as a colorless oil.

Step 4: trans-3-(1-(3-(tert-Butyl)-5-(1-methylcyclopropyl)phenyl)-5-(cyclohexylthio)-4-methyl-1H-pyrrole-3-carboxamido)cyclobutanecarboxylic acid (21)

Compound 21c was saponified, then coupled with trans 3-amino-cyclobutanecarboxylic acid methyl ester hydrochloride and finally again saponified as described in Example 7 and 8, Step 6 to 8 to give compound 21 as a white solid. $^1$H-NMR (400 MHz, $CDCl_3$) δ: 0.76 (t, J=3.2 Hz, 2H), 0.88 (t, J=5.2 Hz, 2H), 1.00-1.11 (m, 5H), 1.33 (s, 9H), 1.42 (s, 3H), 1.54-1.58 (m, 4H), 2.30-2.37 (m, 3H), 2.46 (s, 3H), 2.80-2.84 (m, 2H), 3.10-3.14 (m, 1H), 4.79-4.82 (m, 1H), 5.97-5.99 (m, 1H), 7.00 (s, 1H), 7.14 (s, 1H), 7.29 (s, 1H), 7.45 (s, 1H). MS 523.4 $[M+1]^+$.

Step 5: (trans)-Methyl 3-(1-(3-(tert-butyl)-5-(1-methylcyclopropyl)phenyl)-5-(cyclohexylsulfinyl)-4-methyl-1H-pyrrole-3-carboxamido)cyclobutanecarboxylate (22a) and (trans)-Methyl 3-(1-(3-(tert-butyl)-5-(1-methylcyclopropyl)phenyl)-5-(cyclohexylsulfonyl)-4-methyl-1H-pyrrole-3-carboxamido)cyclobutanecarboxylate (23a)

To a solution of the methylester of compound 21 (115 mg, 0.21 mmol) in DCM (15 mL) was added m-CPBA (52 mg, 0.30 mmol) at 0° C. and the solution was stirred at rt overnight, quenched with sat. $Na_2SO_3$, adjusted pH to 9 with sat. $Na_2CO_3$ and extracted with DCM. The organic layer was washed with brine, dried over $Na_2SO_4$, filtered, concentrated and purified by prep-TLC (PE/EA=2/1) to give compound 22a (40 mg, 33%) as a white solid and compound 23a (70 mg, 59%) as a white solid.

Step 6: trans-3-(1-(3-(tert-Butyl)-5-(1-methylcyclopropyl)phenyl)-5-(cyclohexylsulfinyl)-4-methyl-1H-pyrrole-3-carboxamido)cyclobutanecarboxylic acid (22)

To a solution of compound 22a (80 mg, 0.15 mmol) in a mixture of MeOH (4 mL) and $H_2O$ (1 mL) was added LiOH.$H_2O$ (12 mg, 0.29 mmol) and the solution was stirred at rt overnight, adjusted pH to 4 and extracted with EA. The organic layer was washed with brine, dried over $Na_2SO_4$, filtered, concentrated and purified by prep-HPLC to give compound 22 (27 mg, 35%) as a white solid. $^1$H-NMR (400 MHz, $CD_3OD$) δ: 0.79-0.82 (m, 2H), 0.88-0.97 (m, 4H), 1.10-1.20 (m, 2H), 1.29-1.36 (m, 11H), 1.44 (s, 3H), 1.52-1.60 (m, 2H), 1.77-1.80 (m, 1H), 2.02-2.05 (m, 1H), 2.32-2.39 (m, 2H), 2.50 (s, 3H), 2.59-2.65 (m, 2H), 2.68-2.70 (m, 1H), 3.02-3.07 (m, 1H), 4.60-4.68 (m, 1H), 7.28 (s, 1H), 7.45-7.47 (m, 2H), 7.71 (s, 1H). MS 539.3 $[M+1]^+$.

Step 7: trans-3-(1-(3-(tert-Butyl)-5-(1-methylcyclopropyl)phenyl)-5-(cyclohexylsulfonyl)-4-methyl-1H-pyrrole-3-carboxamido)cyclobutanecarboxylic acid (23)

Compound 23a (110 mg, 0.19 mmol) was treated similar as described in Step 6 above for compound 22a to give compound 23 (70 mg, 65%) as a white solid. $^1$H-NMR (400 MHz, $CD_3OD$) δ: 0.70 (t, J=4.0 Hz, 2H), 0.79 (t, J=4.4 Hz, 2H), 0.96-1.07 (m, 3H), 1.19-1.29 (m, 11H), 1.33 (s, 3H), 1.52-1.55 (d, J=9.2 Hz, 1H), 1.66-1.73 (m, 4H), 2.21-2.28 (m, 2H), 2.33-2.40 (m, 1H), 2.45 (s, 3H), 2.48-2.54 (m, 2H), 2.92-2.97 (m, 1H), 4.51-4.57 (m, 1H), 7.00 (d, J=1.6 Hz, 1H), 7.14 (d, J=1.6 Hz, 1H), 7.34 (s, 1H), 7.42 (s, 1H), 8.19 (d, J=7.2 Hz, 1H). MS 555.3 $[M+1]^+$.

Example 24 and Example 25

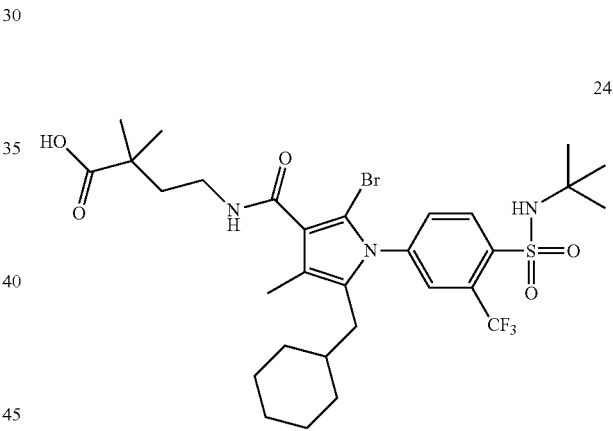

24

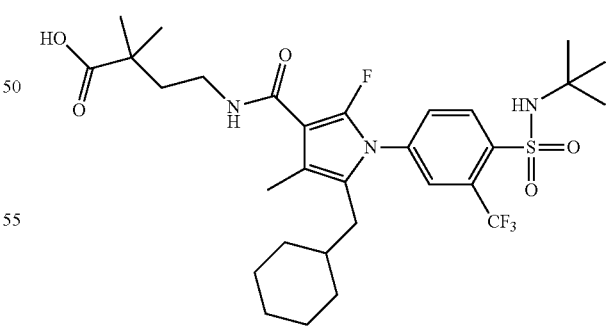

25

Step 1: Ethyl 2-bromo-1-(4-(N-(tert-butyl)sulfamoyl)-3-(trifluoromethyl)phenyl)-5-(cyclohexylmethyl)-4-methyl-1H-pyrrole-3-carboxylate (24a)

To a solution of compound 3f (1.5 g, 2.84 mmol) in dry THF (15 mL) was added a solution of NBS (531 mg, 2.98 mmol) in dry THF (15 mL) at −78° C. under N₂ and the solution was stirred at this temperature for 20 min and quenched with cold aq. NH₄Cl. The organic layer was separated and the aq. layer extracted repeatedly with EA. The combined organic layers were washed with brine, dried over Na₂SO₄, filtered, concentrated and purified by CC (PE/EA=10/1) to give compound 24a (1.0 g, 59%) as a brown solid.

Step 2: 4-(2-Bromo-1-(4-(N-(tert-butyl)sulfamoyl)-3-(trifluoromethyl)phenyl)-5-(cyclohexylmethyl)-4-methyl-1H-pyrrole-3-carboxamido)-2,2-dimethylbutanoic acid (24)

Compound 24a was saponified, then coupled with methyl 4-amino-2,2-dimethylbutanoate hydrochloride and finally again saponified similar as described in Example 7 and 8, Step 6 to 8 to give compound 24 as a white solid.

Step 3: 4-(1-(4-(N-(tert-Butyl)sulfamoyl)-3-(trifluoromethyl)phenyl)-5-(cyclohexylmethyl)-2-fluoro-4-methyl-1H-pyrrole-3-carboxamido)-2,2-dimethylbutanoic acid (25)

To a solution of compound 24 (550 mg, 0.79 mmol) in dry THF (3 mL) was added n-BuLi (2.5M in hexane, 6.4 mL, 16.0 mmol) at −78° C. under N₂ and the solution was stirred at rt for 2 h. Then a solution of NFSI (3.15 g, 10 mmol) in dry THF (20 mL) was added at −78° C. and the solution was stirred at rt overnight, quenched with sat. NH₄Cl and extracted with EA. The organic layer was washed with water and brine, dried over Na₂SO₄, filtered, concentrated and purified by CC (DCM/MeOH=20/1), then prep-HPLC and then prep-TLC (PE/EA=1/2) twice (remove de-Br side product and compound 24) to give compound 25 (11 mg, 2.2%) as a white solid. ¹H-NMR (300 MHz, CDCl₃) δ: 0.63-0.74 (m, 2H), 0.88-1.04 (m, 3H), 1.25 (s, 6H), 1.27 (s, 9H), 1.33-1.40 (m, 2H), 1.53-1.57 (m, 3H), 1.82-1.88 (m, 2H), 2.25 (s, 3H), 2.30 (d, J=6.9 Hz, 2H), 3.40-3.47 (m, 2H), 4.85 (s, 1H), 5.93-5.97 (m, 1H), 7.58 (d, J=8.4 Hz, 1H), 7.72 (s, 1H), 8.44 (d, J=8.4 Hz, 1H). MS 632.3 (M+1)⁺.

Example 26

26

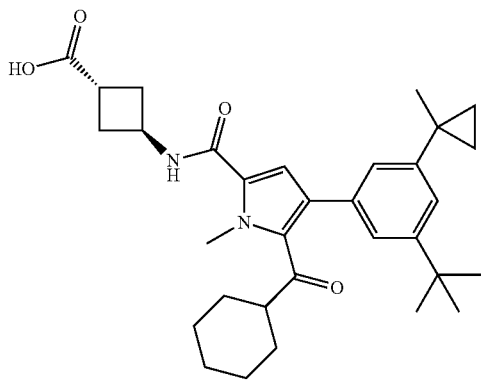

Step 1: Methyl 4-bromo-5-(cyclohexanecarbonyl)-1-methyl-1H-pyrrole-2-carboxylate (26a)

To a solution of i-Pr₂NH (9.1 g, 90.3 mmol) in THF (200 mL) was added n-BuLi (2.5M in hexane, 36 mL) at −78° C. and the mixture was stirred at −78° C. for 30 min, then a solution of methyl 4-bromo-1-methyl-1H-pyrrole-2-carboxylate (9.8 g, 45.2 mmol) was added. The mixture was stirred at −78° C. for 2 h, then cyclohexanecarboxylic acid methoxy-methyl-amide (11.6 g, 67.7 mmol) was added and the mixture was stirred at −78° C. for 2 h, diluted with NH₄Cl and extracted with EA twice. The organic phase was washed with brine, dried over Na₂SO₄, concentrated and purified by CC (PE/EA=50/1) to give compound 26a (11.6 g, 78%) as a yellow oil.

Step 2: Methyl 4-(3-(tert-butyl)-5-(1-methylcyclopropyl)phenyl)-5-(cyclohexanecarbonyl)-1-methyl-1H-pyrrole-2-carboxylate (26b)

A solution of compound 26a (500 mg, 1.53 mmol), 2-(3-(tert-butyl)-5-(1-methylcyclopropyl)phenyl)-4,4,5,5-tetramethyl-1,3,2-dioxaborolane (720 mg, 2.29 mmol), Pd(dppf)Cl₂ (107 mg) and K₂CO₃ (633 mg, 4.59 mmol) in DMF (10 mL) was stirred at 80° C. for 3 h under N₂, cooled to rt, diluted with water and extracted with EA (3×). The combined organic layers were washed by water (3×) and brine consecutively, dried with Na₂SO₄, filtered, concentrated and purified by CC (PE/EA=20/1) to give compound 26b (496 mg, 75%) as a white solid.

Step 3: 4-(3-(tert-Butyl)-5-(1-methylcyclopropyl)phenyl)-5-(cyclohexanecarbonyl)-1-methyl-1 H-pyrrole-2-carboxylic acid (26c)

A solution of compound 26b (500 mg, 1.15 mmol) and KOH (193 mg, 3.45 mmol) in a mixture of MeOH (5 mL), THF (5 mL) and H₂O (3 mL) was stirred at reflux for overnight, cooled to rt, concentrated, diluted with water, adjusted to ph=5 with conc. HCl and the formed solid was collected by filtration and dried in vacuum to give compound 26c (359 mg, 74%) as a white solid.

Step 4: trans-3-(4-(3-(tert-Butyl)-5-(1-methylcyclopropyl)phenyl)-5-(cyclohexanecarbonyl)-1-methyl-1H-pyrrole-2-carboxamido)cyclobutanecarboxylic acid (26)

A solution of compound 26c (130 mg, 0.30 mmol), trans-3-amino-cyclobutanecarboxylic acid HCl salt (61 mg, 0.40 mmol), HATU (141 mg, 0.38 mmol) and DIEA (100 mg, 0.78 mmol) in DMF (6 mL) was stirred at rt for 30 min, diluted with water and extracted by EA twice. The combined organic layers were washed by water (3×) and brine consecutively, dried over Na₂SO₄, filtered, concentrated and purified by prep-HPLC to give compound 26 (31 mg, 20%) as a white solid. ¹H-NMR (CDCl₃, 300 MHz) δ: 0.61-0.73 (m, 4H), 0.83-0.86 (m, 2H), 1.02-1.25 (m, 4H), 1.32 (s, 9H), 1.41 (s, 3H), 1.43-1.59 (m, 5H), 2.28-2.39 (m, 3H), 2.75-2.83 (m, 2H), 3.10-3.17 (m, 1H), 4.02 (s, 3H), 4.71-4.79 (m, 1H), 6.14 (d, J=6.9 Hz, 1H), 6.46 (s, 1H), 6.98 (s, 1H), 7.07 (s, 1H), 7.29 (s, 1H). MS 519.3 (M+1)⁺.

Example 26/1 to 26/4

The following Example was prepared similar as described in Example 26:

| # | Structure | Analytical data |
|---|---|---|
| 26/1 | 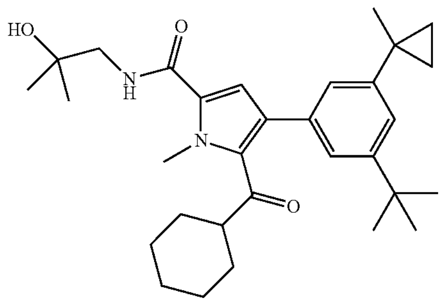 [SMILES: Cn1c(C(=O)NCC(C)(C)O)cc(-c2cc(C(C)(C)C)cc(C3(C)CC3)c2)c1C(=O)C1CCCCC1] | ¹H-NMR (CDCl₃, 300 MHz) δ: 0.62-0.74 (m, 4H), 0.79-0.87 (m, 2H), 0.98-1.23 (m, 3H), 1.31 (s, 6H), 1.34 (s, 9H), 1.48 (s, 3H), 1.53-1.60 (m, 4H), 2.04 (s, 1H), 2.30-2.40 (m, 1H), 3.42 (d, J = 6.0 Hz, 2H), 4.04 (s, 3H), 6.40 (t, J = 6.0 Hz, 1H), 6.50 (s, 1H), 7.00 (t, J = 1.8 Hz, 1H), 7.08 (t, J = 1.8 Hz, 1H), 7.30 (d, J = 1.8 Hz, 1H). MS 493.3 (M + 1)⁺ |
| 26/2 | 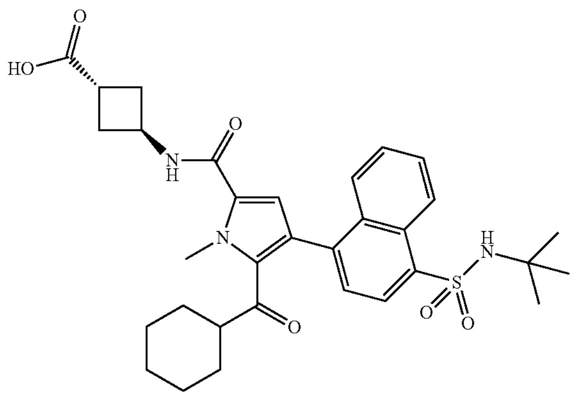 [SMILES: Cn1c(C(=O)N[C@H]2C[C@H](C(=O)O)C2)cc(-c2ccc(S(=O)(=O)NC(C)(C)C)c3ccccc23)c1C(=O)C1CCCCC1] | ¹H-NMR (CDCl₃, 300 MHz) δ: 0.85-1.00 (m, 1H), 1.12-1.21 (m, 4H), 1.25 (s, 9H), 1.30-1.42 (m, 5H), 1.85-1.93 (m, 1H), 2.29-2.39 (m, 2H), 2.76-2.82 (m, 2H), 3.09-3.15 (m, 1H), 4.13 (s, 3H), 4.71-4.81 (m, 2H), 6.24 (d, J = 6.9 Hz, 1H), 6.53 (s, 1H), 7.41 (d, J = 7.5 Hz, 1H), 7.48-7.57 (m, 2H), 7.66-7.71 (m, 1H), 7.85-7.88 (m, 1H), 8.31 (d, J = 7.8 Hz, 1H), 8.65 (d, J = 8.1 Hz, 1H). MS 594.3 (M + 1)⁺ |
| 26/3 | 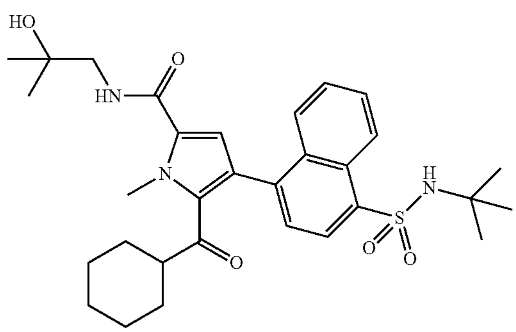 [SMILES: Cn1c(C(=O)NCC(C)(C)O)cc(-c2ccc(S(=O)(=O)NC(C)(C)C)c3ccccc23)c1C(=O)C1CCCCC1] | ¹H-NMR (CD₃OD, 300 MHz) δ: 0.86-1.00 (m, 1H), 1.12-1.21 (m, 4H), 1.18 (s, 9H), 1.22 (s, 6H), 1.30-1.42 (m, 5H), 1.91-1.99 (m, 1H), 3.36 (s, 2H), 4.06 (s, 3H), 6.78 (s, 1H), 7.52-7.54 (m, 2H), 7.69-7.74 (m, 1H), 7.88 (d, J = 8.7 Hz, 1H), 8.30 (d, J = 7.5 Hz, 1H), 8.79 (d, J = 8.7 Hz, 1H). MS 568.3 (M + 1)⁺ |
| 26/4 | 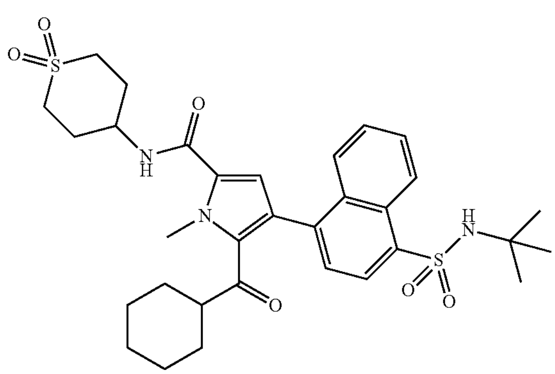 [SMILES: Cn1c(C(=O)NC2CCS(=O)(=O)CC2)cc(-c2ccc(S(=O)(=O)NC(C)(C)C)c3ccccc23)c1C(=O)C1CCCCC1] | ¹H-NMR (CDCl₃, 300 MHz) δ: 0.85-1.55 (m, 19H), 1.79-1.84 (m, 1H), 2.28-2.49 (m, 4H), 3.11-3.17 (m, 2H), 3.42-3.49 (m, 2H), 4.14 (s, 3H), 4.48-4.53 (m, 1H), 5.71 (s, 1H), 6.65 (s, 1H), 6.83 (d, J = 8.7 Hz, 1H), 7.46-7.51 (m, 1H), 7.59-7.67 (m, 2H), 7.73 (d, J = 8.7 Hz, 1H), 8.39 (d, J = 7.5 Hz, 1H), 8.56 (d, J = 8.4 Hz, 1H). MS 628.2 (M + 1)⁺ |

Additional Examples

The following compounds can be prepared in the same manner by using the procedures as described above:

| 157 Structure | 158 -continued Structure |
|---|---|
| 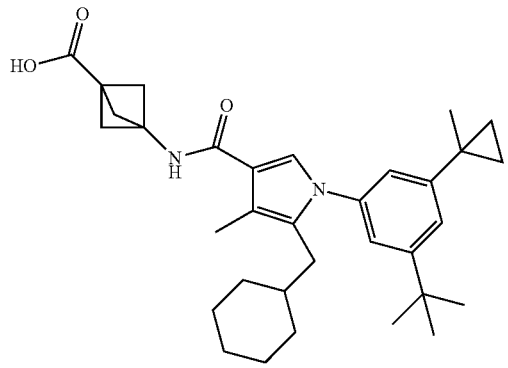 [SMILES: Cc1c(C(=O)NC23CC(C(=O)O)(C2)C3)cn(-c2cc(C(C)(C)C)cc(C3(C)CC3)c2)c1CC1CCCCC1] | 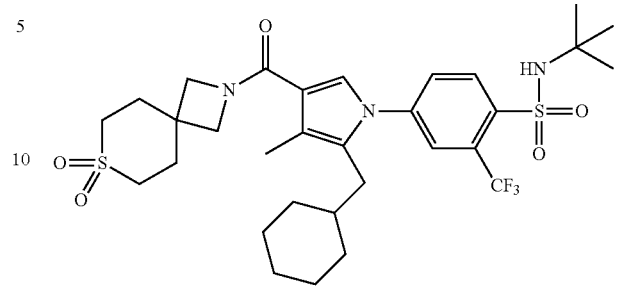 |
| 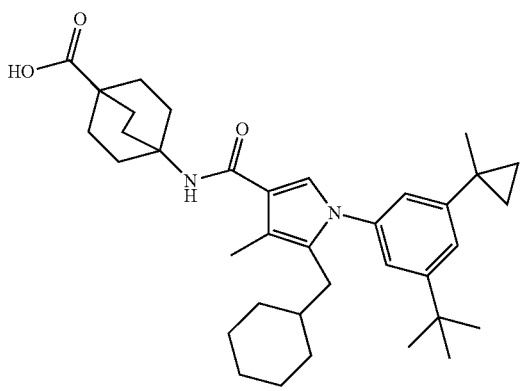 [SMILES: Cc1c(C(=O)NC23CCC(C(=O)O)(CC2)CC3)cn(-c2cc(C(C)(C)C)cc(C3(C)CC3)c2)c1CC1CCCCC1] | 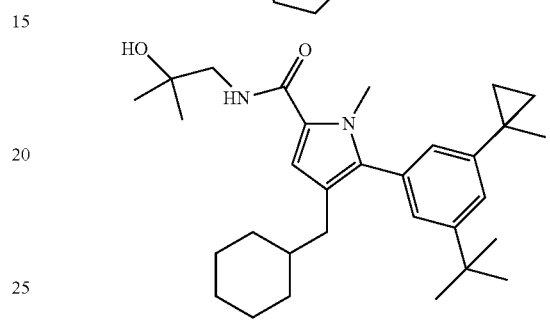 |
| 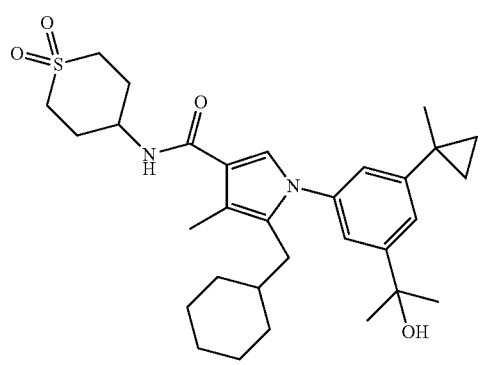 [SMILES: Cc1c(C(=O)NC2CCS(=O)(=O)CC2)cn(-c2cc(C(C)(C)O)cc(C3(C)CC3)c2)c1CC1CCCCC1] | 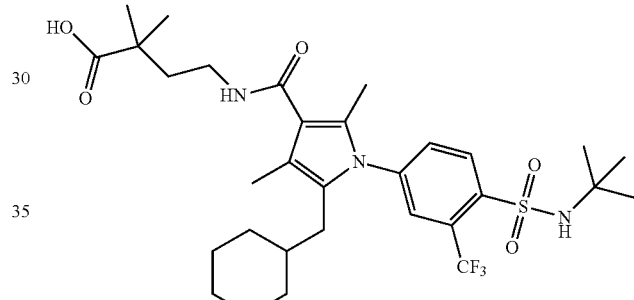 |
| 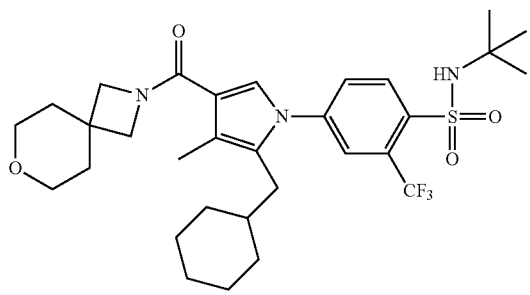 [SMILES: Cc1c(C(=O)N2CC3(CCOCC3)C2)cn(-c2ccc(S(=O)(=O)NC(C)(C)C)c(C(F)(F)F)c2)c1CC1CCCCC1] | 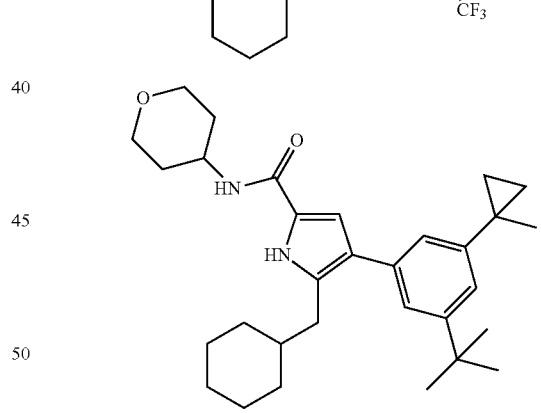 |
| | 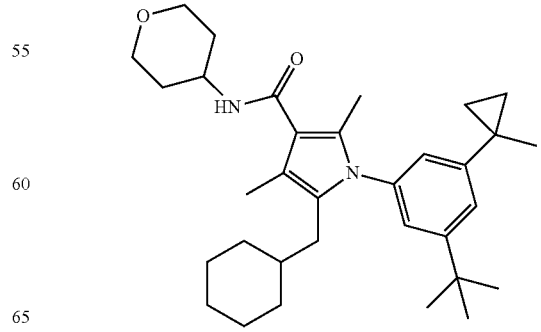 |

| 159 -continued | 160 -continued |
|---|---|
| Structure | Structure |
| 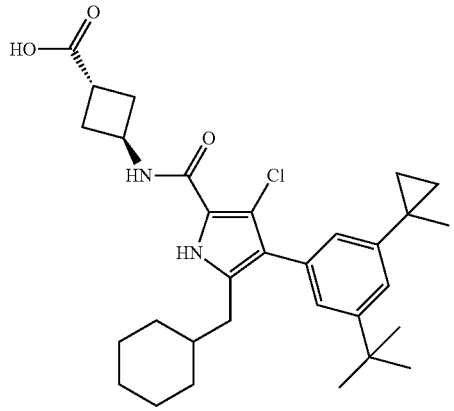 [SMILES: CC(C)(C)c1cc(-c2c(CC3CCCCC3)[nH]c(C(=O)N[C@H]3C[C@H](C(=O)O)C3)c2Cl)cc(C2(C)CC2)c1] | 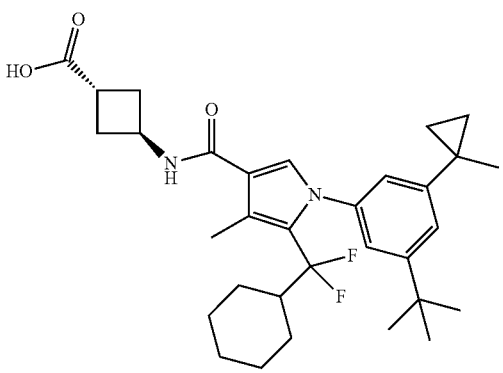 |
| 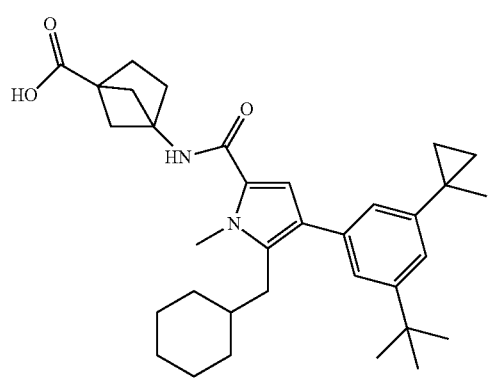 [SMILES: Cn1c(C(=O)NC23CCC(C(=O)O)(C2)C3)cc(-c2cc(C(C)(C)C)cc(C3(C)CC3)c2)c1CC1CCCCC1] | 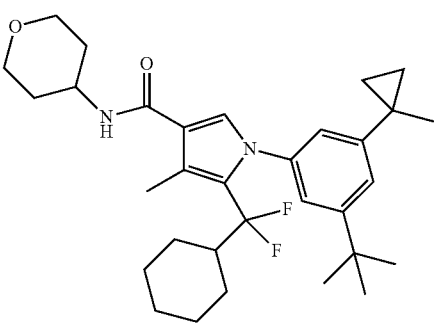 |
| 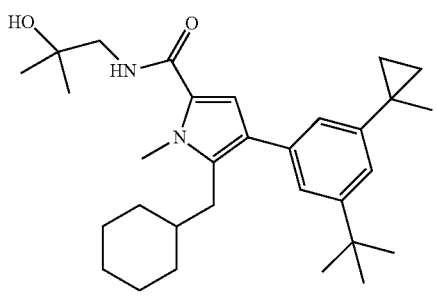 [SMILES: Cn1c(C(=O)NCC(C)(C)O)cc(-c2cc(C(C)(C)C)cc(C3(C)CC3)c2)c1CC1CCCCC1] | 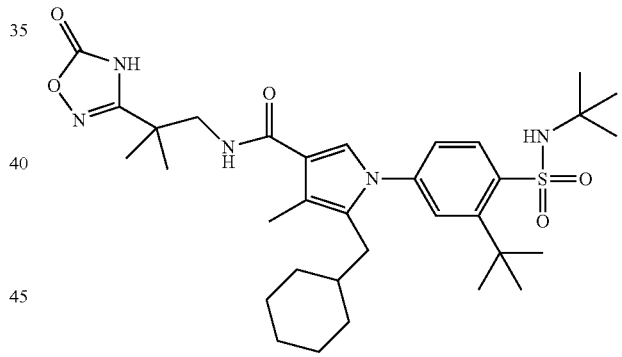 |
| 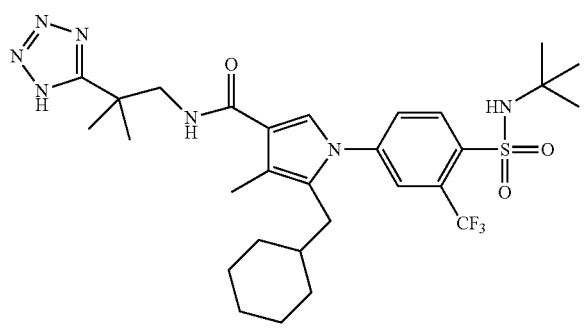 [SMILES: Cc1c(C(=O)NCC(C)(C)c2nnn[nH]2)cn(-c2ccc(S(=O)(=O)NC(C)(C)C)c(C(F)(F)F)c2)c1CC1CCCCC1] | 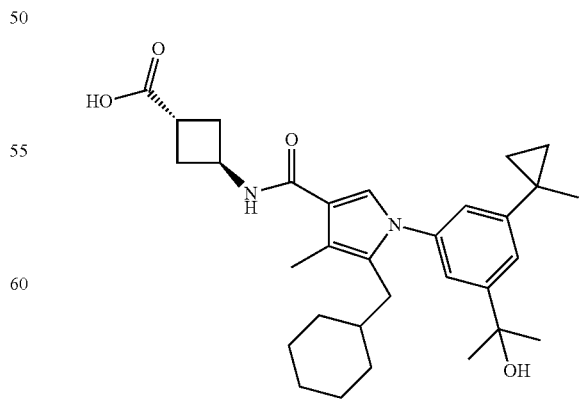 |

| 161 -continued | 162 -continued |
|---|---|
| Structure | Structure |
| 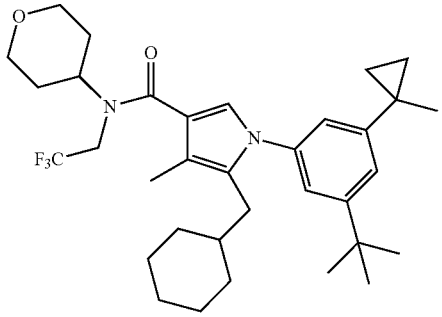 [SMILES: Cc1c(C(=O)N(CC(F)(F)F)C2CCOCC2)cn(-c2cc(C(C)(C)C)cc(C3(C)CC3)c2)c1CC1CCCCC1] | 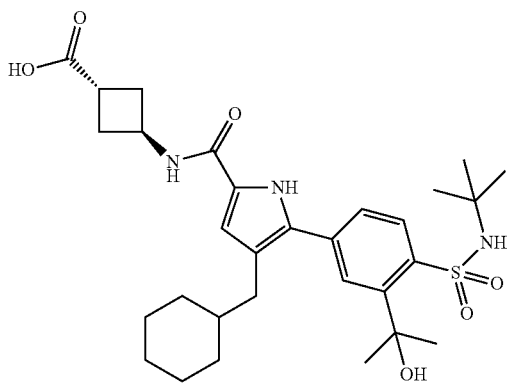 |
| 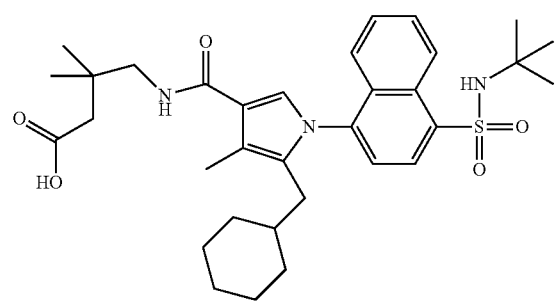 [SMILES: Cc1c(C(=O)NCC(C)(C)CC(=O)O)cn(-c2ccc(S(=O)(=O)NC(C)(C)C)c3ccccc23)c1CC1CCCCC1] | 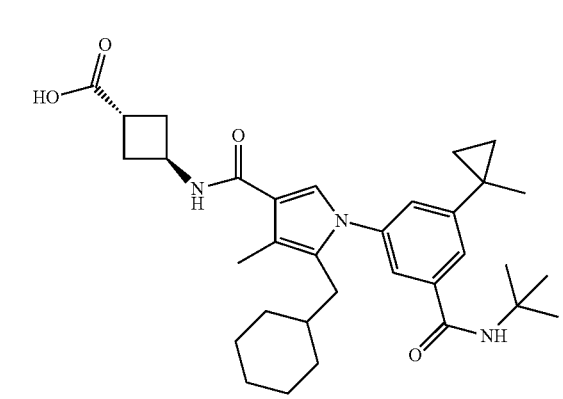 |
| 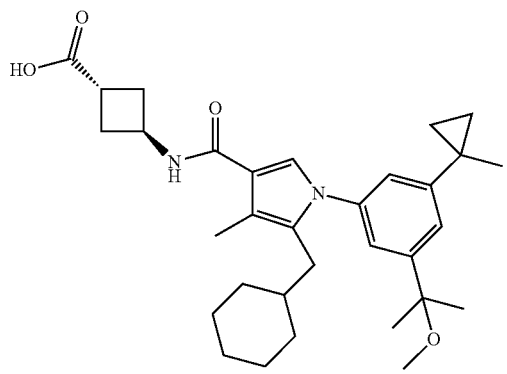 [SMILES: COC(C)(C)c1cc(-n2cc(C(=O)N[C@H]3C[C@H](C(=O)O)C3)c(C)c2CC2CCCCC2)cc(C2(C)CC2)c1] | 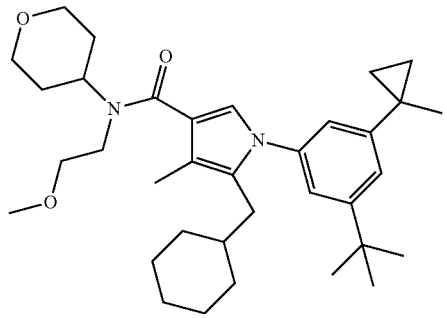 |
| 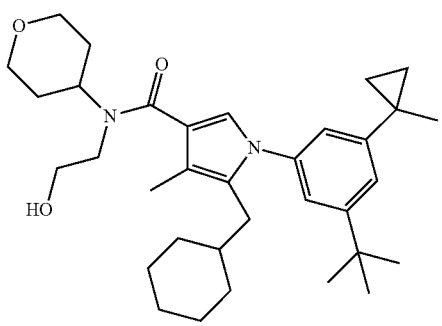 [SMILES: Cc1c(C(=O)N(CCO)C2CCOCC2)cn(-c2cc(C(C)(C)C)cc(C3(C)CC3)c2)c1CC1CCCCC1] | 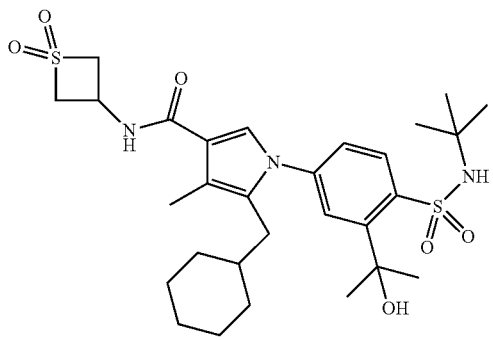 [SMILES: Cc1c(C(=O)NC2CS(=O)(=O)C2)cn(-c2ccc(S(=O)(=O)NC(C)(C)C)c(C(C)(C)O)c2)c1CC1CCCCC1] |

| 163 -continued | 164 -continued |
|---|---|
| Structure | Structure |
| 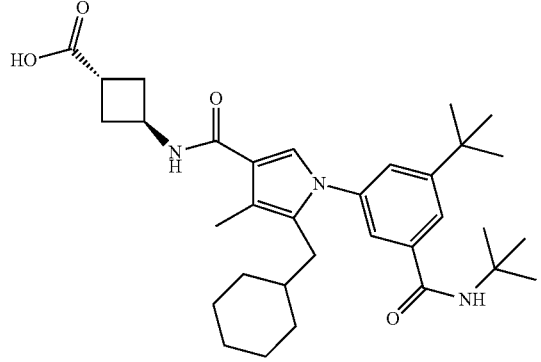 [SMILES: Cc1c(C(=O)N[C@H]2C[C@H](C(=O)O)C2)cn(-c2cc(C(=O)NC(C)(C)C)cc(C(C)(C)C)c2)c1CC1CCCCC1] | 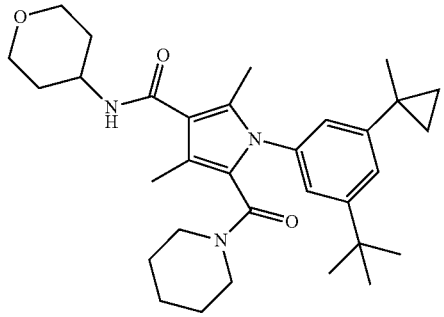 [SMILES: Cc1c(C(=O)NC2CCOCC2)c(Cl)n(-c2cc(C(C)(C)C)cc(C3(C)CC3)c2)c1C(=O)N1CCCCC1] |
| 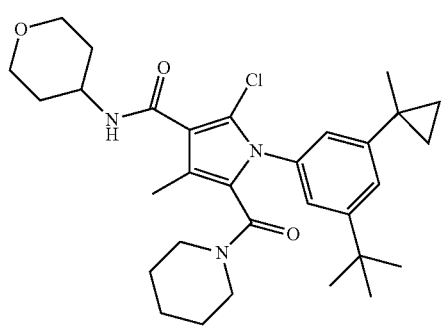 | 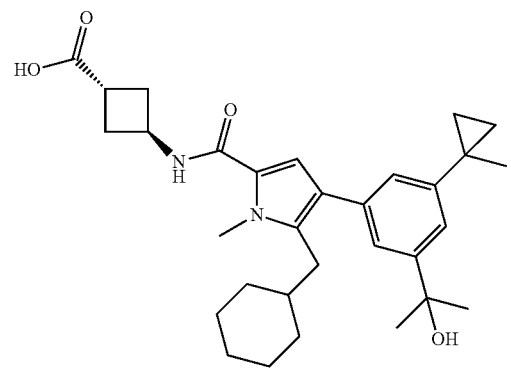 [SMILES: Cn1c(C(=O)N[C@H]2C[C@H](C(=O)O)C2)cc(-c2cc(C(C)(C)O)cc(C3(C)CC3)c2)c1CC1CCCCC1] |
| 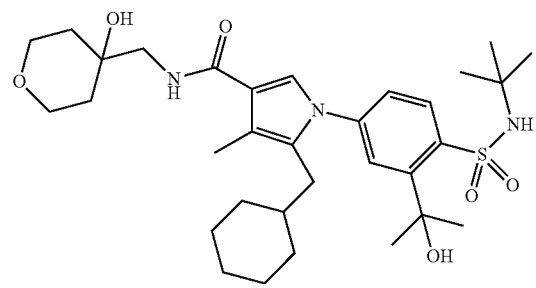 [SMILES: Cc1c(C(=O)NCC2(O)CCOCC2)cn(-c2ccc(S(=O)(=O)NC(C)(C)C)c(C(C)(C)O)c2)c1CC1CCCCC1] | 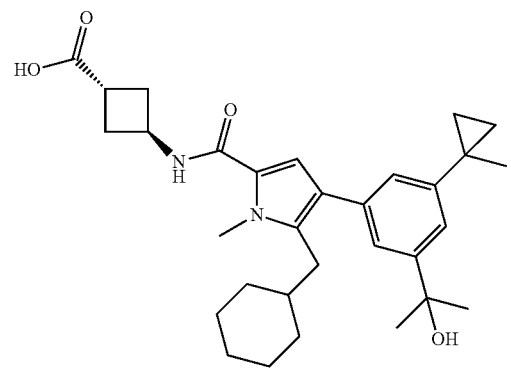 [SMILES: Cn1c(C(=O)N[C@H]2C[C@H](C(=O)O)C2)cc(-c2cc(C(C)(C)O)cc(C3(C)CC3)c2)c1CC1CCCCC1] |
| 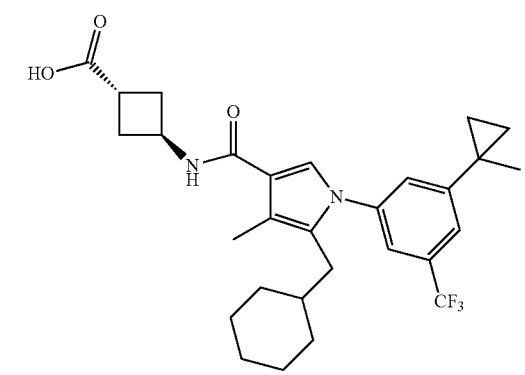 [SMILES: Cc1c(C(=O)N[C@H]2C[C@H](C(=O)O)C2)cn(-c2cc(C(F)(F)F)cc(C3(C)CC3)c2)c1CC1CCCCC1] | 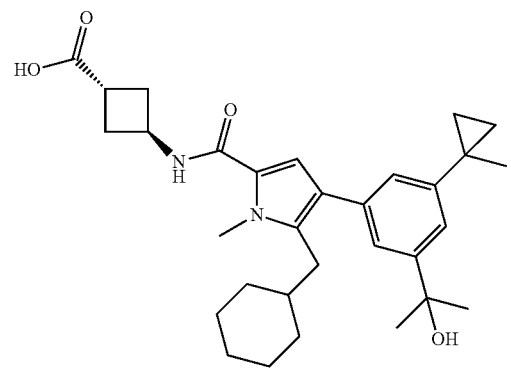 [SMILES: Cn1c(C(=O)N[C@H]2C[C@H](C(=O)O)C2)cc(-c2cc(C(C)(C)O)cc(C3(C)CC3)c2)c1CC1CCCCC1] |

| Structure | Structure |
|---|---|
| 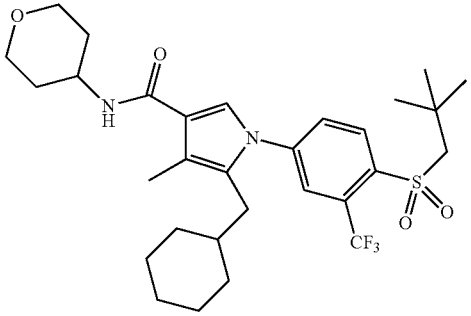 [SMILES: Cc1c(C(=O)NC2CCOCC2)cn(-c2ccc(S(=O)(=O)CC(C)(C)C)c(C(F)(F)F)c2)c1CC1CCCCC1] | 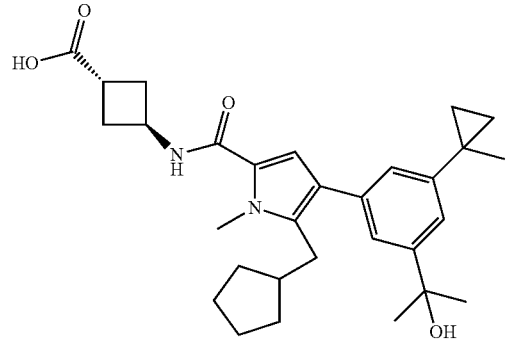 |
| 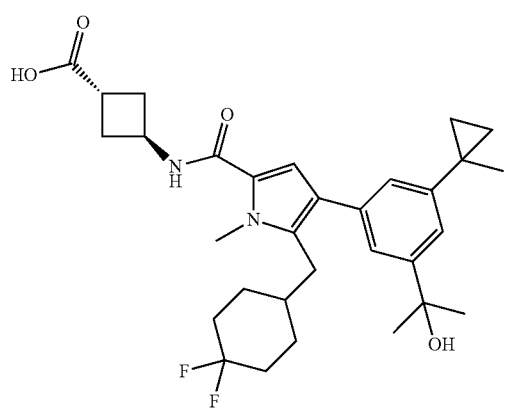 [SMILES: Cn1c(C(=O)N[C@H]2C[C@H](C(=O)O)C2)cc(-c2cc(C(C)(C)O)cc(C3(C)CC3)c2)c1CC1CCC(F)(F)CC1] | 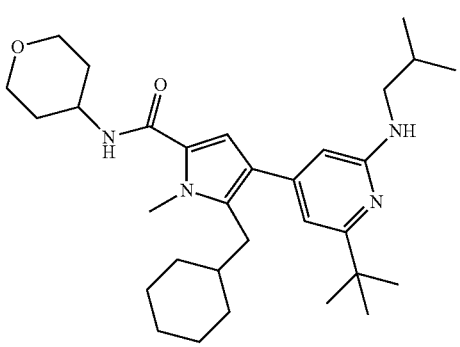 |
| 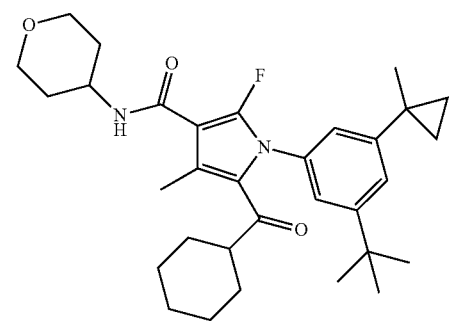 [SMILES: Cc1c(C(=O)NC2CCOCC2)c(F)n(-c2cc(C(C)(C)C)cc(C3(C)CC3)c2)c1C(=O)C1CCCCC1] | 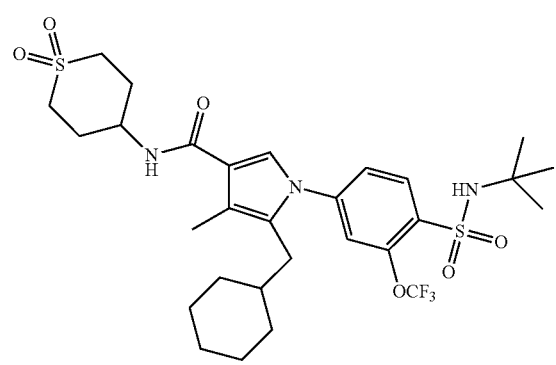 [SMILES: Cc1c(C(=O)NC2CCS(=O)(=O)CC2)cn(-c2ccc(S(=O)(=O)NC(C)(C)C)c(OC(F)(F)F)c2)c1CC1CCCCC1] |
| 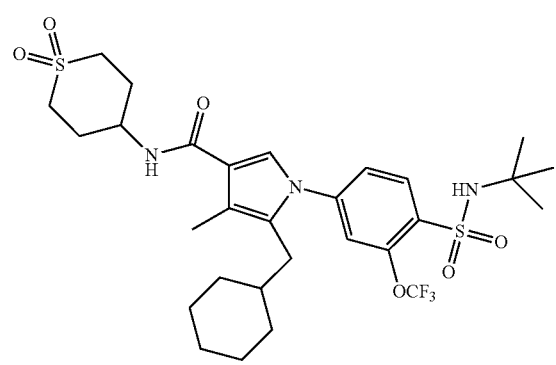 [SMILES: Cc1c(C(=O)NC2CCS(=O)(=O)CC2)cn(-c2ccc(S(=O)(=O)NC(C)(C)C)c(OC(F)(F)F)c2)c1CC1CCCCC1] | 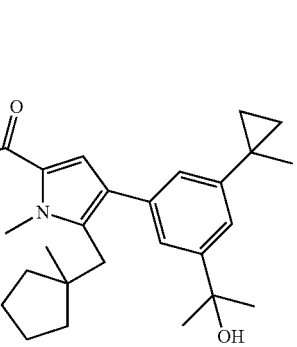 |

| 167 -continued | 168 -continued |
|---|---|
| Structure | Structure |
| 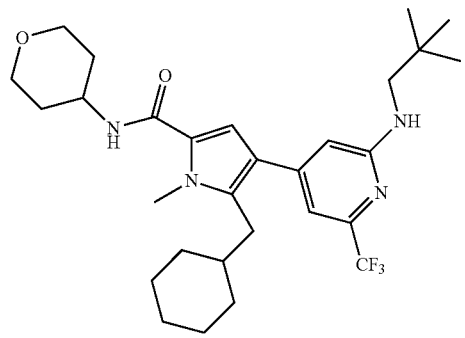 [SMILES: Cn1c(C(=O)NC2CCOCC2)cc(-c2cc(NCC(C)(C)C)nc(C(F)(F)F)c2)c1CC1CCCCC1] | 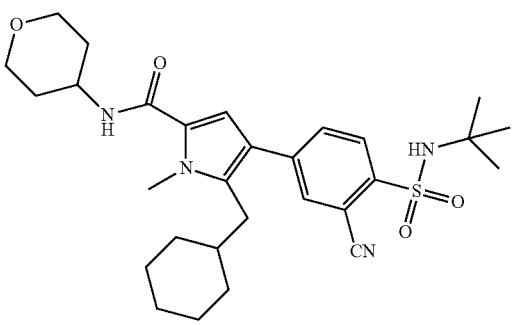 [SMILES: Cn1c(C(=O)NC2CCOCC2)cc(-c2ccc(S(=O)(=O)NC(C)(C)C)c(C#N)c2)c1CC1CCCCC1] |
| 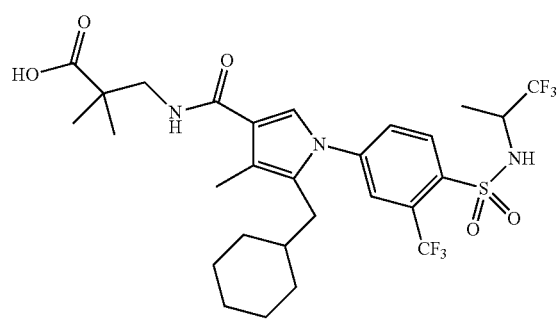 | 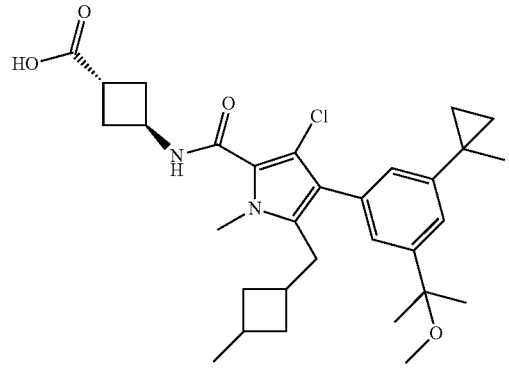 [SMILES: COC(C)(C)c1cc(-c2c(Cl)c(C(=O)N[C@H]3C[C@H](C(=O)O)C3)n(C)c2CC2CC(C)C2)cc(C2(C)CC2)c1] |
| 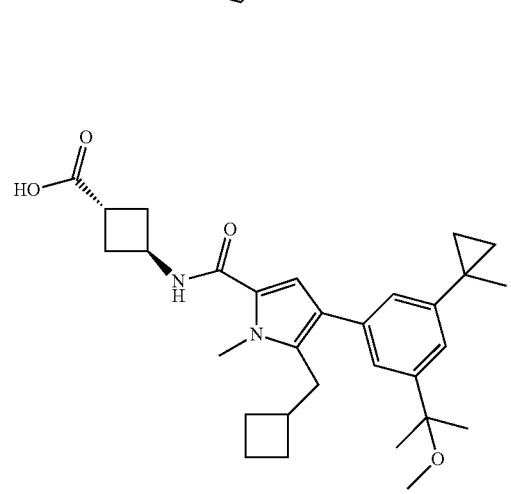 | 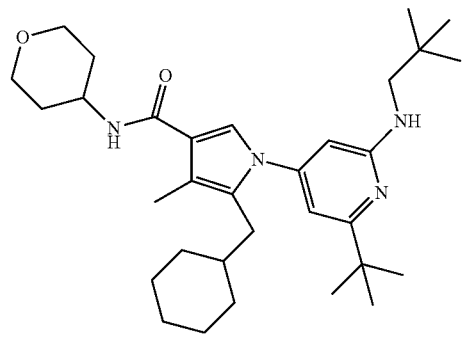 [SMILES: Cc1c(C(=O)NC2CCOCC2)cn(-c2cc(NCC(C)(C)C)nc(C(C)(C)C)c2)c1CC1CCCCC1] |
| 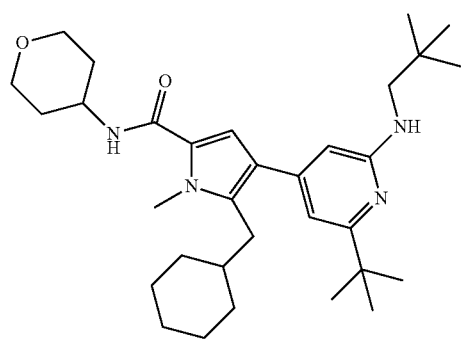 | 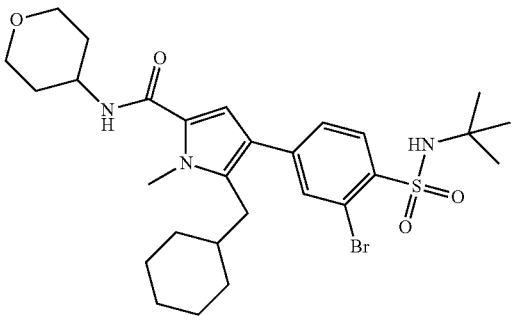 [SMILES: Cn1c(C(=O)NC2CCOCC2)cc(-c2ccc(S(=O)(=O)NC(C)(C)C)c(Br)c2)c1CC1CCCCC1] |

| 169 -continued | 170 -continued |
|---|---|
| Structure | Structure |
| 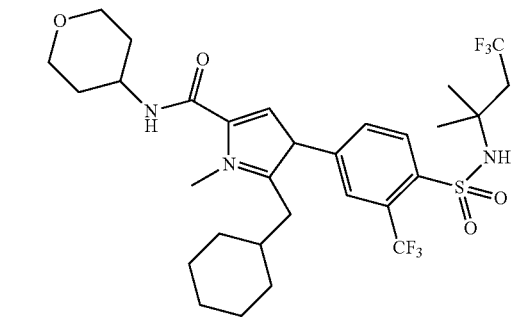 | 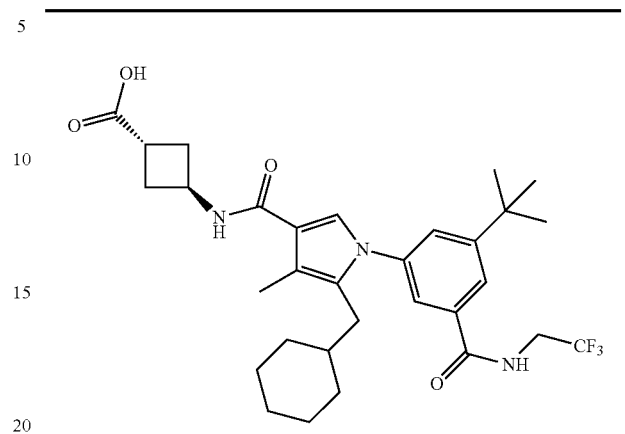 |
| 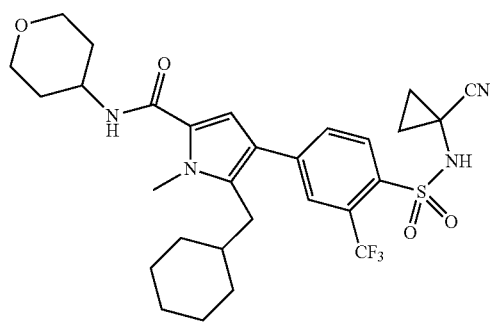 [SMILES: Cn1c(C(=O)NC2CCOCC2)cc(-c2ccc(S(=O)(=O)NC3(C#N)CC3)c(C(F)(F)F)c2)c1CC1CCCCC1] | |
| 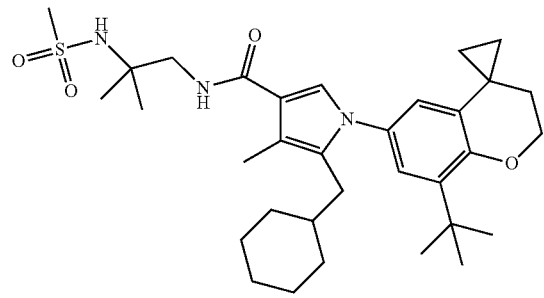 [SMILES: Cc1c(C(=O)NCC(C)(C)NS(C)(=O)=O)cn(-c2cc(C(C)(C)C)c3c(c2)C2(CCO3)CC2)c1CC1CCCCC1] | 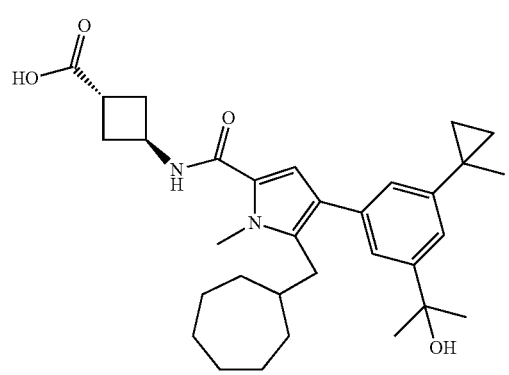 [SMILES: Cn1c(C(=O)N[C@H]2C[C@H](C(=O)O)C2)cc(-c2cc(C(C)(C)O)cc(C3(C)CC3)c2)c1CC1CCCCCC1] |
| 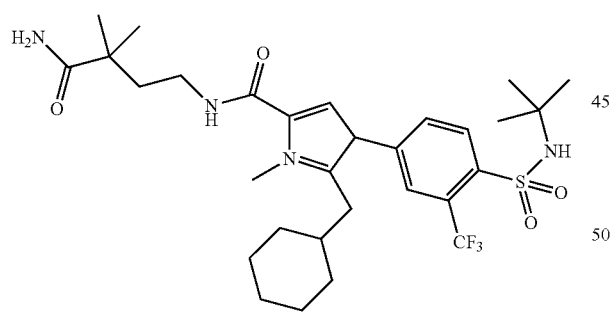 | 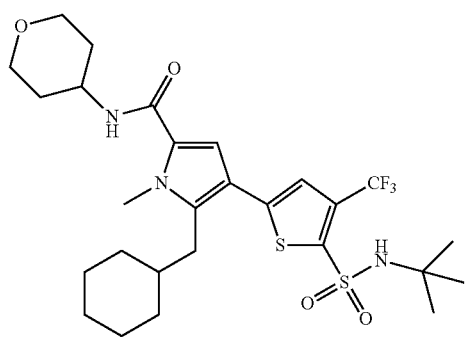 [SMILES: Cn1c(C(=O)NC2CCOCC2)cc(-c2cc(C(F)(F)F)c(S(=O)(=O)NC(C)(C)C)s2)c1CC1CCCCC1] |
| 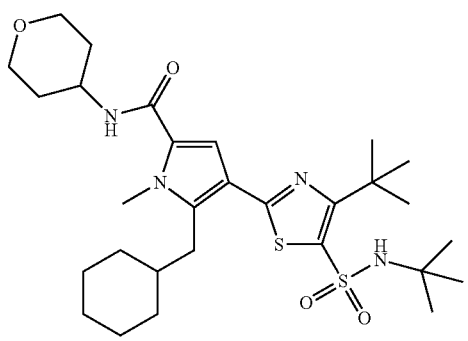 | 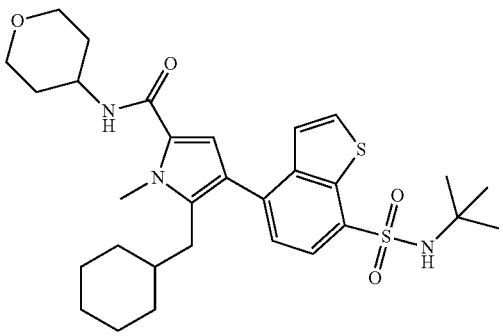 [SMILES: Cn1c(C(=O)NC2CCOCC2)cc(-c2ccc(S(=O)(=O)NC(C)(C)C)c3sccc23)c1CC1CCCCC1] |

| 171 -continued | 172 -continued |
|---|---|
| Structure | Structure |
| 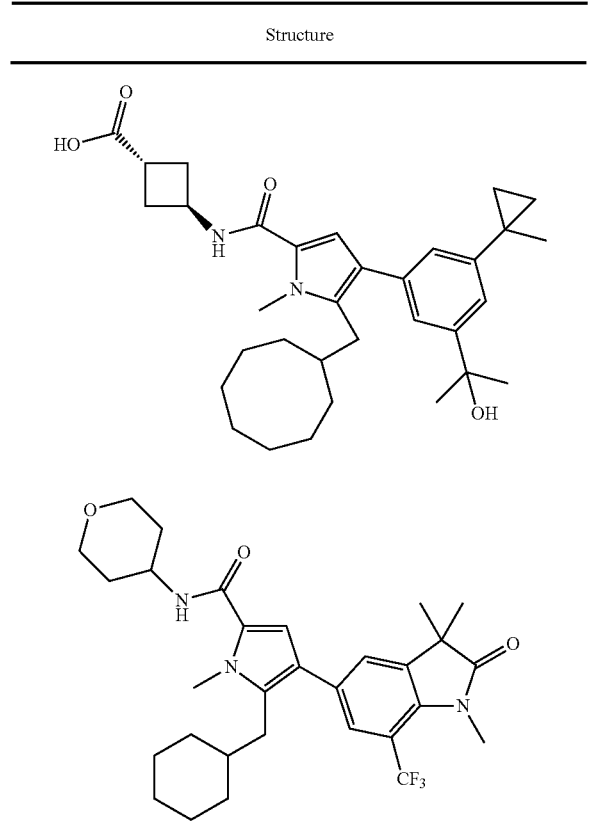 | 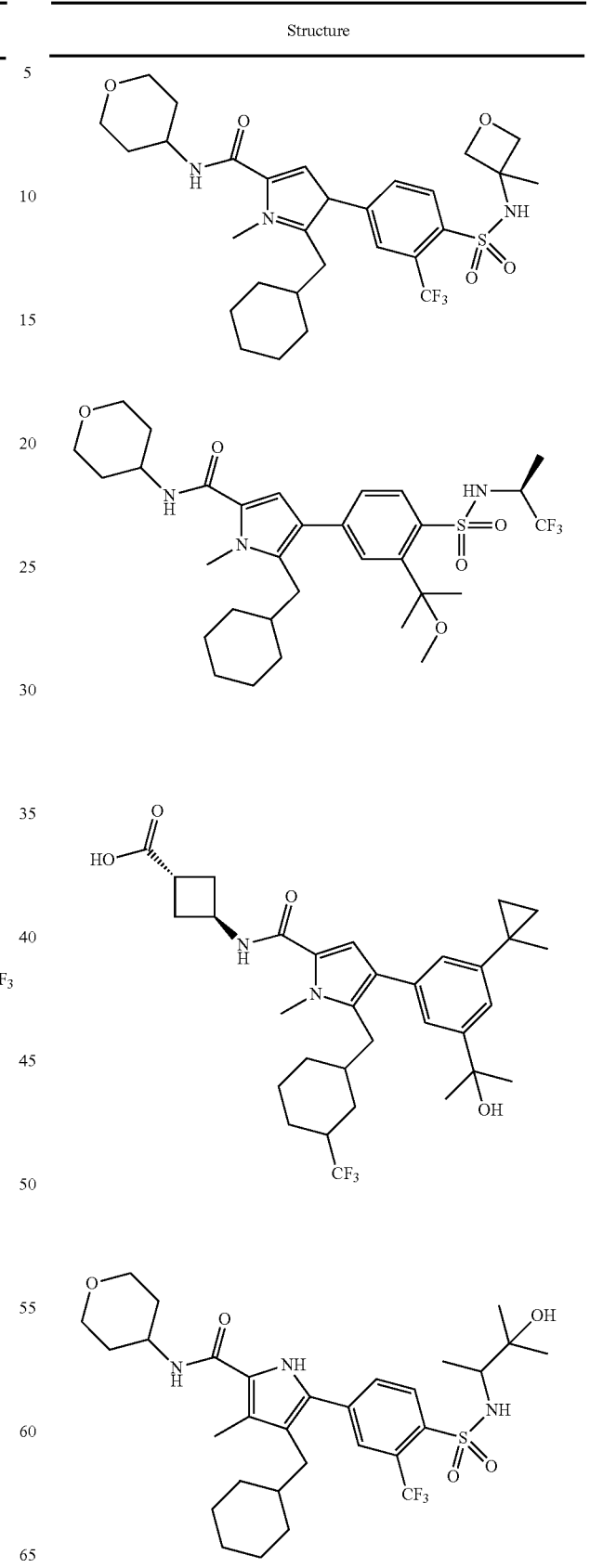 |
| 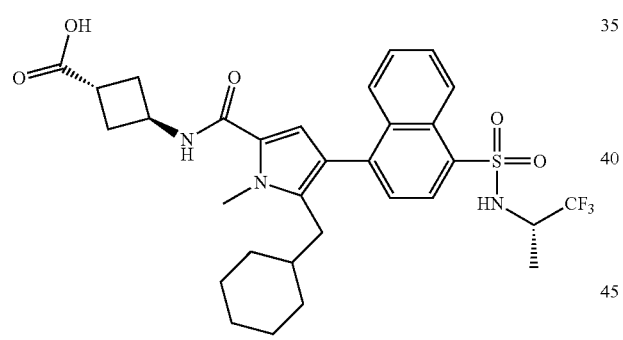 | |
| 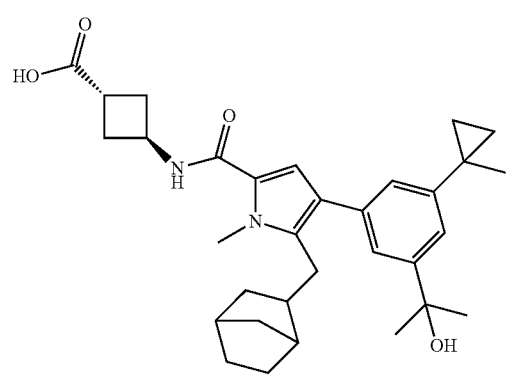 [SMILES: Cn1c(C(=O)N[C@H]2C[C@H](C(=O)O)C2)cc(-c2cc(C(C)(C)O)cc(C3(C)CC3)c2)c1CC1CC2CCC1C2] | |

| 173 -continued | 174 -continued |
|---|---|
| Structure | Structure |
| 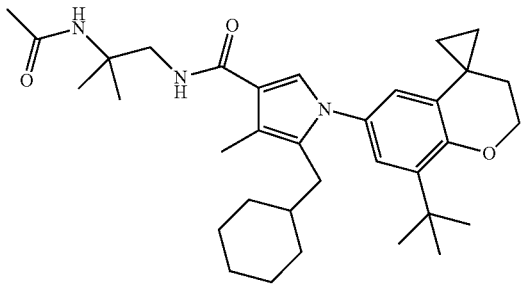 [SMILES: CC(=O)NC(C)(C)CNC(=O)c1cn(-c2cc(C(C)(C)C)c3c(c2)C2(CCO3)CC2)c(CC2CCCCC2)c1C] | 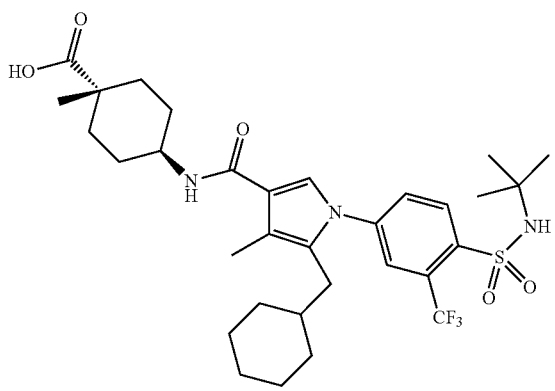 |
| 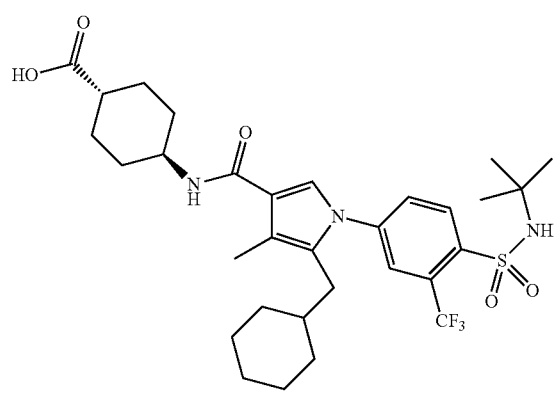 [SMILES: Cc1c(C(=O)N[C@H]2CC[C@H](C(=O)O)CC2)cn(-c2ccc(S(=O)(=O)NC(C)(C)C)c(C(F)(F)F)c2)c1CC1CCCCC1] | 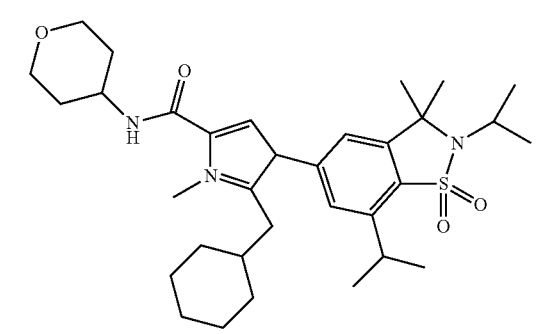 |
| 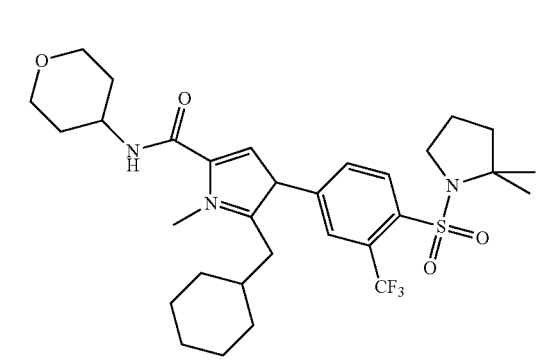 | 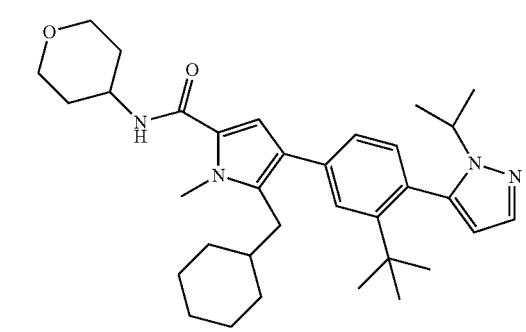 |
| 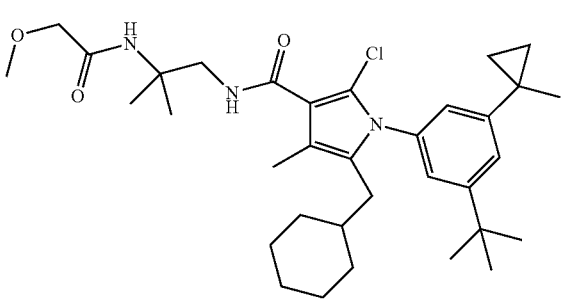 | 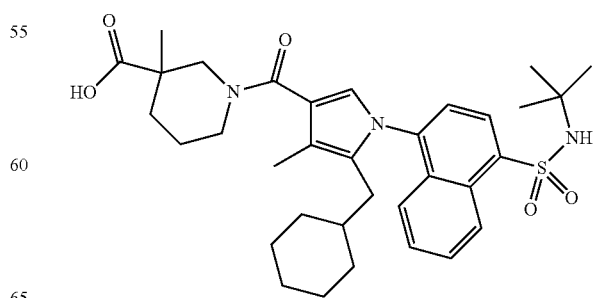 |

| 175 -continued | 176 -continued |
|---|---|
| Structure | Structure |
| 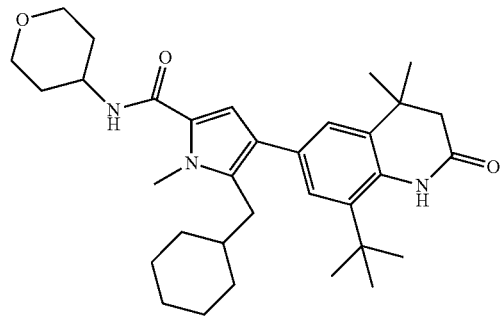 [SMILES: Cn1c(C(=O)NC2CCOCC2)cc(-c2cc(C(C)(C)C)c3c(c2)C(C)(C)CC(=O)N3)c1CC1CCCCC1] | 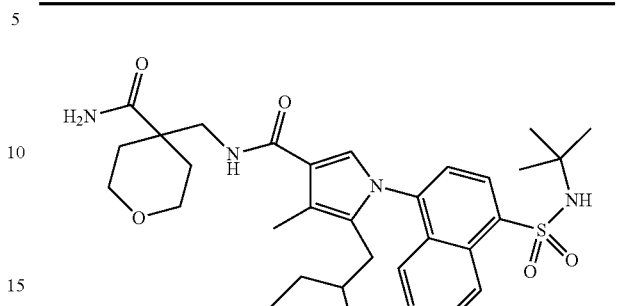 |
| 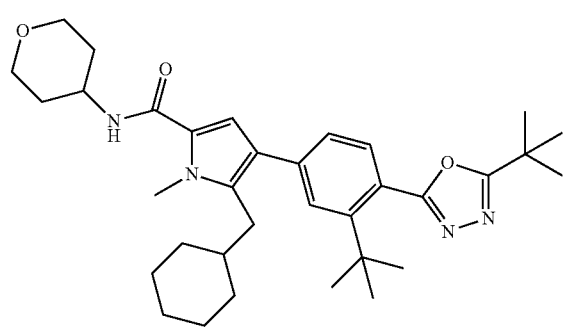 [SMILES: Cn1c(C(=O)NC2CCOCC2)cc(-c2ccc(-c3nnc(C(C)(C)C)o3)c(C(C)(C)C)c2)c1CC1CCCCC1] | 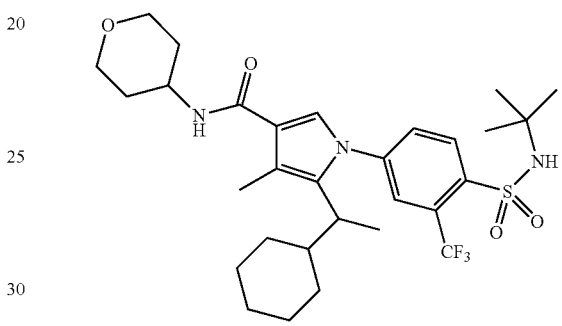 |
| 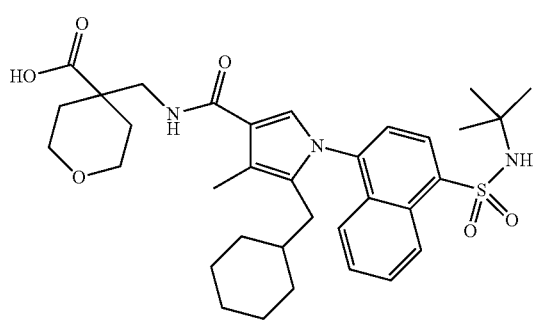 [SMILES: Cc1c(C(=O)NCC2(C(=O)O)CCOCC2)cn(-c2ccc(S(=O)(=O)NC(C)(C)C)c3ccccc23)c1CC1CCCCC1] | Example 100 |
| 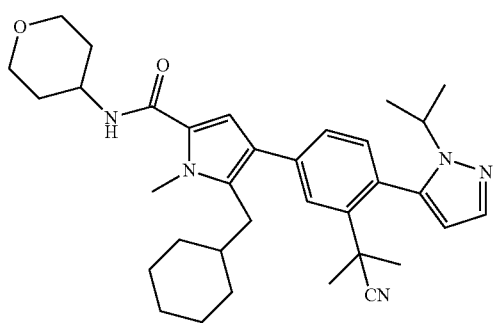 [SMILES: CC(C)n1nccc1-c1ccc(-c2cc(C(=O)NC3CCOCC3)n(C)c2CC2CCCCC2)cc1C(C)(C)C#N] | 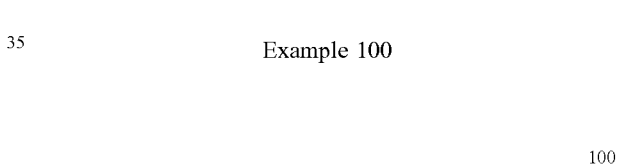 |
| 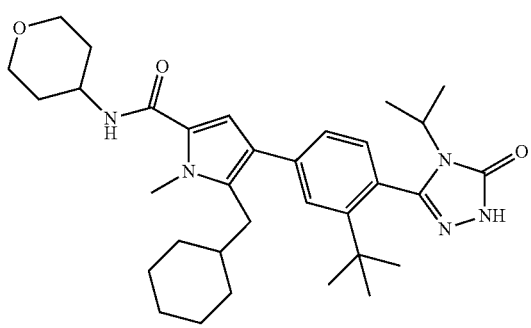 [SMILES: CC(C)n1c(-c2ccc(-c3cc(C(=O)NC4CCOCC4)n(C)c3CC3CCCCC3)cc2C(C)(C)C)n[nH]c1=O] | |

Step 1: Ethyl 1-(cyclohexylmethyl)-5-hydroxy-1H-pyrazole-3-carboxylate (100a)

To a solution of diethyl but-2-ynedioate (1.7 g, 10 mmol) in EtOH (20 mL) was added $K_2CO_3$ (4.1 g, 30 mmol) and (cyclohexylmethyl)hydrazine hydrochloride (1.7 g, 11 mmol). The reaction mixture was stirring at 90° C. overnight, cooled to rt, acidified with 2N HCl, extracted with EA (100 mL) twice, dried over $Na_2SO_4$ and concentrated to afford product 100a (1.5 g, 61%) as a solid.

Step 2: Ethyl 1-(cyclohexylmethyl)-5-(((trifluoromethyl)sulfonyl)oxy)-1H-pyrazole-3-carboxylate (100b)

To a solution of 100a (1.5 g, 6.0 mmol) in DCM (40 mL) at 0° C. was added TEA (1.7 mL, 12 mmol). The solution was stirred at 0° C. for 50 min at which time Tf$_2$O (1.7 g, 6.1 mmol) in DCM (15 mL) was added dropwise, stirred for 2 h, quenched with H$_2$O (10 mL) and extracted with EA twice. The combined organic layers dried over MgSO$_4$, concentrated and purified by CC (PE/EA=10/1) to afford the product 100b (1.8 g, 78%) as a solid.

Step 3: Ethyl 5-(3-(tert-butyl)-5-(1-methylcyclopropyl)phenyl)-1-(cyclohexylmethyl)-1H-pyrazole-3-carboxylate (100c)

To a solution of compound 100b (1.8 g, 4.6 mmol) in dioxane (15 mL) was added Pd(Ph$_3$)$_4$ (100 mg), 2-(3-tert-butyl-5-(1-methylcyclopropyl)phenyl)-4,4,5,5-tetramethyl-1,3,2-dioxaborolane (1.6 g, 5 mmol), K$_2$CO$_3$ (1.6 g, 11 mol) and H$_2$O (3 mL) under N$_2$. The reaction was stirring at 90° C. overnight, concentrated and purified by CC to afford compound 100c (423 mg, 21%) as a white solid.

Step 4: 5434 tert-Butyl)-5-(1-methylcyclopropyl)phenyl)-1-(cyclohexyl methyl)-1H-pyrazole-3-carboxylic acid (100d)

To a solution of compound 100c (423 mg, 1.0 mmol) in THF (5 mL) was added LiOH (100 mg) and H$_2$O (1 mL) under N$_2$. The reaction was stirred at rt overnight, acidified with 2N HCl, extracted with EA (100 mL) twice, dried over Na$_2$SO$_4$ and concentrated to afford compound 100d (390 mg, 99%) as a solid.

Step 5: (trans)-3-(5-(3-(tert-Butyl)-5-(1-methylcyclopropyl)phenyl)-1-(cyclohexylmethyl)-1H-pyrazole-3-carboxamido)cyclobutanecarboxylic acid (100)

To a solution of compound 100d (100 mg, 0.25 mmol) in DCM (5 mL) was added HATU (115 mg, 0.3 mmol), Et$_3$N (55 mg, 0.5 mmol) and trans-3-aminocyclobutanecarboxylic acid (55 mg, 0.5 mmol) and the mixture was stirring overnight, evaporated and was purified by prep-HPLC to afford compound 100 (15 mg, 13%). $^1$H-NMR (400 MHz, DMSO-d$_6$) δ: 8.38 (d, 1H, J=8.0 Hz), 7.31 (s, 1H), 7.24 (s, 1H), 7.07 (s, 1H), 6.71 (s, 1H), 4.56-4.62 (m, 1H), 3.97 (d, 2H, J=7.6 Hz), 2.91-2.87 (m, 1H), 2.38-2.42 (m, 4H), 1.80-1.84 (m, 2H), 0.77-1.83 (m, 27H). LC/MS (ESI): m/z 492.3 (M+H)$^+$.

Examples 100/1 to 100/7

The following Examples were prepared similar as in Example 100 (and the ester optionally saponified as described for Example 4):

| # | Structure | Analytical data |
|---|---|---|
| 100/1 | 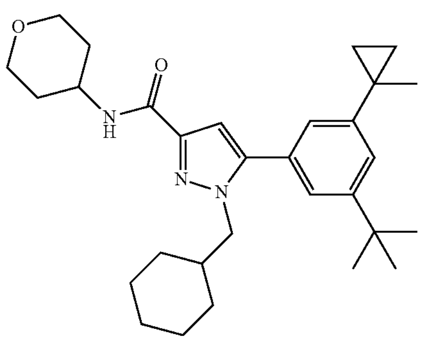 [SMILES: CC(C)(C)c1cc(-c2cc(C(=O)NC3CCOCC3)nn2CC2CCCCC2)cc(C2(C)CC2)c1] | $^1$H-NMR (400 MHz, CD$_3$OD) δ: 7.44 (t, 1H, J = 1.6 Hz), 7.25 (s, 1H), 7.13 (s, 1H), 6.74(s, 1H), 4.13-1.17 (m, 1H), 3.98-4.02 (m, 4H), 3.53-3.59 (m, 2H), 1.48-1.95 (m, 10H), 1.45 (s, 3H), 1.37 (s, 9H), 0.79-1.21 (m, 9H). LC/MS (ESI): m/z 478.3 (M + H)$^+$. |
| 100/2 | 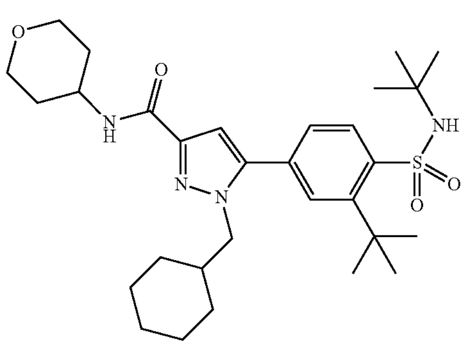 [SMILES: CC(C)(C)NS(=O)(=O)c1ccc(-c2cc(C(=O)NC3CCOCC3)nn2CC2CCCCC2)cc1C(C)(C)C] | $^1$H-NMR (300 MHz, CDCl$_3$) δ: 0.75-0.89 (m, 4H), 1.07-1.37 (m, 15H), 1.44-1.55 (m, 2H), 1.60-1.72 (m, 10H), 1.84-1.86 (m, 1H), 2.01-2.05 (m, 2H), 3.53-3.60 (m, 2H), 3.95 (d, J = 7.5 Hz, 2H), 4.03 (d, J = 11.4 Hz, 2H), 4.18-4.25 (m, 1H), 4.60 (s, 1H), 6.82 (d, J = 8.4 Hz, 1H), 6.86 (s, 1H), 7.32 (d, J = 8.1 Hz, 1H), 7.64 (s, 1H), 8.27 (d, J = 8.1 Hz, 1H). MS 559.3 (M + 1)$^+$ |

| # | Structure | Analytical data |
|---|---|---|
| 100/3 | 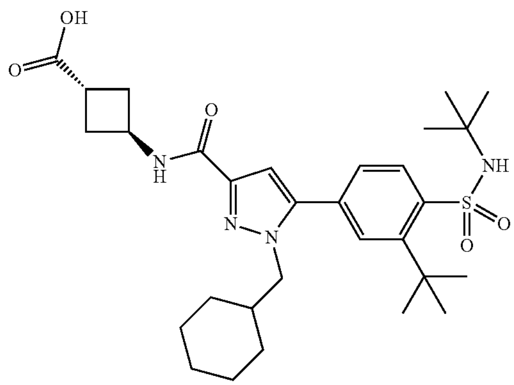 [SMILES: CC(C)(C)NS(=O)(=O)c1ccc(-c2cc(C(=O)N[C@H]3C[C@H](C(=O)O)C3)nn2CC2CCCCC2)cc1C(C)(C)C] | ¹H-NMR (400 MHz, CDCl₃) δ: 0.76-0.84 (m, 2H), 1.10-1.15 (m, 3H), 1.26-1.36 (m, 10H), 1.47-1.49 (m, 2H), 1.56-1.62 (m, 12H), 1.81-1.85 (m, 1H), 2.41-2.48 (m, 2H), 2.79-2.85 (m, 1H), 3.13-3.19 (m, 1H), 3.94 (d, J = 7.6 Hz, 2H), 4.72 (s, 1H), 4.80-4.88 (m, 1H), 6.86 (s, 1H), 7.18 (d, J = 7.6 Hz, 1H), 7.31 (dd, J = 8.4, 1.2 Hz, 1H), 7.62 (d, J = 1.2 Hz, 1H), 8.25 (d, J = 8.8 Hz, 1H). MS 571.3 (M − 1)⁻ |
| 100/4 | 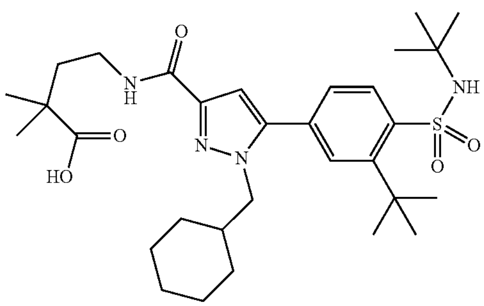 [SMILES: CC(C)(C)NS(=O)(=O)c1ccc(-c2cc(C(=O)NCCC(C)(C)C(=O)O)nn2CC2CCCCC2)cc1C(C)(C)C] | ¹H-NMR (300 MHz, CDCl₃) δ: 0.75-0.83 (m, 2H), 1.06-1.32 (m, 21H), 1.45-1.48 (m, 2H), 1.62 (s, 9H), 1.77-1.84 (m, 1H), 1.92-1.96 (m, 2H), 3.49-3.52(m, 2H), 3.93 (d, J = 7.2 Hz, 2H), 4.76 (s, 1H), 6.84 (s, 1H), 7.06-7.08 (m, 1H), 7.30 (d, J = 8.0 Hz, 1H), 7.62 (s, 1H), 8.24 (d, J = 8.0 Hz, 1H). MS 587.3 (M − 1)⁻ |
| 100/5 | 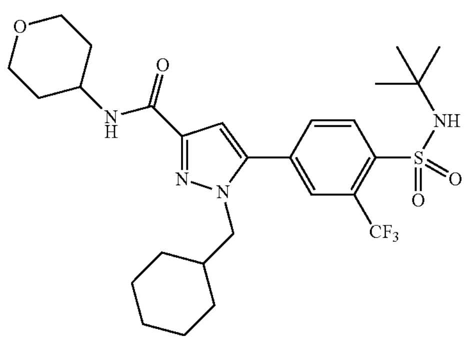 [SMILES: CC(C)(C)NS(=O)(=O)c1ccc(-c2cc(C(=O)NC3CCOCC3)nn2CC2CCCCC2)cc1C(F)(F)F] | ¹H-NMR (300 MHz, CDCl₃) δ: 0.74-0.83 (m, 2H), 1.07-1.18 (m, 3H), 1.29 (s, 9H), 1.47-1.50 (m, 2H), 1.59-1.69 (m, 5H), 1.82-1.88 (m, 1H), 2.00-2.04 (m, 2H), 3.55 (td, J = 11.6, 1.6 Hz, 2H), 3.94 (d, J = 7.2 Hz, 2H), 4.01 (d, J = 8.4 Hz, 2H), 4.16-4.23 (m, 1H), 4.79 (s, 1H), 6.79 (d, J = 8.0 Hz, 1H), 6.92 (s, 1H), 7.69 (dd, J = 8.4, 1.6 Hz, 1H), 7.84 (d, J = 1.2 Hz, 1H), 8.40 (d, J = 8.4 Hz, 1H). MS 571.2 (M + 1)⁺ |
| 100/6 | 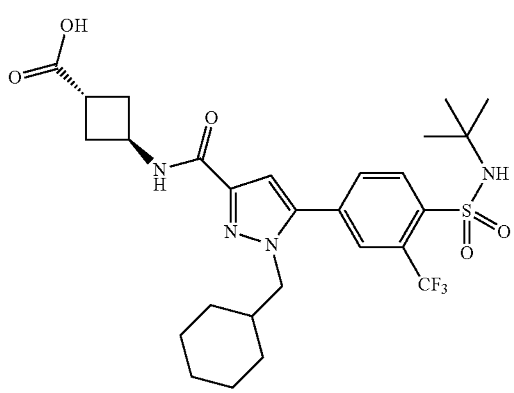 [SMILES: CC(C)(C)NS(=O)(=O)c1ccc(-c2cc(C(=O)N[C@H]3C[C@H](C(=O)O)C3)nn2CC2CCCCC2)cc1C(F)(F)F] | ¹H-NMR (400 MHz, CDCl₃) δ: 0.77-0.82 (m, 2H), 1.12-1.19 (m, 3H), 1.25-1.29 (m, 10H), 1.47-1.50 (m, 2H), 1.62-1.68 (m, 2H), 1.84-1.85 (m, 1H), 2.43-2.47 (m, 2H), 2.78-2.84 (m, 2H), 3.15-3.19 (m, 1H), 3.94 (d, J = 7.2 Hz, 2H), 4.77-4.83 (m, 2H), 6.92 (s, 1H), 7.11 (d, J = 8.0 Hz, 1H), 7.69 (dd, J = 8.4, 1.6 Hz, 1H), 7.84 (d, J = 1.2 Hz, 1H), 8.40 (d, J = 8.4 Hz, 1H). MS 583.2 (M − 1)⁻ |

| # | Structure | Analytical data |
|---|---|---|
| 100/7 | 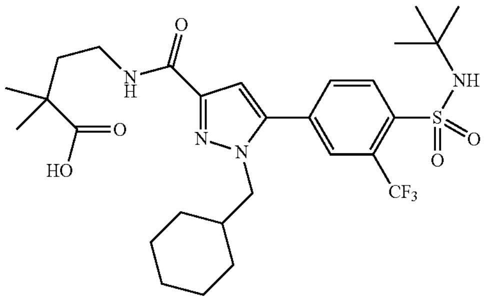 [SMILES: CC(C)(C)NS(=O)(=O)c1ccc(-c2cc(C(=O)NCCC(C)(C)C(=O)O)nn2CC2CCCCC2)cc1C(F)(F)F] | ¹H-NMR (400 MHz, CDCl₃) δ: 0.75-0.88 (m, 2H), 1.11-1.14 (m, 3H), 1.25-1.30 (m, 16H), 1.43-1.49 (m, 2H), 1.63-1.66 (m, 2H), 1.81-1.86 (m, 1H), 1.93-1.96 (m, 2H), 3.48-3.54 (m, 2H), 3.93 (d, J = 7.6 Hz, 2H), 4.78 (s, 1H), 6.91 (s, 1H), 7.02 (t, J = 5.6 Hz, 1H), 7.69 (d, J = 8.4 Hz, 1H), 7.84 (s, 1H), 8.39 (d, J = 8.0 Hz, 1H). MS 599.3 (M − 1)⁻ |

Example 102/1 to 102/3

The following Examples were prepared similar as described for Example 312:

| # | Structure | Analytical data |
|---|---|---|
| 102/1 | 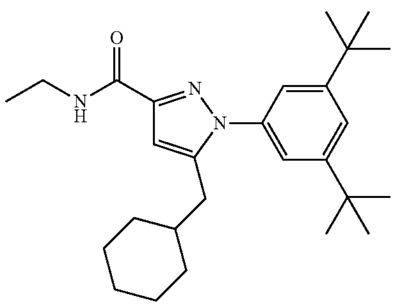 [SMILES: CCNC(=O)c1cc(CC2CCCCC2)n(-c2cc(C(C)(C)C)cc(C(C)(C)C)c2)n1] | ¹H-NMR (CDCl₃, 400 MHz) δ: 0.83-0.89 (2H, m), 1.12-1.16 (3H, m), 1.20-1.26 (3H, m), 1.35 (18H, s), 1.63-1.69 (5H, m), 2.44 (2H, d, J = 6.8 Hz), 6.74 (1H, s), 6.95 (1H, brs), 7.18 (2H, s), 7.50 (1H, s). MS 424 (M + 1)⁺ |
| 102/2 | 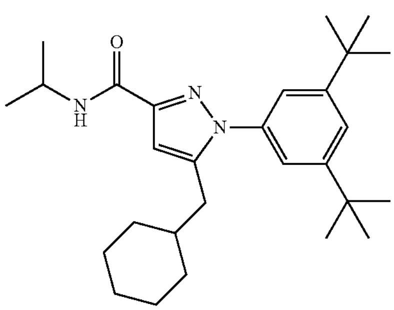 [SMILES: CC(C)NC(=O)c1cc(CC2CCCCC2)n(-c2cc(C(C)(C)C)cc(C(C)(C)C)c2)n1] | ¹H-NMR (CDCl₃, 400 MHz) δ: 0.80-0.88 (2H, m), 1.06-1.19 (3H, m), 1.24 (6H, m), 1.35 (18H, s), 1.58-1.65 (5H, m), 2.43 (2H, d, J = 7.2 Hz), 4.28 (1H, m), 6.73 (1H, s), 6.79 (1H, d, J = 8.0 Hz), 7.18 (2H, d, J = 1.6 Hz), 7.50 (1H, s). MS 438 (M + 1)⁺ |
| 102/3 | 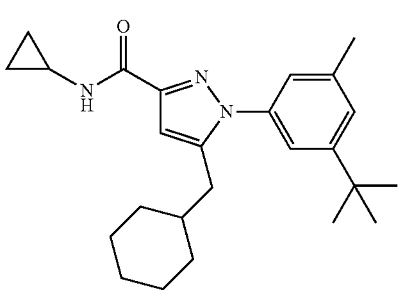 [SMILES: Cc1cc(-n2nc(C(=O)NC3CC3)cc2CC2CCCCC2)cc(C(C)(C)C)c1] | ¹H-NMR (CDCl₃, 300 MHz) δ: 0.58-0.62 (2H, m), 0.77-0.85 (4H, m), 1.10-1.13 (3H, m), 1.33 (9H, s), 1.50 (1H, m), 1.64 (5H, m), 2.41 (3H, s), 2.44 (2H, d, J = 7.2 Hz), 2.86 (1H, m), 6.73 (1H, s), 6.99-7.01 (2H, m), 7.13 (1H, m), 7.26 (1H, m). MS 394 (M + 1)⁺ |

Example 103/1 to 103/8

The following Examples were prepared similar as described for Example 314:

| # | Structure | Analytical data |
|---|-----------|-----------------|
| 103/1 | 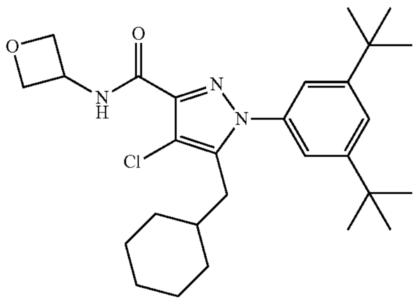 [SMILES: CC(C)(C)c1cc(-n2nc(C(=O)NC3COC3)c(Cl)c2CC2CCCCC2)cc(C(C)(C)C)c1] | ¹H-NMR (CDCl₃, 300 MHz) δ: 0.79-0.81 (3H, m), 0.82-0.85 (4H, m), 1.25-1.27 (20H, m), 1.45-1.48 (2H, m), 2.52 (2H, d, J = 7.2 Hz), 4.59-4.63 (2H, m), 4.93-4.98 (2H, m), 5.22-5.24 (1H, m), 7.17 (2H, d, J = 1.8 Hz), 7.36 (1H, br s), 7.54 (1H, s). MS 486 (M + 1)⁺ |
| 103/2 | 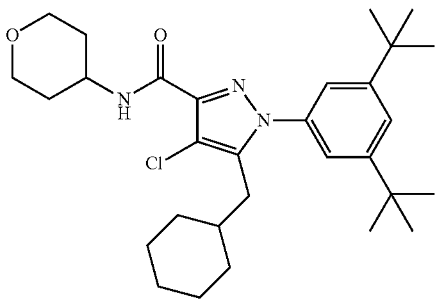 [SMILES: CC(C)(C)c1cc(-n2nc(C(=O)NC3CCOCC3)c(Cl)c2CC2CCCCC2)cc(C(C)(C)C)c1] | ¹H-NMR (CDCl₃, 300 MHz) δ: 0.79-0.81 (2H, m), 0.82-0.85 (3H, m), 1.25-1.27 (19H, m), 1.45-1.62 (7H, m), 2.52 (2H, d, J = 7.2 Hz), 3.47-3.55 (2H, m), 3.95-3.99 (2H, m), 4.20-4.24 (1H, m), 6.80 (1H, br s), 7.17 (1H, s), 7.23 (1H, s), 7.53 (1H, s). MS 514 (M + 1)⁺ |
| 103/3 | 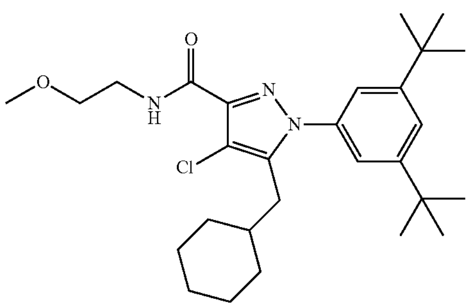 [SMILES: COCCNC(=O)c1nn(-c2cc(C(C)(C)C)cc(C(C)(C)C)c2)c(CC2CCCCC2)c1Cl] | ¹H-NMR (CDCl₃, 300 MHz) δ: 0.80-0.82 (3H, m), 0.83-0.89 (4H, m), 1.25-1.27 (20H, m), 1.45-1.46 (2H, m), 2.51 (2H, d, J = 6.0 Hz), 3.35 (3H, s), 3.55-3.62 (4H, m), 7.16-7.28 (3H, m), 7.51 (1H, s). MS 488 (M + 1)⁺ |
| 103/4 | 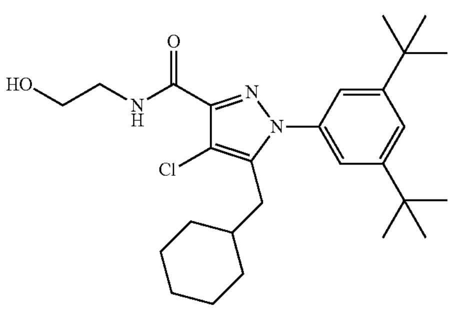 [SMILES: CC(C)(C)c1cc(-n2nc(C(=O)NCCO)c(Cl)c2CC2CCCCC2)cc(C(C)(C)C)c1] | ¹H-NMR (CDCl₃, 300 MHz) δ: 0.80-0.82 (2H, m), 0.83-0.88 (3H, m), 1.25-1.27 (19H, m), 1.45-1.50 (5H, m), 2.52 (2H, d, J = 7.2 Hz), 2.70 (1H, br s), 3.56-3.61 (2H, m), 3.80-3.82 (2H, m), 7.16-7.18 (2H, m), 7.27 (1H, br s), 7.51 (1H, s). MS 474 (M + 1)⁺ |
| 103/5 | 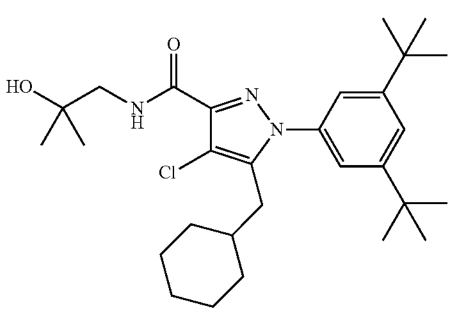 [SMILES: CC(C)(O)CNC(=O)c1nn(-c2cc(C(C)(C)C)cc(C(C)(C)C)c2)c(CC2CCCCC2)c1Cl] | ¹H-NMR (CDCl₃, 300 MHz) δ: 0.80-0.82 (2H, m), 0.83-0.88 (3H, m), 1.04-1.06 (7H, m), 1.27-1.28 (19H, m), 1.52-1.54 (4H, m), 2.53 (2H, d, J = 6.6 Hz), 2.70 (1H, s), 3.42-3.44 (2H, m), 7.16-7.18 (2H, m), 7.26 (1H, br s), 7.52 (1H, s). MS 502 (M + 1)⁺ |

| # | Structure | Analytical data |
|---|---|---|
| 103/6 | 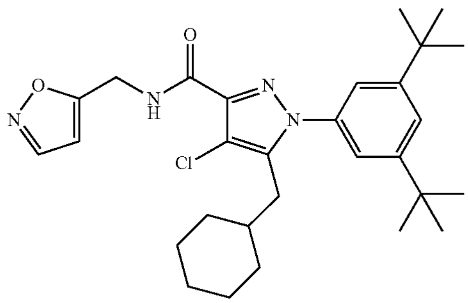 [SMILES: CC(C)(C)c1cc(-n2nc(C(=O)NCc3ccno3)c(Cl)c2CC2CCCCC2)cc(C(C)(C)C)c1] | $^1$H-NMR (CDCl$_3$, 300 MHz) δ: 0.80-0.82 (3H, m), 0.83-0.88 (4H, m), 1.27 (18H, s), 1.52-1.54 (3H, m), 2.52 (2H, d, J = 7.2 Hz), 3.12-3.15 (1H, m), 4.74-4.76 (2H, m), 6.27-6.28 (1H, m), 7.16-7.18 (2H, m), 7.26 (1H, br s), 7.52 (1H, s), 8.17 (1H, s). MS 511 (M + 1)$^+$ |
| 103/7 | 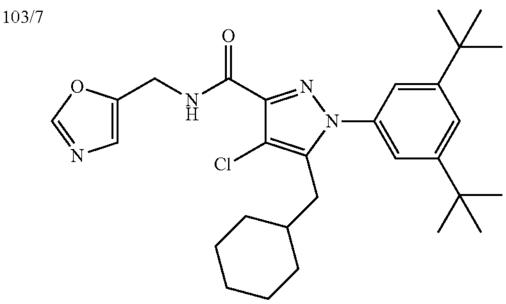 | $^1$H-NMR (CDCl$_3$, 300 MHz) δ: 0.80-0.82 (3H, m), 0.83-0.88 (4H, m), 1.25-1.27 (20H, m), 1.48-1.50 (2H, m), 2.52 (2H, d, J = 7.2 Hz), 4.74-4.76 (2H, m), 7.03 (1H, s), 7.14-7.15 (2H, m), 7.16 (1H, br s), 7.53 (1H, s), 7.80 (1H, s). MS 511 (M + 1)$^+$ |
| 103/8 | 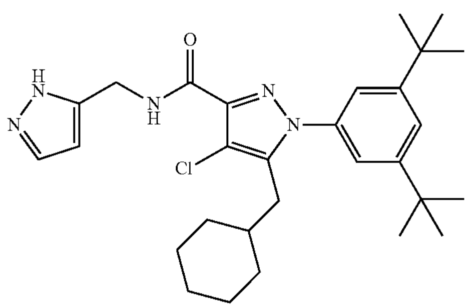 [SMILES: CC(C)(C)c1cc(-n2nc(C(=O)NCc3ccn[nH]3)c(Cl)c2CC2CCCCC2)cc(C(C)(C)C)c1] | $^1$H-NMR (CDCl$_3$, 300 MHz) δ: 0.79-0.82 (2H, m), 0.83-0.88 (3H, m), 1.04-1.06 (3H, m), 1.27 (18H, s), 1.52-1.54 (3H, m), 2.52 (2H, d, J = 7.2 Hz), 4.60-4.62 (2H, m), 6.24-6.25 (1H, m), 7.13-7.14 (2H, m), 7.45-7.51 (2H, m), 7.52 (1H, s). MS 510 (M + 1)$^+$ |

Example 104/1 to 104/4

The following Examples were prepared similar as described for Example 315:

| # | Structure | Analytical data |
|---|---|---|
| 104/1 | 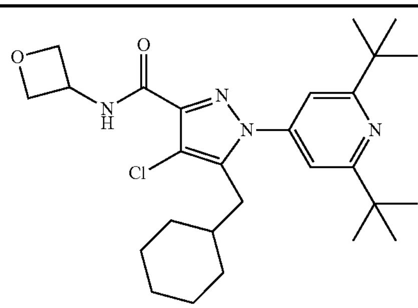 | $^1$H-NMR (CDCl$_3$, 400 MHz) δ: 0.87-0.89 (2H, m), 1.01-1.07 (3H, m), 1.40 (20H, s), 1.47-1.50 (3H, m), 1.53-1.60 (1H, m), 2.62 (2H, d, J = 6.8 Hz), 4.63 (2H, t, J = 6.8 Hz), 4.98 (2H, t, J = 6.8 Hz), 5.26 (1H, m), 7.15 (2H, s), 7.36 (2H, d, J = 6.8 Hz). MS 487 (M + 1)$^+$ |

| # | Structure | Analytical data |
|---|---|---|
| 104/2 | 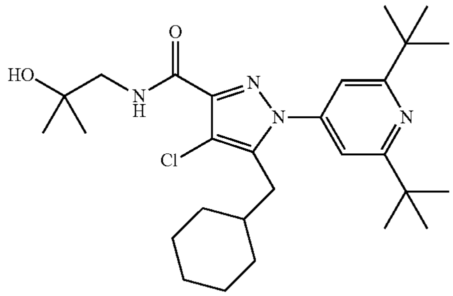 [SMILES: CC(C)(O)CNC(=O)c1nn(-c2cc(C(C)(C)C)nc(C(C)(C)C)c2)c(CC2CCCCC2)c1Cl] | ¹H-NMR (CDCl₃, 400 MHz) δ: 0.87-0.90 (2H, m), 1.08 (3H, m), 1.28 (6H, s), 1.39 (20H, s), 1.48-1.54 (3H, m), 2.47 (1H, s), 2.63 (2H, d, J = 6.8 Hz), 3.45 (2H, d, J = 6.4 Hz), 7.15 (2H, s), 7.26 (1H, s). MS 503 (M + 1)⁺ |
| 104/3 | 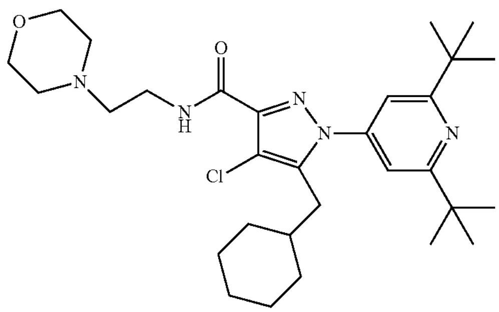 [SMILES: CC(C)(C)c1cc(-n2nc(C(=O)NCCN3CCOCC3)c(Cl)c2CC2CCCCC2)cc(C(C)(C)C)n1] | ¹H-NMR (CDCl₃, 400 MHz) δ: 0.88-0.91 (2H, m), 1.05-1.09 (3H, m), 1.38 (18H, s), 1.51-1.62 (6H, m), 2.50 (4H, m), 2.58 (2H, t, J = 6.0 Hz), 2.65 (2H, d, J = 6.8 Hz), 3.55 (2H, t, J = 6.0 Hz), 3.70 (4H, m), 7.17 (2H, s), 7.30 (1H, br s). MS 544 (M + 1)⁺ |
| 104/4 | 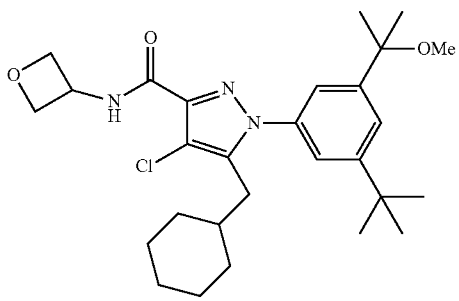 [SMILES: COC(C)(C)c1cc(-n2nc(C(=O)NC3COC3)c(Cl)c2CC2CCCCC2)cc(C(C)(C)C)c1] | ¹H-NMR (CDCl₃, 300 MHz) δ: 0.79-0.87 (2H, m), 0.99-1.05 (3H, m), 1.37 (9H, s), 1.40-1.48 (3H, m), 1.56 (6H, m), 1.58-1.62 (3H, m), 2.55 (2H, d, J = 7.2 Hz), 3.11 (3H, s), 4.62 (1H, t, J = 6.6 Hz), 4.97 (1H, t, J = 7.2 Hz), 5.25 (1H, m), 7.22 (1H, t, J = 1.8 Hz), 7.26 (1H, d, J = 1.8 Hz), 7.38 (1H, d, J = 8.1 Hz), 7.58 (1H, d, J = 1.8 Hz). MS 502 (M + 1)⁺ |

Example 105

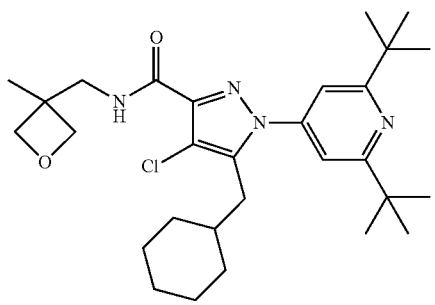

Step 1: Ethyl 4-cyclohexyl-3-oxobutanoate (105a)

1-Cyclohexylpropan-2-one (10.0 g, 71.3 mmol) and diethyl oxalate (10.5 g, 71.3 mmol) were mixed together and then added to a solution of NaOEt (78.4 mmol) which was made by dried EtOH (200 mL) and Na (1.8 g, 78.4 mmol) with stirring at 0° C. under N₂. After stirring for 15 min, the solution was warmed up to rt and stirred overnight, diluted with aq. NH₄Cl (200 mL) and extracted twice with EA. The combined organic phases were washed with brine, dried over Na₂SO₄, filtered, concentrated and purified by CC (PE/EA=20/1) to afford compound 105a (8.6 g, 57%) as a colorless oil.

Step 2: Ethyl 5-(cyclohexylmethyl)-1H-pyrazole-3-carboxylate (105b)

To a stirred solution of compound 105a (5.5 g, 25.9 mmol) in dry EtOH (50 mL) at 0° C. was added a solution of N₂H₄H₂O (1.3 g, 29.8 mmol) in EtOH (10 mL). The resulting solution was stirred at rt for 1 h, heated at reflux for 4 h, concentrated and purified by CC (PE/EA=6/1) to afford compound 105b (3.9 g, 64%) as a white solid.

Step 3: Ethyl 5-(cyclohexylmethyl)-1-(2,6-di-tert-butylpyridin-4-yl)-1H-pyrazole-3-carboxylate (105c)

A solution of compound 105b (2.7 g, 11.4 mmol), P10 (2.6 g, 17.2 mmol), Cu(OAc)₂ (3.1 g, 17.2 mmol) and pyridine (0.5 mL) in dry DMF (30 mL) was stirred at 85° C. overnight under N₂. The resulting solution was concentrated, diluted with water and extracted twice with DCM. The combined organic phases were washed with brine, dried over Na$_2$SO$_4$, filtered, concentrated and purified by CC (PE/EA=15/1) to give compound 105c (800 mg, 17%) as a white solid.

Step 4: Ethyl 4-chloro-5-(cyclohexylmethyl)-1-(2,6-di-tert-butylpyridin-4-yl)-1H-pyrazole-3-carboxylate (105d)

To a solution of compound 105c (400 mg, 0.95 mmol) in DCM (10 mL) was added dropwise SO$_2$Cl$_2$ (0.22 mL, 2.72 mmol). The solution was stirred at rt for 2 h, quenched with aq. NaHCO$_3$ and extracted with DCM. The organic phase was washed with brine, dried over Na$_2$SO$_4$, filtered, concentrated and purified by CC (PE/EA=20/1) to afford compound 105d (110 mg, 26%) as a white solid.

Step 5: 4-Chloro-5-(cyclohexylmethyl)-1-(2,6-di-tert-butylpyridin-4-yl)-1H-pyrazole-3-carboxylic acid (105e)

To a solution of compound 105d (100 mg, 0.24 mmol) in a mixture of THF (5 mL) and H$_2$O (2 mL) was added LiOH.H$_2$O (100 mg, 2.4 mmol) and the solution was stirred at 60° C. for 2 h. The solution was concentrated, the pH was adjusted to 2 with 2N HCl and the mixture was extracted with DCM. The organic phase was washed with brine, dried over Na$_2$SO$_4$, filtered, concentrated and purified by CC (PE/EA=10/1) to afford compound 105e (80 mg, 77%) as a white solid.

Step 6: 4-Chloro-5-(cyclohexylmethyl)-1-(2,6-di-tert-butylpyridin-4-yl)-N-((3-methyloxetan-3-yl)methyl)-1H-pyrazole-3-carboxamide (105)

A solution of compound 105e (80 mg, 0.185 mmol), HATU (90 mg, 0.236 mmol), DIPEA (33 mg, 0.236 mmol) and (3-methyloxetan-3-yl) methylamine (37 mg, 0.370 mmol) in DMF (5 mL) was stirred for 20 min at rt, diluted with H$_2$O and EA. The organic layer was washed with water (3×) and brine consecutively, dried over Na$_2$SO$_4$, filtered, concentrated and purified by prep-TLC to afford compound 105 (40 mg, 42%) as a white powder. $^1$H-NMR (400 MHz, CDCl$_3$) δ: 7.14 (s, 2H), 7.12-7.10 (m, 1H), 4.58 (d, J=6.0 Hz, 2H), 4.39 (d, J=6.0 Hz, 2H), 3.62 (d, J=6.0 Hz, 2H), 2.62 (d, J=7.6 Hz, 2H), 1.56-1.51 (m, 3H), 1.51 (s, 3H), 1.40-1.36 (m, 21H), 1.09-1.06 (m, 3H), 0.93-0.90 (m, 2H). A NOE was observed between cyclohexyl-CH$_2$ and pyridine-H. MS 515 (M+1)$^+$.

Example 106

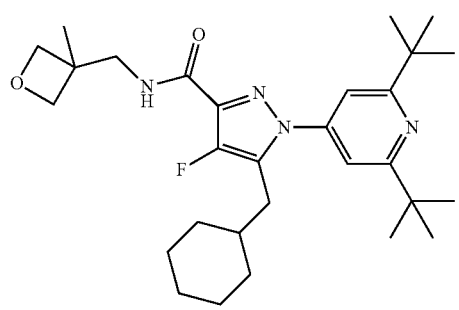

Step 1: Ethyl 5-(cyclohexylmethyl)-4-fluoro-1H-pyrazole-3-carboxylate (106a)

To a solution of compound 105b (1.0 g, 4.2 mmol) in MeCN (10 mL) was added Selectfluor (2.0 g, 5.7 mmol), and the solution was stirred overnight at rt. The formed solid was filtered off, the filtrate was concentrated and purified by CC (PE/EA=15/1) to give compound 106a (410 mg, 38%) as a yellow solid.

Step 2: 5-(Cyclohexylmethyl)-1-(2,6-di-tert-butylpyridin-4-yl)-4-fluoro-N-((3-methyloxetan-3-yl)methyl)-1H-pyrazole-3-carboxamide (106)

Example 106 was obtained from intermediate 106a following similar procedures as described for example 105. 1-HNMR (400 MHz, CDCl$_3$) δ: 7.15 (s, 2H), 6.99 (m, 1H), 4.58 (d, J=6.0 Hz, 2H), 4.40 (d, J=6.0 Hz, 2H), 3.63 (d, J=6.0 Hz, 2H), 2.58 (d, J=7.6 Hz, 2H), 1.64-1.54 (m, 6H), 1.42-1.38 (m, 21H), 1.15-1.11 (m, 3H), 0.93-0.90 (m, 2H). A NOE was observed between cyclohexyl-CH$_2$ and pyridine-H. MS 499 (M+1)$^+$.

Example 107

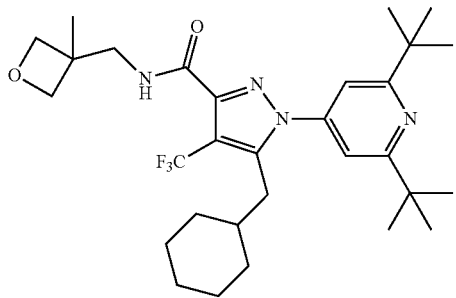

Step 1: Diethyl 4-(trifluoromethyl)-1H-pyrazole-3,5-dicarboxylate (107a)

To a solution of ethyl 4,4,4-trifluorobut-2-ynoate (2.0 g, 12 mmol) in dry Et$_2$O (30 mL) was added dropwise ethyl diazoacetate (1.4 g, 12 mmol) at 0° C. The solution was stirred at 0° C. for 15 min, then warmed to rt and stirred for further 13 h, concentrated and purified by CC (PE/EA=10/1) to afford compound 107a (2.0 g, 59%) as a white solid.

Step 2: 5-(Cyclohexylmethyl)-1-(2,6-di-tert-butylpyridin-4-yl)-N-((3-methyloxetan-3-yl)methyl)-4-(trifluoromethyl)-1H-pyrazole-3-carboxamide (107)

Example 107 was prepared from intermediate 107a using similar procedures as described for example 315 without pyrazole chlorination. $^1$H-NMR (300 MHz, CDCl$_3$) δ: 7.10 (s, 2H), 4.55 (d, J=6.0 Hz, 2H), 4.39 (d, J=6.0 Hz, 2H), 3.60 (d, J=6.6 Hz, 2H), 2.66 (d, J=7.5 Hz, 2H), 1.60-1.54 (m, 2H), 1.53-1.40 (m, 4H), 1.39-1.33 (m, 21H), 1.09-1.03 (m, 3H), 0.83-0.72 (m, 2H). A NOE effect was observed between cyclohexyl-CH$_2$ and pyridine-H. MS 549 (M+1)$^+$.

Example 108

Example 109

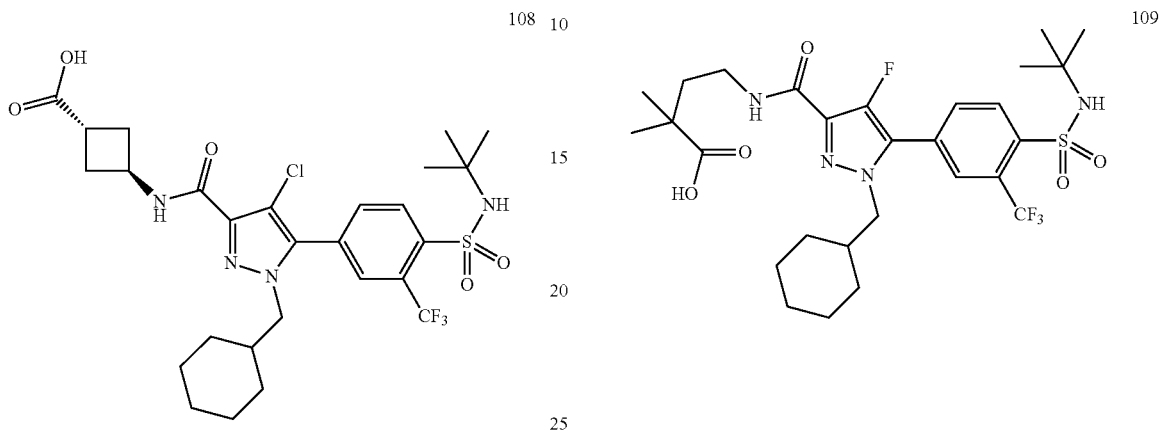

Step 1: trans-Methyl 3-(5-(4-(N-(tert-butyl)sulfamoyl)-3-(trifluoromethyl)phenyl)-4-chloro-1-(cyclohexylmethyl)-1H-pyrazole-3-carboxamido)cyclobutanecarboxylate (108a)

To a solution of the methyl ester of compound 100/6 (100 mg, 0.16 mmol) in MeCN (2 mL) was added a solution of NCS (22 mg, 0.16 mmol) in MeCN (1 mL) and the solution was stirred at 50° C. for 2 h, quenched with water and extracted with EA. The organic layer was washed with brine, dried over Na$_2$SO$_4$, filtered, concentrated and purified by CC (PE/EA=2/1) and then prep-TLC to give compound 108a (64 mg, 75%) as a white solid.

Step 2: trans-3-(5-(4-(N-(tert-Butyl)sulfamoyl)-3-(trifluoromethyl)phenyl)-4-chloro-1-(cyclohexylmethyl)-1H-pyrazole-3-carboxamido)cyclobutanecarboxylic acid (108)

To a solution of compound 108a (64 mg, 0.10 mmol) in a solution of MeOH (2 mL) and H$_2$O (1 mL) was added LiOH.H$_2$O (42 mg, 1.0 mmol) and the solution was stirred overnight at rt, concentrated, diluted with H$_2$O, adjusted to pH=5 with 1N HCl and extracted with DCM. The organic layer was washed with brine, dried over Na$_2$SO$_4$, filtered, concentrated and purified by prep-TLC to give compound 108 (45 mg, 72%) as a white solid. $^1$H-NMR (300 MHz, CDCl$_3$) δ: 0.75-0.84 (m, 2H), 1.08-1.14 (m, 3H), 1.18-1.27 (m, 13H), 1.45-1.49 (m, 2H), 1.64-1.66 (m, 3H), 1.79-1.85 (m, 1H), 2.43-2.53 (m, 2H), 2.79-2.87 (m, 2H), 3.17-3.23 (m, 1H), 3.89 (d, J=7.5 Hz, 2H), 4.75-4.84 (m, 2H), 7.05 (d, J=7.8 Hz, 1H), 7.73 (dd, J=8.1, 1.5 Hz, 1H), 7.85 (s, 1H), 8.47 (d, J=8.1 Hz, 1H). MS 617.2 (M−1)$^−$.

Step 1: Methyl 4-(5-(4-(N-(tert-butyl)sulfamoyl)-3-(trifluoromethyl)phenyl)-1-(cyclohexylmethyl)-4-fluoro-1H-pyrazole-3-carboxamido)-2,2-dimethylbutanoate (109a)

To a solution of the methyl ester of compound 100/7 (230 mg, 0.37 mmol) in MeCN (5 mL) was added Selectfluor (400 mg, 1.12 mmol) at rt and then the solution was stirred for 4 h at 90° C. A second batch of Selectfluor (260 mg, 0.75 mmol) was added and the solution was stirred at 90° C. for 2 h again, quenched with water and extracted with EA twice. The combined organic layers were washed with water and brine, dried with Na$_2$SO$_4$, filtered, concentrated and purified by prep-TLC to give crude compound 109a (110 mg, with 30% starting material) as a yellow solid.

Step 2: 4-(5-(4-(N-(tert-Butyl)sulfamoyl)-3-(trifluoromethyl)phenyl)-1-(cyclohexylmethyl)-4-fluoro-1H-pyrazole-3-carboxamido)-2,2-dimethylbutanoic acid (109)

To a solution of compound 109a (110 mg) in a mixture of MeOH (4 mL) and H$_2$O (0.5 mL) was added KOH (22 mg, 0.52 mmol) and the solution was stirred at 80° C. for 1 h, concentrated, adjusted with 1N HCl to pH=6 and extracted with EA twice. The combined organic layers were washed with brine, dried over Na$_2$SO$_4$, filtered, concentrated and purified by SFC to give compound 109 (50 mg, 39% over two steps) as a white solid. $^1$H NMR (400 MHz, CDCl$_3$) δ: 0.76-0.84 (m, 2H), 1.07-1.20 (m, 3H), 1.26-1.30 (m, 16H), 1.45-1.48 (m, 2H), 1.60-1.64 (m, 2H), 1.79-1.81 (m, 1H), 1.92-1.96 (m, 2H), 3.49-3.54 (m, 2H), 3.90 (d, J=7.2 Hz, 2H), 4.78 (s, 1H), 6.79 (t, J=5.2 Hz, 1H), 7.73 (d, J=8.4 Hz, 1H), 7.86 (s, 1H), 8.44 (d, J=8.0 Hz, 1H). MS 619.2 (M+1)$^+$.

Example 110

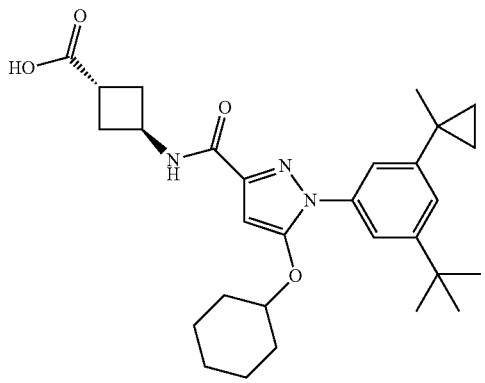

Step 1: Ethyl 5-(cyclohexyloxy)-1H-pyrazole-3-carboxylate (110a)

To the stirred suspension of ethyl 5-hydroxy-1H-pyrazole-3-carboxylate (7.00 g, 45.0 mmol) and K₂CO₃ (24.9 g, 180 mmol) in ACN (500 mL) was added cyclohexyl chloride (5.34 g, 45.0 mmol) and the suspension was refluxed for 16 h, cooled to rt, filtered and the solid was washed with ACN. The combined filtrates were concentrated and purified by CC (PE/EA=2/1) to give compound 110a (8.36 g, 78%) as a white solid. A NOE between cyclohexyl-H and pyrazole-H was observed by NOE spectrum.

Step 2: Ethyl 1-(3-(tert-butyl)-5-(1-methylcyclopropyl)phenyl)-5-(cyclohexyloxy)-1H-pyrazole-3-carboxylate (110b)

A suspension of compound 110a (7.50 g, 31.5 mmol), 2-(3-(tert-butyl)-5-(1-methylcyclopropyl)phenyl)-4,4,5,5-tetramethyl-1,3,2-dioxaborolane (15.7 g, 50.0 mmol), pyridine (3.16 g, 40 mmol) and Cu(OAc)₂ (9.98 g, 50 mmol) in DMF (200 mL) was stirred at 40° C. under N₂ for 36 h, cooled to rt and the solid was filtered off. The filtrate was concentrated and purified by CC (PE/EA=3/1) to give compound 110b (2.45 g, 18%) as a pale yellow solid.

Step 3: Potassium 1-(3-(tert-butyl)-5-(1-methylcyclopropyl)phenyl)-5-(cyclohexyloxy)-1H-pyrazole-3-carboxylate (110c)

To a solution of compound 110b (187 mg, 0.44 mmol) in a solution of MeOH (5 mL) and H₂O (0.5 mL) was added KOH (28 mg, 0.50 mmol) and then the solution was stirred at rt for 4 h. The resulting solution was concentrated to give crude compound 110c (190 mg) as a pale yellow solid.

Step 4: trans-3-(1-(3-(tert-Butyl)-5-(1-methylcyclopropyl)phenyl)-5-(cyclohexyloxy)-1H-pyrazole-3-carboxamido)cyclobutanecarboxylic acid (110)

To a solution of compound 110c (190 mg, 0.44 mmol) and DIEA (115 mg, 0.89 mmol) in DMF (6 mL) was added trans-3-aminocyclobutanecarboxylic acid (72 mg, 0.44 mmol) and HATU (168 mg, 0.44 mmol) at 0° C. under N₂ and the solution was stirred at rt for 4 h, diluted with water and extracted with EA (3×). The combined organic layers were washed with water (3×) and brine consecutively, dried over Na₂SO₄, filtered, concentrated and purified by prep-HPLC to give compound 110 (70 mg, 32% over two steps) as a white solid. $^1$H-NMR (CDCl₃, 300 MHz) δ: 0.74-0.78 (m, 2H), 0.89-0.92 (m, 2H), 1.25-1.41 (m, 12H), 1.44 (s, 3H), 1.53-1.79 (m, 5H), 1.96-2.02 (m, 2H), 2.34-2.45 (m, 2H), 2.75-2.83 (m, 2H), 3.09-3.15 (m, 1H), 4.26-4.31 (m, 1H), 4.79-4.86 (m, 1H), 6.21 (s, 1H), 7.28 (t, J=1.8 Hz, 1H), 7.37 (t, J=1.8 Hz, 1H), 7.48 (t, J=1.8 Hz, 1H). MS 494.3 (M+1)⁺.

Example 111

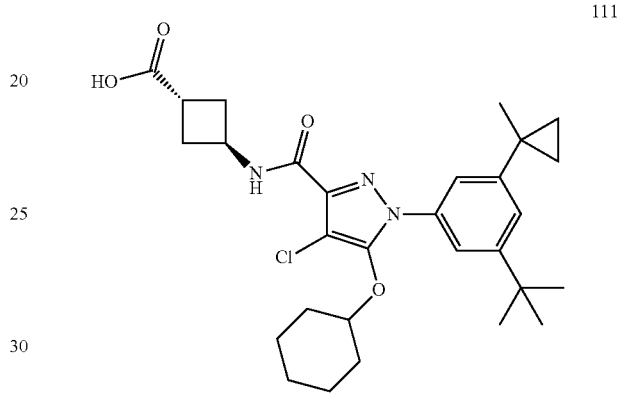

Step 1: Ethyl 1-(3-(tert-butyl)-5-(1-methylcyclopropyl)phenyl)-4-chloro-5-(cyclohexyloxy)-1H-pyrazole-3-carboxylate (111a)

To a solution of compound 110b (1.00 g, 2.36 mmol) in DMF (15 mL) at 0° C. was added NCS (446 mg, 3.43 mmol) portionwise and the solution was stirred at 55° C. for overnight, cooled to rt, quenched with water and extracted with EA twice. The combined organic layers were washed with brine, dried over Na₂SO₄, filtered, concentrated and purified by CC (PE/EA=3/1) to give compound 111a (990 mg, 91%) as a white solid.

Step 2: trans-3-(1-(3-(tert-Butyl)-5-(1-methylcyclopropyl)phenyl)-4-chloro-5-(cyclohexyloxy)-1H-pyrazole-3-carboxamido)cyclobutanecarboxylic acid (111)

Compound 111a was treated as described in Example 110, Step 3 and 4 to give compound 111 (36 mg, 16% over two steps) as a white solid. $^1$H-NMR (CDCl₃, 300 MHz) δ: 0.76-0.79 (m, 2H), 0.88-0.91 (m, 2H), 1.16-1.25 (m, 3H), 1.35 (s, 9H), 1.44 (s, 6H), 1.52-1.64 (m, 2H), 1.78-1.82 (m, 2H), 2.38-2.49 (m, 2H), 2.73-2.82 (m, 2H), 3.09-3.20 (m, 1H), 4.40-4.48 (m, 1H), 4.69-4.81 (m, 1H), 7.10 (d, J=7.2 Hz, 1H), 7.29 (t, J=1.8 Hz, 1H), 7.31 (t, J=1.8 Hz, 1H), 7.39 (t, J=1.8 Hz, 1H). MS 528.3 [M+1]+.

Example 111/1

The following Example was prepared similar as described for Example 111:

| # | Structure | Analytical data |
|---|---|---|
| 111/1 | 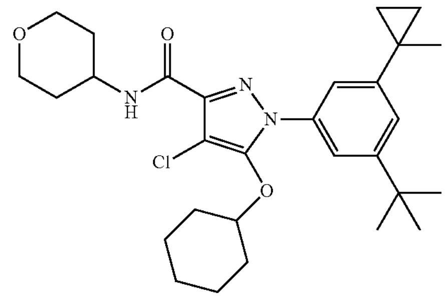 [SMILES: CC(C)(C)c1cc(-n2nc(C(=O)NC3CCOCC3)c(Cl)c2OC2CCCCC2)cc(C2(C)CC2)c1] | $^1$H-NMR (CDCl$_3$, 300 MHz) δ: 0.76-0.79 (m, 2H), 0.88-0.91 (m, 2H), 1.17-1.24 (m, 3H), 1.35 (s, 9H), 1.44 (s, 6H), 1.55-1.63 (m, 4H), 1.76-1.84 (m, 2H), 1.97-2.03 (m, 2H), 3.52 (td, J = 12.0 Hz, 2.4 Hz, 2H), 3.96-4.02 (m, 2H), 4.14-4.24 (m, 1H), 4.39-4.49 (m, 1H), 6.80 (d, J = 11.6 Hz, 1H), 7.29 (t, J = 1.8 Hz, 1H), 7.31 (t, J = 1.8 Hz, 1H), 7.40 (t, J = 1.8 Hz, 1H). MS 514.3 (M + 1)$^+$ |

Example 112

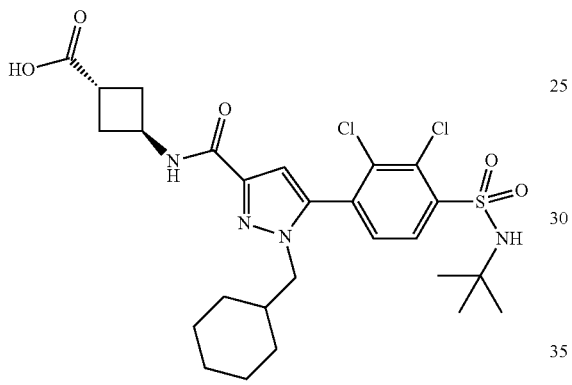

Step 1: 4-Acetyl-N-(tert-butyl)-2,3-dichlorobenzenesulfonamide (112a)

A mixture of 4-bromo-N-(tert-butyl)-2,3-dichlorobenzenesulfonamide (2.04 g, 5.65 mmol), tri(o-tolyl)phosphine (345 mg, 1.13 mmol) and TEA (2 g, 19.8 mmol) in ACN (20 mL) was bubbled with N$_2$ for 10 min and then Pd(OAc)$_2$ (125 mg, 0.57 mmol) and 1-(vinyloxy)butane (680 mg, 6.78 mmol) were added. The mixture was stirred at 80° C. for 16 h under N$_2$, cooled to rt, diluted with 2N HCl, stirred for 1 h at rt, extracted with EA, washed with brine, dried over Na$_2$SO$_4$, filtered, concentrated and purified by CC (EA/PE=1/4) to give compound 112a (730 mg, 40%) as a white solid.

Step 2: Ethyl 4-(4-(N-(tert-butyl)sulfamoyl)-2,3-dichlorophenyl)-2,4-dioxobutanoate (112b)

Na (63 mg, 2.72 mmol) was slowly added to dry EtOH (20 mL) at rt. After the Na was dissolved, the solution was added to a solution of compound 112a (730 mg, 2.26 mmol) in EtOH (30 mL) under cooling with an ice-bath and stirred for further 1 h. Diethyl oxalate (400 mg, 2.72 mmol) was added and the mixture was stirred overnight at rt, concentrated, diluted with EA and washed it with 1N HCl. The organic layer was washed with water (3×) and brine consecutively, dried over Na$_2$SO$_4$, filtered and concentrated to give compound 112b (850 mg, 89%) as yellow oil.

Step 3: Ethyl 5-(4-(N-(tert-butyl)sulfamoyl)-2,3-dichlorophenyl)-1-(cyclohexylmethyl)-1H-pyrazole-3-carboxylate (112c)

To a solution of compound 112b (850 mg, 2.0 mmol) in EtOH (5 mL) was added (cyclohexylmethyl)hydrazine (347 mg, 2.1 mmol) and conc. HCl (0.2 mL) in one portion. The mixture was stirred overnight at rt, concentrated, diluted with water and EA, adjusted to pH=7-8 with sat. NaHCO$_3$ solution, washed with water and brine, dried over Na$_2$SO$_4$, filtered, concentrated and purified by prep-TLC (EA/PE=1/4) to give compound 112c (680 mg, 66%) as white solid.

Step 4: trans-3-(5-(4-(N-(tert-Butyl)sulfamoyl)-2,3-dichlorophenyl)-1-(cyclohexylmethyl)-1H-pyrazole-3-carboxamido)cyclobutanecarboxylic acid (112)

Compound 112c was saponified and coupled with the amine similar as described in Example 100 to give compound 112 as a white solid. $^1$H-NMR (400 MHz, CD$_3$OD) δ: 0.78-0.84 (m, 2H), 1.09-1.22 (m, 3H), 1.25 (s, 9H), 1.44-1.48 (m, 2H), 1.60-1.63 (m, 3H), 1.77-1.82 (m, 1H), 2.45-2.53 (m, 2H), 2.63-2.68 (m, 2H), 3.07-3.12 (m, 1H), 3.89 (d, J=6.8 Hz, 2H), 4.74-4.78 (m, 1H), 6.85 (s, 1H), 7.60 (d, J=8.0 Hz, 1H), 8.22 (d, J=8.0 Hz, 1H). MS 585.2 [M+1]$^+$.

Example 112/1 to 112/2

The following Example was prepared similar as described for Example 112:

| # | Structure | Analytical data |
|---|---|---|
| 112/1 | 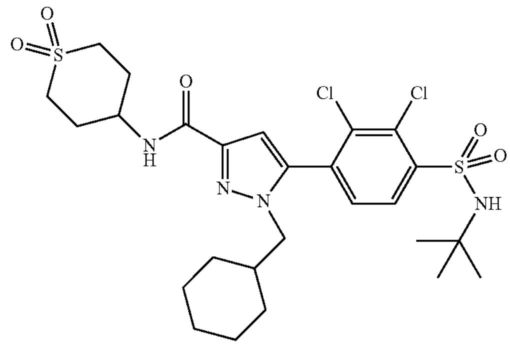 [SMILES: CC(C)(C)NS(=O)(=O)c1ccc(-c2cc(C(=O)NC3CCS(=O)(=O)CC3)nn2CC2CCCCC2)c(Cl)c1Cl] | ¹H-NMR (400 MHz, DMSO-d₆) δ: 0.69-0.75 (m, 2H), 1.01-1.10 (m, 3H), 1.15 (s, 9H), 1.33-1.36 (m, 2H), 1.50-1.52 (m, 3H), 1.65-1.70 (m, 1H), 1.99-2.20 (m, 4H), 3.05-3.10 (m, 2H), 3.28-3.39 (m, 2H), 3.78-3.82 (m, 2H), 4.17-4.21 (m, 1H), 6.86 (s, 1H), 7.67 (d, J = 8.4 Hz, 1H), 8.05 (s, 1H), 8.12 (d, J = 8.0 Hz, 1H), 8.34 (d, J = 8.8 Hz, 1H). MS 619.3 [M + 1]⁺ |
| 112/2 | 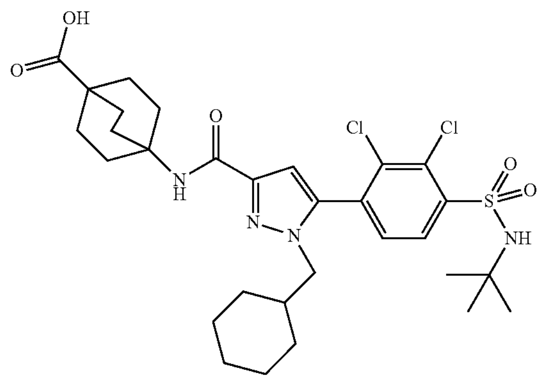 [SMILES: CC(C)(C)NS(=O)(=O)c1ccc(-c2cc(C(=O)NC34CCC(C(=O)O)(CC3)CC4)nn2CC2CCCCC2)c(Cl)c1Cl] | ¹H-NMR (400 MHz, DMSO-d₆) δ: 0.64-0.73 (m, 2H), 0.85-1.09 (m, 3H), 1.14 (s, 9H), 1.23-1.34 (m, 2H), 1.48-1.51 (m, 3H), 1.60-1.64 (m, 1H), 1.79-1.81 (m, 6H), 1.93-1.99 (m, 6H), 3.79 (d, J = 6.4 Hz, 2H), 6.80 (s, 1H), 7.16 (s, 1H), 7.66 (d, J = 8.4 Hz, 1H), 8.06 (s, 1H), 8.11 (d, J = 8.0 Hz, 1H). MS 639.3 [M + 1]⁺ |

Example 113

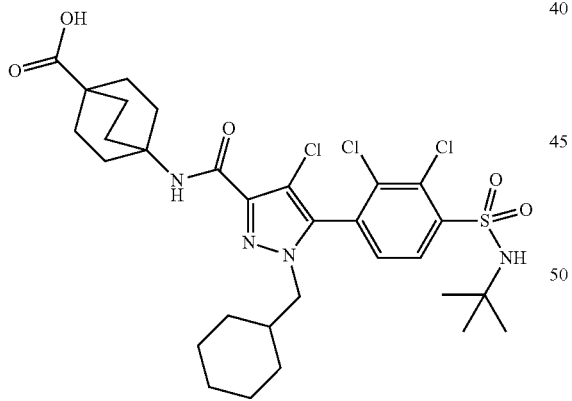

113

Step 1: Ethyl 5-(4-(N-(tert-butyl)sulfamoyl)-2,3-dichlorophenyl)-4-chloro-1-(cyclohexylmethyl)-1H-pyrazole-3-carboxylate (113a)

To a solution of compound 112c (150 mg, 0.291 mmol) in ACN (10 mL) was added NCS (200 mg, 1.50 mmol) at rt. The solution was stirred overnight at 80° C., cooled, concentrated under and purified by prep-TLC to give compound 113a (150 mg, 94%) as a white solid.

Step 2: 4-(5-(4-(N-(tert-Butyl)sulfamoyl)-2,3-dichlorophenyl)-4-chloro-1-(cyclohexylmethyl)-1H-pyrazole-3-carboxamido)bicyclo[2.2.2]octane-1-carboxylic acid (113)

Compound 113a was saponified and coupled with the appropriate amine similar as described in Example 100 to give compound 113 as a white solid. ¹H-NMR (400 MHz, DMSO-d₆) δ: 0.71-0.78 (m, 2H), 0.99-1.08 (m, 3H), 1.15 (s, 9H), 1.30-1.42 (m, 2H), 1.51-1.63 (m, 4H), 1.77-1.80 (m, 6H), 1.93-1.97 (m, 6H), 3.67-3.73 (m, 1H), 3.87-3.92 (m, 1H), 7.31 (s, 1H), 7.71 (d, J=8.4 Hz, 1H), 8.10 (s, 1H), 8.17 (d, J=8.4 Hz, 1H), 12.09 (br s, 1H). MS 673.2 [M+1]⁺.

Example 114

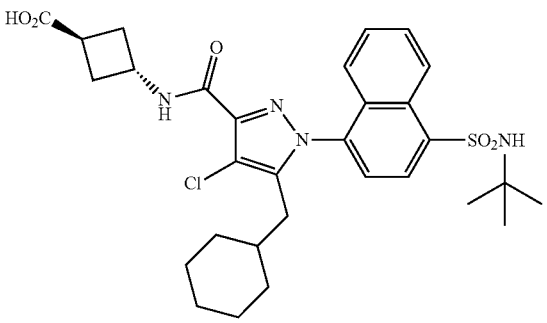

114

Step 1: N-(tert-Butyl)-4-hydrazinylnaphthalene-1-sulfonamide (114a)

A solution of 4-bromo-N-(tert-butyl)naphthalene-1-sulfonamide (1.0 g, 2.93 mmol) and 85% hydrazine hydrate (1 mL) in methoxyl ethanol (10 mL) was heated under reflux for 3 h, cooled to rt, concentrated and purified by CC (PE/EA=5/1) to give compound 114a as a white solid (300 mg, 35%).

Step 2: Ethyl 5-cyclohexyl-2,4-dioxopentanoate (114b)

Sodium hydride (223 mg, 9.28 mmol) was added slowly with stirring under $N_2$ to NaCl/ice bath-cooled EtOH (10 mL). 1-Cyclohexylpropan-2-one (1.0 g, 7.14 mmol) and diethyloxalate (1.04 g, 7.14 mmol) were mixed together and then added to the cold NaOEt solution. After stirring for 5 min. the reaction was warmed to rt. After 10 min. the reaction solidified and an additional 10 mL EtOH was added. After stirring for 5 h, the reaction was quenched at 0° C. with 1N HCl and extracted with DCM. The combined organic layers were washed with $H_2O$, dried with $Na_2SO_4$, filtered, concentrated and purified by CC (PE/EA=5:1) to obtain compound 114b (1.0 g, 59%) as a yellow oil.

Step 3: Ethyl 1-(4-(N-(tert-butyl)sulfamoyl)naphthalen-1-yl)-5-(cyclohexylmethyl)-1H-pyrazole-3-carboxylate (114c)

A solution of 114a (200 mg, 0.68 mmol) and 114b (196 mg, 0.82 mmol) in acetic acid (10 mL) was refluxed for 16 h, cooled to rt and the solvent was removed. The residue was partitioned between EA and $H_2O$. The organic layer was washed with water, saturated bicarbonate and brine, and dried over $Na_2SO_4$, filtered and concentrated. The crude material was purified by CC (PE/EA=5:1) to give compound 114c (200 mg, 59%) as a syrup.

Step 4: Ethyl 1-(4-(N-(tert-butyl)sulfamoyl)naphthalen-1-yl)-4-chloro-5-(cyclohexylmethyl)-1H-pyrazole-3-carboxylate (114d)

To a solution of compound 114c (200 mg, 0.4 mmol) in DCM (10 mL) at 0° C. was added $SO_2Cl_2$ (38.8 µL, 0.48 mmol). The mixture was allowed to warm to rt and stirred at rt for 5 h, washed with saturated aq. $Na_2CO_3$ (4×30 mL), the organic phase was dried ($Na_2SO_4$) and concentrated to give compound 114d (200 mg, 94%) as a yellow oil.

Step 5: 1-(4-(N-(tert-Butyl)sulfamoyl)naphthalen-1-yl)-4-chloro-5-(cyclohexylmethyl)-1H-pyrazole-3-carboxylic acid (114e)

To a solution of compound 114d (100 mg, 0.23 mmol) in MeOH (10 mL) was added 4M NaOH (18.4 mg, 0.46 mmol) at rt. The resulting solution was stirred at rt for 1 h, then warmed to reflux for additional 5 h. Water (50 mL) was added, then acidified by 2N HCl and extracted with EA (50 mL×3). The combined EA phases were concentrated to give compound 114e (80 mg, 84%) as a colorless solid.

Step 6: (trans)-Methyl 3-(1-(4-(N-(tert-butyl)sulfamoyl)naphthalen-1-yl)-4-chloro-5-(cyclohexyl-methyl)-1H-pyrazole-3-carboxamido)cyclobutanecarboxylate (114f)

To a solution of compound 114e (100 mg, 0.2 mmol) in DMF (5 mL) at rt under $N_2$ was added HATU (91.2 mg, 0.24 mmol) and DIPEA (66 µL, 0.4 mmol) and the resulting solution was stirred at rt for 45 min. Then (trans)-methyl 3-aminocyclobutanecarboxylate (33 mg, 0.2 mmol) was added and stirring was continued for additional 2 h. Water (50 mL) was added and the mixture was extracted with EA (50 mL×3). The combined EA layers were concentrated to give crude compound 114f (100 mg, 84%) as a yellow oil.

Step 7: (trans)-3-(1-(4-(N-(tert-Butyl)sulfamoyl)naphthalen-1-yl)-4-chloro-5-(cyclohexyl-methyl)-1H-pyrazole-3-carboxamido)cyclobutanecarboxylic acid (114)

To a solution of compound 114f (100 mg, 0.16 mmol) in MeOH (5 mL) was added 4N NaOH (12.8 mg, 0.32 mmol) at rt. The resulting solution was stirred at this temperature for 1 h and then warmed to reflux for additional 5 h. Water (50 mL) was added, then acidified by 2N aq. HCl and extracted with EA (50 mL×3). The combined organic phases were concentrated to give the crude product, which was purified by prep-HPLC to afford compound 114 (25 mg, 26%) as a white solid. $^1$H-NMR (400 MHz, CDCl$_3$) δ: 8.74 (d, 1H, J=8.8 Hz), 8.48 (d, 1H, J=8.0 Hz), 8.80-8.78 (t, 1H, J=7.6 Hz) 7.68-7.65 (t, 1H, J=8.0 Hz), 7.59 (d, 1H, J=7.6 Hz) 7.04 (d, 1H, J=7.6 Hz), 4.78-4.74 (m, 1H), 4.71 (s, 1H), 3.15-3.11 (m, 1H), 2.80-2.74 (m, 2H), 2.46-2.38 (m, 3H), 2.28-2.25 (m, 1H), 1.53 (m, 4H), 1.43 (m, 2H), 1.24 (s, 9H), 0.97-0.92 (m, 3H), 0.74-0.71 (m, 2H). MS 601.3 (M+1)$^+$.

Example 114/1

The following example was prepared similar to example 114.

| # | Structure | Analytical data |
|---|---|---|
| 114/1 | (structure shown) | $^1$H-NMR (400 MHz, CDCl$_3$) δ: 8.75 (d, 1H, J = 8.8 Hz), 8.49 (d, 1H, J = 7.6 Hz), 7.82-7.78 (t, 1H, J = 7.2 Hz), 7.68-7.64 (t, 1H, J = 7.2 Hz), 7.59 (d, 1H, J = 7.6 Hz), 6.83 (d, 1H, J = 8.0 Hz), 4.69 (s, 1H), 4.31-4.26 (m, 1H), 3.19-3.08 (m, 4H), 2.44-2.20 (m, 5H), 1.59-1.54 (m, 4H), 1.43-1.40 (m, 2H), 1.24 (s, 9H), 0.99-0.91 (m, 3H), 0.78-0.72 (m, 2H). MS 635.2 (M + 1)$^+$ |

Additional Examples
The following compounds can be prepared in the same manner by using the procedures as described above:
| Structure |
| --- |
| 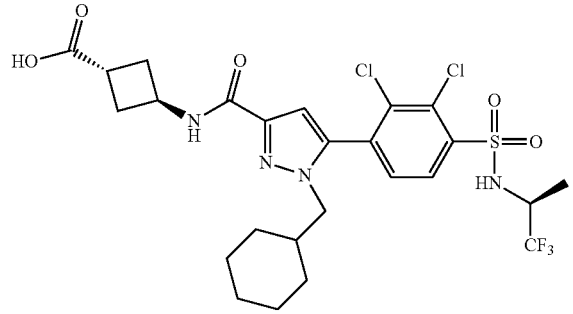 [SMILES: C[C@H](NS(=O)(=O)c1ccc(-c2cc(C(=O)N[C@H]3C[C@H](C(=O)O)C3)nn2CC2CCCCC2)c(Cl)c1Cl)C(F)(F)F] |
| 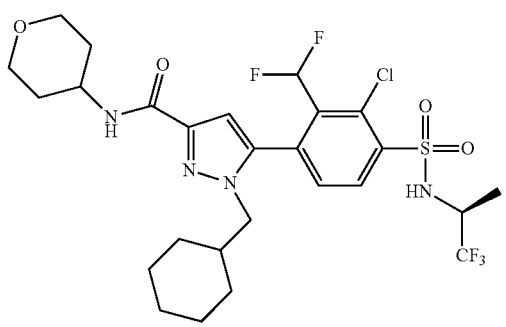 [SMILES: C[C@H](NS(=O)(=O)c1ccc(-c2cc(C(=O)NC3CCOCC3)nn2CC2CCCCC2)c(C(F)F)c1Cl)C(F)(F)F] |
| 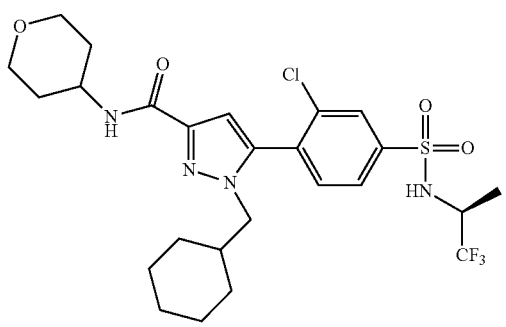 [SMILES: C[C@H](NS(=O)(=O)c1ccc(-c2cc(C(=O)NC3CCOCC3)nn2CC2CCCCC2)c(Cl)c1)C(F)(F)F] |
| 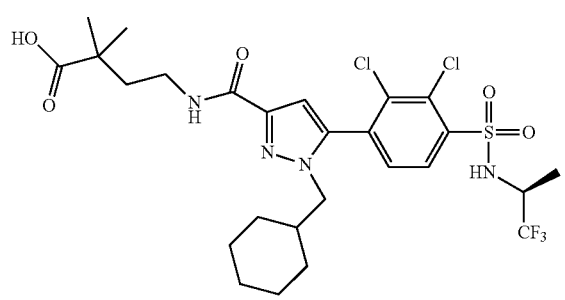 [SMILES: C[C@H](NS(=O)(=O)c1ccc(-c2cc(C(=O)NCCC(C)(C)C(=O)O)nn2CC2CCCCC2)c(Cl)c1Cl)C(F)(F)F] |
-continued
| Structure |
| --- |
| 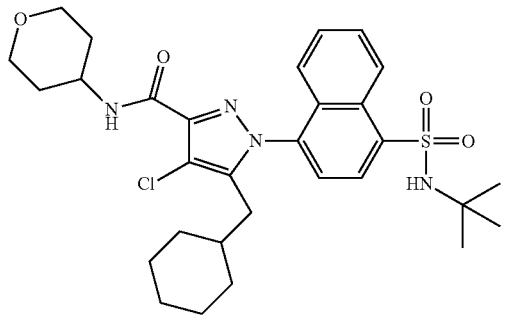 [SMILES: CC(C)(C)NS(=O)(=O)c1ccc(-n2nc(C(=O)NC3CCOCC3)c(Cl)c2CC2CCCCC2)c2ccccc12] |
| 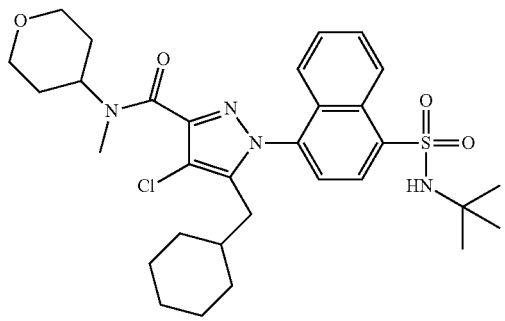 [SMILES: CN(C(=O)c1nn(-c2ccc(S(=O)(=O)NC(C)(C)C)c3ccccc23)c(CC2CCCCC2)c1Cl)C1CCOCC1] |
| 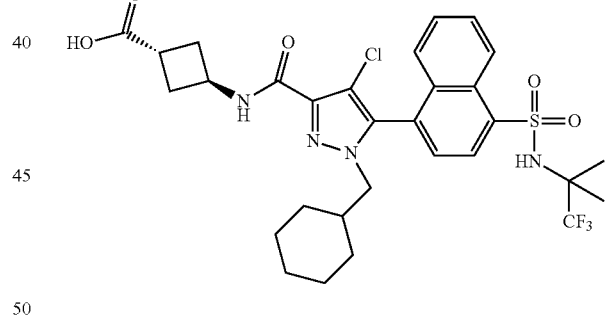 |
| 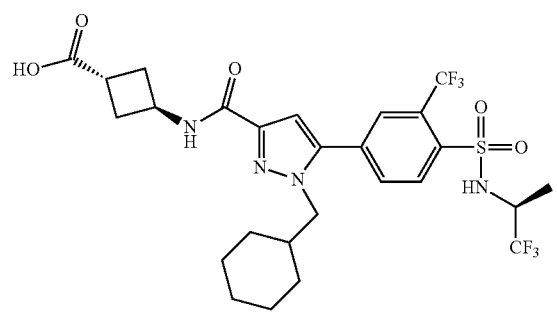 [SMILES: C[C@H](NS(=O)(=O)c1ccc(-c2cc(C(=O)N[C@H]3C[C@H](C(=O)O)C3)nn2CC2CCCCC2)cc1C(F)(F)F)C(F)(F)F] |

203
-continued

Structure

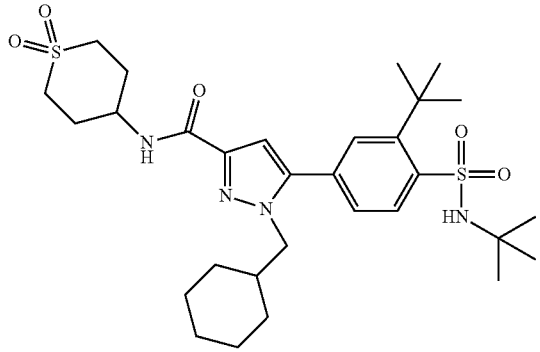 [SMILES: CC(C)(C)NS(=O)(=O)c1ccc(-c2cc(C(=O)NC3CCS(=O)(=O)CC3)nn2CC2CCCCC2)cc1C(C)(C)C]

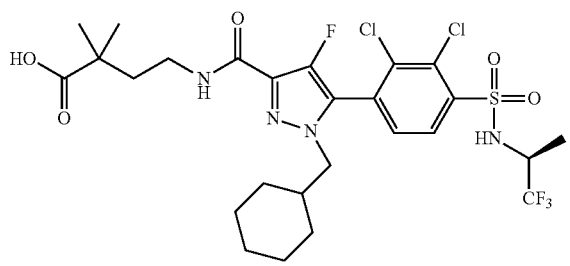 [SMILES: C[C@H](NS(=O)(=O)c1ccc(-c2c(F)c(C(=O)NCCC(C)(C)C(=O)O)nn2CC2CCCCC2)c(Cl)c1Cl)C(F)(F)F]

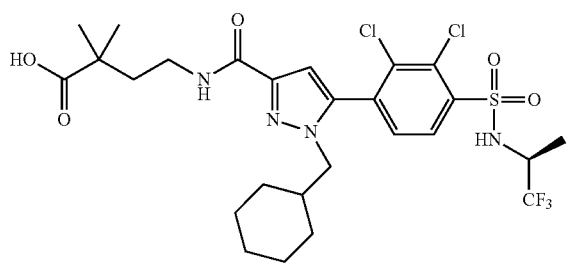 [SMILES: C[C@H](NS(=O)(=O)c1ccc(-c2cc(C(=O)NCCC(C)(C)C(=O)O)nn2CC2CCCCC2)c(Cl)c1Cl)C(F)(F)F]

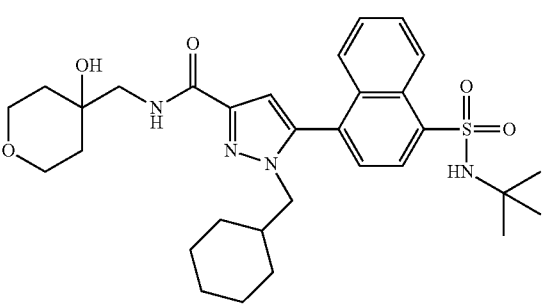 [SMILES: CC(C)(C)NS(=O)(=O)c1ccc(-c2cc(C(=O)NCC3(O)CCOCC3)nn2CC2CCCCC2)c2ccccc12]

204
Example 300 and Example 301

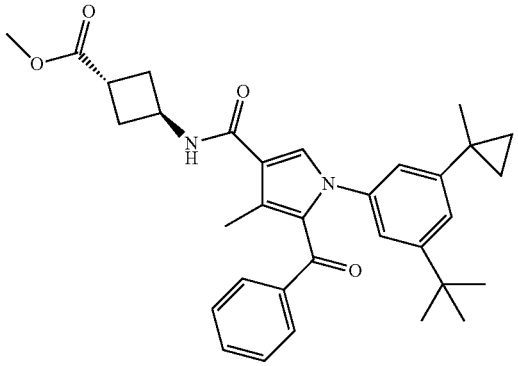

300

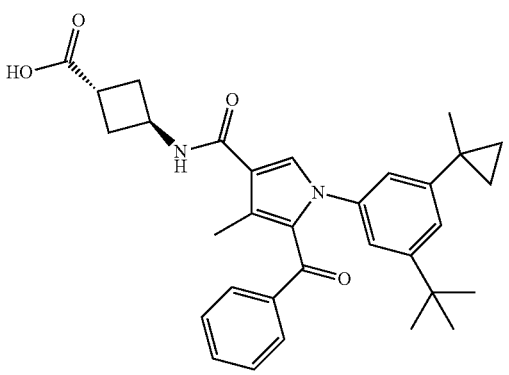

301

Step 1: Ethyl 5-formyl-4-methyl-1-((2-(trimethylsilylethoxy)methyl)-1H-pyrrole-3-carboxylate (300a)

To a solution of compound 5a (9.0 g, 50 mmol) in DMF (80 mL) was added NaH (60%, 2.6 g, 65 mmol) in portions at 0° C. and the solution was stirred at rt for 1 h, SEMCl (10.0 g, 60 mmol) was added dropwise, then heated at 30° C. for 1 h, poured into sat. NH$_4$Cl and extracted with EA. The organic layer was washed with brine, dried over Na$_2$SO$_4$, filtered, concentrated and purified by CC (PE/EA=25/1) to give compound 300a (13.2 g, 85%) as a yellow oil.

Step 2: Ethyl 5-(hydroxy(phenyl)methyl)-4-methyl-4-((2-(trimethylsilylethoxy)methyl)-1H-pyrrole-3-carboxylate (300b)

To a solution of compound 300a (3.81 g, 12.2 mmol) in dry THF (150 mL) was added PhMgBr (1M solution in THF, 14.7 mL) at 0° C. and the solution was stirred at rt for 2 h, quenched with sat. NH$_4$Cl and extracted with EA. The organic layer was washed with water and brine consecutively, dried by Na$_2$SO$_4$, filtered and concentrated to give crude compound 300b (6.11 g) as a yellow oil.

Step 3: Ethyl 5-benzoyl-4-methyl-1-((2-(trimethylsilylethoxy)methyl)-1H-pyrrole-3-carboxylate (300c)

To a solution of compound 300b (6.11 g, 15.7 mmol) in DCM (200 mL) was added Dess-Martin periodinane (13.0 g, 30.6 mmol) and the solution was stirred at rt for 2 h, diluted with sat. NaHCO₃ and extracted with DCM. The organic layer was washed with water and brine consecutively, dried with Na₂SO₄, filtered, concentrated and purified by CC (PE/EA=50/1) to give compound 300c (3.52 g, 58% over two steps) as a yellow oil.

Step 4: Ethyl 5-benzoyl-4-methyl-1H-pyrrole-3-carboxylate (300d)

Compound 300c (3.52 g, 9.08 mmol) was dissolved in a solution of TBAF (1M in THF, 120 mL) and the solution was refluxed overnight, cooled to rt, quenched with sat. NH₄Cl and extracted with EA. The organic layer was washed by water and brine consecutively, dried over Na₂SO₄, filtered, concentrated and purified by CC (PE/EA=25/1) to give compound 300d (2.10 g, 90%) as a white solid.

Step 5: Ethyl 5-benzoyl-1-(3-(tert-butyl)-5-(1-methylcyclopropyl)phenyl)-4-methyl-1H-pyrrole-3-carboxylate (300e)

Compound 300d (350 mg, 1.36 mmol), compound P2b (400 mg, 1.50 mmol), (1R,2R)-1N,2N-dimethylcyclohexane-1,2-diamine (197 mg, 1.36 mmol), CuI (259 mg, 1.36 mmol), K₃PO₄ (577 mg, 2.72 mmol) was added to toluene (30 mL) and the suspension was refluxed for 48 h under N₂, filtered and the cake was washed with EA. The combined filtrates were washed with water and brine consecutively, dried by Na₂SO₄, filtered, concentrated and purified by CC (PE/EA=50/1) to give compound 300e (190 mg, 32%) as a white solid.

Step 6: 5-Benzoyl-1-(3-(tert-butyl)-5-(1-methylcyclopropyl)phenyl)-4-methyl-1H-pyrrole-3-carboxylic acid (300f)

The solution of compound 300e (190 mg, 428 μmol) and t-BuOK (576 mg, 5.14 mmol) in a mixture of DMSO (3.5 mL) and H₂O (0.5 mL) was stirred at 90° C. overnight, cooled to 0° C., diluted with water, adjusted to pH=5 with conc. HCl and extracted with EA (3×). The combined organic layers were washed with water (3×) and brine consecutively, dried over Na₂SO₄, filtered and concentrated to give compound 300f (150 mg, 84%) as a pale yellow solid.

Step 7: (trans)-Methyl 3-(5-benzoyl-1-(3-(tert-butyl)-5-(1-methylcyclopropyl)phenyl)-4-methyl-1H-pyrrole-3-carboxamido)cyclobutanecarboxylate (300)

The solution of compound 300f (150 mg, 0.36 mmol), trans methyl 3-aminocyclobutane carboxylate HCl salt (66 mg, 0.40 mmol), HATU (206 mg, 0.54 mmol) and DIPEA (140 mg, 1.08 mmol) in DMF (5 mL) was stirred at rt overnight, quenched with water and extracted with EA twice. The combined organic layers were washed by water (3×) and brine consecutively, dried over Na₂SO₄, filtered and concentrated to give compound 300 (160 mg, 84%) as a yellow solid.

Step 8: (trans)-3-(5-Benzoyl-1-(3-(tert-butyl)-5-(1-methylcyclopropyl)phenyl)-4-methyl-1H-pyrrole-3-carboxamido)cyclobutanecarboxylic acid (301)

Compound 300 (160 mg, 0.304 mmol) was deprotected as described for Example 6 to give compound 301 (52 mg, 33%) as a pale yellow solid. ¹H-NMR (400 MHz, CDCl₃) δ: 0.64-0.71 (m, 4H), 1.18 (s, 9H), 1.28 (s, 3H), 2.31-2.40 (m, 5H), 2.80-2.86 (m, 2H), 3.11-3.16 (m, 1H), 4.80-4.86 (m, 1H), 6.04 (d, J=6.8 Hz, 2H), 6.82 (d, J=1.6 Hz, 1H), 6.90 (t, J=1.6 Hz, 1H), 7.02 (s, 1H), 7.21 (t, J=8.0 Hz, 2H), 7.34 (t, J=7.2 Hz, 1H), 7.44 (s, 1H), 7.54 (d, J=6.8 Hz, 2H). MS 513.3 (M+1)⁺.

Example 302

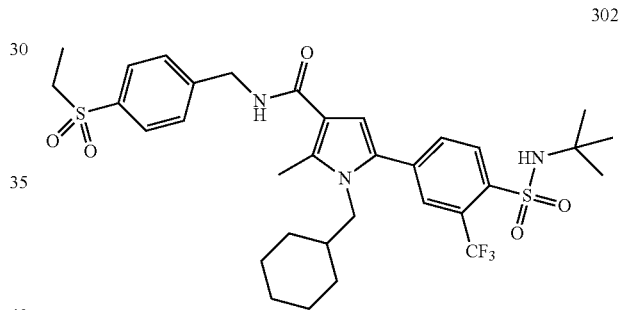

5-(4-(N-(tert-Butyl)sulfamoyl)-3-(trifluoromethyl) phenyl)-1-(cyclohexylmethyl)-N-(4-(ethylsulfonyl) benzyl)-2-methyl-1H-pyrrole-3-carboxamide (302)

5-(4-(N-(tert-butyl)sulfamoyl)-3-(trifluoromethyl)phenyl)-1-(cyclohexylmethyl)-2-methyl-1H-pyrrole-3-carboxylic acid (synthesis as described in EP12004186.8 or U.S. 61/566,055) was coupled with (4-(ethylsulfonyl)phenyl)methanamine similar as described above to give compound 302. ¹H-NMR (400 MHz, CDCl₃) δ: 0.61-0.67 (m, 2H), 0.97-1.06 (m, 3H), 1.25-1.58 (m, 18H), 2.65 (s, 3H), 3.09 (dd, J=7.2 Hz, 7.6 Hz, 2H), 3.82 (d, J=6.8 Hz, 2H), 4.68-4.70 (m, 3H), 6.27 (t, J=6.0 Hz, 1H), 6.42 (s, 1H), 7.53 (d, J=8.0 Hz, 2H), 7.62 (d, J=6.8 Hz, 1H), 7.80 (s, 1H), 7.86 (d, J=8.4 Hz, 2H), 8.31 (d, J=8.4 Hz, 1H). MS 682.2 (M+1)⁺.

Example 302/1 to 302/8

The following Examples were prepared similar as in Example 302:

| # | Structure | Analytical data |
|---|---|---|
| 302/1 | 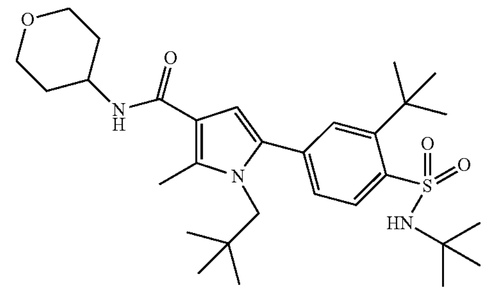 [SMILES: Cc1c(C(=O)NC2CCOCC2)cc(-c2ccc(S(=O)(=O)NC(C)(C)C)c(C(C)(C)C)c2)n1CC(C)(C)C] | ¹H-NMR (CDCl₃, 300 MHz) δ: 0.63 (s, 9H), 1.30 (s, 9H), 1.51-1.57 (m, 2H), 1.62 (s, 9H), 1.94-2.03 (m, 2H), 2.65 (s, 3H), 3.50-3.56 (m, 2H), 3.75-3.79 (m, 1H), 3.98-4.01 (m, 2H), 4.09-4.22 (m, 2H), 4.46 (s, 1H), 5.63 (t, J = 7.6 Hz, 1H), 6.30 (s, 1H), 7.25 (d, J = 1.2 Hz, 1H), 7.59 (d, J = 1.6 Hz, 1H), 8.19 (d, J = 8.8 Hz, 1H). MS 546.4 (M + 1)⁺ |
| 302/2 | 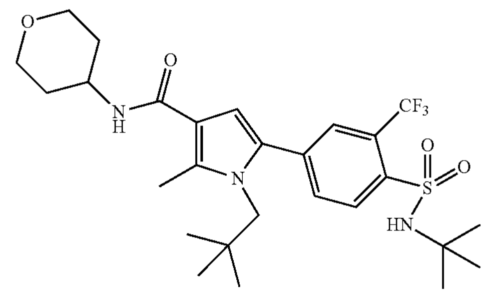 [SMILES: Cc1c(C(=O)NC2CCOCC2)cc(-c2ccc(S(=O)(=O)NC(C)(C)C)c(C(F)(F)F)c2)n1CC(C)(C)C] | ¹H-NMR (CDCl₃, 300 MHz) δ: 0.64 (s, 9H), 1.25 (s, 9H), 1.53-1.58 (m, 2H), 1.97-2.00 (m, 2H), 2.66 (s, 3H), 3.50-3.56 (m, 2H), 3.91-4.01 (m, 4H), 4.15-4.19 (m, 2H), 4.71 (s, 1H), 5.64 (t, J = 7.6 Hz, 1H), 6.39 (s, 1H), 7.61 (dd, J = 1.4 Hz, 8.0 Hz, 1H), 7.80 (d, J = 1.2 Hz, 1H), 8.31 (d, J = 8.4 Hz, 1H). MS 558.3 (M + 1)⁺ |
| 302/3 | 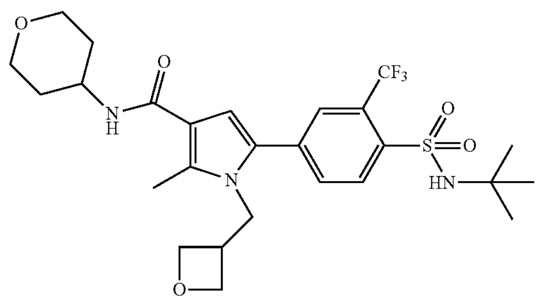 [SMILES: Cc1c(C(=O)NC2CCOCC2)cc(-c2ccc(S(=O)(=O)NC(C)(C)C)c(C(F)(F)F)c2)n1CC1COC1] | ¹H-NMR (400 MHz, CDCl₃) δ: 1.28 (s, 9H), 1.47-1.53 (m, 2H), 1.98 (dd, J = 12.0 Hz, 2.0 Hz, 2H), 2.65 (s, 3H), 3.01-3.09 (m, 1H), 3.52 (td, J = 12.0 Hz, 2.0 Hz, 2H), 3.99 (dd, J = 12.0 Hz, 2.0 Hz, 2H), 4.11 (t, J = 6.0 Hz, 2H), 4.15-4.21 (m, 1H), 4.33 (d, J = 7.2 Hz, 2H), 4.57 (d, J = 7.2 Hz, 2H), 4.71 (s, 1H), 5.61 (d, J = 7.6 Hz, 1H), 6.38 (s, 1H), 7.63 (dd, J = 8.4 Hz, 1.6 Hz, 1H), 7.79 (s, 1H), 8.35 (d, J = 8.4 Hz, 1H). MS 558 (M + 1)⁺ |
| 302/4 | 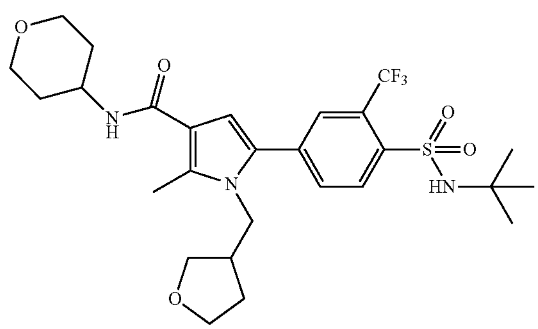 [SMILES: Cc1c(C(=O)NC2CCOCC2)cc(-c2ccc(S(=O)(=O)NC(C)(C)C)c(C(F)(F)F)c2)n1CC1CCOC1] | ¹H-NMR (400 MHz, CDCl₃) δ: 1.27 (s, 9H), 1.30-1.39 (m, 1H), 1.52-1.56 (m, 2H), 1.75-1.85 (m, 1H), 1.98 (d, J = 12.4 Hz, 2H), 2.25-2.35 (m, 1H), 2.67 (s, 3H), 3.21-3.25 (m, 1H), 3.45-3.65 (m, 5H), 3.99 (dd, J = 7.6 Hz, 2.8 Hz, 2H), 4.15-4.20 (m, 1H), 4.72 (s, 1H), 5.63 (d, J = 8.0 Hz, 1H), 6.40 (s, 1H), 7.64 (d, J = 8.4 Hz, 1H), 7.82 (s, 1H), 8.33 (d, J = 8.4 Hz, 1H). MS 572 (M + 1)⁺ |
| 302/5 | 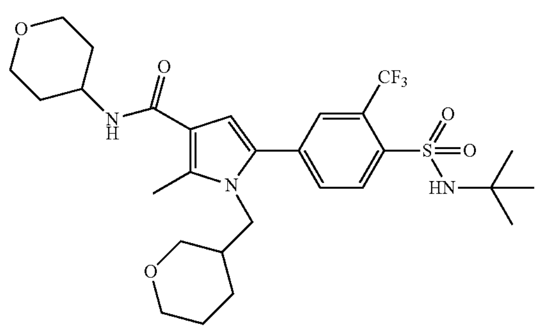 [SMILES: Cc1c(C(=O)NC2CCOCC2)cc(-c2ccc(S(=O)(=O)NC(C)(C)C)c(C(F)(F)F)c2)n1CC1CCCOC1] | ¹H-NMR (400 MHz, CDCl₃) δ: 0.95-1.10 (m, 1H), 1.26 (s, 9H), 1.30-1.40 (m, 2H), 1.51-1.56 (m, 3H), 1.65-1.70 (m, 1H), 1.97-2.01 (m, 2H), 2.64 (s, 3H), 2.81-2.93 (m, 1H), 3.25-3.75 (m, 5H), 3.89-4.00 (m, 4H), 4.10-4.25 (m, 1H), 4.70 (s, 1H), 5.61 (d, J = 7.6 Hz, 1H), 6.38 (s, 1H), 7.63 (dd, J = 8.4 Hz, 1.6 Hz, 1H), 7.80 (d, J = 0.8 Hz, 1H), 8.33 (d, J = 8.4 Hz, 1H). MS 586 (M + 1)⁺ |

| # | Structure | Analytical data |
|---|---|---|
| 302/6 | 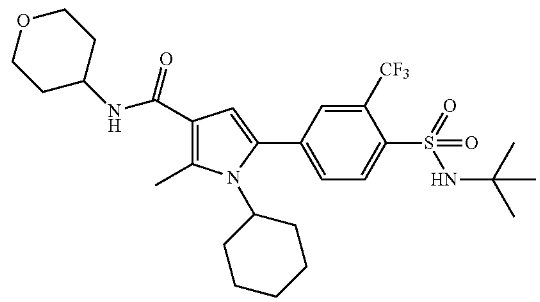 [SMILES: Cc1c(C(=O)NC2CCOCC2)cc(-c2ccc(S(=O)(=O)NC(C)(C)C)c(C(F)(F)F)c2)n1C1CCCCC1] | $^1$H-NMR (400 MHz, CDCl$_3$) δ: 1.14-1.25 (m, 3H), 1.28 (s, 9H), 1.47-1.55 (m, 2H), 1.65-1.70 (m, 1H), 1.85-1.88 (m, 4H), 1.96-1.99 (m, 4H), 2.76 (s, 3H), 3.52 (td, J = 12.0 Hz, 2.0 Hz, 2H), 3.96-3.99 (m, 3H), 4.15-4.16 (m, 1H), 4.71 (s, 1H), 5.60 (d, J = 7.6 Hz, 1H), 6.30 (s, 1H), 7.57 (dd, J = 8.4 Hz, 1.6 Hz, 1H), 7.76 (d, J = 1.6 Hz, 1H), 8.31 (d, J = 8.4 Hz, 1H). MS 570.3 (M + 1)$^+$ |
| 302/7 | 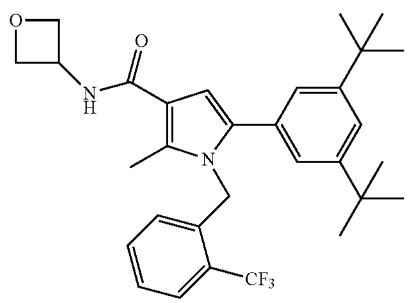 [SMILES: Cc1c(C(=O)NC2COC2)cc(-c2cc(C(C)(C)C)cc(C(C)(C)C)c2)n1Cc1ccccc1C(F)(F)F] | $^1$H-NMR (400 MHz, DMSO-d$_6$) δ: 8.41 (m, 1H), 7.79 (m, 1H), 7.70 (m, 1H), 7.52 (m, 1H), 7.32 (s, 1H), 6.98 (s, 2H), 6.85 (s, 1H), 6.60 (m, 1H), 5.27 (s, 2H), 4.99 (m, 1H), 4.76 (m, 2H), 4.60 (m, 2H), 2.38 (s, 3H), 1.13 (s, 18H). MS 527.3 (M + 1)$^+$ |
| 302/8 | 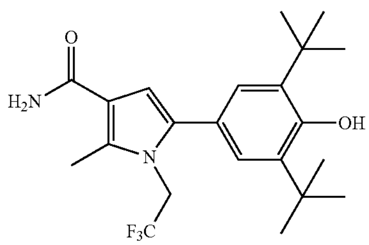 [SMILES: Cc1c(C(N)=O)cc(-c2cc(C(C)(C)C)c(O)c(C(C)(C)C)c2)n1CC(F)(F)F] | $^1$H-NMR (CDCl$_3$, 400 MHz) δ: 7.26 (s, 1H), 7.09 (s, 1H), 6.22 (s, 1H), 5.35-5.43 (m, 2H), 4.35-4.41 (m, 2H), 2.65 (s, 3H), 1.44 (s, 18H). MS 411.5 (M + 1)$^+$ |

Example 303

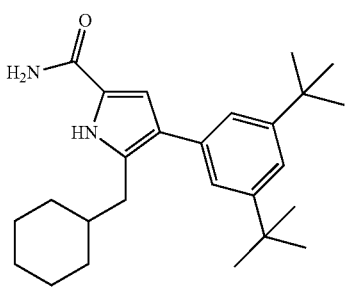

303

Step 1: Cyclohexyl(1H-pyrrol-2-yl)methanone (303a)

To a 3M solution of MeMgBr (30 mL, 90 mmol) was added 6.04 g (90 mmol) pyrrole in dry Et$_2$O (50 mL) at rt. The mixture was heated to reflux for 30 min, cooled to 0° C. and then cyclohexane carbonyl chloride (6.6 g, 45 mmol) dissolved in dry Et$_2$O (10 mL) was added dropwise to the reaction mixture. After addition was complete, the mixture was heated to reflux for 2 h, cooled to rt and poured into sat. NH$_4$Cl. The organic layer was separated and extracted with EA. The combined organic layer was washed with brine, dried over Na$_2$SO$_4$, filterede, evaporated and purified by CC (EA/PE=10/1) to give compound 303a (4.9 g, 62%) as an oil.

Step 2: 2-(Cyclohexylmethyl)-1H-pyrrole (303b)

A mixture of compound 303a (17.7 g, 100 mmol) and 99% hydrazine hydrate (6.0 mL) was heated under reflux in diethyl glycol (70 mL) for 1.5 h. The excess hydrazine hydrate and water were distilled off and the mixture was cooled. KOH (12 g, 210 mmol) was added portionwise and the mixture was then heated under reflux for 4 h, cooled, poured into water (500 mL) and extracted with Et$_2$O (3×) and the combined organic layer was washed with water and dried over Na$_2$SO$_4$, filtered, evaporated and used directly in the next reaction.

Step 3: tert-Butyl 2-(cyclohexylmethyl)-1H-pyrrole-1-carboxylate (303c)

To a solution of compound 303b (16.3 g, 100 mmol) dissolved in DCM (100 mL) was added DMAP (1.22 g, 10 mmol). The mixture was stirred at rt overnight, diluted with 1N HCl (50 mL) and the organic layer was separated and the aq. layer was extracted with EA (3×). The combined organic layer was washed with water, brine and dried over Na$_2$SO$_4$, filtered, evaporated and purified by CC (PE/EA=100/1) to give compound 303c (17.8 g, 68%) as an oil.

Step 4: 1-tert-Butyl 2-methyl 5-(cyclohexylmethyl)-1H-pyrrole-1,2-dicarboxylate (303d)

A 1.6M solution of n-BuLi in hexane (46.5 mL, 75 mmol) was added to a solution of 2,2,6,6-tetramethyl piperidine (12.6 mL, 75 mmol) in dry THF (250 mL) at −78° C. under Ar. The mixture was stirred for 30 min, then compound 303c (15.8 g, 60 mmol) in dry THF (50 mL) was added. The mixture was stirred at −78° C. for 1 h, then another hour at 0° C., then transferred into methyl chloroformate (6.95 mL) and stirred for further 1 h at 0° C. Sat. NH₄Cl (100 mL) was added at rt. The organic layer was separated and the aq. layer was extracted with EA (3×). The combined organic layer was washed with brine and dried over Na₂SO₄, filtered, evaporated and purified by CC (PE/EA=100/1) to give compound 303d (11.6 g, 62%).

Step 5: Methyl 5-(cyclohexylmethyl)-1H-pyrrole-2-carboxylate (303e)

Compound 303d (11.6 g, 36 mmol) was treated with a 20% TFA/DCM (20 mL) solution. After the reaction was over, the solvents were removed to give compound 303e (quant.).

Step 6: Methyl 4-bromo-5-(cyclohexylmethyl)-1H-pyrrole-2-carboxylate (303f)

NBS (1.96 g, 11 mmol) was added portionwise over 1 h to an ice-cooled solution of compound 303e (2.21 g, 10 mmol) in dry CHCl₃ (50 mL) and the mixture was stirred for 12 h at rt, poured into ice-cooled 2N NaOH (20 mL) and extracted with CHCl₃. The combined extracts were washed twice with water (20 mL) and dried over Na₂SO₄, evaporated and purified by CC (PE/EA=100/1) to give compound 303f (2.04 g, 68%).

Step 7: 1-tert-Butyl 2-methyl 4-bromo-5-(cyclohexylmethyl)-1H-pyrrole-1,2-dicarboxylate (303q)

To a solution of compound 303f (2.04 g, 6.8 mmol) in DCM (20 mL) was added DMAP (0.22 g, 0.06 mmol). The mixture was stirred at rt overnight, diluted with 1N HCl (20 mL) and extracted with EA (3×). The combined organic layer was washed with water, brine and dried over Na₂SO₄, filtered, evaporated and purified by a CC (PE/EA=100/1) to give compound 303g (2.39 g, 88%).

Step 8: methyl 5-(cyclohexylmethyl)-4-(3,5-di-tert-butylphenyl)-1H-pyrrole-2-carboxylate (303h)

To a sealed microwave vessel was added compound 303g (100 mg, 0.25 mmol), boronic ester (100 mg, 0.32 mmol), Cs₂CO₃ (200 mg, 0.62 mmol), Pd(dppf)Cl₂ (30 mg), dioxane (3 mL) and five drops water under Ar. The mixture was heated to 130° C. for 1 h with microwave irradiation, diluted with water (20 mL) and EA (20 mL). The organic layer was separated and the aq. layer was extracted with EA (3×). The combined organic layer was washed with brine, dried over Na₂SO₄, filtered, evaporated and purified by CC (PE/EA=100/1) to give compound 303h (68 mg, 67%).

Step 9: 5-(Cyclohexylmethyl)-4-(3,5-di-tert-butylphenyl)-1H-pyrrole-2-carboxylic acid (303i)

Compound 303h (68 mg, 0.17 mmol) was treated with 4N NaOH (5 mL) and MeOH (10 mL) at 60° C. for 4 h. The mixture was cooled to 0° C. and adjusted to pH<4 with 2N HCl (11 mL), extracted with EA (3×). The combined organic layer was washed with brine and dried over Na₂SO₄, filtered and evaporated to give compound 303i.

Step 10: 5-(Cyclohexylmethyl)-4-(3,5-di-tert-butylphenyl)-1H-pyrrole-2-carboxamide (303)

To a solution of compound 303i (62 mg, 0.17 mmol) in DMF (3 mL) was added HATU (77 mg, 0.2 mmol) and TEA (40 mg, 0.4 mmol). The mixture was stirred at rt for 30 min, then NH₄Cl (42 mg, 0.8 mmol) was added. The mixture was stirred overnight, diluted with water (10 mL) and EA (10 mL) and extracted with EA (3×). The combined organic layer was washed with brine, dried over Na₂SO₄, filtered, evaporated and purified by prep-HPLC to give pure compound 303 (26%). ¹H-NMR (400 MHz, CDCl₃) δ: 9.18 (br s, 1H), 7.32 (s, 1H), 7.21 (s, 2H), 6.69 (s, 1H), 5.57 (br s, 2H), 2.62 (d, 2H, J=6.0 Hz), 1.80-1.65 (m, 6H), 1.36 (s, 18H), 1.25-1.10 (m, 3H), 1.00-0.90 (m, 2H). MS 395 (M+1).

Example 304

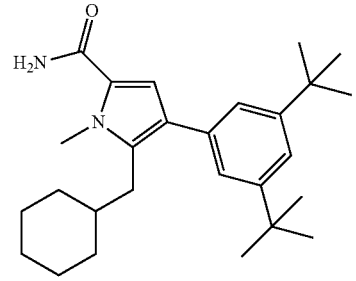

304

Step 1: Methyl 5-(cyclohexylmethyl)-4-(3,5-di-tert-butylphenyl)-1-methyl-1H-pyrrole-2-carboxylate (304a)

To a solution of compound 303h (102 mg, 0.25 mmol) in DMF (10 mL) was added NaH (16 mg, 60%, 0.4 mmol) in one portion at 0° C. under N₂. The mixture was stirred at 0° C. for 30 min, then CH₃I (42 mg, 0.3 mmol) was added. The mixture was stirred at rt for 2 h, diluted with water (10 mL) and EA (10 mL) and extracted with EA (3×). The combined organic layer was washed with brine, dried over Na₂SO₄, filtered and evaporated to give a crude product (84 mg, 80%).

Step 2: 5-(Cyclohexylmethyl)-4-(3,5-di-tert-butylphenyl)-1-methyl-1H-pyrrole-2-carboxylic acid (304b)

Compound 304a (84 mg, 0.2 mmol) was treated with 4N NaOH (5 mL) and MeOH (10 mL) at 60° C. for 4 h. The mixture was cooled to 0° C., adjusted to pH<4 with 2N HCl (11 mL), extracted with EA (3×). The combined organic layer was washed with brine and dried over Na₂SO₄, filtered was evaporated to give compound 304b.

Step 3: 5-(Cyclohexylmethyl)-4-(3,5-di-tert-butyl-phenyl)-1-methyl-1H-pyrrole-2-carboxamide (304)

To a solution of compound 304b (84 mg, 0.2 mmol) in DMF (3 mL) was added HATU (77 mg, 0.2 mmol) and TEA (40 mg, 0.4 mmol). The mixture was stirred at rt for 30 min, then NH₄Cl (42 mg, 0.8 mmol) was added. The mixture was stirred overnight, diluted with water (10 mL) and EA (10 mL) and extracted with EA (3×). The combined organic layer was washed with brine, dried over Na₂SO₄, filtered, evaporated and purified by prep-HPLC to give pure compound 304 (20%). ¹H-NMR (400 MHz, CDCl₃) δ: 7.32 (s, 1H), 7.17 (s, 2H), 6.69 (s, 1H), 5.51 (br s, 2H), 3.92 (s, 3H), 2.62 (d, 2H, J=6.0 Hz), 1.65-1.55 (m, 6H), 1.35 (s, 18H), 1.20-1.05 (m, 3H), 0.90-0.80 (m, 2H). MS 409 (M+1).

Example 305

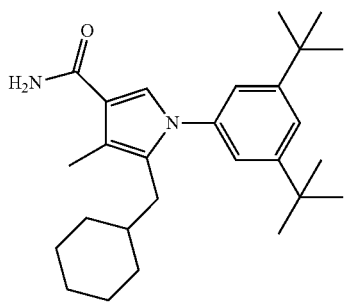

305

5-(Cyclohexylmethyl)-1-(3,5-di-tert-butylphenyl)-4-methyl-1H-pyrrole-3-carboxamide (305)

Compound 305 was prepared similar as described in Example 1. ¹H-NMR (400 MHz, CDCl₃) δ: 0.71-0.76 (m, 2H), 0.96-1.02 (m, 3H), 1.08-1.12 (m, 1H), 1.33 (s, 18H), 1.41-1.49 (m, 2H), 1.54-1.56 (m, 1H), 1.78 (m, 2H), 2.29 (s, 3H), 2.35 (d, J=7.2 Hz, 2H), 5.58 (br s, 2H), 7.07 (d, J=1.6 Hz, 2H), 7.23 (s, 1H), 7.42-7.43 (m, 1H). MS 409 (M+1).

Example 306

Step 1: Methyl 5-bromo-1H-1,2,4-triazole-3-carboxylate (306a)

Methyl 5-amino-1H-1,2,4-triazole-3-carboxylate (6.5 g, 45 mmol) was suspended in a mixture of conc. H₂SO₄ (6 mL) and water (100 mL). Then an aq. solution of NaNO₂ (6.4 g, 67 mmol) was added to the suspension at −3° C. After 30 min at −3° C. a freshly prepared aq. solution of CuBr (4.2 g, 21 mmol) and KBr (13.0 g, 91 mmol) was added dropwise. After stirring for 3 h at 25° C. the mixture was extracted with EA. The crude product was purified by CC (DCM/CH₃OH=20/1) to give compound 306a (5.5 g, 58%) as a white solid.

Step 2: Methyl 5-bromo-1-(cyclohexylmethyl)-1H-1,2,4-triazole-3-carboxylate (306b)

To a suspension of 60% NaH (1.00 g, 25 mmol) in dry DMF (50 mL) at 0° C. was added a solution of compound 306a (4.10 g, 20 mmol) in dry DMF (50 mL) dropwise. The resulting suspension was stirred at the same temperature for 30 min and treated with a solution of (bromomethyl)cyclohexane (3.54 g, 20 mmol) in dry DMF (20 mL). The resulting mixture was stirred at rt overnight, poured into ice and extracted with Et₂O twice. The combined organic layers were dried over Na₂SO₄, evaporated and purified by prep-HPLC to give compound 306b (1.5 g, 24%) as a white solid and 2.3 g of the undesired regioisomer.

Step 3: 5-Bromo-1-(cyclohexylmethyl)-1H-1,2,4-triazole-3-carboxamide (306c)

Compound 306b (1.0 g, 3.3 mmol) was suspended in a 10% NH₃/CH₃OH solution (50 mL) and stirred at rt for 2 d. The solvent was evaporated to give compound 306c (0.9 g, 95%) as a white solid.

Step 4: 1-(Cyclohexylmethyl)-5-(3,5-di-tert-butyl-4-hydroxyphenyl)-1H-1,2,4-triazole-3-carboxamide (306)

Compound P8 (1.5 g, 5.0 mmol), Pd(PPh₃)₄ (150 mg, 0.20 mmol), K₂CO₃ (0.6 g, 4.3 mmol) and compound 306c (0.5 g, 1.6 mmol) were suspended in dioxane/H₂O (3:1, 40 mL) and heated at 120° C. overnight under N₂, cooled to rt, concentrated and purified by prep-HPLC to give compound 306 (65 mg, 11%) as a white solid. ¹H-NMR (CDCl₃, 400 MHz) δ: 0.95-1.01 (m, 2H), 1.17-1.34 (m, 3H), 1.50 (s, 18H), 1.65-1.73 (m, 5H), 2.12-2.20 (m, 1H), 4.05 (d, J=8 Hz, 2H), 5.57 (s, 1H), 5.74 (s, 1H), 7.12 (s, 1H), 7.41 (s, 2H). MS 413 (M+1).

Example 307

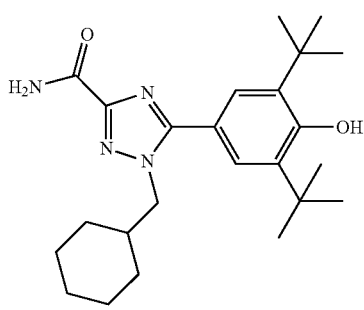

306

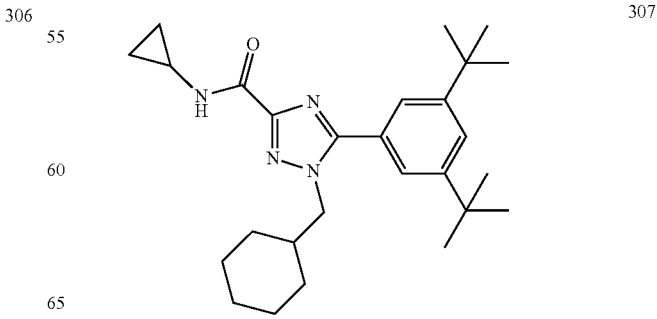

307

Step 1: Methyl 1-(cyclohexylmethyl)-5-(3,5-di-tert-butylphenyl)-1H-1,2,4-triazole-3-carboxylate (307a)

A solution of compound 306a (2.0 g, 6.7 mmol), Pd(PPh$_3$)$_4$ (800 mg, 0.7 mmol), K$_2$CO$_3$ (1.9 g, 13.4 mmol) and (3,5-di-tert-butylphenyl)boronic acid (3.7 g, 16.8 mmol) in DMF (50 mL) of was heated at 90° C. overnight under N$_2$. The mixture was cooled to rt, diluted with water and extracted with EA. The mixture was concentrated and purified by CC (PE/EA=10/1) to give compound 307a (1.7 g, 62%) as a white solid.

Step 2: 1-(Cyclohexylmethyl)-5-(3,5-di-tert-butylphenyl)-1H-1,2,4-triazole-3-carboxylic acid (307b)

To a solution of compound 307a (0.9 g, 2.18 mmol) in THF (15 mL) was added a solution of LiOH.H$_2$O (700 mg, 16.7 mmol) in water (5 mL). After stirring at rt overnight, the resulting solution was concentrated, diluted with water (10 mL), adjusted to pH=5 and extracted with EA twice. The combined organic layers were dried over Na$_2$SO$_4$, filtered, concentrated and purified by CC (PE/EA=5/1) to give compound 307b (650 mg, 75%) as a white solid.

Step 3: 1-(Cyclohexylmethyl)-N-cyclopropyl-5-(3,5-di-tert-butylphenyl)-1H-1,2,4-triazole-3-carboxamide (307)

To the solution of compound 307b (200 mg, 0.50 mmol) in dry DCM (10 mL) was added oxalyl chloride (200 mg, 1.6 mmol) and one drop DMF consecutively at 0° C. and the solution was stirred for 1 h at rt, concentrated, diluted with THF (3 mL) and cyclopropylamine (0.5 mL) were added. The mixture was stirred for 1 h at rt, concentrated and purified by CC (EA/PE=2/3) to give compound 307 (100 mg, 50%) as a white solid. $^1$H-NMR (CDCl$_3$, 400 MHz) δ: 0.67-0.69 (2H, m), 0.86-0.90 (4H, m), 1.15-1.21 (4H, m), 1.36 (18H, s), 1.58-1.64 (4H, m), 2.08 (1H, m), 2.98 (1H, m), 4.01 (2H, d, J=8.0 Hz), 7.29 (1H, s), 7.37 (2H, s), 7.57 (1H, s). MS 437 (M+1).

Example 308

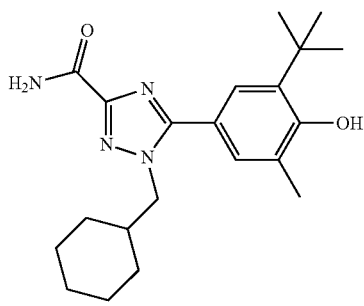

308

Step 1: Methyl 5-(3-(tert-butyl)-4-(methoxymethoxy)-5-methylphenyl)-1-(cyclohexylmethyl)-1H-1,2,4-triazole-3-carboxylate (308a)

A solution of compound 306a (400 mg, 1.3 mmol), Pd(PPh$_3$)$_4$ (120 mg, 0.1 mmol), K$_2$CO$_3$ (400 mg, 3.0 mmol) and compound P9 (1.5 g, 6.0 mmol) in DMF (10 mL) was heated at 80° C. overnight under N$_2$. The resulting solution was cooled to rt, diluted with water and extracted with EA (3×). The combined organic layers were washed with water (3×) and brine consecutively, concentrated and purified by CC (PE/EA=10/1) to give compound 308a (100 mg, 18%) as a white solid.

Step 2: Methyl 5-(3-(tert-butyl)-4-hydroxy-5-methylphenyl)-1-(cyclohexylmethyl)-1H-1,2,4-triazole-3-carboxylate (308b)

To a solution of compound 308a (100 mg, 0.23 mmol) in dioxane (5 mL) was added 6N HCl (5 mL) and the solution was stirred at rt for 2 h, concentrated, diluted with water and extracted with EA. The organic layer was dried over Na$_2$SO$_4$, filtered, concentrated and purified by CC (PE/EA=5/1) to give compound 308b (80 mg, 90%) as a solid.

Step 3: 5-(3-(tert-Butyl)-4-hydroxy-5-methylphenyl)-1-(cyclohexylmethyl)-1H-1,2,4-triazole-3-carboxamide (308)

A solution of compound 308b (80 mg, 0.21 mmol) in NH$_3$/MeOH (6M, 10 mL) was placed in a sealed tube and stirred at 70° C. overnight, concentrated and purified by CC (EA/PE=1/10) to give compound 308 (28 mg, 36%) as a white solid. $^1$H-NMR (CDCl$_3$, 400 MHz) δ: 0.82-0.95 (2H, m), 1.11-1.26 (4H, m), 1.45 (9H, s), 1.60-1.68 (4H, m), 2.08 (1H, m), 2.32 (3H, s), 4.04 (2H, d, J=8.0 Hz), 5.16 (1H, s), 5.67 (1H, s), 7.07 (1H, s), 7.28 (1H, s), 7.35 (1H, s). MS 371 (M+1).

Examples 308/1 to 308/10

The following Examples were prepared similar as described in Example 308.

| # | Structure | Analytical data |
|---|---|---|
| 308/1 | 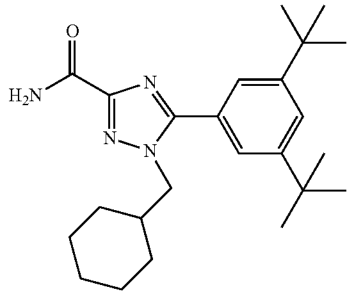 [SMILES: CC(C)(C)c1cc(-c2nc(C(N)=O)nn2CC2CCCCC2)cc(C(C)(C)C)c1] | ¹H-NMR (CDCl₃, 400 MHz) δ: 0.86-0.95 (2H, m), 1.10-1.18 (4H, m), 1.33 (18H, s), 1.61-1.68 (4H, m), 2.08 (1H, m), 4.04 (2H, d, J = 8.0 Hz), 5.87 (1H, s), 7.13 (1H, s), 7.40 (2H, s), 7.60 (1H, s). MS 397 (M + 1) |
| 308/2 | 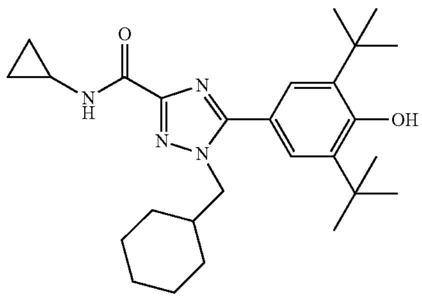 [SMILES: CC(C)(C)c1cc(-c2nc(C(=O)NC3CC3)nn2CC2CCCCC2)cc(C(C)(C)C)c1O] | ¹H-NMR (CDCl₃, 300 MHz) δ: 7.34 (2H, s), 3.99-4.00 (2H, d, J = 7.2 Hz), 2.94-2.97 (1H, m), 2.07-2.12 (1H, m), 1.62-1.67 (2H, m), 1.47-1.50 (18H, s), 1.13-1.37 (6H, m), 0.84-0.96 (4H, m), 0.63-0.67 (2H, m). MS 453 (M + 1) |
| 308/3 | 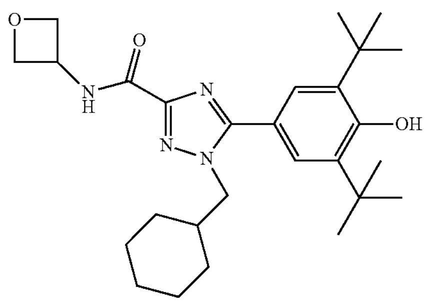 [SMILES: CC(C)(C)c1cc(-c2nc(C(=O)NC3COC3)nn2CC2CCCCC2)cc(C(C)(C)C)c1O] | ¹H-NMR (CDCl₃, 300 MHz) δ: 7.77 (1H, d, J = 8.4 Hz), 7.26-7.39 (2H, s), 5.32-5.37 (1H, m), 4.98-5.02 (2H, d, J = 10.4 Hz), 4.63-4.67 (2H, d, J = 13.2 Hz), 4.01-4.03 (2H, d, J = 7.2 Hz), 2.08-2.10 (1H, m), 1.61-1.70 (4H, m), 1.48 (18H, s), 1.11-1.28 (4H, m), 0.88-1.11 (2H, m). MS 469 (M + 1) |
| 308/4 | 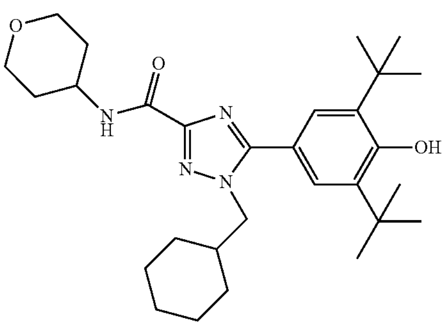 [SMILES: CC(C)(C)c1cc(-c2nc(C(=O)NC3CCOCC3)nn2CC2CCCCC2)cc(C(C)(C)C)c1O] | ¹H-NMR (CDCl₃, 300 MHz) δ: 7.35 (2H, s), 7.16 (1H, d, J = 8.4 Hz), 4.23-4.30 (1H, m), 3.99-4.01 (4H, m), 3.51-3.56 (2H, t, J = 22 Hz), 2.08-2.13 (1H, m), 1.99-2.02 (2H, m), 1.60-1.661 (6H, m), 1.53-1.57 (18H, s), 1.11-1.38 (4H, m), 0.78-0.90 (2H, m). MS 497 (M + 1) |
| 308/5 | 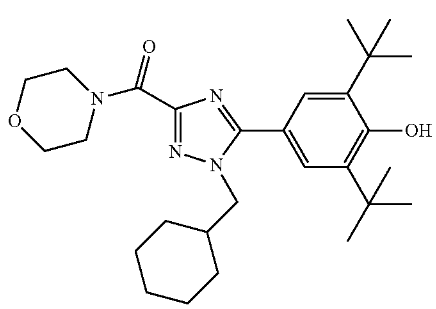 [SMILES: CC(C)(C)c1cc(-c2nc(C(=O)N3CCOCC3)nn2CC2CCCCC2)cc(C(C)(C)C)c1O] | ¹H-NMR (CDCl₃, 400 MHz) δ: 7.39 (2H, s), 3.98-4.02 (4H, m), 3.69-3.74 (4H, m), 2.05 (1H, s), 1.65-1.71 (4H, m), 1.47 (18H, s), 1.18-1.28 (4H, m), 0.94-0.97 (2H, m). MS 483 (M + 1) |

| # | Structure | Analytical data |
|---|---|---|
| 308/6 | 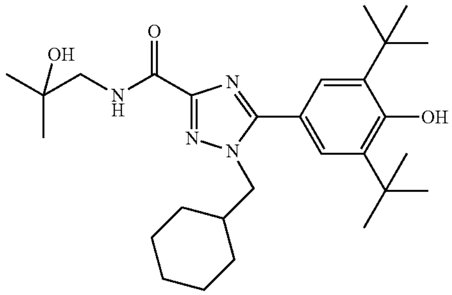 [SMILES: CC(C)(O)CNC(=O)c1nc(-c2cc(C(C)(C)C)c(O)c(C(C)(C)C)c2)n(CC2CCCCC2)n1] | $^1$H-NMR (CDCl$_3$, 400 MHz) δ: 7.61-7.62 (1H, m), 7.37 (2H, s), 4.00-4.02 (2H, d, J = 7.6 Hz), 3.49-3.51 (2H, d, J = 6.0 Hz), 2.49 (1H, s), 2.11-2.12 (1H, m), 1.63-1.70 (4H, m), 1.48 (18H, s), 1.30 (6H, s), 1.11-1.14 (4H, m), 0.86-0.95 (2H, m). MS 485 (M + 1) |
| 308/7 | 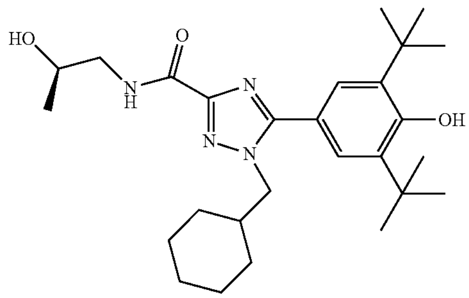 [SMILES: C[C@@H](O)CNC(=O)c1nc(-c2cc(C(C)(C)C)c(O)c(C(C)(C)C)c2)n(CC2CCCCC2)n1] | $^1$H-NMR (CDCl$_3$, 400 MHz) δ: 7.59-7.62 (1H, m), 7.37 (2H, s), 4.09-4.13 (1H, m), 4.01-4.02 (2H, d, J = 9.8 Hz), 3.61-3.67 (1H, m), 3.34-3.41 (1H, m), 2.64-2.66 (1H, m), 2.08-2.14 (1H, m), 1.62-1.70 (4H, m), 1.48 (18H, s), 1.38-1.40 (3H, d, J = 10 Hz), 1.07-1.33 (4H, m), 0.88-0.97 (2H, m). MS 471 (M + 1) |
| 308/8 | 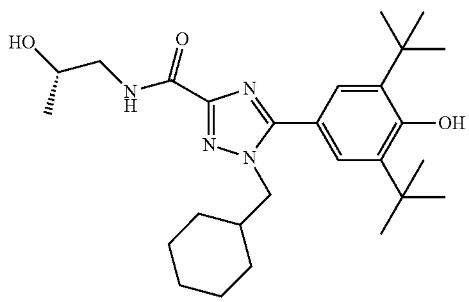 [SMILES: C[C@H](O)CNC(=O)c1nc(-c2cc(C(C)(C)C)c(O)c(C(C)(C)C)c2)n(CC2CCCCC2)n1] | $^1$H-NMR (CDCl$_3$, 400 MHz) δ: 7.60-7.63 (1H, m), 7.37 (2H, s), 4.02-4.05 (1H, m), 4.01-4.02 (2H, d, J = 9.8 Hz), 3.61-3.67 (1H, m), 3.35-3.40 (1H, m), 2.68 (1H, m), 2.05-2.12 (1H, m), 1.62-1.69 (4H, m), 1.48 (18H, s), 1.32-1.33 (3H, d, J = 10 Hz), 1.11-1.24 (4H, m), 0.88-0.97 (2H, m). MS 471 (M + 1) |
| 308/9 | 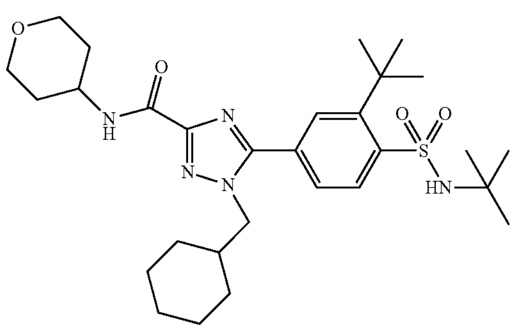 [SMILES: CC(C)(C)NS(=O)(=O)c1ccc(-c2nc(C(=O)NC3CCOCC3)nn2CC2CCCCC2)cc1C(C)(C)C] | $^1$H-NMR (CDCl$_3$, 400 MHz) δ: 0.81-0.89 (m, 2H), 1.07-1.20 (m, 3H), 1.32 (s, 9H), 1.54-1.62 (m, 5H), 1.65 (s, 9H), 2.00-2.07 (m, 3H), 3.51-3.57 (m, 2H), 3.99-4.06 (m, 4H), 4.26-4.29 (m, 1H), 4.56 (s, 1H), 7.07 (d, 1H, J = 8.4 Hz), 7.54-7.57 (dd, J = 8.4, 1.6 Hz), 7.85-7.86 (m, 1H), 8.33 (d, 1H, J = 8.0 Hz). MS 560 (M + 1) |
| 308/10 | 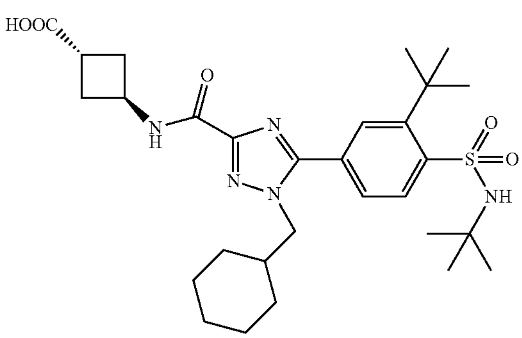 [SMILES: CC(C)(C)NS(=O)(=O)c1ccc(-c2nc(C(=O)N[C@H]3C[C@H](C(=O)O)C3)nn2CC2CCCCC2)cc1C(C)(C)C] | $^1$H-NMR (CDCl$_3$, 400 MHz) δ: 0.78-0.90 (m, 2H), 1.03-1.17 (m, 3H), 1.33 (s, 9H), 1.49-1.56 (m, 2H), 1.65 (s, 9H), 1.73-1.75 (m, 3H), 2.02-2.06 (m, 1H), 2.38-2.44 (m, 2H), 2.80 (m, 2H), 3.13-3.15 (m, 1H), 4.02-4.07 (dd, 2H, J = 18.8, 7.2 Hz), 4.72 (s, 1H), 4.85-4.91 (m, 1H), 7.47 (d, 1H, J = 8.0 Hz), 7.56 (d, 1H, J = 7.6 Hz), 7.85 (s, 1H), 8.34 (d, 1H, J = 8.4 Hz). MS 574 (M + 1) |

Example 309

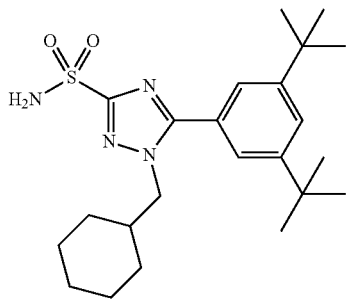

309

Step 1: 2-(Cyclohexylmethyl)hydrazinecarbothioamide (309a)

A mixture of cyclohexanecarbaldehyde (5.00 g, 44.6 mmol) and hydrazinecarbothioamide (4.06 g, 44.6 mmol) in MeOH (35 mL) was stirred at rt overnight. NaBH$_4$ (4.41 g, 117 mmol) was added slowly at rt and the mixture was stirred for 2 h, quenched with sat. aq. NH$_4$Cl, concentrated and extracted with EA. The combined organic layers were dried over Na$_2$SO$_4$, filtered and concentrated to give crude compound 309a (9.5 g) as a colorless solid.

Step 2: 2-(Cyclohexylmethyl)-2-(3,5-di-tert-butyl-benzoyl)hydrazinecarbothioamide (309b)

To a solution of 3,5-di-tert-butylbenzoic acid (4.14 g, 17.7 mmol) and DMF (0.1 mL) in dry DCM (20 mL) was added (COCl)$_2$ (4 mL, 420 mmol) at rt and the mixture was stirred for 1 h at rt, concentrated and diluted with dry DCM (10 mL). To a solution of 2-(cyclohexylmethyl)hydrazinecarbothioamide (3.31 g, 17.7 mmol) and DIPEA (9.5 mL, 53.1 mmol) in dry DCM (30 mL) was added the first mentioned solution of 3,5-di-tert-butylbenzoyl chloride in dry DCM at rt and the mixture was stirred at rt for 1 h, concentrated and purified by prep. HPLC to give compound 309b (2.0 g, 28%) as a yellow solid.

Step 3: 1-(Cyclohexylmethyl)-5-(3,5-di-tert-butylphenyl)-1H-1,2,4-triazole-3(2H)-thione (309c)

A suspension of compound 309b (1.96 g, 4.86 mmol) in 10% aq. sodium carbonate (40 mL) was heated under reflux for 2 h, cooled to rt and acidified with conc. HCl to pH 3-4. The precipitate was filtered and dried in vacuo to give compound 309c (1.70 g, 90%) as a white solid.

Step 4: 1-(Cyclohexylmethyl)-5-(3,5-di-tert-butylphenyl)-1H-1,2,4-triazole-3-sulfonamide (309)

A solution of compound 309c (425 mg, 1.10 mmol), NCS (585 mg, 4.43 mmol) in DCM (10 mL) was stirred for 2 h, diluted with water and extracted with DCM. The combined organic layers were washed with brine, concentrated and diluted with acetone (10 mL). To this solution was added NH$_3$OH (30 mL) at rt and the resulting solution was stirred for 15 min, concentrated and diluted with EA. The organic layer was dried, concentrated and purified by CC (EA/PE=1/3) to give compound 309 (121 mg, 26%) as a colorless solid.

$^1$H-NMR (300 MHz, CDCl$_3$) δ: 0.85-0.96 (m, 2H), 1.13-1.23 (m, 4H), 1.34 (s, 18H), 1.57-1.65 (m, 4H), 2.00-2.04 (m, 1H), 4.08 (d, J=7.5 Hz, 2H), 5.30 (s, 2H), 7.39 (d, J=1.8 Hz, 2H), 7.59 (t, J=1.8 Hz, 1H). MS 433 (M+1).

Example 310

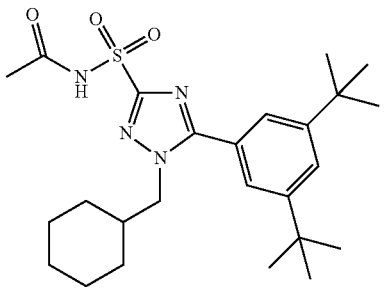

310

N-((1-(Cyclohexylmethyl)-5-(3,5-di-tert-butylphenyl)-1H-1,2,4-triazol-3-yl)sulfonyl)acetamide Compound 309 was treated with Ac$_2$O in pyridine and catalytic amounts of DMAP to obtain compound 310 after usual aq. workup. $^1$H-NMR (400 Hz) δ: 0.92-1.01 (m, 2H), 1.15-1.36 (m, 6H), 1.38 (s, 18H), 1.38-1.69 (m, 3H), 2.01-2.20 (m, 3H), 4.12 (d, J=7.6 Hz, 2H), 7.46 (d, J=1.2 Hz, 2H), 7.67 (s, 1H). MS 475.2 (M+1)$^+$.

Example 311

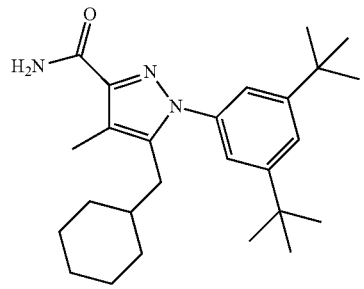

311

Step 1: (E/Z)-Methyl 2-chloro-2-(2-(3,5-di-tert-butylphenyl)hydrazono)acetate (311a)

To a solution of 3,5-di-tert-butylaniline (3.85 g, 19 mmol) in MeOH (30 mL) was added 6N aq. HCl (18 mL) and the solution was cooled to 0° C. NaNO$_2$ (2.59 g, 38 mmol) was then slowly added as a solid. The reaction was stirred for 15 min at 0° C. after which time NaOAc was added as a solid to adjust the reaction to pH=5. Subsequently, a solution of methyl 2-chloroacetoacetate (2.34 mL, 19 mmol) in MeOH (10 mL) was slowly added at 0° C. The reaction was then allowed to warm to 25° C. and stirred for 12 h, after which time the MeOH was removed under reduced pressure and EA (100 mL) was added. The organic layer was separated and washed with saturated NaHCO$_3$ and brine prior to drying over Na$_2$SO$_4$. The organic layer was concentrated under reduced pressure to give 5.3 g of the title compound as a yellow solid, which was utilized without further purification (87%).

Step 2: Methyl 5-((benzylperoxy)methyl)-1-(3,5-di-tert-butylphenyl)-4-methyl-4,5-dihydro-1H-pyrazole-3-carboxylate (311b)

To a solution of 311a (5.3 g, 16.3 mmol) and (E)-benzyl but-2-enoate (3.01 g, 17.1 mmol) in dioxane (80 mL) at 25° C. was added $Ag_2CO_3$ (11.3 g, 40.75 mmol). The reaction was protected from light and stirred at 25° C. for 48 h. Subsequently, the reaction mixture was filtered through a pad of celite and the filtrate was concentrated under reduced pressure. The crude product mixture was purified by CC (PE/EA=25/1) to give 5.2 g of compound 311b as a yellow solid (68%).

Step 3: 5-Benzyl 3-methyl 1-(3,5-di-tert-butylphenyl)-4-methyl-1H-pyrazole-3,5-dicarboxylate (311c)

To a solution of 311b (5.2 g, 11.2 mmol) in 30 mL THF and 30 mL $H_2O$ at 0° C. was added ceric ammonium nitrate (12.3 g, 22.4 mmol) under $N_2$. The reaction mixture was stirred at 0° C. for 1 h. The reaction was quenched with sat. aq. $NaHCO_3$ (30 mL), the mixture was extracted with EA (3×30 mL). The organic phase was washed with brine, dried over $Na_2SO_4$, then concentrated and purified by CC (PE/EA=15/1) to give 4.67 g of the title compound 311c as a yellow solid (90%).

Step 4: 1-(3,5-Di-tert-butylphenyl)-3-(methoxycarbonyl)-4-methyl-1H-pyrazole-5-carboxylic acid (311 d)

To a solution of 311c (3.0 g, 6.5 mmol) in 30 mL MeOH was added Pd/C (0.5 g) and the mixture was stirred at rt overnight under $H_2$ (30 psi). The reaction mixture was filtered and the filtrate was concentrated to give 2.0 g of compound 311d as a white solid (83%).

Step 5: Ethyl 5-(cyclohexylmethyl)-1-(3,5-di-tert-butylphenyl)-4-methyl-1H-pyrrole-3-carboxylate (311e)

To a solution of 311d (2.0 g, 5.37 mmol) in 30 mL of dry THF at 0° C. was added $BH_3$/THF solution (10.8 mL, 10.8 mmol) dropwise. The mixture was stirred at rt for 1 h and at reflux for 2 h, quenched with sat. aq. $NaHCO_3$ (30 mL) and extracted with EA (3×30 mL). The organic phase was washed with brine, dried over $Na_2SO_4$, concentrated and purified by CC (DCM) to give 0.7 g of the title compound 311e as a white solid (36%).

Step 6: Methyl 1-(3,5-di-tert-butylphenyl)-5-((dimethoxyphosphoryl)methyl)-4-methyl-1H-pyrazole-3-carboxylate (311f)

To a solution of 311e (0.7 g, 1.95 mmol) in 30 mL of DCM at 0° C., $SOCl_2$ (0.3 mL, 3.91 mmol) was added dropwise. The reaction mixture was stirred at rt for 1 h, quenched with sat. aq. $NaHCO_3$ (30 mL) and extracted with DCM (2×30 mL). The organic phase was washed with brine, dried over $Na_2SO_4$ and concentrated to give 0.66 g of residue as a yellow oil. A solution of this residue (0.5 g, 1.33 mmol) in 20 mL of trimethylphosphite was stirred and refluxed at 150° C. for 4 h. The mixture was concentrated under reduced pressure to give 0.60 g of crude compound 311f as a colorless oil (99%).

Step 7: Methyl 5-(cyclohexylmethyl)-1-(3,5-di-tert-butylphenyl)-4-methyl-1H-pyrazole-3-carboxylate (311g)

To a solution of NaH (0.1 g, 2.66 mmol) in 20 mL of dry THF was added dropwise a solution of compound 311f (0.6 g, 1.33 mmol) in 10 mL of dry THF. The reaction mixture was stirred at rt for 0.5 h and then cyclohexanone (0.13 g, 1.33 mmol) was added. The mixture was stirred at rt overnight. After quenching with water (30 mL), the mixture was extracted with EA (2×30 mL). The organic phase was washed with brine, dried over $Na_2SO_4$ and concentrated to give 0.3 g of crude compound 311g as a yellow oil (55%).

Step 8: Methyl 5-(cyclohexylmethyl)-1-(3,5-di-tert-butylphenyl)-4-methyl-1H-pyrazole-3-carboxylate (311h)

To a solution of compound 311g (0.3 g, 0.73 mmol) in 30 mL of MeOH was added Pd/C (0.1 g). The reaction mixture was stirred at rt overnight under $H_2$ (30 psi), filtered and concentrated to give 0.18 g of crude compound 311h as a yellow solid (60%).

Step 9: 5-(Cyclohexylmethyl)-1-(3,5-di-tert-butylphenyl)-4-methyl-1H-pyrazole-3-carboxamide (311)

To a solution of compound 311h (175 mg, 0.44 mmol) in of MeOH (6 mL) was added 2N aq. NaOH (0.9 mmol) at rt and the reaction mixture was stirred at rt for 1 h, concentrated and diluted with 1N HCl to adjust the pH to ca. 3. The aq. mixture was extracted twice with EA and the combined organic layers were washed with brine, dried over $Na_2SO_4$ and concentrated to give the crude acid. To a solution of the crude acid in DCM (10 mL) and 1 drop DMF at 0° C. was added dropwise oxalyl chloride (0.09 mL, 0.88 mmol). The reaction mixture was stirred at rt for 0.5 h and the resulting solution was concentrated under reduced pressure. A solution of the crude residue in 5 mL of dry THF was added to 20 mL of $NH_3$/THF solution and the mixture stirred at rt for 1 h, quenched with sat. aq. $NaHCO_3$ (30 mL) and extracted with EA (3×30 mL). The organic phase was washed with brine, dried over $Na_2SO_4$, concentrated and purified by CC (DCM) to give 40 mg of compound 311 as a white solid (22%). $^1$H-NMR (CDCl$_3$, 400 MHz) δ: 0.77-0.80 (2H, m), 1.01-1.05 (2H, m), 1.29 (18H, s), 1.45-1.48 (2H, m), 1.50-1.57 (5H, m), 2.34 (3H, s), 2.38 (2H, d, J=7.2 Hz), 5.23 (1H, br s), 6.84 (1H, br s), 7.17 (2H, d, J=2.0 Hz), 7.49 (1H, s, J=1.6 Hz). MS 410 (M+1).

Example 312

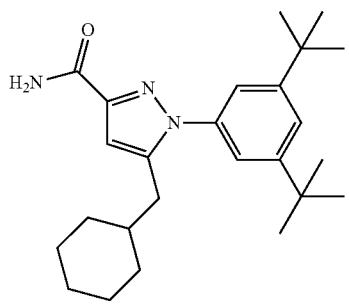

312

Step 1: 5-Benzyl 3-methyl 1-(3,5-di-tert-butylphenyl)-1H-pyrazole-3,5-dicarboxylate (312a)

To a solution of compound 311a (7.75 g, 24 mmol) and benzyl propiolate (7.65 g, 45 mmol) in toluene (240 mL) at 25° C. was added TEA (12.1 g, 0.12 mol). The mixture was stirred at 120° C. for 0.5 h, cooled, filtered through a pad of celite, concentrated and purified by CC (PE/EA=40/1) to give 2.86 g of compound 312a as a yellow solid (27%).

Step 2: 5-(Cyclohexylmethyl)-1-(3,5-di-tert-butylphenyl)-1H-pyrazole-3-carboxamide (312)

Example 312 was prepared from compound 312a by using similar procedures as described for the steps from intermediate 311c. $^1$H-NMR (CDCl$_3$, 400 MHz) δ: 0.84-0.87 (2H, m), 1.12-1.20 (3H, m), 1.36 (18H, s), 1.59-1.67 (5H, m), 2.46 (2H, d, J=7.6 Hz), 6.76 (1H, s), 6.85 (1H, br s), 7.19 (2H, d, J=1.6 Hz), 7.51 (1H, d, J=1.6 Hz). MS 396 (M+1)$^+$.

Example 312/1 to 312/2

The following Examples were prepared similar as described for Example 312:

Example 313

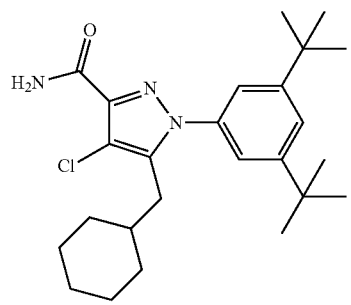

4-Chloro-5-(cyclohexylmethyl)-1-(3,5-di-tert-butylphenyl)-1H-pyrazole-3-carboxamide (313)

To a solution of compound 312 (100 mg, 0.25 mmol) in DCM (5 mL) at 0° C. was added dropwise SO$_2$Cl$_2$ (1 mL)

| # | Structure | Analytical data |
|---|---|---|
| 312/1 | 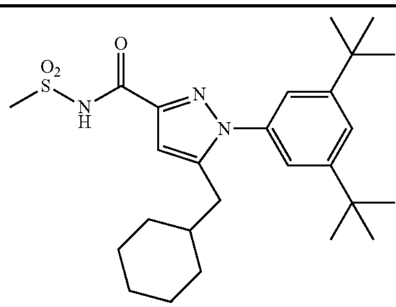 | $^1$H-NMR (CDCl$_3$, 400 MHz) δ: 0.84-0.87 (2H, m), 1.13-1.26 (3H, m), 1.37 (18H, s), 1.62-1.65 (5H, m), 2.48 (2H, d, J = 7.2 Hz), 3.39 (3H, s), 6.81 (1H, s), 7.16 (2H, s), 7.54 (1H, s). MS 474 (M + 1)$^+$ |
| 312/2 | | $^1$H-NMR (CDCl$_3$, 300 MHz) δ: 0.83-0.91 (2H, m), 1.11-1.19 (3H, m), 1.34 (10H, s), 1.49-1.68 (5H, m), 2.42 (3H, s), 2.47 (2H, d, J = 7.2 Hz), 5.35 (2H, m), 6.27-6.28 (1H, m), 6.75 (1H, s), 6.82 (1H, m), 7.02 (1H, s), 7.17 (1H, s), 7.28 (1H, s). MS 354 (M + 1)$^+$ | and the solution was stirred at rt for 1 h, quenched with sat. aq. NaHCO₃ and extracted with DCM twice. The combined organic layers were washed with brine, dried over Na₂SO₄, filtered and concentrated to give 36 mg of compound 313 as a white solid (36%). ¹H-NMR (CDCl₃, 300 MHz) δ: 0.82-0.85 (2H, m), 1.03-1.06 (3H, m), 1.35 (18H, s), 1.43-1.51 (2H, m), 1.55-1.58 (4H, m), 2.54 (2H, d, J=6.8 Hz), 5.42 (1H, br s), 6.79 (1H, br s), 7.17 (1H, d, J=1.6 Hz), 7.53 (1H, s). MS 430 (M+1)⁺.

Example 314

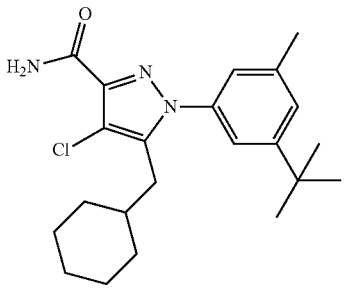

314

Step 1: Methyl 1-(3-(tert-butyl)-5-methylphenyl)-5-(cyclohexylidenemethyl)-1H-pyrazole-3-carboxylate (314a)

To a solution of NaH (60%, 225 mg, 5.64 mmol) in dry THF (20 mL) was added dropwise a solution of methyl 1-(3-(tertbutyl)-5-methylphenyl)-5-((dimethoxyphosphoryl)methyl)-1H-pyrazole-3-carboxylate (740 mg, 1.88 mmol, prepared similar as described for intermediate 311f) in dry THF (10 mL). The mixture was stirred for 0.5 h at rt and then cyclohexanone (368 mg, 3.76 mmol) was added, stirred at rt overnight, quenched with water and extracted twice with EA. The combined organic layers were washed with brine, dried over Na₂SO₄ and concentrated to give 580 mg of crude compound 314a as a yellow oil (84%).

Step 2: Methyl 1-(3-(tert-butyl)-5-methylphenyl)-5-(cyclohexylmethyl)-1H-pyrazole-3-carboxylate (314b)

To a solution of compound 314a (580 mg, 1.60 mmol) in MeOH (10 mL) was added Pd/C (0.2 g). The reaction mixture was stirred under H₂ (30 psi) at rt overnight, filtered off and the filtrate was concentrated to give 450 mg of compound 314b as a yellow solid (73%).

Step 3: Methyl 1-(3-(tert-butyl)-5-methylphenyl)-4-chloro-5-(cyclohexylmethyl)-1H-pyrazole-3-carboxylate (314c)

To a solution of compound 314b (110 mg, 0.3 mmol) in DCM (5 mL) at 0° C. was added dropwise SO₂Cl₂ (0.5 mL) and the solution was stirred at rt for 1 h, quenched with aq. NaHCO₃ and extracted twice with DCM. The combined organic layers were washed with brine, dried over Na₂SO₄, filtered and concentrated to give 120 mg of compound 314c as a white solid (100%).

Step 4: 1-(3-(tert-Butyl)-5-methylphenyl)-4-chloro-5-(cyclohexylmethyl)-1H-pyrazole-3-carbonyl chloride (314d)

To a solution of compound 314c (120 mg, 0.3 mmol) in MeOH (5 mL) was added 2N NaOH (0.3 mL, 0.6 mmol) at rt and the reaction mixture was stirred at rt for 1 h, concentrated and adjusted pH=3 with 1N HCl and extracted twice with EA. The combined organic layers were washed with brine, dried over Na₂SO₄ and concentrated to give the crude acid. To a solution of crude acid and 1 drop DMF in dry DCM (5 mL) at 0° C. was added dropwise oxalyl chloride (10 mg, 0.56 mmol), stirred at rt for 0.5 h and concentrated to give crude 314d as a yellow oil.

Step 5: 1-(3-(tert-butyl)-5-methylphenyl)-4-chloro-5-(cyclohexylmethyl)-1H-pyrazole-3-carboxamide (314)

A solution of crude 314d in dry DCM (1 mL) was added to a solution of NH₃ (1M in THF, 2.0 mL, 2.0 mmol) and the solution was stirred at rt for 1 h, quenched with aq. NaHCO₃ and extracted with EA (3×). The combined organic layers were washed with brine, dried over Na₂SO₄, filtered, concentrated and purified by prep-TLC to give 41 mg of compound 314 as a white solid (35%). ¹H-NMR (CDCl₃, 300 MHz) δ: 0.81-0.85 (2H, m), 1.03-1.10 (3H, m), 1.33 (9H, s), 1.46-1.54 (2H, m), 1.56-1.60 (4H, m), 2.42 (3H, s), 2.56 (2H, d, J=6.9 Hz), 5.52 (1H, s), 6.77 (1H, s), 7.00 (1H, s), 7.16 (1H, s), 7.30 (1H, s). MS 388 (M+1)⁺.

Example 315

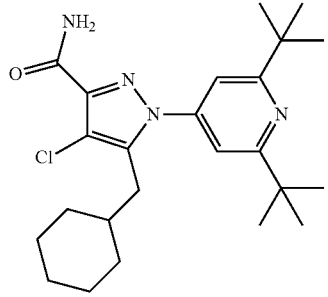

315

Step 1: Dimethyl 1-(2,6-di-tert-butylpyridin-4-yl)-1H-pyrazole-3,5-dicarboxylate (315a)

A mixture of dimethyl 1H-pyrazole-3,5-dicarboxylate (2.09 g, 11.4 mmol), compound P10 (3.60 g, 11.4 mmol), Cu(OTf)₂ (4.11 g, 11.4 mmol) and pyridine (1.80 g, 22.7 mmol) in DMF (50 mL) was stirred at 85° C. overnight under N₂ and diluted with a saturated solution of NaHCO₃. The aqueous layer was extracted with DCM twice. The combined organic layers were dried over Na₂SO₄, concentrated and purified by CC (EA/PE=1/20) to give compound 315a (3.10 g, 73%) as a white solid.

Step 2: 1-(2,6-Di-tert-butylpyridin-4-yl)-3-(methoxycarbonyl)-1H-pyrazole-5-carboxylic acid (315b)

To a solution of 315a (3.10 g, 8.31 mmol) in of MeOH (60 mL) was added 2N NaOH (4.16 mL, 8.31 mmol) and the mixture was stirred overnight at rt, quenched with brine and extracted twice with EA. The combined organic layers were washed with brine, dried over Na₂SO₄ and concentrated to give compound 315b (2.41 g, 81%) as a white solid.

Step 3: 4-Chloro-5-(cyclohexylmethyl)-1-(2,6-di-tert-butylpyridin-4-yl)-1H-pyrazole-3-carboxamide (315)

Compound 315 was prepared from intermediate 315b using similar procedures as described for compound 314. $^1$H-NMR (CDCl$_3$, 400 MHz) δ: 0.85-0.93 (2H, m), 1.06-1.09 (3H, m), 1.39 (20H, s), 1.43-1.49 (3H, m), 1.54-1.61 (1H, m), 2.64 (2H, d, J=7.2 Hz), 5.54 (1H, br s), 6.78 (1H, br s), 7.15 (2H, s). MS 431 (M+1)$^+$.

Example 315/1

The following Examples were prepared similar as described for Example 315:

| # | Structure | Analytical data |
|---|---|---|
| 315/1 | 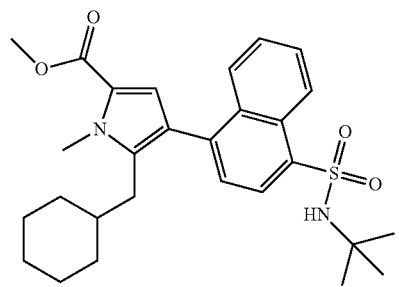 | $^1$H-NMR (CDCl$_3$, 300 MHz) δ: 0.80-0.87 (2H, m), 1.00-1.06 (3H, m), 1.36 (9H, s), 1.40-1.49 (3H, m), 1.55 (6H, m), 1.59-1.66 (3H, m), 2.56 (2H, d, J = 7.2 Hz), 3.10 (3H, s), 5.54 (1H, br s), 6.78 (1H, br s), 7.22 (1H, d, J = 1.8 Hz), 7.26 (1H, s), 7.56 (1H, d, J = 1.8 Hz). MS 446 (M + 1)$^+$ |

Example 316 and Example 317

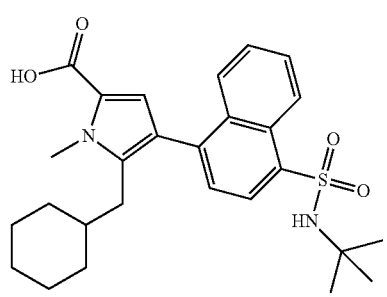

316

317

Step 1: Methyl 4-(4-(N-(tert-butyl)sulfamoyl)naphthalen-1-yl)-5-(cyclohexylmethyl)-1-methyl-1H-pyrrole-2-carboxylate (316)

The solution of compound 7d (1.1 g, 3.67 mmol), N-(tert-butyl)-4-(4,4,5,5-tetramethyl-1,3,2-dioxaborolan-2-yl) naphthalene-1-sulfonamide (1.7 g, 4.4 mmol), Pd(dppf)Cl$_2$ (110 mg) and K$_2$CO$_3$ (1.0 g, 7.34 mmol) in DMF (11 mL) was stirred overnight at 80° C. under N$_2$, cooled to rt, diluted with water and extracted with EA (3×). The combined organic layers were washed by water (3×) and brine consecutively, dried by Na$_2$SO$_4$, filtered, concentrated and purified by CC (PE/EA=8/1) to give compound 316 (1.5 g, 82%) as a white solid.

Step 2: 4-(4-(N-(tert-Butyl)sulfamoyl)naphthalen-1-yl)-5-(cyclohexylmethyl)-1-methyl-1H-pyrrole-2-carboxylic acid (317)

The solution of compound 316 (1.5 g, 3.0 mmol) and KOH (1.7 g, 30.0 mmol) in a mixture of EtOH (30 mL) and H$_2$O (15 mL) was stirred for 4 h at 80° C., concentrated, diluted with water, adjusted to pH=5 with 2N HCl and extracted with EA. The organic layer was dried with Na$_2$SO$_4$, filtered, concentrated and purified by CC (DCM/MeOH=20/1) to give compound 317 (1.4 g, 97%) as a white solid. $^1$H-NMR (CDCl$_3$, 400 MHz) δ: 0.49-0.55 (m, 2H), 0.89-0.98 (m, 3H), 1.18 (s, 9H), 1.22-1.47 (m, 6H), 2.45 (br s, 2H), 3.98 (s, 3H), 4.60 (s, 1H), 7.17 (s, 1H), 7.41 (d, J=7.6 Hz, 1H), 7.51-7.54 (m, 1H), 7.65-7.68 (m, 1H), 7.94 (d, J=8.4 Hz, 1H), 8.32 (d, J=7.6 Hz, 1H), 8.64 (d, J=8.4 Hz, 1H). MS 481.0 (M−1)$^−$.

Example 318

318

Step 1: Ethyl 2-amino-2-(2-(2-cyclohexylacetyl)hydrazono)acetate (318a)

To a solution of ethyl 2-amino-2-hydrazonoacetate (13.1 g, 100 mmol) in dry THF (100 mL) was added 2-cyclohexylacetyl chloride (16.0 g, 100 mmol) at 0° C. under $N_2$ and the solution was stirred for 30 min at rt. The formed solid was collected by filtration and washed with DCM and dried in vacuum to give compound 318a (12.8 g, 50%) as a tan solid.

Step 2: Ethyl 5-(cyclohexylmethyl)-1H-1,2,4-triazole-3-carboxylate (318b)

The suspension of compound 318a (4.5 g, 17.6 mmol) in xylene (100 mL) was heated in a Dean-Stark apparatus at 140° C. for 1 h, cooled, concentrated and purified by CC (PE/EA=2/1) to give compound 318b (1.6 g, 41%) as a white solid.

Step 3: Methyl 1-(3-(tert-butyl)-4-(N-(tert-butyl)sulfamoyl)phenyl)-5-(cyclohexylmethyl)-1H-1,2,4-triazole-3-carboxylate (318c)

A solution of (3-(tert-butyl)-4-(N-(tert-butyl)sulfamoyl)phenyl)boronic acid (2.28 g, 7.31 mmol), compound 318b (1.20 g, 5.06 mmol), $Cu(OAc)_2$ (912 mg, 2.53 mmol) and pyridine (360 mg, 4.54 mmol) in DCM (20 mL) was stirred overnight at rt under $N_2$, concentrated and purified by CC (PE/EA=5/1) to give compound 318c (540 mg, 19%) as a white solid. The NMR shows a NOE effect between $CH_2$ and aryl.

Step 4: 1-(3-(tert-Butyl)-4-(N-(tert-butyl)sulfamoyl)phenyl)-5-(cyclohexylmethyl)-1H-1,2,4-triazole-3-carboxylic acid (318d)

A solution of compound 318c (200 mg, 0.40 mmol) and $LiOH.H_2O$ (168 mg, 4.0 mmol) in a mixture of water (1 mL) and THF (5 mL) was stirred overnight at 60° C., concentrated, treated with a 2N HCl and stirred for additional 30 min. The resulting precipitate was collected by filtration, washed with water and dried in vacuum to give compound 318d (160 mg, 85%) as a white solid.

Step 5: trans-Methyl 3-(1-(3-(tert-butyl)-4-(N-(tert-butyl)sulfamoyl)phenyl)-5-(cyclohexylmethyl)-1H-1,2,4-triazole-3-carboxamido)cyclobutanecarboxylate (318e)

To a solution of compound 318d (300 mg, 0.63 mmol), trans methyl 3-aminocyclobutanecarboxylate hydrochloride (115 mg, 0.69 mmol), DIEA (162 mg, 1.26 mmol) and HATU (229 mg, 0.63 mmol) in DMF (5 mL) was stirred at rt for 3 h, diluted with water and extracted with EA (3×). The combined organic layers were washed with water (3×) and brine consecutively, dried over $Na_2SO_4$, filtered, concentrated and purified by CC (PE/EA=3/1) to give compound 318e (275 mg, 77%) as a white solid.

Step 6: trans-3-(1-(3-(tert-Butyl)-4-(N-(tert-butyl)sulfamoyl)phenyl)-5-(cyclohexylmethyl)-1H-1,2,4-triazole-3-carboxamido)cyclobutanecarboxylic acid (318)

To a solution of compound 318e (275 mg, 0.47 mmol) in THF (5 mL) and water (2 mL) was added $LiOH.H_2O$ (168 mg, 4.0 mmol) and the solution was stirred overnight at rt, diluted with water and extracted with $Et_2O$. The aqueous layer was adjusted with 1N HCl to pH=2 and then extracted with DCM. The combined organic phase was washed with brine, dried over $Na_2SO_4$, filtered, concentrated and purified by prep-HPLC to give compound 318 (50 mg, 20%) as a white solid. $^1$H-NMR ($CDCl_3$, 400 MHz) δ: 0.87-0.94 (m, 2H), 1.12-1.30 (m, 4H), 1.32 (s, 9H), 1.58-1.66 (m, 15H), 1.75-1.88 (m, 1H), 2.41-2.49 (m, 2H), 2.69 (d, J=7.2 Hz, 2H), 2.80-2.85 (m, 2H), 3.11-3.21 (m, 1H), 4.61 (s, 1H), 4.84-4.90 (m, 1H), 7.40 (d, J=8.4 Hz, 2H), 7.68 (d, J=2.0 Hz, 1H), 8.34 (d, J=8.4 Hz, 1H). MS 574.3 $(M+1)^+$.

Example 318/1

The following Example was prepared similar as described for Example 318:

| # | Structure | Analytical data |
|---|---|---|
| 318/1 | 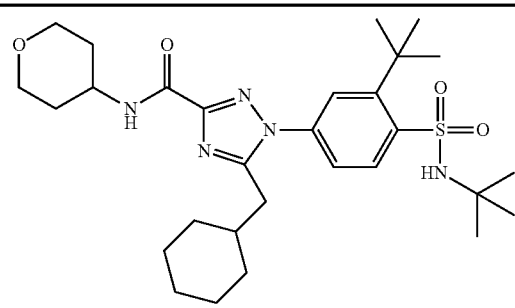 | $^1$H-NMR ($CDCl_3$, 400 MHz) δ: 0.77-0.98 (m, 2H), 1.11-1.30 (m, 4H), 1.32 (s, 9H), 1.62-1.66 (m, 15H), 1.75-1.88 (m, 1H), 2.00-2.09 (m, 2H), 2.68 (d, J = 7.2 Hz, 2H), 3.54 (td, J = 11.2 Hz, 2.0 Hz, 2H), 3.98-4.08 (m, 2H), 4.25-4.37 (m, 1H), 4.53 (s, 1H), 7.05 (d, J = 8.4 Hz, 1H), 7.41 (dd, J = 8.4 Hz, 2.0 Hz, 1H), 7.68 (d, J = 2.0 Hz, 1H), 8.34 (d, J = 8.4 Hz, 1H). MS 560.3 $(M + 1)^+$ |

Example 319

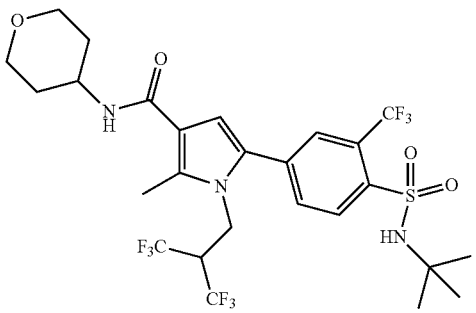

Step 1: N-Benzyl-3,3,3-trifluoro-2-(trifluoromethyl)propanamide (319a)

To a solution of 3,3,3-trifluoro-2-(trifluoromethyl)propanoic acid (15 g, 76.5 mmol) in DCM (250 mL) was added (COCl)$_2$ (9.6 g, 76.5 mmol) and the solution was stirred at rt for 2 h. Then NH$_2$Bn (9.8 g, 91.8 mmol) and DIPEA (19 g, 153 mmol) were added dropwise at 0° C. and the solution was stirred at rt for 2 h, quenched with aq. NH$_4$Cl, and the organic layer was concentrated to give compound 319a (13 g, 60%) as a white solid.

Step 2: N-Benzyl-3,3,3-trifluoro-2-(trifluoromethyl)propan-1-amine (319b)

A solution of compound 319a (1.0 g, 35 mmol) and BH$_3$ (1M in THF, 40 mL, 40 mmol) was heated at reflux for 48 h, cooled, quenched with MeOH (30 mL), heated to reflux for 1 h, concentrated, poured into water and extracted with EA. The organic layer was washed with brine, dried by Na$_2$SO$_4$, filtered and concentrated to give compound 319b (0.99 g, 100%) as a colorless oil.

Step 3: 3,3,3-Trifluoro-2-(trifluoromethyl)propan-1-amine 4-methylbenzenesulfonate (319c)

A suspension of compound 319b (2.0 g, 7.4 mmol) and 10% Pd/C (wet, 200 mg) in MeOH (30 mL) was stirred under H$_2$ (50 Psi) at rt overnight. TsOH.H$_2$O (3.0 g, 15 mmol) was added. The residue was filtered and washed with Et$_2$O and dried in vacuum to give compound 319c (1.4 g, 54%) as a white solid.

Step 4: 2,2-Dimethyl-5-(1-((3,3,3-trifluoro-2-(trifluoromethyl)propyl)amino)ethylidene)-1,3-dioxane-4,6-dione (319d)

A solution of compound 319c (1.0 g, 7.0 mmol), 5-(methoxyethylidene)-2,2-dimethyl-1,3-dioxane-4,6-dione (1.68 g, 8.4 mmol) in iso-propanol (20 mL) was refluxed for 22 h, cooled, concentrated and purified by CC (PE/EA=5/1) to compound 319d (1.0 g, 47%) as a white solid.

Step 5: Ethyl 3-((3,3,3-trifluoro-2-(trifluoromethyl)propyl)amino)but-2-enoate (319e)

To a solution of compound 319d (1.0 g, 2.87 mmol) in EtOH (10 mL) was added NaOEt (1M in EtOH, 3.0 mL, 3.0 mmol) and the solution was refluxed overnight under N$_2$, cooled, quenched with water and extracted with EA (3×). The combined organic phases were washed with water and brine, dried over Na$_2$SO$_4$, filtered, concentrated and purified by CC (PE/EA=10/1) to give compound 319e (350 mg, 42%) as a pale yellow oil.

Step 6: Ethyl 5-(4-(N-tert-butyl)sulfamoyl)-3-(trifluoromethyl)phenyl)-2-methyl-1-(3,3,3-trifluoro-2-(trifluoromethyl)propyl)-1H-pyrrole-3-carboxylate (319f)

The solution of compound 319e (2.0 g, 6.8 mmol), 4-(2-bromoacetyl)-N-(tert-butyl)-2-(trifluoromethyl)benzenesulfonamide (3.17 g, 7.9 mmol) and DIPEA (2.0 g, 16.0 mmol) in DMF (20 mL) were stirred at 160° C. for 30 min, cooled, concentrated and purified by CC (PE/EA=4/1) to give compound 319f (190 mg, 5%) as a brown oil.

Step 7: 5-(4-(N-(tert-Butyl)sulfamoyl)-3-(trifluoromethyl)phenyl)-2-methyl-1-(3,3,3-trifluoro-2-(trifluoromethyl)propyl)-1H-pyrrole-3-carboxylic acid (319q)

A solution of compound 319f (190 mg, 0.32 mmol) and KOH (22.4 mg, 0.40 mmol) in MeOH (5 mL) was stirred for 2 d at rt, concentrated, diluted with water, adjusted to pH=5 with 1N HCl and extracted with DCM. The organic layer was washed with brine, dried over Na$_2$SO$_4$, filtered, concentrated and purified by CC (PE/EA=1/2) to give compound 319g (30 mg, 17%) as a pale yellow solid.

Step 8: 5-(4-(N-(tert-Butyl)sulfamoyl)-3-(trifluoromethyl)phenyl)-2-methyl-N-(tetrahydro-2H-pyran-4-yl)-1-(3,3,3-trifluoro-2-(trifluoromethyl)propyl)-1H-pyrrole-3-carboxamide (319)

Compound 319g (30 mg. 53 µmol), 2H-3,4,5,6-tetrahydropyran-4-yl-amine (6 mg, 60 µmol), HATU (22 mg, 60 µmol) and DIPEA (12 mg, 0.1 mmol) in DMF (2 mL) were stirred at rt for 1 h, concentrated and purified by prep-HPLC and then SFC to give compound 319 (2.8 mg, 8%) as a white solid. $^1$H-NMR (CDCl$_3$, 300 MHz) δ: 1.25 (s, 9H), 1.45-1.60 (m, 2H), 1.94-2.03 (m, 2H), 2.68 (s, 3H), 2.86-2.96 (m, 1H), 3.48-3.57 (m, 2H), 3.97-4.01 (m, 2H), 4.11-4.18 (m, 1H), 4.54 (d, J=6.6 Hz, 2H), 4.72 (s, 1H), 5.63 (d, J=11.4 Hz, 1H), 6.42 (s, 1H), 7.62 (d, J=8.4 Hz, 1H), 7.80 (s, 1H), 8.38 (d, J=8.4 Hz, 1H). MS 652.2 (M+1)$^+$.

Example 320

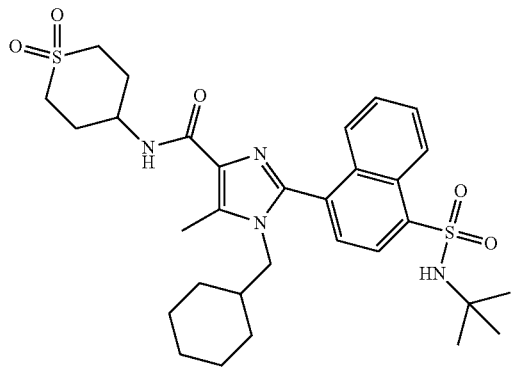

Step 1: Ethyl 1-(cyclohexylmethyl)-5-methyl-1H-imidazole-4-carboxylate (320a)

A solution of ethyl 5-methyl-1H-imidazole-4-carboxylate (400 mg, 2.59 mmol) and KOH (291 mg, 5.19 mmol) in DMSO (25 mL) was stirred at rt for 0.5 h. Then cyclohexylmethyl bromide (918 mg, 5.19 mmol) and TBAB (100 mg, 0.30 mmol) were added and the mixture was stirred at 30° C. for 8 h, diluted with water and extracted with DCM. The organic layer was dried over $Na_2SO_4$, filtered, concentrated and purified by CC (PE/EA=1/1) to give compound 320a (130 mg, 20%) as a pale brown solid. The NOE effect between imidazole-CH$_3$ and cyclohexylmethyl was observed by NOE spectrum.

Step 2: Ethyl 2-bromo-1-(cyclohexylmethyl)-5-methyl-1H-imidazole-4-carboxylate (320b)

To a solution of compound 320a (100 mg, 0.40 mmol) in DMF (10 mL) was added NBS (142 mg, 0.80 mmol) and the mixture was stirred at 90° C. for 6 h, diluted with water and extracted with DCM. The organic layer was dried over $Na_2SO_4$, filtered, concentrated and purified by CC (PE/EA=4/1) to give compound 320b (75 mg, 57%) as a white solid.

Step 3: Ethyl 2-(4-(N-(tert-butyl)sulfamoyl)naphthalen-1-yl)-1-(cyclohexylmethyl)-5-methyl-1H-imidazole-4-carboxylate (320c)

To a solution of compound 320b (300 mg, 0.912 mmol) in DMF (15 mL) was added N-(tert-butyl)-4-(4,4,5,5-tetramethyl-1,3,2-dioxaborolan-2-yl)naphthalene-1-sulfonamide (428 mg, 1.09 mmol), Pd(dppf)Cl$_2$ (67.0 mg, 91 μmol) and $K_2CO_3$ (503 mg) and the mixture was stirred at 95° C. for 18 h, diluted with water was added and extracted with DCM. The organic layer was dried over $Na_2SO_4$, filtered, concentrated and purified by CC (PE/EA=3/1) to give compound 320c (150 mg, 32%) as a white solid.

Step 4: 2-(4-(N-(tert-Butyl)sulfamoyl)naphthalen-1-yl)-1-(cyclohexylmethyl)-5-methyl-1H-imidazole-4-carboxylic acid (320d)

The solution of compound 320c (120 mg, 0.235 mmol) and KOH (79.0 mg, 1.41 mmol) in a mixture of EtOH (12 mL) and water (2 mL) was stirred refluxed for 6 h, cooled to rt, diluted with water and acidified to pH=6 with 2N HCl. The formed solid was collected by filtration, washed with water and dried in vacuum to give compound 320d (100 mg, 88%) as a white solid.

Step 5: 2-(4-(N-(tert-Butyl)sulfamoyl)naphthalen-1-yl)-1-(cyclohexylmethyl)-N-(1,1-dioxidotetrahydro-2H-thiopyran-4-yl)-5-methyl-1H-imidazole-4-carboxamide (320)

A solution of compound 320d (120 mg, 248 μmol), 4-aminotetrahydro-2H-thiopyran 1,1-dioxide (46 mg, 248 μmol), HATU (94 mg, 248 μmol) and DIEA (128 mg, 994 μmol) in DCM (6 mL) was stirred at rt for 1.5 h under $N_2$, concentrated and purified by prep-HPLC to give compound 320 (65 mg, 43%) as a white solid. $^1$H-NMR (CDCl$_3$, 300 MHz) δ: 0.50-0.54 (m, 2H), 0.89-0.92 (m, 9H), 1.28-1.32 (m, 3H), 1.50-1.52 (m, 3H), 2.19-2.27 (m, 2H), 2.34-2.41 (m, 2H), 2.70 (s, 3H), 3.08-3.12 (m, 4H), 3.53 (d, J=7.2 Hz, 2H), 4.22-4.25 (m, 1H), 4.72 (s, 1H), 7.19 (d, J=7.8 Hz, 1H), 7.59-7.65 (m, 3H), 7.70-7.76 (m, 1H), 8.41 (d, J=7.5 Hz, 1H), 8.69 (d, J=8.7 Hz, 1H). MS 615.3 (M+1)$^+$.

Example 321

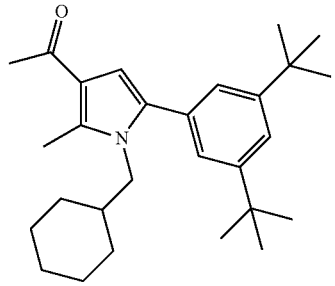

321

Step 1: 1-(Cyclohexylmethyl)-5-(3,5-di-tert-butylphenyl)-N-methoxy-N,2-dimethyl-1H-pyrrole-3-carboxamide (321a)

To a solution of 1-(cyclohexylmethyl)-5-(3,5-di-tert-butylphenyl)-2-methyl-1H-pyrrole-3-carboxylic acid (2.9 g, 7.08 mmol) in dry DCM (40 mL) was added DMF (0.1 mL) and this mixture was cooled to 0° C. Oxalyl dichloride (1.8 mL) was added and the resulting mixture was stirred at rt overnight and concentrated in vacuo to give crude acid chloride as a brown oil. To a stirred solution of N-methoxymethanamine hydrochloride (898 mg, 9.2 mmol) in DCM (10 mL) was added DIPEA (3.52 mL) and the mixture was stirred at rt. for 30 min. To this mixture was added a solution of the crude acid chloride in DCM (30 mL) at 0° C. and the resulting mixture was stirred at rt overnight, diluted with DCM, washed with water and brine, dried over $Na_2SO_4$, concentrated and purified by CC (PE/EA=8:1 to 5:1) to give compound 321a (2.7 g, 84%) as yellow semisolid.

Step 2: 1-(1-(Cyclohexylmethyl)-5-(3,5-di-tert-butylphenyl)-2-methyl-1H-pyrrol-3-yl)ethanone (321)

To a solution of compound 321a (453 mg, 1 mmol) in dry THF (4 mL) at rt was added CH$_3$MgBr (3M in THF, 1.8 mL) and the resulting mixture was stirred at rt. overnight, quenched with aq. NH$_4$Cl and extracted with Et$_2$O. The combined extracts were washed with aq. NH$_4$Cl and brine, dried over $Na_2SO_4$, concentrated and purified by CC (PE to PE/EA=30/1 to 20/1) to give compound 321 (371 mg, 91%) as colorless solid. $^1$H-NMR (400 MHz, CDCl$_3$): δ 7.41 (s, 1H), 7.16 (s, 2H), 6.47 (s, 1H), 3.71 (d, J=6.4 Hz, 2H), 2.61 (s, 3H), 2.42 (s, 3H), 1.57-1.52 (m, 4H), 1.35 (s, 18H), 1.35-1.25 (m, 4H), 0.99-0.86 (m, 3H), 0.67-0.64 (m, 2H). MS 408.4 (M+1)$^+$.

Example 321/1

Using similar procedures as that described in Example 321 the following Example was prepared:

| # | Structure | Analytical Data |
|---|---|---|
| 321/1 | 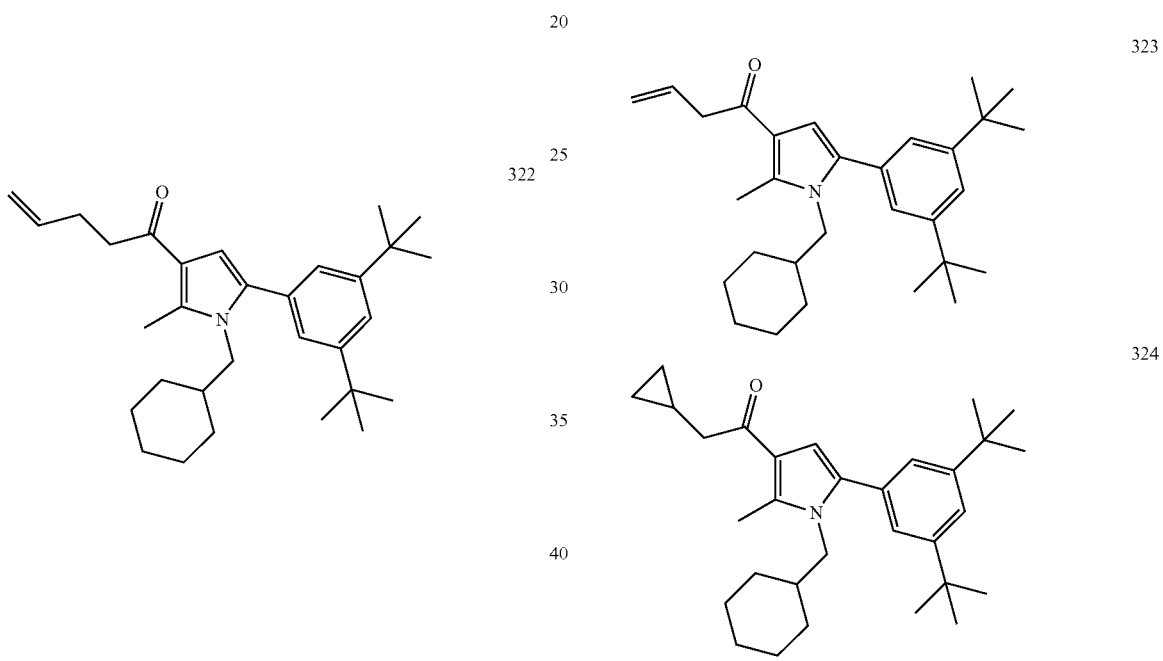 | $^1$H-NMR (400 MHz, CDCl$_3$) δ: 7.41 (s, 1H), 7.18 (s, 2H); 6.65 (s, 1H), 3.73 (d, J = 7.2 Hz, 2H), 2.62 (s, 3H), 2.46-2.44 (m, 1H), 1.56-1.51 (m, 4H), 1.35 (s, 18H), 1.42-1.24 (m, 4H), 1.14-1.12 (m, 2H), 1.01-0.96 (m, 3H), 0.88-0.85 (m, 2H), 0.67-0.64 (m, 2H). MS 434.5 (M + 1)$^+$. |

Example 322

1-(1-(Cyclohexylmethyl)-5-(3,5-di-tert-butylphenyl)-2-methyl-1H-pyrrol-3-yl)pent-4-en-1-one (322)

A mixture of Mg (124 mg, 5.1 mmol) and catalytic amounts of I$_2$ in dry THF (2 mL) was treated with (bromomethyl)cyclopropane (448 mg, 3.3 mmol) in dry THF (1 mL) and the resulting mixture was refluxed for 2 h and then cooled to rt. A solution of compound 321a (240 mg, 0.53 mmol) in dry THF (1 mL) was added and the resulting mixture was stirred at rt overnight, quenched with aq. NH$_4$Cl and extracted with Et$_2$O. The combined organic layers were washed with aq. NH$_4$Cl and brine, dried over Na$_2$SO$_4$, concentrated and purified by CC (PE to PE/EA=30/1 to 20/1) to give compound 322 (184 mg, 78%) as a colorless solid. $^1$H-NMR (400 MHz, CDCl$_3$) δ: 7.40 (s, 1H), 7.16 (s, 2H), 6.49 (s, 1H), 5.93-5.90 (m, 1H), 5.07 (d, J=17.2 Hz, 1H), 4.97 (d, J=10.0 Hz, 1H), 3.72 (d, J=5.6 Hz, 2H), 2.90-2.85 (m, 2H), 2.62 (s, 3H), 2.48-2.45 (m, 2H), 1.56-1.52 (m, 4H), 1.35 (s, 18H), 1.35-1.19 (m, 4H), 1.01-0.95 (m, 3H), 0.68-0.64 (m, 2H). MS 448.6 (M+1)$^+$.

Example 323 and Example 324

Step 1: 1-(1-(Cyclohexylmethyl)-5-(3,5-di-tert-butylphenyl)-2-methyl-1H-pyrrol-3-yl)but-3-en-1-one (323)

A mixture of Mg (80 mg, 3.32 mmol) and catalytic amounts of I$_2$ in dry Et$_2$O (2 mL) was treated with 3-bromoprop-1-ene (267 mg, 2.21 mmol) in dry Et$_2$O (1 mL) and the resulting mixture was refluxed for 1 h and then cooled to rt. A solution of compound 321a (200 mg, 0.44 mmol) in dry THF (1 mL) was added and the resulting mixture was stirred at 40° C. overnight, quenched with aq. NH$_4$Cl and extrated with Et$_2$O. The combined organic layers were washed with aq.NH$_4$Cl and brine, dried over Na$_2$SO$_4$, concentrated and purified by CC (PE to PE/EA=50/1 to 20/1) to give compound 323 (138 mg, 72%) as a colorless solid. $^1$H-NMR (400 MHz, CDCl$_3$) δ: 7.41 (s, 1H), 7.16 (s, 2H), 6.49 (s, 1H), 6.14-6.7 (m, 1H), 5.19-5.15 (m, 2H), 3.71 (d, J=6.8 Hz, 2H), 3.56 (d, J=6.8 Hz, 2H), 2.62 (s, 3H), 1.58-1.52 (m, 3H), 1.35 (s, 18H), 1.42-1.28 (m, 4H), 1.01-0.96 (m, 3H), 0.69-0.61 (m, 2H).

Step 2: 1-(1-(Cyclohexylmethyl)-5-(3,5-di-tert-butylphenyl)-2-methyl-1H-pyrrol-3-yl)-2-cyclopropylethanone (324)

To a solution of N-methyl-N-nitro-N-nitrosoguanidine (50% in water, 543 mg, 1.84 mmol) in Et$_2$O (4 mL) was added 40% NaOH (1.5 mL) dropwise at 0° C. and the mixture was stirred for 30 min. Then the mixture was decanted and the yellow liquid was added dropwise to a solution of compound 323 (80 mg, 0.184 mmol) and Pd(OAc)$_2$ (5 mg) in DCM (2 mL) at −20° C. The mixture was stirred at −20° C. for 1 h and then at rt overnight, diluted with DCM and washed with 5% AcOH, Na$_2$CO$_3$, water and brine, dried over Na$_2$SO$_4$, concentrated and purified by prep-HPLC to give compound 324 as a colorless solid (36 mg, 43%). $^1$H-NMR (400 MHz, CDCl$_3$) δ: 7.40 (s, 1H), 7.15 (s, 2H), 6.43 (s, 1H), 3.71 (d, J=6.8 Hz, 2H), 2.68 (d, J=6.4 Hz, 2H), 2.64 (s, 3H), 1.56-1.51 (m, 4H), 1.34 (s, 18H), 1.35-1.17 (m, 4H), 1.05-0.99 (m, 4H), 0.67-0.63 (m, 2H), 0.56 (d, J=7.6 Hz, 2H), 0.17 (d, J=4.4 Hz, 2H). MS 448.1 (M+1)$^+$.

Example 325

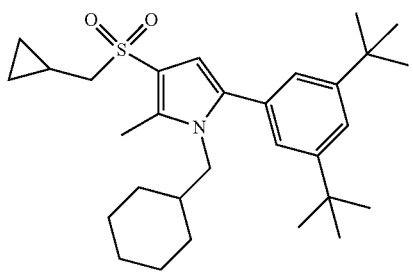

325

Step 1: Ethyl 1-(cyclohexylmethyl)-4-((cyclopropylmethyl)sulfonyl)-5-methyl-1H-pyrrole-2-carboxylate (325a)

To a solution of ethyl 4-(chlorosulfonyl)-1-(cyclohexylmethyl)-5-methyl-1H-pyrrole-2-carboxylate (15 g, 43.2 mmol) in acetone (100 mL) was added a solution of Na$_2$SO$_3$ (4.4 g, 35 mmol) in H$_2$O (50 mL) and the solution was stirred for 10 min at 80° C. A solution of Na$_2$CO$_3$ (9.2 g, 86 mmol) in H$_2$O (100 mL) was then added and the mixture was refluxed for 2 h. After cooling the crude sulfinic acid intermediate was precipitated by addition of 2M HCl to pH=2. After filtration, the solid was dissolved in a mixture of H$_2$O (200 mL) and EtOH (300 mL) followed by addition of Na$_2$CO$_3$ until pH=10. Bromocyclopropylmethane (4.0 g, 30 mmol) was then added and the solution was refluxed for 2 h, cooled, evaporated and diluted with H$_2$O (100 mL), followed by addition of conc. HCl until pH=2. The resulting colorless solid was filtered off and purified by CC (PE/EA=5/1) to give compound 325a (1.2 g, 51%).

Step 2: 1-(Cyclohexylmethyl)-4-((cyclopropylmethyl)sulfonyl)-5-methyl-1H-pyrrole-2-carboxylic acid (325b)

To a mixture of compound 325a (1.2 g, 3.2 mmol) in a mixture of H$_2$O (20 mL) and EtOH (40 mL) was added LiOH.H$_2$O (500 mg, 11.9 mmol) and the mixture was stirred at 80° C. for 4 h, concentrated and diluted with water (20 mL). 1M HCl was added to adjust pH to 4 and the suspension was extracted with EtA. The organic layer was dried over Na$_2$SO$_4$, filtered and concentrated to give crude compound 325b (1.0 g, 92%) as a colorless solid.

Step 3: 1-(Cyclohexylmethyl)-3-((cyclopropylmethyl)sulfonyl)-2-methyl-1H-pyrrole (325c)

A mixture of compound 325b (1.0 g, 2.5 mmol) in 4N HCl (20 mL) and EtOH (20 mL) was refluxed overnight, concentrated and extracted with EA twice. The combined organic layers were washed with water and brine consecutively, dried over Na$_2$SO$_4$, filtered, concentrated and purified by CC (PE/EA=5/1) to give compound 325c (700 mg, 95%) as a brown oil.

Step 4: 5-Bromo-1-(cyclohexylmethyl)-3-((cyclopropylmethyl)sulfonyl)-2-methyl-1H-pyrrole (325d)

To a solution of compound 325c (700 mg, 2.4 mmol) in THF (20 mL) was added a solution of NBS (409 mg, 2.3 mmol) in THF (8 mL) at −78° C. and the solution was stirred for 30 min, quenched with water and extracted with EA. The organic layer was washed with water twice and brine consecutively, dried over Na$_2$SO$_4$, filtered, concentrated and purified by CC (PE/EA=5/1) to give compound 325d (700 mg, 79%) as a brown solid.

Step 5: 1-(Cyclohexylmethyl)-3-((cyclopropylmethyl)sulfonyl)-5-(3,5-di-tert-butylphenyl)-2-methyl-1H-pyrrole (325)

A solution of compound 325d (700 mg, 1.9 mmol), Pd(dppf)Cl$_2$ (120 mg), K$_2$CO$_3$ (580 mg, 4.2 mmol) and (3,5-di-tert-butylphenyl)boronic acid (735.6 mg, 3.1 mmol) in DMF (30 mL) was heated at 120° C. overnight under N$_2$, cooled to rt, diluted with water and extracted with EA (3×). The combined organic layers were washed with water (3×) and brine twice, dried over Na$_2$SO$_4$, filtered, concentrated and purified by CC (PE/EA=10/1) to give compound 325 (85 mg, 10%) as a colorless solid. $^1$H-NMR (CDCl$_3$, 300 MHz) δ: 0.24 (2H, m), 0.58-0.71 (4H, m), 0.97-1.15 (4H, m), 1.34 (21H, s), 1.50-1.54 (3H, m), 2.55 (3H, s), 2.99 (2H, d, J=7.2 Hz), 3.74 (2H, d, J=7.2 Hz), 6.45 (1H, s), 7.14 (2H, d, J=1.8 Hz), 7.40 (1H, t, J=1.8 Hz). MS 484.9 (M+1)$^+$.

Example 325/1

Using similar procedures as that described in Example 325 the following Example was prepared:

| # | Structure | Analytical Data |
|---|---|---|
| 325/1 | 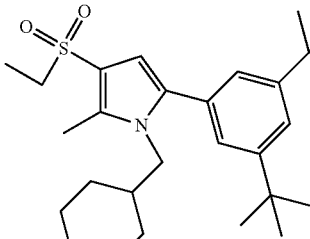 | $^1$H-NMR (CDCl$_3$, 300 MHz) δ: 0.56-0.66 (2H, m), 0.90-1.06 (3H, m), 1.27-1.40 (24H, m), 1.50-1.57 (3H, m), 2.54 (3H, s), 3.10 (2H, q, J = 7.5 Hz), 3.74 (2H, d, J = 7.2 Hz), 6.44 (1H, s), 7.15 (2H, d, J = 1.8 Hz), 7.41 (1H, t, J = 1.8 Hz). MS 458.4 (M + 1)$^+$ |
Additional Examples
The following compounds can be prepared in the same manner by using the procedures as described above:
| Structure |
|---|
| 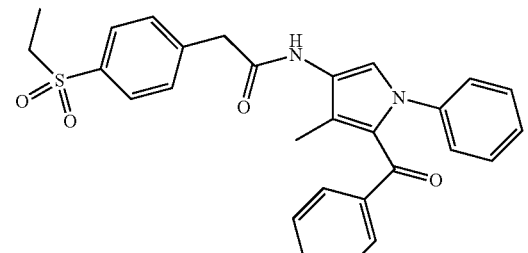 |
| 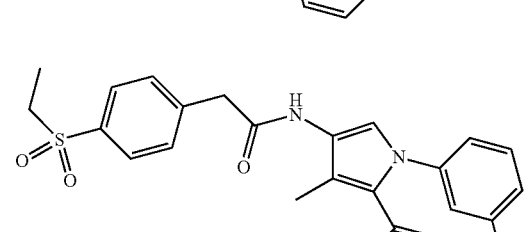 |
| 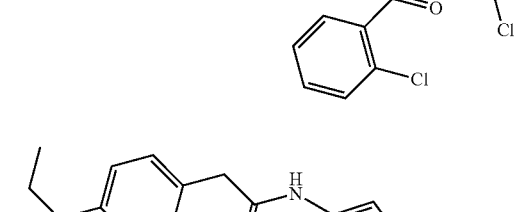 |
-continued
| Structure |
|---|
| 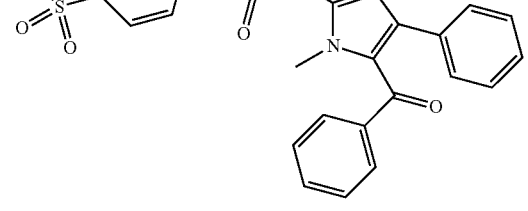 |
| 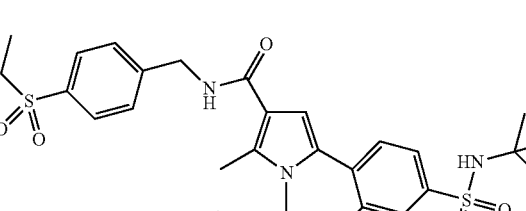 |
| 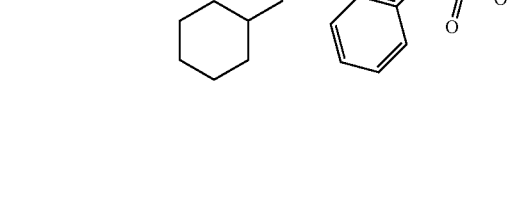 |
|  |

| Structure | Structure |
|---|---|
| 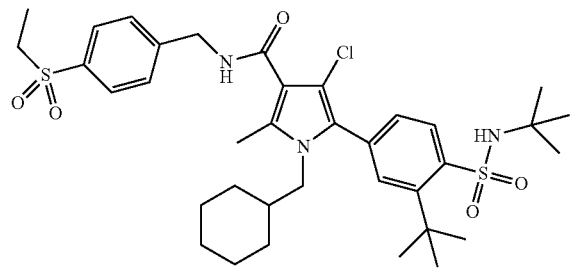 [SMILES: CCS(=O)(=O)c1ccc(CNC(=O)c2c(Cl)c(-c3ccc(S(=O)(=O)NC(C)(C)C)c(C(C)(C)C)c3)n(CC3CCCCC3)c2C)cc1] | 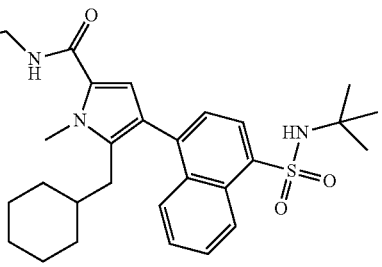 |
| 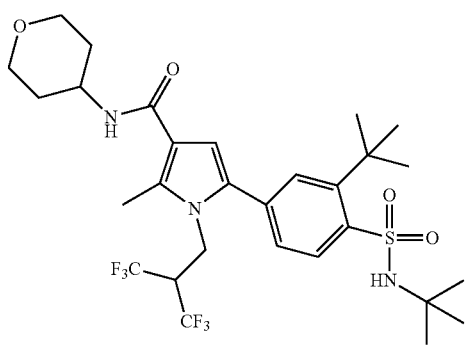 [SMILES: Cc1c(C(=O)NC2CCOCC2)cc(-c2ccc(S(=O)(=O)NC(C)(C)C)c(C(C)(C)C)c2)n1CC(C(F)(F)F)C(F)(F)F] | 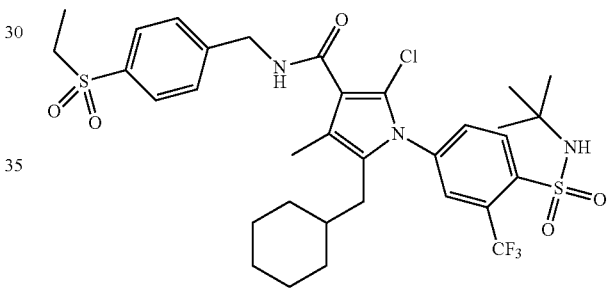 |
| 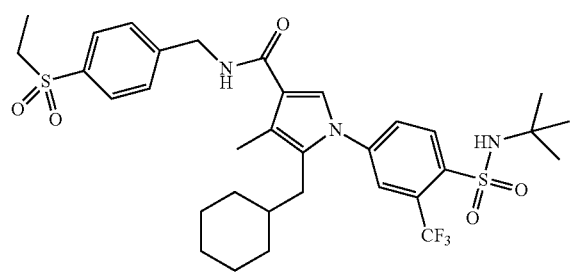 [SMILES: CCS(=O)(=O)c1ccc(CNC(=O)c2cn(-c3ccc(S(=O)(=O)NC(C)(C)C)c(C(F)(F)F)c3)c(CC3CCCCC3)c2C)cc1] | |

Protein Expression and Purification

Protein expression and purification was done as described in WO2010/049144.

TR-FRET Activity Assay

This method measures the ability of putative ligands to modulate the interaction between the purified bacterial expressed RORγ ligand binding domain (LBD) and synthetic N-terminally biotinylated peptides which are derived from nuclear receptor coactivator proteins such as but not limited to SRC1 (NcoA1), SRC2 (NcoA2, TIF2), SRC3 (NcoA3), PGC1α, PGC1β, CBP, GRIP1, TRAP220, RIP140. The peptides used are listed in Table 1 below:

TABLE 1

| Peptide Name (aa range) | DB entry Protein | DB entry DNA | Sequence |
|---|---|---|---|
| SRC1(676-700) | NP_003734 | NM_003743.4 | $NH_2$-CPSSHSSLTERHKILHRLLQEGSPS-COOH |
| TRAP220(631-655) | NP_004765 | NM_004774.3 | $NH_2$-PVSSMAGNTKNHPMLMNLLKDNPAQ-COOH |
| TIF2(628-651) | NP_006531 | NM_006540.2 | $NH_2$-GQSRLHDSKGQTKLLQLLTTKSDQ-COOH |

The ligand-binding domain (LBD) of RORγ was expressed as fusion protein with GST in BL-21 (BL3) cells using the vector pDEST15. Cells were lysed by lysozyme-treatment and sonication, and the fusion proteins purified over glutathione sepharose (Pharmacia) according to the manufacturers instructions. For screening of compounds for their influence on the RORγ-peptide interaction, the LANCE technology (Perkin Elmer) was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection assays were done in a final volume of 25 μL in a 384 well plate, in a Tris-based buffer system (20 mM Tris-HCl pH6.8; 60 mM KCl, 1 mM DTT; 5 mM MgCl$_2$; 35 ng/μL BSA), containing 20-60 ng/well recombinantly expressed RORγ-LBD fused to GST, 200-600 nM N-terminally biotinylated peptide, 200 ng/well Streptavidin-xlAPC conjugate (Prozyme) and 6-10 ng/well Eu W1024-antiGST (Perkin Elmer). DMSO content of the samples was kept at 1%.

After generation of the Tris-based buffer system, the potentially RORγ modulating ligands were diluted. After his step, protein, peptide and fluorescent acceptor and donor solutions were mixed in the Tris-based buffer system and have been added to the compound dilutions, after this addition of 'detection mix', the assay was equilibrated for one hour in the dark at rt in FIA-plates black 384 well (Corning). The LANCE signal was detected by a Perkin Elmer EnVision™ Multilabel Counter. The results were visualized by plotting the ratio between the emitted light at 665 nm and 615 nm. A basal level of RORγ-peptide formation is observed in the absence of added ligand. Ligands that promote the complex formation induce a concentration-dependent increase in time-resolved fluorescent signal. Compounds which bind equally well to both monomeric RORγ and to the RORγ-peptide complex would be expected to give no change in signal, whereas ligands, which bind preferentially to the monomeric receptor would be expected to induce a concentration-dependent decrease in the observed signal.

To assess the antagonistic potential of the compounds, IC$_{50}$ values were determined using a Ligand Sensing Assay based on Time-resolved Fluorescence Energy Transfer (TR-FRET) as described above. The normalised TR-FRET assay values, using the following equation: 1000*665 nm measurement value/615 nm measurement value, were transferred to the program GraphPad Prism to generate graphs and dose response curves using the following equation:

Equation: Sigmoidal dose-response (variable slope)

$$Y=Bottom+(Top-Bottom)/(1+10^{\wedge}((\log EC50-X)*HillSlope))$$

X is the logarithm of the concentration. Y is the response. Y starts at Bottom and goes to Top with a sigmoidal shape.

This is identical to the "four parameter logistic equation". The IC$_{50}$ values are calculated using this equation. Examples listed below do reduce the signal in the TR-FRET assay in a dose dependent manner. The Examples of the present invention usually have an inhibition activity (IC$_{50}$ FRET) ranging from below 100 nM to about 20 μM. The RORγ modulating compounds of the invention desirably have an inhibition in the TR-FRET Activity Assay ranging from below 100 nM to about 1 μM. Table 2 lists the pIC$_{50}$-value of compounds of the invention. Is is understood that the data illustrated below may have reasonable variation depending on the specific conditions and procedures used by the person conducting the test.

RORγ Gal4 Reporter Gene Assay

Determination of a ligand mediated Gal4 promoter driven transactivation to quantify ligand binding to RORγ was performed as follows: DNA encoding three different RORγ. protein fragments was cloned into vector pCMV-BD (Stratagene). Expression was under control of a CMV promoter and as fusion to the DNA-binding domain of the yeast protein GAL4. The amino acid boundaries of the three proteins and the respective database entries are listed in Table 3. Other vectors used were pFR-Luc (Stratagene) as regulated reporter plasmid. pFR-Luc contains a synthetic promoter with five tandem repeats of the yeast GAL4 binding sites that control expression of the Photinus pyralis (American firefly) luciferase gene. In order to improve experimental accuracy the plasmid pRL-CMV was cotransfected. pRL-CMV contains the constitutive CMV promoter, controlling the expression of the Renilla reniformis luciferase.

TABLE 3

| construct name | aa borders (RefSeq) | Ref sequence ID |
|---|---|---|
| hRORg-LBD | aa259-518 | NP_005051.2 |
| hRORgt | aa1-497 | NP_001001523 (RORg, t isoform, 497aa) |
| mRORg-LBD | aa264-516 | NP_035411 |

All Gal4 reporter gene assays were done in 293T cells (DSMZ (German Collection of Microorganisms and Cell Cultures), Braunschweig, Germany, ACC635) grown in Minimum Essential Medium (MEM) with Phenol Red. The medium is supplemented with 10% fetal bovine serum, 0.1 mM nonessential amino acids, 1 mM sodium pyruvate, 1% Glutamax and 100 units Penicilin/Streptavidin per mL at 37° C. in 5% CO$_2$.

For the assay, 5×10$^5$ cells were plated per well in 96 well plates in 100 μL per well, incubated over night at 37° C. in 5% CO$_2$. The following day, medium was discarded and the cells were transiently transfected using 20 μL per well of a OptiMEM—PEI-based transfection-reagent (Sigma-Aldrich, 408727) including the three plasmids described above. About 4 h after addition of the transfection solution, fresh Minimal Essential Medium (MEM, same composition as used for plating cells, but without serum) was added. Then compound stocks, prediluted in MEM (same composition as used for plating cells) were added (final vehicle concentration not exceeding 0.1%).

Cells were incubated for additional 16 h before firefly (FF) and renilla (REN) luciferase activities were measured sequentially in the same cell extract using a Dual-Light-Luciferase-Assay system (Dyer et al., Anal. Biochem. 2000, 282:158). All experiments were done at least in triplicates.

Applying the Gal4 reporter gene assay as described above, the Examples of the present invention usually have an inhibition activity (IC$_{50}$ FF resp. IC$_{50}$ RENnorm) ranging from below 10 nM to about 20 μM, and typically, from about 10 nM to about 1 μM. The RORγ modulating compounds of the invention desirably have an inhibition in the Gal4 reporter gene assay ranging from below 10 nM to about 1 μM. Table 2 lists the pIC$_{50}$-value of typical examples of compounds of the invention that have an RORγ activity in the Gal4 reporter gene assay for firefly (FF) and renilla normalised (RENnorm) luciferase measurements (nt=not tested). It is understood that the data illustrated below may have reasonable variation depending on the specific conditions and procedures used by the person conducting the test. The efficacy was determined in comparison to the RORγt inhibitor T0901317 (equals 100%) and the pIC$_{50}$-value is underlined, when the efficacy of the compound is below 50% of the reference.

TABLE 2

| Ex. # | pIC$_{50}$ (FRET/FF/REN) | Ex. # | pIC$_{50}$ (FRET/FF/REN) | Ex. # | pIC$_{50}$ (FRET/FF/REN) |
|---|---|---|---|---|---|
| 1 | 6.9/7.3/7.3 | 1/1 | 6.7/7.4/7.5 | 1/2 | 6.5/7.5/7.4 |
| 1/3 | 6.1/6.9/6.9 | 1/4 | 6.4/7.2/7.2 | 1/5 | 6.0/7.6/8.0 |
| 1/6 | 6.6/7.2/7.2 | 2 | 5.9/6.4/6.5 | 4 | 6.3/7.2/7.7 |
| 4/1 | 5.9/7.2/7.3 | 4/2 | 6.2/7.3/7.5 | 4/3 | 6.4/7.6/7.6 |
| 6 | 6.3/7.9/8.0 | 8 | 6.0/7.6/7.7 | 8/1 | 5.7/7.0/7.0 |
| 8/2 | 6.4/7.1/7.3 | 8/3 | 6.3/7.1/7.3 | 8/4 | 6.0/7.7/.8 |
| 8/5 | 6.0/7.6/7.6 | 8/6 | 6.3/7.8/7.9 | 8/7 | 6.3/7.8/7.9 |
| 8/8 | 5.7/8.4/8.4 | 8/9 | 5.9/7.5/7.5 | 8/10 | 6.1/7.4/7.5 |
| 8/11 | 5.9/7.3/7.4 | 8/12 | 6.0/7.7/7.8 | 8/13 | 5.6/7.4/7.6 |
| 8/14 | 5.7/7.4/7.6 | 8/15 | 5.7/7.2/7.4 | 8/16 | 5.8/7.5/7.6 |
| 8/17 | 6.0/7.7/7.9 | 8/18 | 6.1/6.7/6.7 | 8/19 | 6.1/6.8/6.8 |
| 9 | 6.1/8.4/8.4 | 10 | 5.8/6.9/6.9 | 12 | 6.0/6.9/6.8 |
| 12/2 | 5.9/6.6/6.6 | 13 | 6.0/7.1/7.1 | 13/1 | 6.0/6.7/6.8 |
| 14 | 5.7/6.1/6.3 | 14/1 | 5.8/6.6/6.6 | 15 | 6.2/7.0/7.0 |
| 16 | 5.8/6.6/6.7 | 17 | 5.9/6.4/6.3 | 17/1 | 6.1/7.0/7.1 |
| 18 | 5.9/6.6/6.5 | 18/1 | 6.1/6.6/6.7 | 19/1 | 6.1/7.2/7.2 |
| 19/2 | 6.3/6.9/6.9 | 20 | 5.4/7.2/7.3 | 21 | 6.1/8.0/8.2 |
| 22 | 5.7/7.1/7.1 | 23 | 5.8/6.4/6.5 | 25 | 6.2/8.3/8.3 |
| 26 | 6.3/8.5/8.5 | 26/1 | nt/7.8/7.9 | 26/2 | nt/7.0/7.2 |
| 26/3 | nt/7.5/7.8 | 26/4 | nt/7.7/7.8 | | |
| 100 | 6.3/6.9/7.0 | 100/1 | 7.1/7.3/7.4 | 100/2 | 6.1/7.3/7.4 |
| 100/3 | 6.1/7.0/7.1 | 100/4 | 5.7/6.6/6.7 | 100/5 | 6.3/7.1/7.2 |
| 100/6 | 6.5/6.3/6.3 | 100/7 | 5.9/6.2/6.3 | 102/1 | 6.2/5.9/6.0 |
| 102/2 | 6.2/<4.7/<4.7 | 102/3 | 5.5/5.7/6.1 | 103/1 | 6.7/6.6/6.7 |
| 103/2 | 6.5/6.3/6.4 | 103/3 | 6.4/<4.7/<4.7 | 103/4 | 6.0/<4.7/<4.7 |
| 103/5 | 6.5/6.2/6.3 | 103/6 | 6.2/6.1/6.2 | 103/7 | 6.6/6.3/6.3 |
| 103/8 | 6.1/<4.7/<4.7 | 104/1 | 6.8/6.4/6.3 | 104/2 | 6.8/6.5/6.5 |
| 104/3 | 6.8/6.7/6.5 | 104/4 | 6.2/6.6/6.6 | 105 | 5.2/<4.7/<4.7 |
| 106 | 6.9/6.7/6.6 | 107 | 5.9/<4.7/<4.7 | 108 | 6.3/6.4/6.4 |
| 109 | 6.3/6.7/6.8 | 110 | nt/6.5/6.5 | 111 | nt/7.3/7.5 |
| 111/1 | nt/6.6/6.6 | 112 | 6.5/6.9/6.9 | 112/1 | 6.3/7.5/7.6 |
| 112/2 | 6.1/6.9/7.0 | 113 | nt/7.5/7.6 | 114 | nt/6.8/6.8 |
| 114/1 | nt/6.9/7.0 | | | | |
| 301 | 6.3/6.7/6.8 | 302 | 8.2/7.6/7.8 | 302/1 | 5.8/6.3/6.4 |
| 302/2 | 5.3/6.1/6.1 | 302/3 | 4.8/6.3/6.2 | 302/4 | 5.4/<4.7/<4.7 |
| 302/5 | 6.1/6.2/6.3 | 302/6 | 6.0/6.5/6.7 | 303 | 6.3/<4.7/<4.7 |
| 304 | 6.9/6.1/6.1 | 305 | 6.7/6.3/6.3 | 306 | 6.1/5.9/6.0 |
| 307 | 6.1/5.9/6.1 | 308 | 5.1/6.0/5.9 | 308/1 | 5.6/6.0/6.0 |
| 308/2 | 6.2/6.2/6.3 | 308/3 | 6.1/6.3/6.4 | 308/4 | 6.0/6.3/6.4 |
| 308/5 | 5.4/5.5/<4.7 | 308/6 | 6.0/6.5/6.5 | 308/7 | 5.6/5.7/5.9 |
| 308/8 | 5.8/6.2/6.3 | 308/9 | 5.1/5.6/5.6 | 308/10 | 5.2/<4.7/<4.7 |
| 309 | 5.5/<4.7/<4.7 | 310 | 4.9/<4.7/<4.7 | 311 | 6.5/6.0/5.9 |
| 312 | 6.6/6.2/6.3 | 312/1 | 5.2/<4.7/<4.7 | 312/2 | 5.1/<4.7/<4.7 |
| 313 | 7.0/6.3/6.4 | 314 | 5.4/5.6/5.5 | 315 | 6.9/6.7/6.7 |
| 315/1 | 6.0/6.0/6.0 | 317 | 5.9/6.9/6.9 | 318 | 5.7/<4.7/<4.7 |
| 318/1 | 5.6/6.2/6.2 | 319 | 5.3/6.0/5.8 | 320 | nt/5.9/6.0 |
| 321 | 6.1/5.8/6.0 | 322 | 5.8/<4.7/<4.7 | 324 | 6.2/<4.7/<4.7 |
| 325 | 6.4/6.1/6.1 | 325/1 | 6.6/6.0/6.3 | | |

The invention claimed is:

1. A compound represented by Formula (1), Formula (2), Formula (3), Formula (4) or Formula (5):

(1)

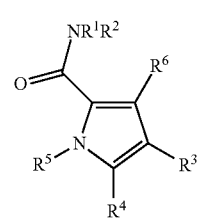

(2)

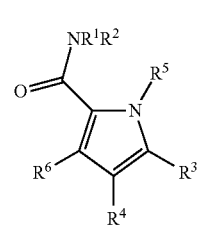

(3)

-continued

-continued

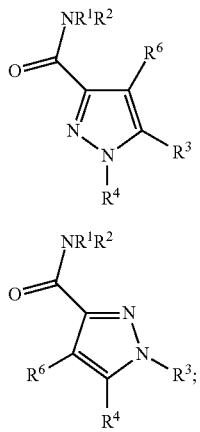

(4)

(5)

or an enantiomer, a diastereomer, a tautomer, an N-oxide, a formulation or a pharmaceutically acceptable salt thereof;

wherein:

$R^1$ is independently selected from $C_{1-10}$-alkyl, $C_{2-10}$-alkenyl, $C_{2-10}$-alkynyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered heteroaryl) and $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from the group consisting of oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_2R^{11}$, $SO_3H$, $SO_2NR^{11}R^{12}$; $NR^{11}COR^{11}$; $NR^{11}SO_2R^{11}$; $NR^{11}$—CO—$NR^{11}R^{12}$, $NR^{11}$—$SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

$R^2$ is $R^1$ or H;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo;

$R^3$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl is optionally substituted with 1 to 5 substituents independently selected from the group consisting of halogen, $C_{1-6}$-alkyl, $C_{2-6}$-alkenyl, $C_{2-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered heteroaryl), $C_{1-6}$-alkylene-O—$R^{31}$, $C_{0-6}$-alkylene-CN, $C_{0-6}$-alkylene-$N(R^{31})_2$, O—$C_{3-10}$-cycloalkyl, O—$C_{1-6}$-alkylene-O—$R^{31}$, O—$C_{3-10}$-heterocycloalkyl, $C_{0-6}$-alkylene-$COOR^{31}$, $C_{0-6}$-alkylene-$C(O)R^{31}$, $C_{0-6}$-alkylene-$C(O)N(R^{31})_2$, $C_{0-6}$-alkylene-$N(R^{31})C(O)R^{31}$, $C_{0-6}$-alkylene-SO—$R^{31}$, $C_{0-6}$-alkylene-$SO_2$—$R^{31}$, $C_{0-6}$-alkylene-$SO_2$—$N(R^{31})_2$, $C_{0-6}$-alkylene-$N(R^{31})SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkyl, alkenyl, alkynyl, alkylene, cycloalkyl, heterocycloalkyl and the 5- or 6-membered heteroaryl is unsubstituted or substituted by 1 to 4 substituents independently selected from the group consisting of halogen, CN, $C_{1-3}$-alkyl, halo-$C_{1-3}$-alkyl, OH, oxo, =N—$OR^{32}$, O—$C_{1-3}$-alkyl and O-halo-$C_{1-3}$-alkyl, or wherein two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 7 substituents independently selected from the group consisting of halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl;

$R^4$ is $(CR^8R^9)R^{40}$, $(C=O)R^{40}$, $(C=O)NR^{13}R^{14}$, O—$R^{40}$, $C_{3-10}$-cycloalkylidenemethyl, $C_3$-cycloalkylene-$R^{40}$ or $SO_y$—$R^7$;

$R^5$ is H, $C_{1-3}$-alkyl, $C_{3-6}$-cycloalkyl or halo-$C_{1-3}$-alkyl, wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

$R^6$ is independently H, halogen, CN, $C_{1-3}$-alkyl, $C_{3-6}$-cycloalkyl, halo-$C_{1-3}$-alkyl or $CONHR^{61}R^{62}$, wherein alkyl, cycloalkyl and haloalkyl are unsubstituted or substituted with 1 to 3 substituents independently selected from the group consisting of OH, oxo, O—$C_{1-6}$-alkyl and O-halo-$C_{1-6}$-alkyl;

$R^7$ is $C_{3-10}$-cycloalkyl or $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-7}$-cycloalkyl and 3 to 7-membered heterocycloalkyl;

$R^8$ is H, F, $C_{1-3}$-alkyl, halo-$C_{1-3}$-alkyl, OH, O—$C_{1-3}$-alkyl or O-halo-$C_{1-3}$-alkyl;

$R^9$ is H, F, $C_{1-3}$-alkyl or halo-$C_{1-3}$-alkyl;

$R^{11}$ is independently selected from H, $C_{1-6}$-alkyl, $C_{0-6}$-alkylene-$C_{3-10}$-cycloalkyl and $C_{0-6}$-alkylene-$C_{3-10}$-heterocycloalkyl, wherein alkyl, alkylene, cycloalkyl and heterocycloalkyl is unsubstituted or substituted with 1 to 6 substituents selected from the group consisting of halogen, CN, OH, oxo, $C_{1-3}$-alkyl, halo-$C_{1-3}$-alkyl, O—$C_{1-3}$-alkyl, O-halo-$C_{1-3}$-alkyl, $NH_2$, $NH(C_{1-3}$-alkyl), $N(C_{1-3}$-alkyl$)_2$, $C_{3-6}$-heterocycloalkyl, $C_{3-6}$-cycloalkyl and $SO_2$—$C_{1-3}$-alkyl, wherein cycloalkyl and heterocycloalkyl is unsubstituted or substituted with 1 to 3 substituents independently selected from the group consisting of F, OH, oxo, $CH_3$ and $CF_3$;

$R^{12}$ is independently selected from H, $C_{1-6}$-alkyl, halo-$C_{1-6}$-alkyl and $C_{3-6}$-cycloalkyl;

$R^{13}$ and $R^{14}$ taken together with the nitrogen to which they are attached complete a 3- to 10-membered ring containing carbon atoms, wherein this ring is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl and $C_{3-6}$-cycloalkyl;

$R^{31}$ is independently selected from H, $C_{1-6}$-alkyl, halo-$C_{1-6}$alkyl, $C_{0-6}$-alkylene-$C_{3-8}$-cycloalkyl, $C_{0-6}$-alkylene-$C_{3-8}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from the group consisting of halogen, CN, OH, oxo, =N—$OR^{32}$, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally when two $R^{31}$ are attached to a nitrogen atom, they may complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl;

$R^{32}$ is independently selected from H, $C_{1-6}$-alkyl, halo-$C_{1-6}$-alkyl and $C_{3-6}$-cycloalkyl;

$R^{40}$ is $C_{3-10}$-cycloalkyl, which is unsubstituted or substituted with 1 to 5 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-8}$-cycloalkyl and $C_{3-8}$-heterocycloalkyl;

$R^{61}$ and $R^{62}$ are independently selected from the group consisting of H, $C_{1-3}$-alkyl and halo-$C_{1-3}$-alkyl; and x and y is independently selected from 0, 1 and 2;

with the proviso that the compound is not 5-(cyclopentylmethyl)-1-(2,4-dichlorophenyl)-4-methyl-N-(piperidin-1-yl)-1H-pyrazole-3-carboxamide and the compounds of Formula (5) are not compounds wherein $R^4$ is $OR^{40}$.

2. The compound according to claim 1 wherein:
$R^5$ is H or $C_{1-3}$-alkyl; and
$R^6$ is H, F, Cl, CN, $C_{1-3}$-alkyl or halo-$C_{1-3}$-alkyl.

3. The compound according to claim 1 wherein:
$R^4$ is $CH_2R^{40}$, $CH(CH_3)R^{40}$, $OR^{40}$ or $(C=O)R^{40}$; and
$R^{40}$ is $C_{3-8}$-cycloalkyl, which is unsubstituted or substituted with 1 to 3 substituents independently selected from the group consisting of F, $CH_3$ and $CF_3$.

4. The compound according to claim 1 wherein:
$R^1$ is selected from $C_{1-10}$-alkyl, $C_{3-10}$-cycloalkyl, $C_{3-10}$-heterocycloalkyl, $C_{1-10}$-alkylene-$C_{3-10}$-cycloalkyl, $C_{1-10}$-alkylene-$C_{3-10}$-heterocycloalkyl and $C_{1-10}$-alkylene-(5-membered heteroaryl), wherein alkyl, alkylene, cycloalkyl, heterocycloalkyl and heteroaryl is unsubstituted or substituted with 1 to 7 substituents independently selected from the group consisting of oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $CONR^{11}SO_2R^{11}$, $COR^{11}$, $SO_xR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $SO_2$—$NR^{11}R^{12}$, $C_{3-10}$-cycloalkyl, O—$C_{3-10}$-cycloalkyl, $C_{3-10}$-heterocycloalkyl, O—$C_{3-10}$-heterocycloalkyl and $NR^{11}R^{12}$;

$R^2$ is selected from H, $C_{1-6}$-alkyl, halo-$C_{1-6}$-alkyl and hydroxy-$C_{1-6}$-alkyl;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of halogen, oxo, CN, $OR^{11}$, $SO_xR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $CONR^{11}SO_2R^{11}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-8}$-cycloalkyl, O—$C_{3-8}$-cycloalkyl, $C_{3-8}$-heterocycloalkyl and O—$C_{3-8}$-heterocycloalkyl, wherein cycloalkyl and heterocycloalkyl are unsubstituted or substituted with 1 to 4 substituents independently selected from the group consisting of halogen, $C_{1-3}$-alkyl, halo-$C_{1-3}$-alkyl, OH, O—$C_{1-3}$-alkyl, O-halo-$C_{1-3}$-alkyl, $SO_2$—$C_{1-3}$-alkyl, COOH and oxo.

5. The compound according to claim 1 wherein $NR^1R^2$ is selected from:

NHMe, NHEt, NH$^i$Pr, NH$^t$Bu, NHCH$_2$CONH$_2$, NHCH$_2$CONMe$_2$, NHCH$_2$CH$_2$OH, NHCH$_2$CH$_2$OMe, NHCH$_2$CH$_2$SO$_2$Me, NHCH$_2$CH$_2$SO$_2$NH$_2$, NH(CH$_2$)$_3$OH, NH(CH$_2$)$_3$OMe, NH(CH$_2$)$_4$OH, NH(CH$_2$)$_4$OMe, NH(CH$_2$)$_5$OH, NH(CH$_2$)$_2$CO$_2$H, NH(CH$_2$)$_3$CO$_2$H, NH(CH$_2$)$_4$CO$_2$H, NH(CH$_2$)$_5$CO$_2$H, NHCH$_2$CH(CF$_3$)OH, NHCH$_2$C(Me)(CF$_3$)OH, NHCH$_2$CMe$_2$OH, NHCH$_2$CH$_2$CMe$_2$OH, NHCH$_2$CMe$_2$NHCH$_2$CF$_3$, NHCH(Me)CMe$_2$OH, NHCH$_2$CMe$_2$OMe, NHCH$_2$CMe$_2$CO$_2$H, NHCH$_2$CMe$_2$CONHMe, NHCH$_2$CMe$_2$CONMe$_2$, NHCH$_2$CMe$_2$NHSO$_2$Me, NH(CH$_2$)$_3$SOMe, NH(CH$_2$)$_5$SO$_2$Me, NH(CH$_2$)$_5$SO$_2$NH$_2$, NH(CH$_2$)$_3$NHSO$_2$Me, NH(CH$_2$)$_2$O(CH$_2$)$_2$OH, NHCH$_2$CHMeOH, NH(CH$_2$)$_5$SOMe, NH(CH$_2$)$_3$SO$_2$Me, NHC(CH$_2$OH)$_3$, NHCH$_2$CH(OH)CH$_2$OH, N(CH$_2$CH$_2$OH)$_2$,

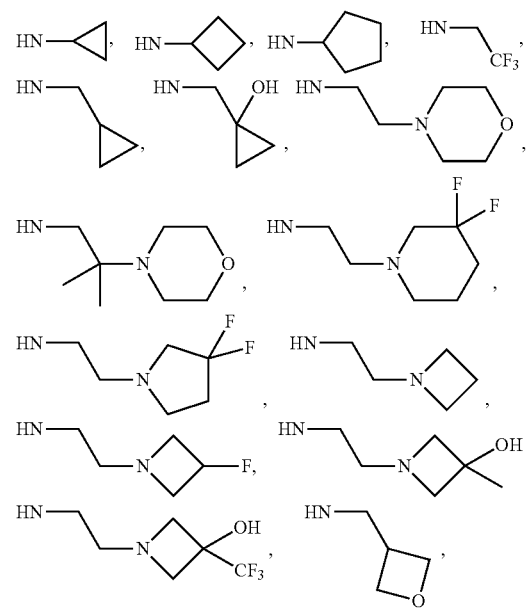

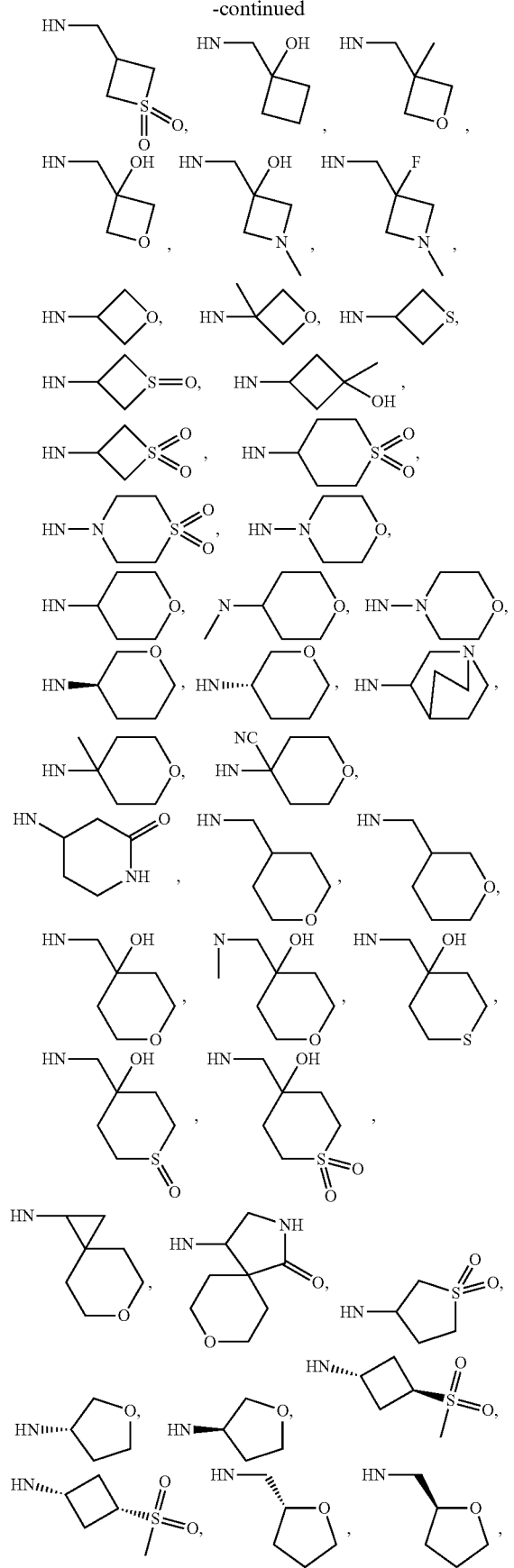
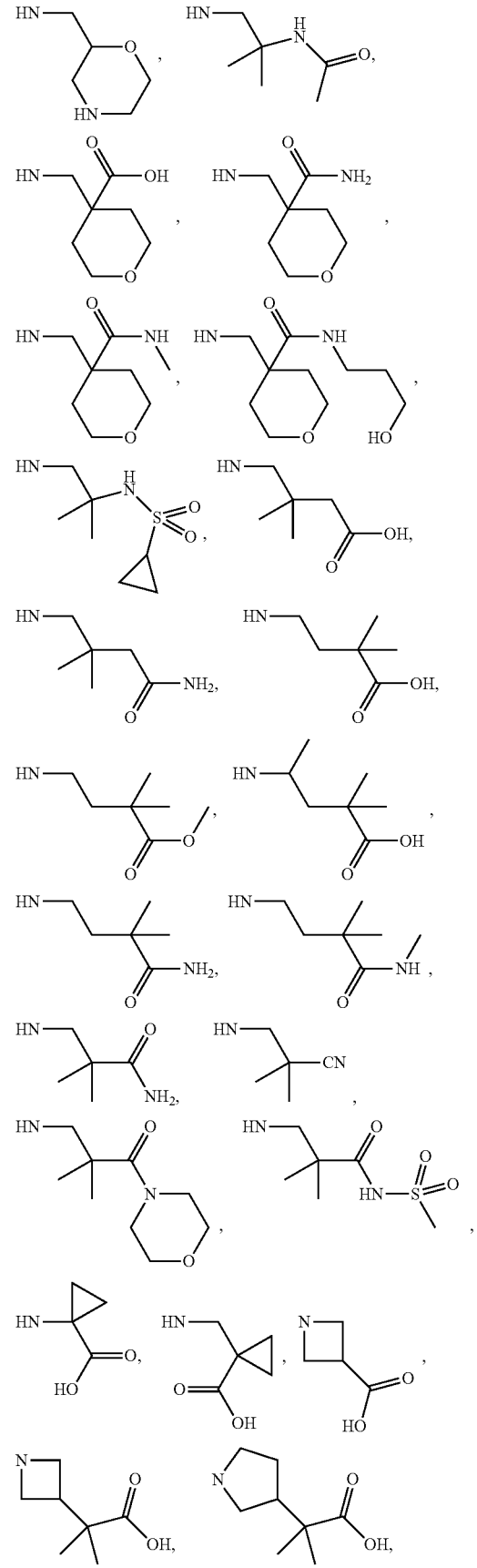

255
-continued
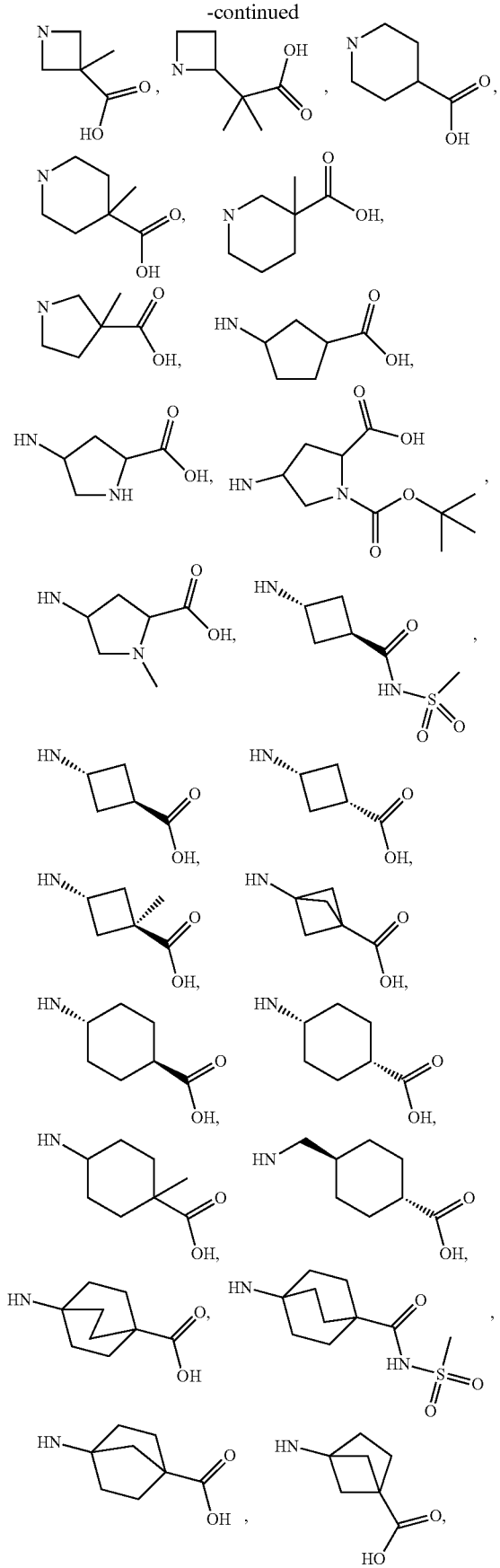
256
-continued
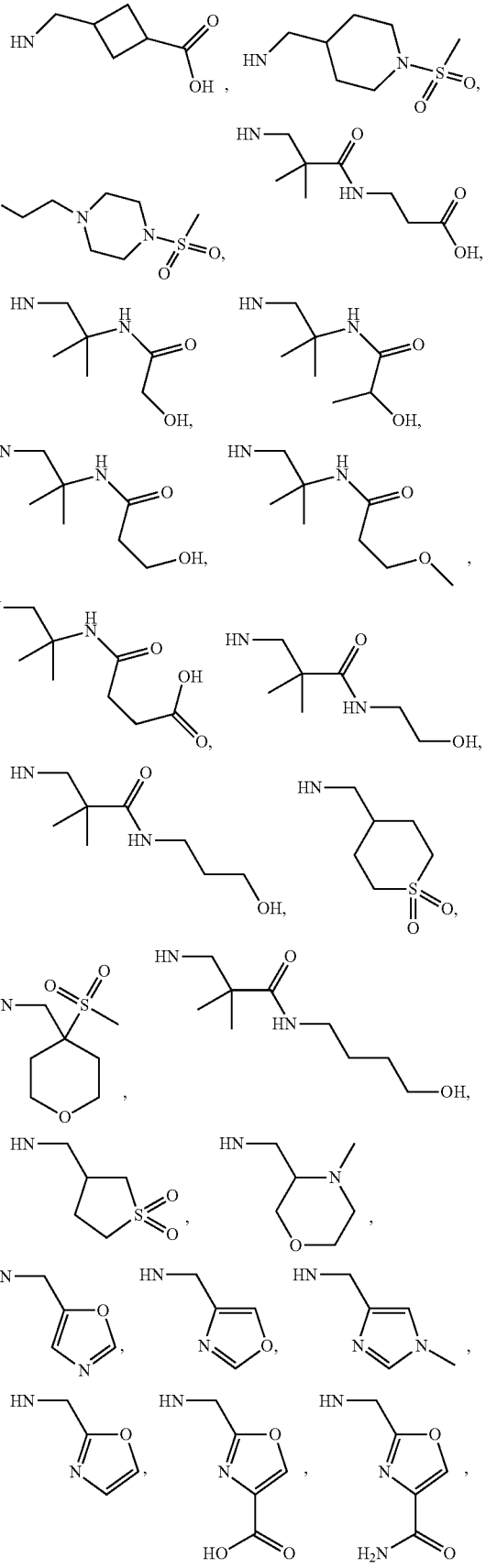

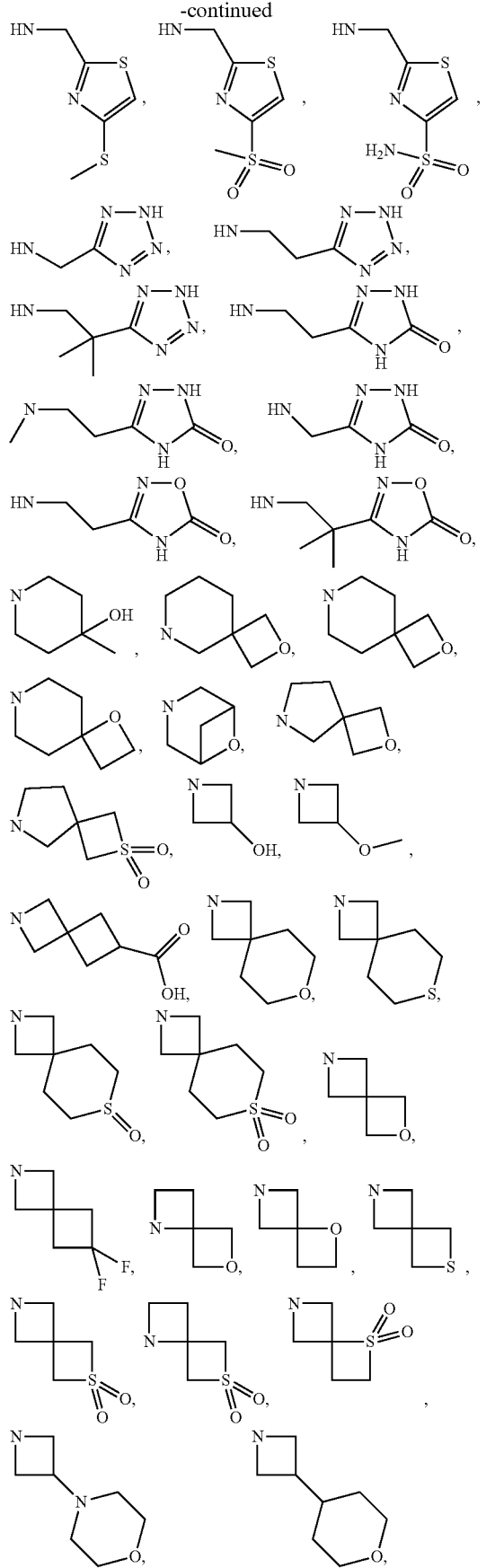
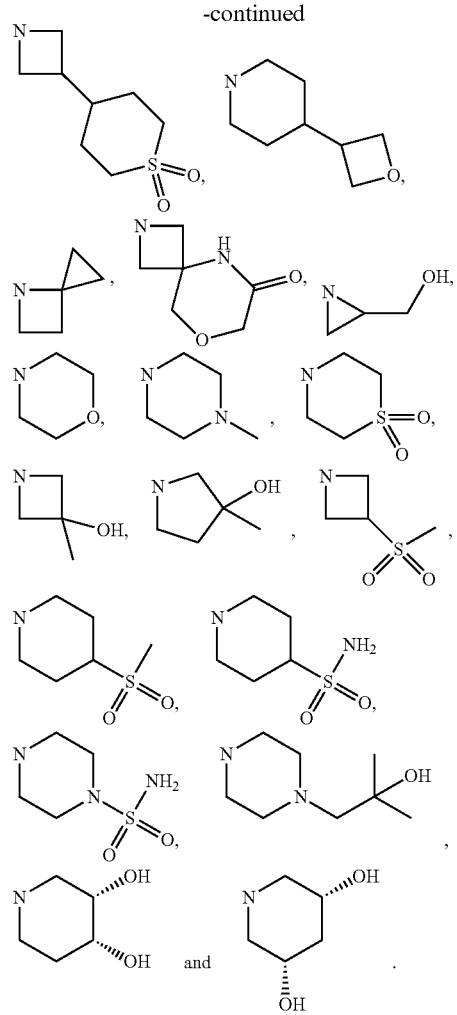

6. The compound according to claim 1 wherein:
R³ is a 6-10 membered mono- or bicyclic aryl or a 5-10 membered mono- or bicyclic heteroaryl containing 1 to 4 heteroatoms independently selected from the group consisting of N, O and S,
  wherein aryl and heteroaryl are unsubstituted or substituted with 1 to 5 substituents independently selected from the group consisting of halogen, CN, $C_{1-6}$-alkyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-COOR³¹, $C_{0-6}$-alkylene-C(O)R³¹, $C_{0-6}$-alkylene-C(O)N(R³¹)$_2$, $C_{0-6}$-alkylene-SO$_2$—N(R³¹)$_2$, $C_{0-6}$-alkylene-SO$_2$—R³¹, $C_{0-6}$-alkylene-(5-membered heteroaryl) and $C_{0-6}$-alkylene-(6-membered heteroaryl),
  wherein alkyl, alkylene, cycloalkyl, heterocycloalkyl and heteroaryl are unsubstituted or substituted by 1 to 3 substituents independently selected from the group consisting of halogen, OH, oxo, O—$C_{1-3}$-alkyl and CN;
  or wherein two adjacent substituents may complete a 3- to 8-membered saturated or partially unsaturated ring containing carbon atoms and optionally containing 1 to 3 heteroatoms selected from O, S or N, wherein the ring is unsubstituted or substituted with 1 to 7 substituents independently selected from the group consisting of halogen, oxo, OH, O—C$_{1-6}$-alkyl, O-halo-C$_{1-6}$-alkyl, C$_{1-6}$-alkyl, C$_{3-6}$-cycloalkyl and halo-C$_{1-6}$-alkyl.

7. The compound according to claim 1 wherein R$^3$ is selected from:

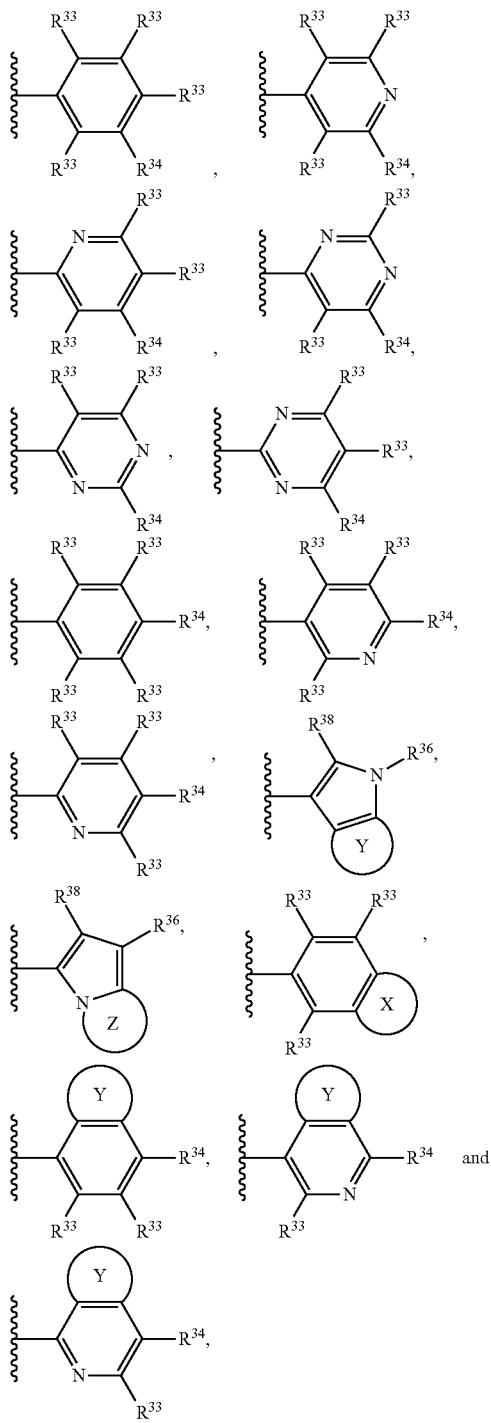

wherein:

R$^{33}$ is independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl and C$_{3-10}$-cycloalkyl, wherein alkylene is unsubstituted or substituted with 1 to 3 substituents selected from F and cycloalkyl is unsubstituted or substituted with 1 to 3 substituents independently selected from the group consisting of F, C$_{1-3}$-alkyl and fluoro-C$_{1-3}$-alkyl;

R$^{34}$ is independently selected from H, halogen, CN, C$_{1-6}$-alkyl, fluoro-C$_{1-6}$-alkyl, C$_{1-4}$-alkylene-OH, C$_{1-4}$-alkylene-O—C$_{1-3}$-alkyl, C$_{1-4}$-alkylene-O-fluoro-C$_{1-3}$-alkyl, OH, O—C$_{1-6}$-alkyl, O-fluoro-C$_{1-6}$-alkyl, NH—C$_{1-6}$-alkyl, NH-fluoro-C$_{1-6}$-alkyl, C$_{3-10}$-cycloalkyl, C$_{0-6}$-alkylene-C$_{3-10}$-heterocycloalkyl, 5-membered heteroaryl, 6-membered heteroaryl, C(O)N(R$^{37}$)$_2$ and SO$_2$N(R$^{37}$)$_2$, wherein alkylene is unsubstituted or substituted with 1 to 3 substituents selected from F and cycloalkyl, heterocycloalkyl and heteroaryl is unsubstituted or substituted with 1 to 3 substituents independently selected from the group consisting of F, C$_{1-3}$-alkyl, fluoro-C$_{1-3}$-alkyl, OH, O—C$_{1-3}$-alkyl and fluoro-O—C$_{1-3}$-alkyl;

R$^{35}$ is selected from halogen, C$_{1-6}$-alkyl, halo-C$_{1-6}$-alkyl, C$_{3-6}$-cycloalkyl, C$_{3-6}$-heterocycloalkyl, oxo, OH, O—C$_{1-6}$-alkyl and O-halo-C$_{1-6}$-alkyl;

R$^{36}$ is selected from C$_{1-6}$-alkyl, fluoro-C$_{1-6}$-alkyl, C(O)N(R$^{37}$)$_2$ and SO$_2$N(R$^{37}$)$_2$;

R$^{37}$ is independently selected from H, C$_{1-6}$-alkyl, halo-C$_{1-6}$-alkyl, C$_{0-4}$-alkylene-C$_{3-6}$-cycloalkyl and C$_{0-4}$-alkylene-C$_{3-6}$-heterocycloalkyl, wherein alkyl and alkylene is unsubstituted or substituted with 1 to 4 substituents selected from the group consisting of halogen, OH, O—C$_{1-3}$-alkyl and CN; and wherein cycloalkyl or heterocycloalkyl is unsubstituted or substituted with 1 to 3 substituents independently selected from the group consisting of F, CN, OH, oxo, C$_{1-3}$-alkyl and fluoro-C$_{1-3}$-alkyl;

or wherein two R$^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, C$_{1-4}$-alkyl and halo-C$_{1-4}$-alkyl;

R$^{38}$ is selected from H, C$_{1-3}$-alkyl and fluoro-C$_{1-3}$-alkyl;

X is an annelated saturated heterocycle selected from the group consisting of

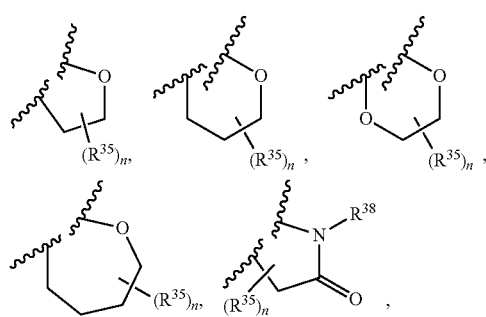

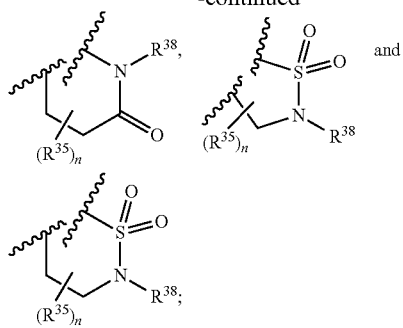

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from the group consisting of halogen, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from the group consisting of fluoro, $C_{1-3}$-alkyl and fluoro-$C_{1-3}$-alkyl;

n is selected from 1 to 4.

8. The compound according to claim 1 wherein $R^3$ is selected from:

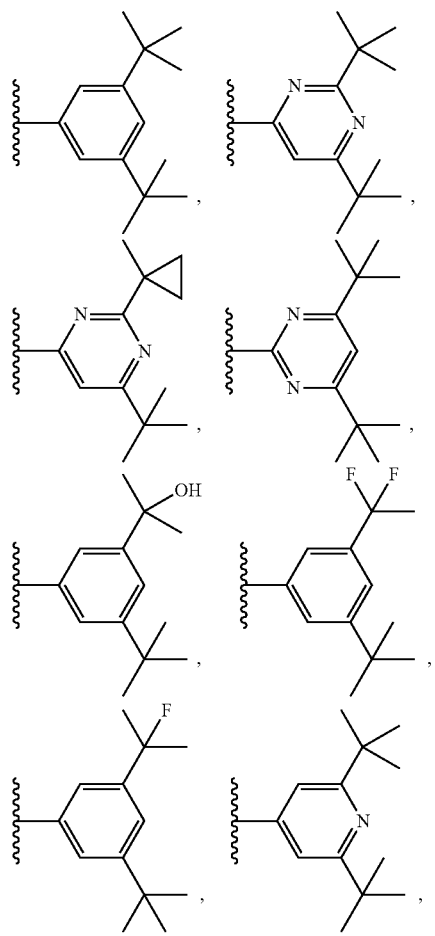

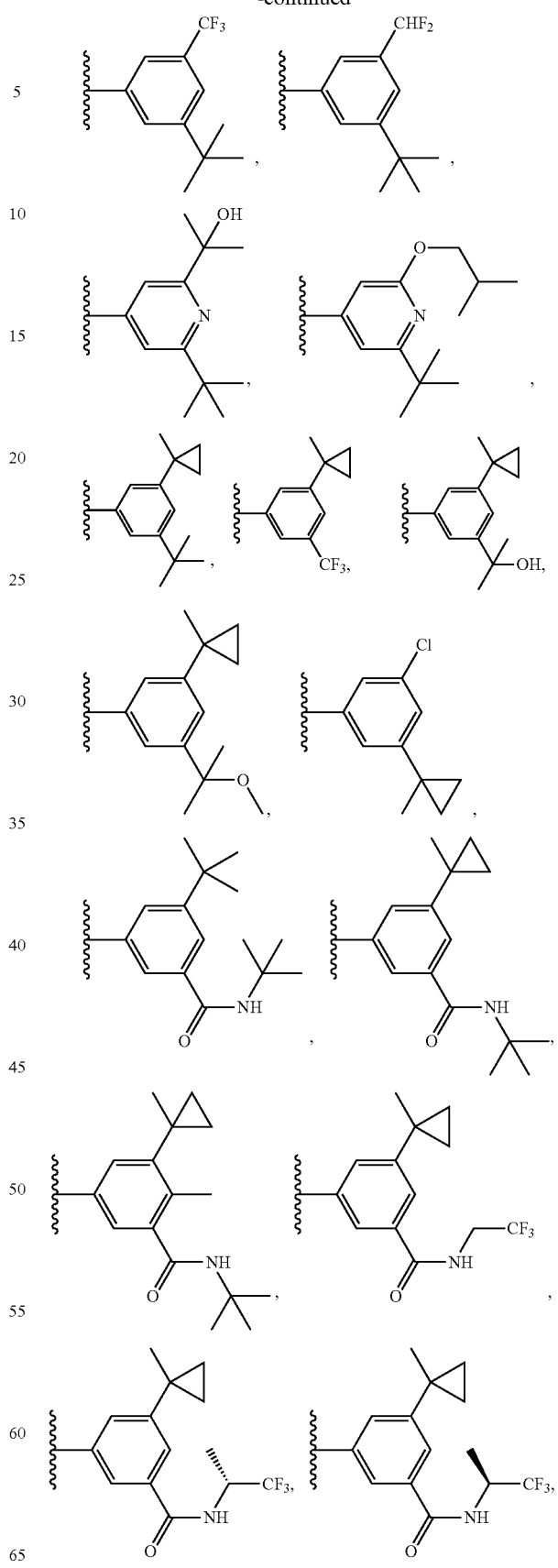

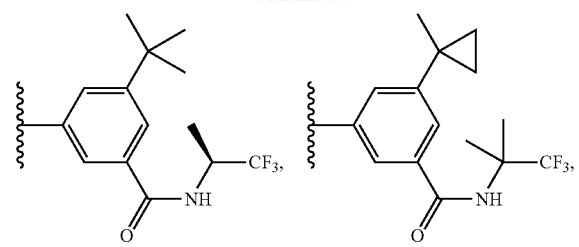
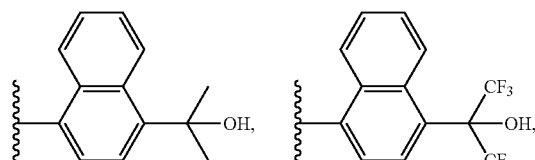
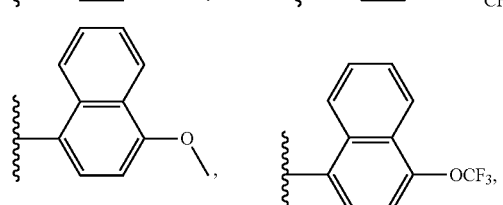
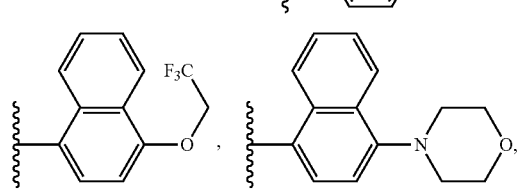
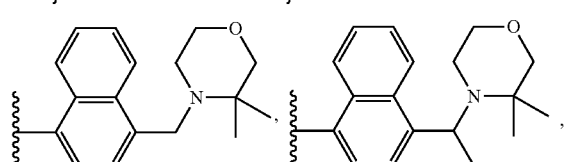
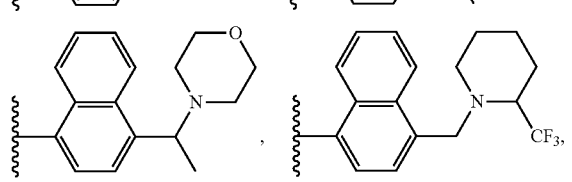
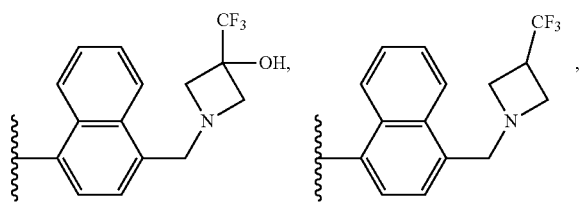
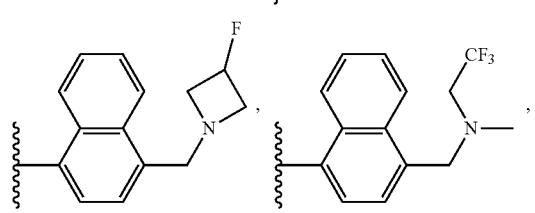
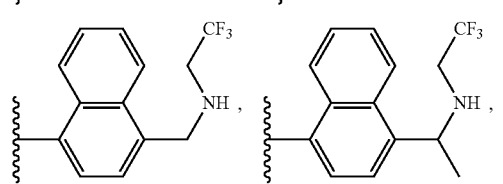
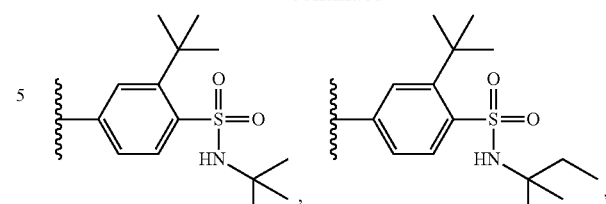
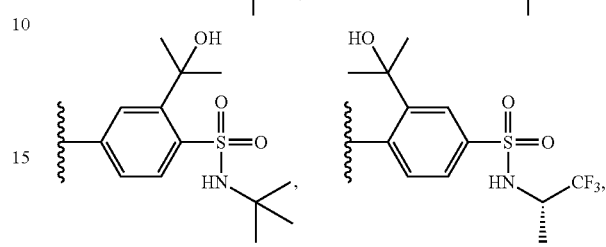
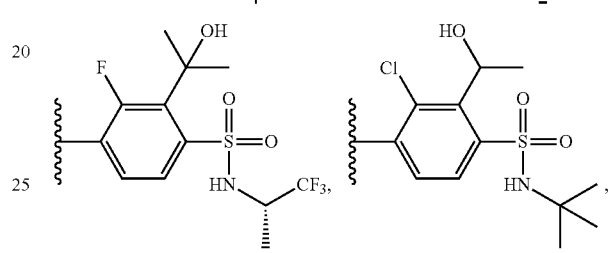
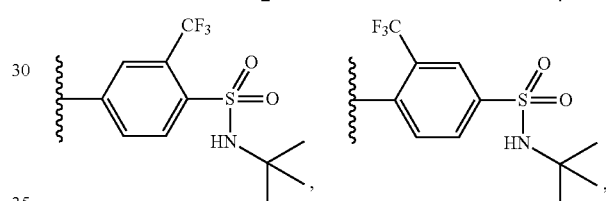
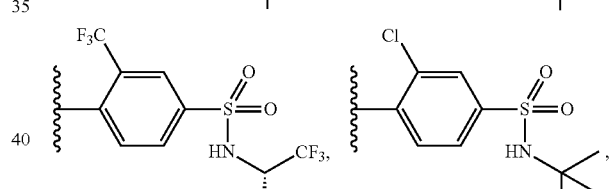
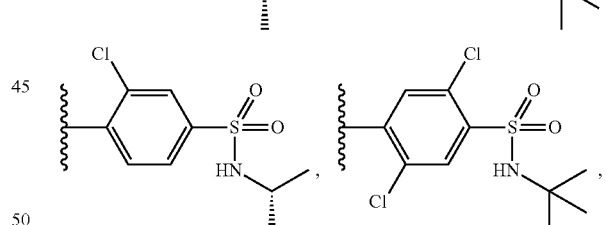
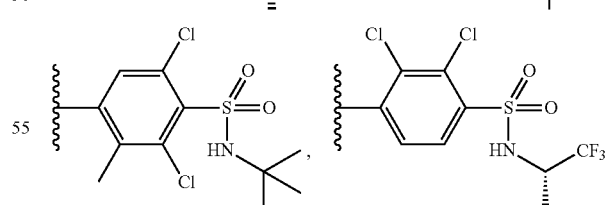
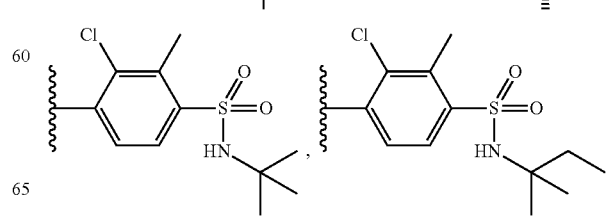

265
-continued
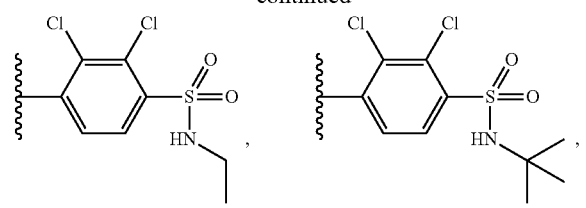
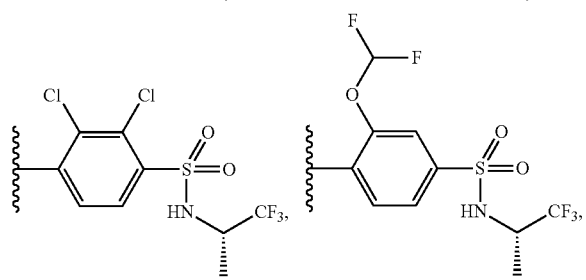
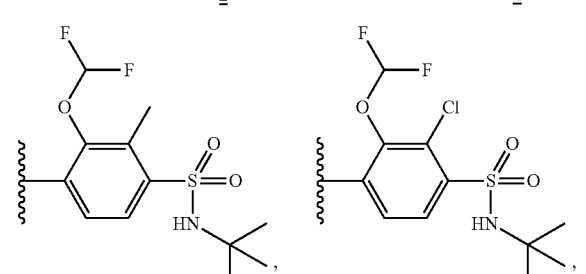
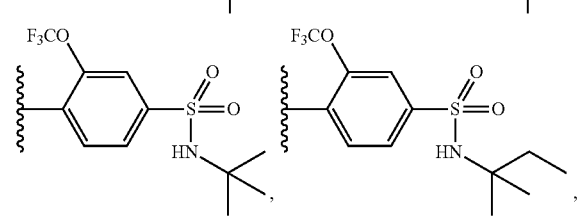
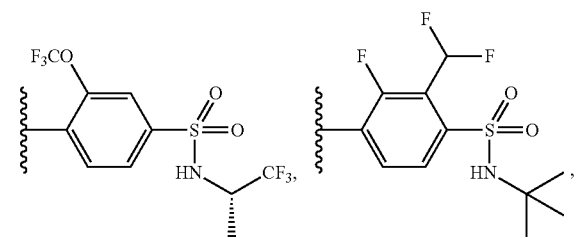
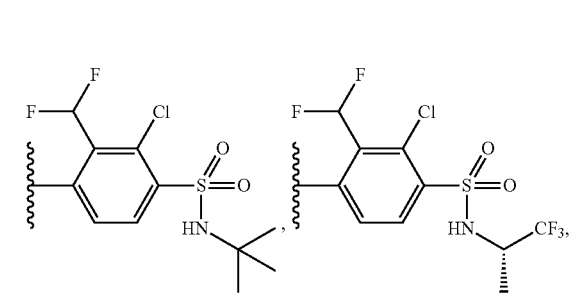
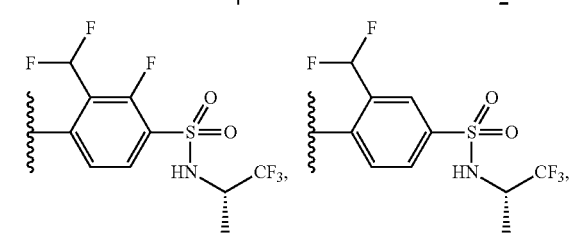
266
-continued
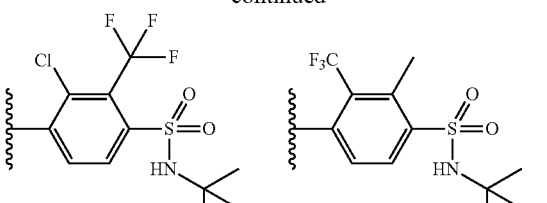
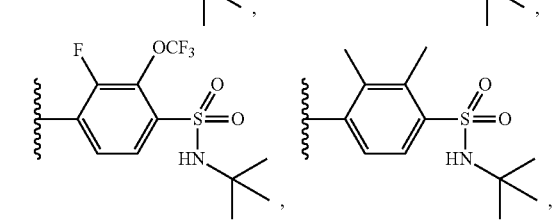
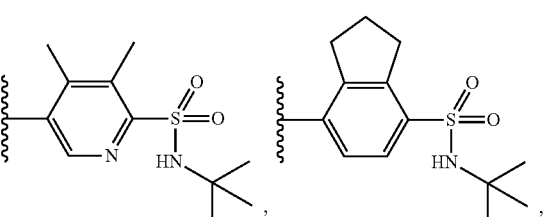
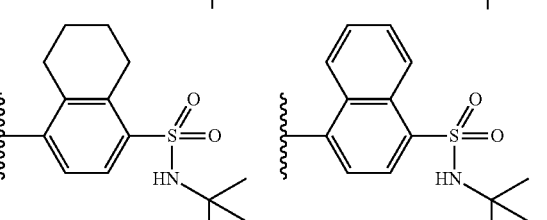
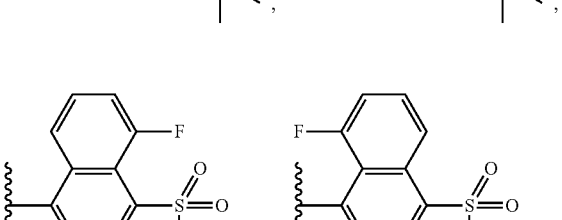
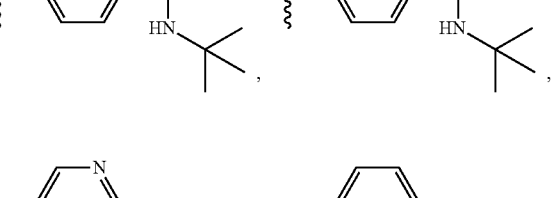
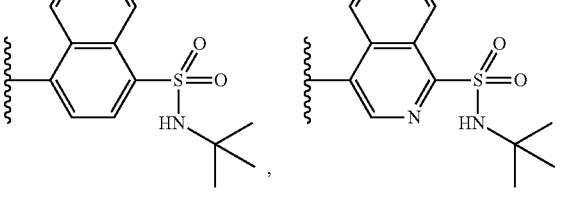
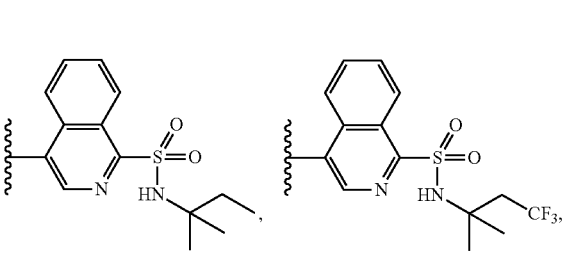

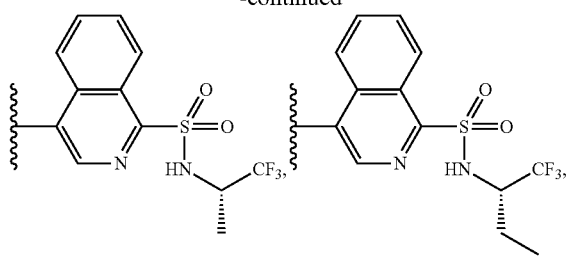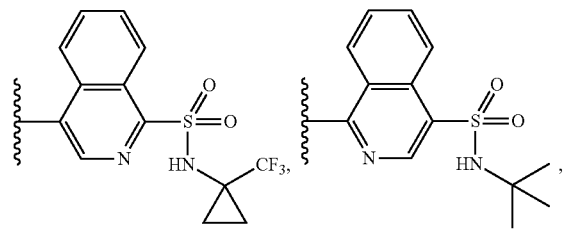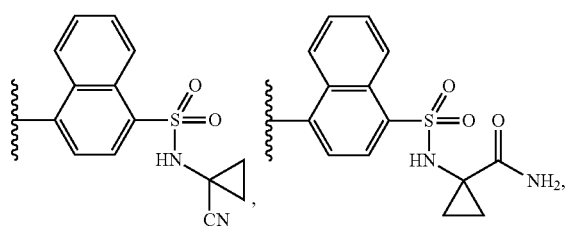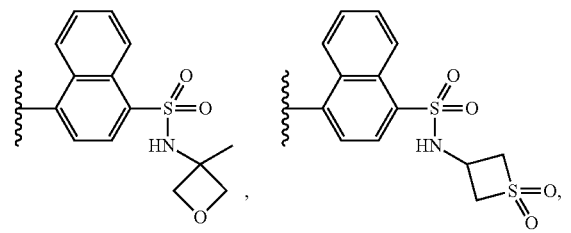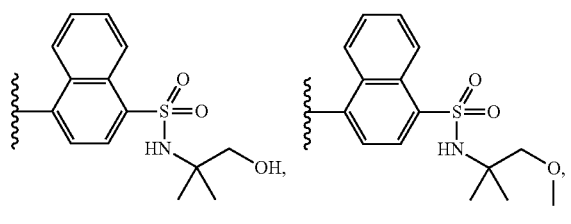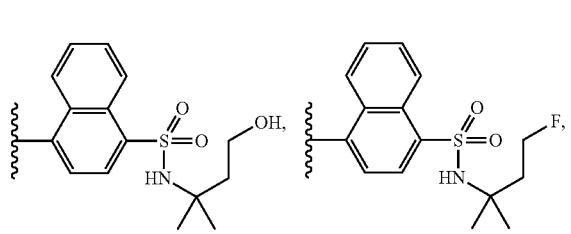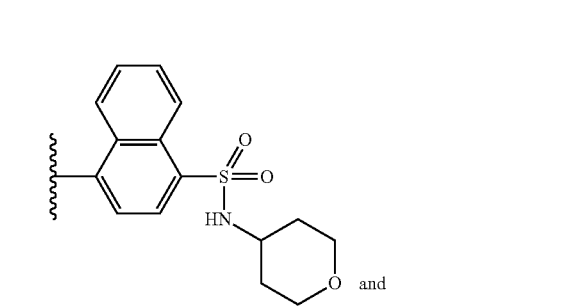and
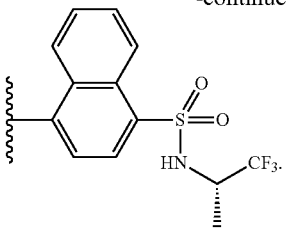
9. The compound according to claim 1 represented by Formula (1) to Formula (3).
10. The compound according to claim 1 represented by Formula (4) and Formula (5).
11. The compound according to claim 1, wherein the compound is selected from:
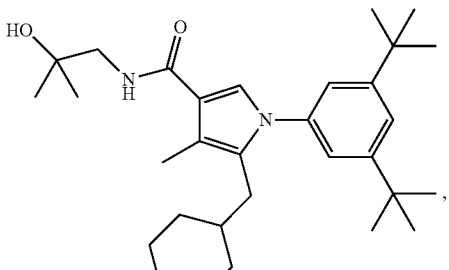,
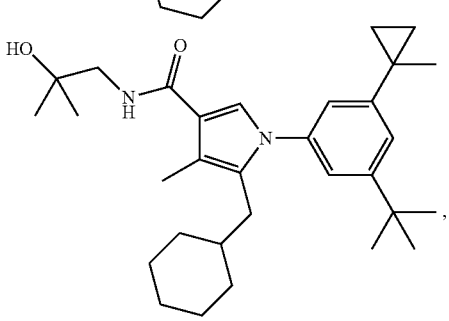,
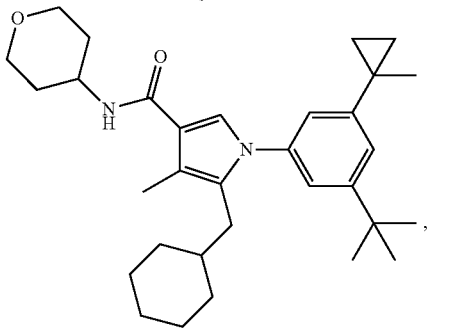,
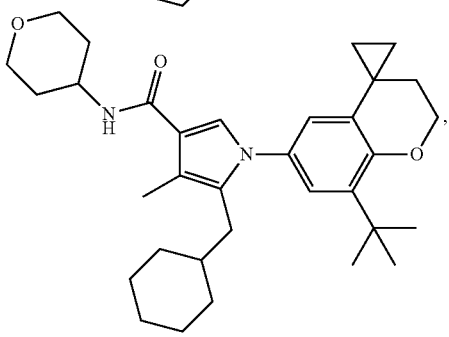, 269
-continued
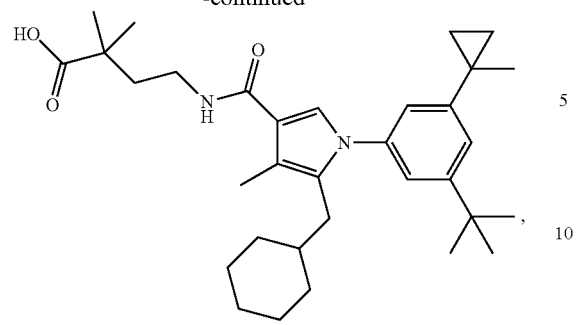
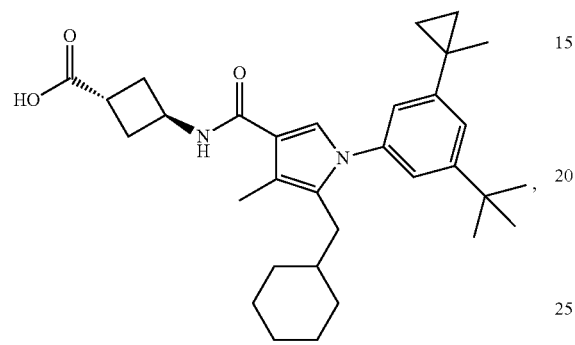
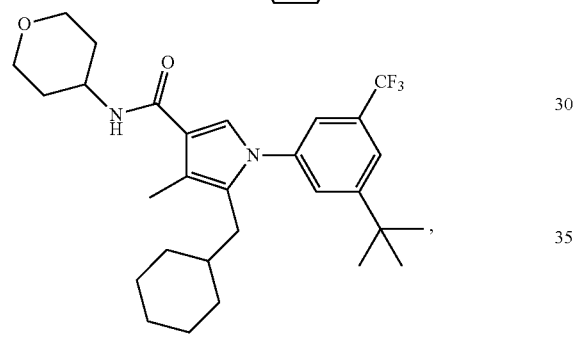
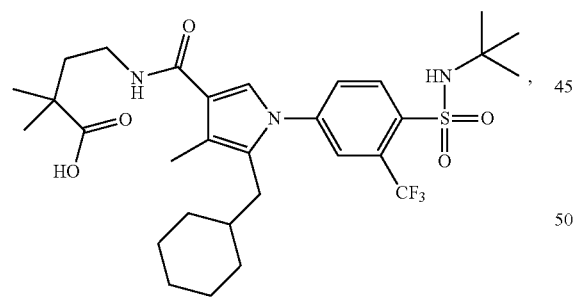
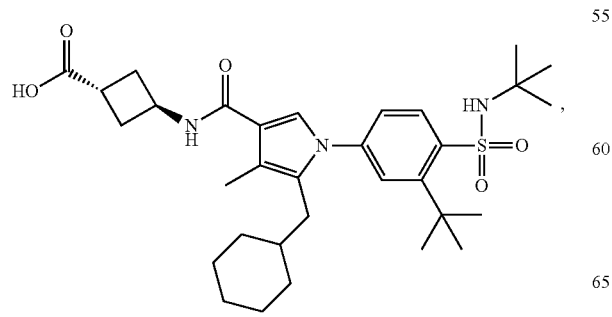
270
-continued
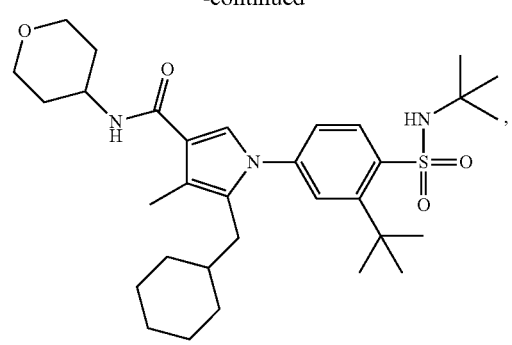
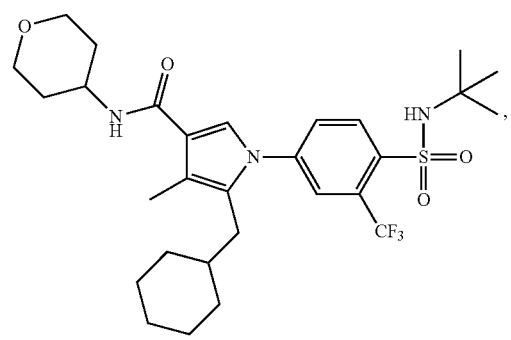
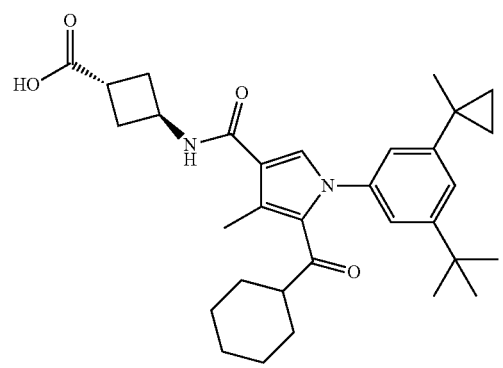
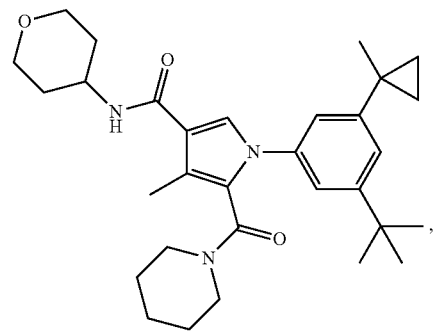
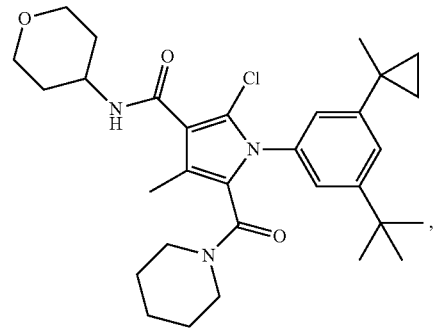

271
-continued
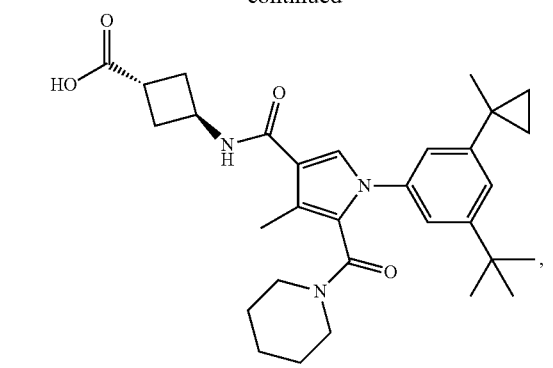
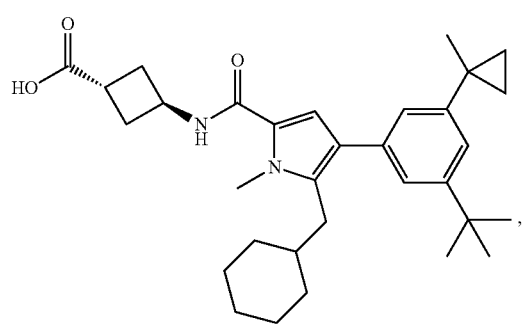
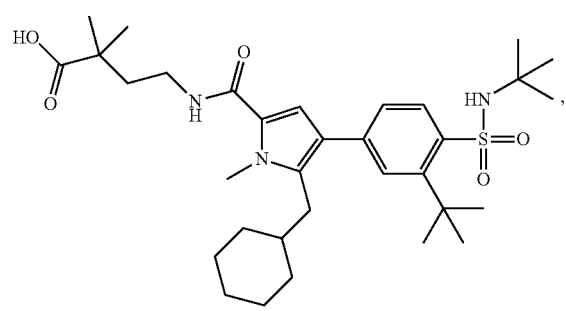
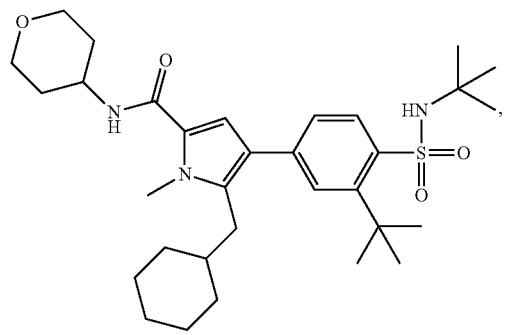
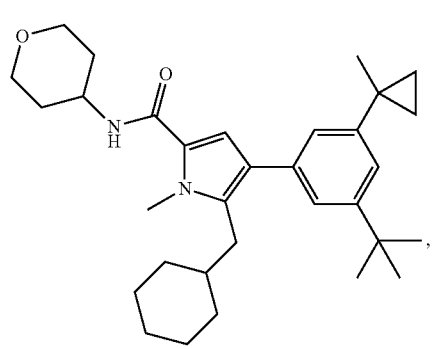
272
-continued
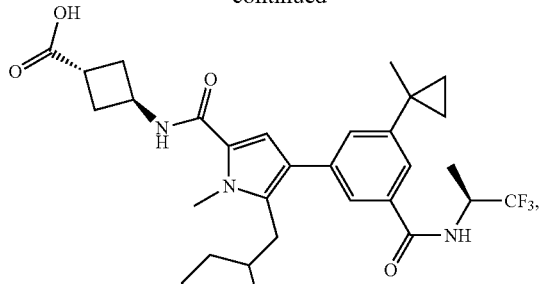
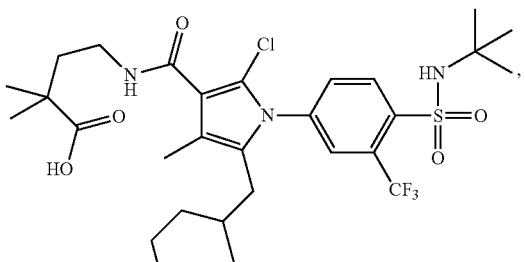
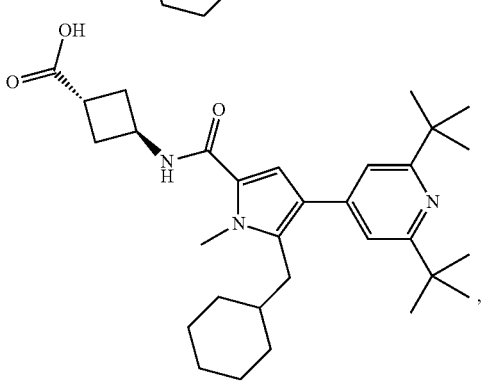
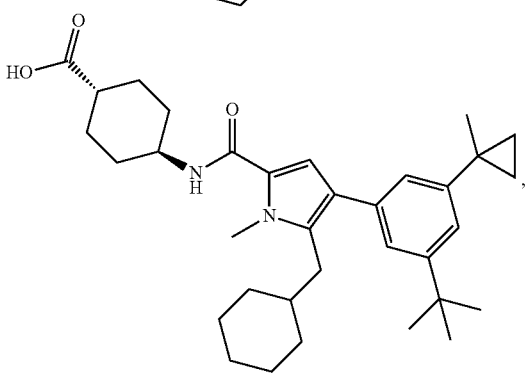
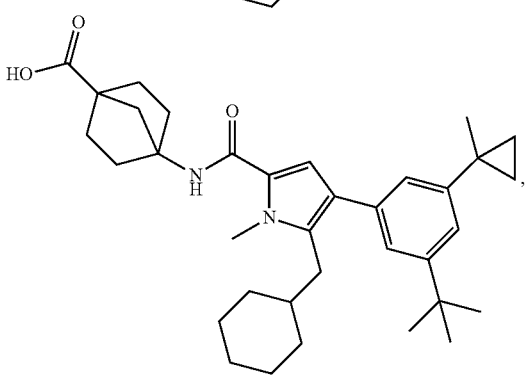

273
-continued
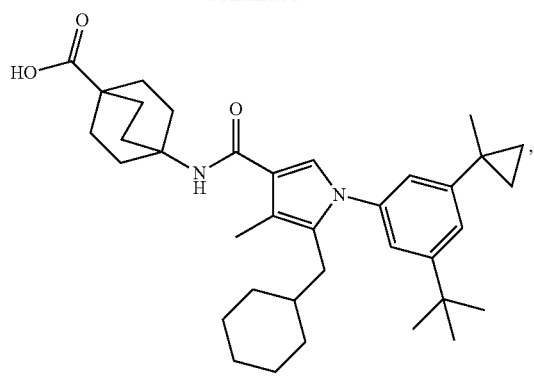
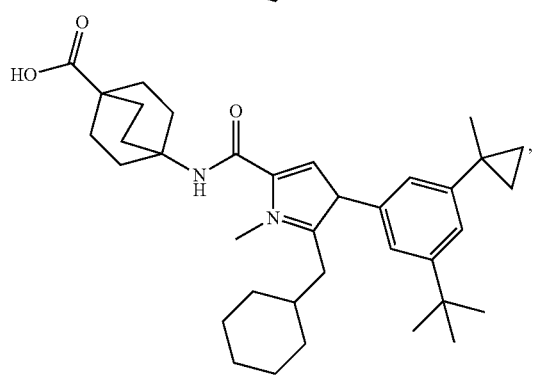
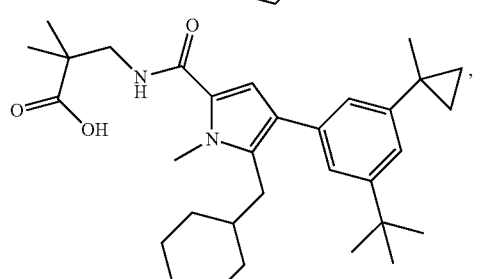
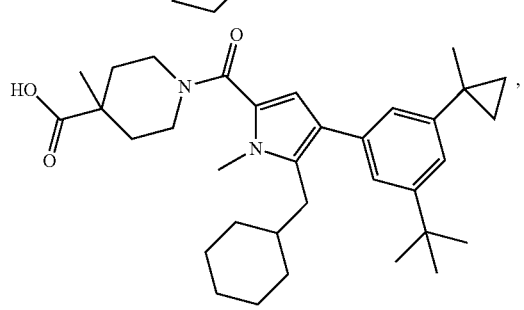
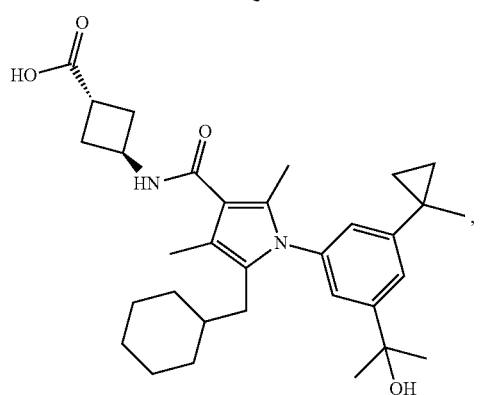
274
-continued
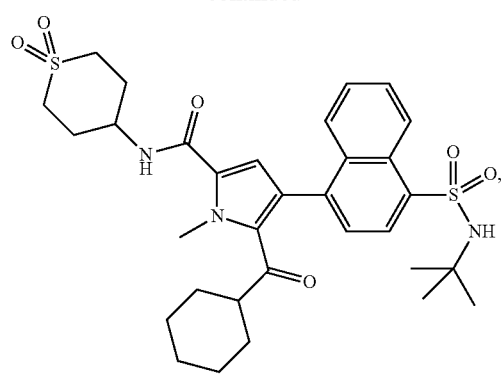
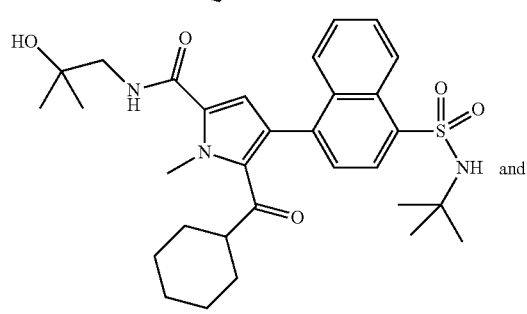
and
12. A method for the treatment of a disease or disorder in a mammal associated with the inhibition or activation of the RORγ receptor, wherein the method comprises administering to the mammal an effective amount of a compound according to Formula (6), Formula (7), Formula (8) or Formula (9):
(6)
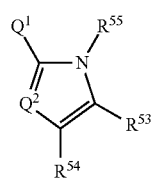
(7)
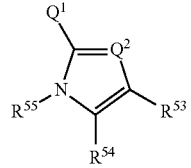

-continued

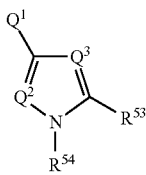
(8)

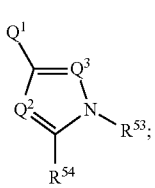
(9)

or an enantiomer, a diastereomer, a tautomer, a formulation or a pharmaceutically acceptable salt thereof, wherein:

$Q^1$ is CO—$NR^{51}R^{52}$, CO—$R^{52}$, $CO_2R^{51}$, $SO_2$—$NR^{51}R^{52}$, $SO_2$—$R^{52}$, $NR^{52}CO$—$R^{51}$ or $NR^{52}SO_2$—$R^{51}$;

$Q^2$ and $Q^3$ are independently selected from N and $CR^{56}$;

$R^{51}$ and $R^{52}$ are independently selected from the group consisting of H, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene 5 to 10-membered heteroaryl and $C_{0-10}$-alkylene-aryl, wherein alkyl, alkenyl, alkynyl, alkylene, cycloalkyl, heterocycloalkyl, aryl and heteroaryl are unsubstituted or substituted with 1 to 7 substituents independently selected from the group consisting of oxo, CN, $OR^{61}$, O—$C_{2-6}$-alkylene-$OR^{61}$, $C_{1-6}$-alkyl, halo-$C_{1-6}$-alkyl, halogen, $CO_2R^{61}$, $CONR^{61}R^{62}$, $CONR^{61}SO_2R^{62}$, $COR^{61}$, $SO_xR^{61}$, $SO_3H$, $SO_2NR^{61}R^{62}$, $NR^{61}COR^{61}$, $NR^{61}SO_2R^{61}$, $NR^{61}$—CO—$NR^{61}R^{62}$, $NR^{61}$—$SO_2$—$NR^{61}R^{62}$, $C_{3-6}$-cycloalkyl, O—$C_{3-6}$-cycloalkyl, $C_{3-6}$-heterocycloalkyl, O—$C_{3-6}$-heterocycloalkyl and $NR^{61}R^{62}$;

or $R^{51}$ and $R^{52}$ when taken together with the nitrogen to which they are attached complete a 3- to 8-membered ring containing carbon atoms and optionally containing 1 or 2 heteroatoms independently selected from the group consisting of O, S and N, wherein the ring is unsubstituted or substituted with 1 to 4 substituents independently selected from the group consisting of halogen, oxo, CN, $OR^{61}$, $SO_xR^{61}$, $SO_3H$, $NR^{61}SO_2R^{61}$, $SO_2NR^{61}R^{62}$, $CO_2R^{61}$, $CONR^{61}R^{62}$, $CONR^{61}SO_2R^{62}$, $COR^{61}$, $NR^{61}$—CO—$R^{61}$, $NR^{61}$—CO—$NR^{61}R^{62}$, $NR^{61}$—$SO_2$—$NR^{61}R^{62}$, $NR^{61}R^{62}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl;

$R^{53}$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl are unsubstituted or substituted with 1 to 5 substituents independently selected from the group consisting of halogen, CN, $C_{1-6}$-alkyl, $C_{2-6}$-alkenyl, $C_{2-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-$COOR^{81}$, $C_{0-6}$-alkylene-C(O)$R^{81}$, $C_{0-6}$-alkylene-C(O)N($R^{81}$)$_2$, $C_{0-6}$-alkylene-N($R^{81}$)$_2$, $C_{0-6}$-alkylene-$SO_2$—N($R^{81}$)$_2$, $C_{0-6}$-alkylene-$SO_2$—$R^{81}$, $C_{0-6}$-alkylene-(6-10-membered mono- or bicyclic aryl), and $C_{0-6}$-alkylene-(6-10-membered mono- or bicyclic heteroaryl), wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—$OR^{82}$, N($R^{81}$)$_2$, O—$C_{1-6}$-alkyl, O-halo-$C_{1-6}$-alkyl, COOH, CON($R^{81}$)$_2$, CN, $NR^{81}$—$COR^{81}$, $C_{3-10}$-cycloalkyl, $C_{3-10}$-heterocycloalkyl, 6-10-membered mono- or bicyclic aryl, and 6-10-membered mono- or bicyclic heteroaryl, or wherein two adjacent substituents may complete a 4- to 8-membered saturated or partially unsaturated ring containing carbon atoms and optionally containing 1 to 3 members selected from the group consisting of O, S, SO, $SO_2$ and $NR^{81}$, wherein the ring is unsubstituted or substituted with 1 to 4 substituents independently selected from the group consisting of halogen, oxo, =N—$OR^{82}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;

$R^{54}$ is $C_{0-6}$-alkylene-$R^{57}$, $C_3$-cycloalkyl-$R^{57}$, O—$C_{0-5}$-alkylene-$R^{57}$, $NR^{91}$—$C_{0-5}$-alkylene-$R^{57}$ and $SO_x$—$C_{0-5}$-alkylene-$R^{57}$, wherein alkylene is optionally substituted with 1 to 5 substituents independently selected from the group consisting of halogen, OH, oxo, =N—$OR^{82}$, N($R^{81}$)$_2$, O—$C_{1-6}$-alkyl, COOH, CON($R^{81}$)$_2$, CN, $NR^{81}$—$COR^{81}$, $C_{3-6}$-cycloalkyl and $C_{3-6}$-heterocycloalkyl;

$R^{55}$ is independently selected from H, $C_{1-6}$-alkyl and $C_{3-6}$-cycloalkyl, wherein alkyl and cycloalkyl is optionally substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

$R^{56}$ is independently selected from the group consisting of H, halogen, CN, $C_{1-6}$-alkyl, $C_{3-6}$-cycloalkyl, O—$C_{1-6}$-alkyl and $CONHR^{61}R^{62}$, wherein alkyl and cycloalkyl is unsubstituted or substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

$R^{57}$ is $C_{1-10}$-alkyl, $C_{3-10}$-cycloalkyl, $C_{3-10}$-heterocycloalkyl, 6-10-membered mono- or bicyclic aryl or 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-10}$-cycloalkyl and 5 to 10-membered heterocycloalkyl;

$R^{61}$ and $R^{81}$ are independently selected from the group consisting of H, $C_{1-6}$-alkyl, $C_{3-10}$-cycloalkyl, $C_{3-10}$-heterocycloalkyl, phenyl, 5-6-membered heteroaryl containing 1 to 4 heteroatoms independently selected from the group consisting of N, O and S, wherein alkyl, cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 10-membered heteroaryl, halogen, $NH_2$, NH($C_{1-6}$-alkyl), N($C_{1-6}$- alkyl)$_2$, C$_{3-10}$-heterocycloalkyl, C$_{3-10}$-cycloalkyl, SO$_2$—C$_{1-3}$-alkyl, oxo, and CN,
  wherein cycloalkyl and heterocycloalkyl are unsubstituted or substituted with 1 to 3 substituents independently selected from the group consisting of C$_{1-6}$-alkyl, halo-C$_{1-6}$-alkyl, OH, O—C$_{1-6}$-alkyl, O-halo-C$_{1-6}$-alkyl, phenyl, 5 to 6-membered heteroaryl, halogen, NH$_2$, NH(C$_{1-6}$-alkyl), N(C$_{1-6}$-alkyl)$_2$ and C$_{3-10}$-cycloalkyl,
  wherein phenyl and heteroaryl are unsubstituted or substituted with 1 to 3 substituents independently selected from the group consisting of OH, O—C$_{1-6}$-alkyl, O-halo-C$_{1-6}$-alkyl, halogen, C$_{1-6}$-alkyl, halo-C$_{1-6}$-alkyl, NH$_2$, NH(C$_{1-6}$-alkyl), N(C$_{1-6}$-alkyl)$_2$ and C$_{3-10}$-cycloalkyl;
R$^{62}$ and R$^{82}$ are independently selected from the group consisting of H, C$_{1-6}$-alkyl, halo-C$_{1-6}$-alkyl and C$_{3-10}$-cycloalkyl;
R$^{91}$ is H, C$_{1-6}$-alkyl, C$_{3-6}$-cycloalkyl or C$_{3-6}$-heterocycloalkyl,
  wherein alkyl, cycloalkyl and heterocycloalkyl are unsubstituted or substituted with 1 to 3 substituents independently selected from the group consisting of OH, oxo, CN, halogen, O—C$_{1-6}$-alkyl, O-halo-C$_{1-6}$-alkyl, C$_{3-6}$-heterocycloalkyl and C$_{3-6}$-cycloalkyl;
x is independently selected from 0, 1 and 2.

13. The method according to claim 12 wherein:
Q$^1$ is selected from CO—NR$^{51}$R$^{52}$; and
Q$^2$ and Q$^3$ is nitrogen.

14. The method according to claim 12 wherein:
Q$^1$ is CO—NR$^{51}$R$^{52}$; and
Q$^2$ and Q$^3$ is CR$^{56}$.

15. The method according to claim 12 wherein:
R$^{51}$ is selected from the group consisting of H, C$_{1-10}$-alkyl, C$_{0-10}$-alkylene-C$_{3-10}$-cycloalkyl, C$_{0-10}$-alkylene-C$_{3-10}$-heterocycloalkyl, C$_{0-10}$-alkylene 5 to 10-membered heteroaryl and C$_{0-10}$-alkylene-aryl, wherein alkyl, alkenyl, alkynyl, alkylene, cycloalkyl, heterocycloalkyl, aryl and heteroaryl are unsubstituted or substituted with 1 to 7 substituents independently selected from the group consisting of oxo, CN, OR$^{61}$, O—C$_{2-6}$-alkylene-OR$^{61}$, C$_{1-6}$-alkyl, halo-C$_{1-6}$-alkyl, halogen, CO$_2$R$^{61}$, CONR$^{61}$R$^{62}$, CONR$^{61}$SO$_2$R$^{62}$, COR$^{61}$, SO$_x$R$^{61}$, SO$_3$H, SO$_2$NR$^{61}$R$^{62}$, NR$^{61}$COR$^{61}$, NR$^{61}$SO$_2$R$^{61}$, NR$^{61}$—CO—NR$^{61}$R$^{62}$, NR$^{61}$—SO$_2$—NR$^{61}$R$^{62}$, C$_{3-6}$-cycloalkyl, O—C$_{3-6}$-cycloalkyl, C$_{3-6}$-heterocycloalkyl, O—C$_{3-6}$-heterocycloalkyl and NR$^{61}$R$^{62}$; and
R$^{52}$ is selected from the group consisting of H, C$_{1-6}$ alkyl and halo-C$_{1-6}$ alkyl;
or R$^{51}$ and R$^{52}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, OR$_{61}$, SO$_x$R$_{61}$, SO$_3$H, NR$^{61}$SO$_2$R$^{61}$, SO$_2$NR$^{61}$R$^{62}$, CO$_2$R$^{61}$, CONR$^{61}$R$^{62}$, CONR$^{61}$SO$_2$R$^{62}$, COR$^{61}$, NR$^{61}$—CO—R$^{61}$, NR$^{61}$—CO—NR$^{61}$R$^{62}$, NR$^{61}$—SO$_2$—NR$^{61}$R$^{62}$, NR$^{61}$R$^{62}$, C$_{1-6}$-alkyl, halo-C$_{1-6}$-alkyl, hydroxy-C$_{1-6}$-alkyl, C$_{3-6}$-cycloalkyl, O—C$_{3-6}$-cycloalkyl, C$_{3-6}$-heterocycloalkyl and O—C$_{3-6}$-heterocycloalkyl.

16. The method according to claim 12 wherein R$^{53}$ is selected from:

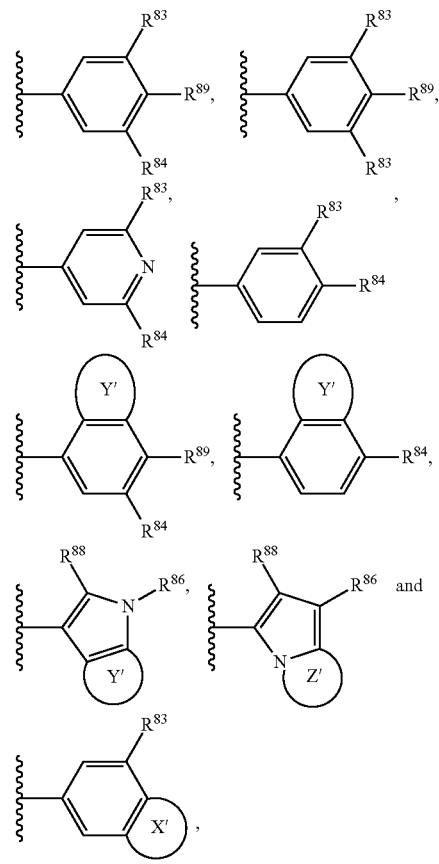

wherein
R$^{83}$ is independently selected from halogen, C$_{1-6}$-alkyl, fluoro-C$_{1-6}$-alkyl, C$_{1-4}$-alkylene-OH, C$_{1-4}$-alkylene-CN, C$_{1-4}$-alkylene-O—C$_{1-3}$-alkyl, C$_{1-4}$-alkylene-O-fluoro-C$_{1-3}$-alkyl, O—C$_{1-6}$-alkyl, O-fluoro-C$_{1-6}$-alkyl, NH—C$_{1-6}$-alkyl, NH-fluoro-C$_{1-6}$-alkyl, C$_{3-10}$-cycloalkyl, C(O)N(R$^{87}$)$_2$,
  wherein alkylene is unsubstituted or substituted with 1 to 3 substituents selected from F, and cycloalkyl is unsubstituted or substituted with 1 to 3 substituents independently selected from F, C$_{1-3}$-alkyl and fluoro-C$_{1-3}$-alkyl;
R$^{84}$ is selected from C$_{1-4}$-alkylene-OH, C$_{1-4}$-alkylene-O—C$_{1-3}$-alkyl, C$_{1-4}$-alkylene-O-fluoro-C$_{1-3}$-alkyl, C$_{3-10}$-cycloalkyl, C(O)N(R$^{87}$)$_2$, S(O$_2$)N(R$^{87}$)$_2$,
  wherein alkylene is unsubstituted or substituted with 1 to 3 substituents selected from F, and cycloalkyl is unsubstituted or substituted with 1 to 3 substituents independently selected from F, C$_{1-3}$-alkyl and fluoro-C$_{1-3}$-alkyl;
R$^{86}$ is selected from C$_{1-6}$-alkyl, fluoro-C$_{1-6}$-alkyl, C(O)N(R$^{87}$)$_2$, S(O$_2$)N(R$^{87}$)$_2$,
R$^{87}$ is independently selected from H, C$_{1-6}$-alkyl, fluoro-C$_{1-6}$-alkyl, C$_{0-3}$-alkylene-C$_{1-6}$-cycloalkyl, C$_{1-6}$-alkylene-OH, C$_{1-6}$-alkylene-O—C$_{1-3}$-alkyl, C$_{1-6}$-alkylene-CN, wherein alkylene and cycloalkyl is unsubstituted or substituted with 1 to 3 substituents independently selected from F, C$_{1-3}$-alkyl and fluoro-C$_{1-3}$-alkyl,
and wherein two R$^{87}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, oxo, $C_{1-4}$-alkyl and halo-$C_{1-4}$-alkyl;
$R^{88}$ is selected from H, $C_{1-3}$-alkyl and fluoro-$C_{1-3}$-alkyl;
$R^{89}$ is selected from H, F or OH;
X' is an annelated saturated heterocycle selected from the group consisting of

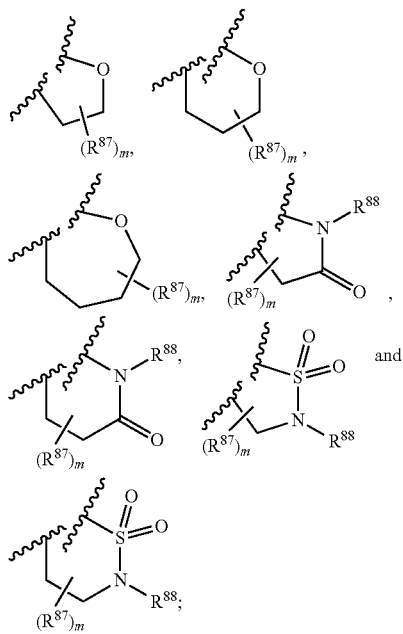

Y' is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from the group consisting of fluoro, $C_{1-3}$-alkyl and fluoro-$C_{1-3}$-alkyl;
Z' is an annelated 6-membered cycle forming a heteroaryl containing 1 to 3 heteroatoms selected from the group consisting of O, S and N, wherein the heteroaryl is unsubstituted or substituted with 1 to 3 substituents selected from the group consisting of fluoro, $C_{1-3}$-alkyl and fluoro-$C_{1-3}$-alkyl; and
m is selected from 1 to 4.

17. The method according to claim 12 wherein:
$R^{54}$ is selected from $C_1$-alkylene-$R^{57}$ and $SO_2$—$R^{57}$, wherein alkylene is unsubstituted or substituted once with OH, oxo, O—$C_{1-6}$-alkyl, CN $C_{3-6}$-cycloalkyl or fluoro or twice with fluoro; and
$R^{57}$ is selected from $C_{1-10}$-alkyl, $C_{3-10}$-cycloalkyl, $C_{3-10}$-heterocycloalkyl, 6-10-membered mono- or bicyclic aryl and 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-3}$-alkyl, O-halo-$C_{1-3}$-alkyl, $C_{1-3}$-alkyl, cycloalkyl and heterocycloalkyl.

18. The method according to claim 12 wherein the disease or disorder is selected from rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, epidermal hyperplasia, glomerulonephritis, chronic obstructive pulmonary disease and amyotrophic lateral sclerosis.

19. A pharmaceutical composition comprising a pharmaceutically acceptable carrier or excipient and a compound according to Formula (6), Formula (7), Formula (8) or Formula (9):

 (6)

 (7)

 (8)

 (9)

or an enantiomer, a diastereomer, a tautomer or a pharmaceutically acceptable salt thereof,
wherein:
$Q^1$ is CO—$NR^{51}R^{52}$, CO—$R^{52}$, $CO_2R^{51}$, $SO_2$—$NR^{51}R^{52}$, $SO_2$—$R^{52}$, $NR^{52}CO$—$R^{51}$ or $NR^{52}SO_2$—$R^{51}$;
$Q^2$ and $Q^3$ are independently selected from N and $CR^{56}$;
$R^{51}$ and $R^{52}$ are independently selected from the group consisting of H, $C_{1-10}$-alkyl, $C_{2-10}$-alkenyl, $C_{2-10}$-alkynyl, $C_{0-10}$-alkylene-$C_{3-10}$-cycloalkyl, $C_{0-10}$-alkylene-$C_{3-10}$-heterocycloalkyl, $C_{0-10}$-alkylene 5 to 10-membered heteroaryl and $C_{0-10}$-alkylene-aryl, wherein alkyl, alkenyl, alkynyl, alkylene, cycloalkyl, heterocycloalkyl, aryl and heteroaryl are unsubstituted or substituted with 1 to 7 substituents independently selected from the group consisting of oxo, CN, $OR^{61}$, O—$C_{2-6}$-alkylene-$OR^{61}$, $C_{1-6}$-alkyl, halo-$C_{1-6}$-alkyl, halogen, $CO_2R^{61}$, $CONR^{61}R^{62}$, $CONR^{61}SO_2R^{62}$, $COR^{61}$, $SO_2R^{61}$, $SO_3H$, $SO_2NR^{61}R^{62}$, $NR^{61}COR^{61}$, $NR^{61}SO_2R^{61}$, $NR^{61}$—CO—$NR^{61}R^{62}$, $NR^{61}$—$SO_2$—$NR^{61}R^{62}$, $O_{3-6}$-cycloalkyl, O—$C_{3-6}$-cycloalkyl, $C_{3-6}$-heterocycloalkyl, O—$C_{3-6}$-heterocycloalkyl and $NR^{61}R^{62}$;

or $R^{51}$ and $R^{52}$ when taken together with the nitrogen to which they are attached complete a 3- to 8-membered ring containing carbon atoms and optionally containing 1 or 2 heteroatoms independently selected from the group consisting of O, S and N, wherein the ring is unsubstituted or substituted with 1 to 4 substituents independently selected from the group consisting of halogen, oxo, CN, $OR^{61}$, $SO_xR^{61}$, $SO_3H$, $NR^{61}SO_2R^{61}$, $SO_2NR^{61}R^{62}$, $CO_2R^{61}$, $CONR^{61}R^{62}$, $CONR^{61}SO_2R^{62}$, $COR^{61}$, $NR^{61}$—CO—$R^{61}$, $NR^{61}$—CO—$NR^{61}R^{62}$, $NR^{61}$—$SO_2$—$NR^{61}R^{62}$, $NR^{61}R^{62}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl;

$R^{53}$ is a 6-10 membered mono- or bicyclic aryl or a 5-14 membered mono-, bi- or tricyclic heteroaryl containing 1 to 5 heteroatoms independently selected from the group consisting of N, O and S, wherein aryl and heteroaryl are unsubstituted or substituted with 1 to 5 substituents independently selected from the group consisting of halogen, CN, $C_{1-6}$-alkyl, $C_{2-6}$-alkenyl, $C_{2-6}$-alkynyl, halo-$C_{1-6}$-alkyl, OH, O—$C_{1-6}$-alkyl, O-halo-$C_{1-6}$-alkyl, $C_{0-6}$-alkylene-$C_{3-10}$-cycloalkyl, $C_{0-6}$-alkylene-O—$C_{3-10}$-cycloalkyl, $C_{0-6}$-alkylene-$C_{3-10}$-heterocycloalkyl, $C_{0-6}$-alkylene-$COOR^{81}$, $C_{0-6}$-alkylene-$C(O)R^{81}$, $C_{0-6}$-alkylene-$C(O)N(R^{81})_2$, $C_{0-6}$-alkylene-$N(R^{81})_2$, $C_{0-6}$-alkylene-$SO_2$—$N(R^{81})_2$, $C_{0-6}$-alkylene-$SO_2$—$R^{81}$, $C_{0-6}$-alkylene-(6-10-membered mono- or bicyclic aryl), and $C_{0-6}$-alkylene-(6-10-membered mono- or bicyclic heteroaryl), wherein alkyl, alkenyl, alkynyl, alkylene, cycloalkyl, heterocycloalkyl and heteroaryl are unsubstituted or substituted by 1 to 3 substituents independently selected from the group consisting of $C_{1-6}$-alkyl, halo-$C_{1-6}$-alkyl, halogen, OH, oxo, =N—$OR^{82}$, $N(R^{81})_2$, O—$C_{1-6}$-alkyl, O-halo-$C_{1-6}$-alkyl, COOH, $CON(R^{81})_2$, CN, $NR^{81}$—$COR^{81}$, $C_{3-10}$-cycloalkyl, $C_{3-10}$-heterocycloalkyl, 6-10-membered mono- or bicyclic aryl, and 6-10-membered mono- or bicyclic heteroaryl, or wherein two adjacent substituents may complete a 4- to 8-membered saturated or partially unsaturated ring containing carbon atoms and optionally containing 1 to 3 members selected from the group consisting of O, S, SO, $SO_2$ and $NR^{81}$, wherein the ring is unsubstituted or substituted with 1 to 4 substituents independently selected from the group consisting of halogen, oxo, =N—$OR^{82}$, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;

$R^{54}$ is $C_{0-6}$-alkylene-$R^{57}$, $C_3$-cycloalkyl-$R^{57}$, O—$C_{0-5}$-alkylene-$R^{57}$, $NR^{91}$—$C_{0-5}$-alkylene-$R^{57}$ and $SO_x$—$C_{0-5}$-alkylene-$R^{57}$, wherein alkylene is optionally substituted with 1 to 5 substituents independently selected from the group consisting of halogen, OH, oxo, =N—$OR^{82}$, $N(R^{81})_2$, O—$C_{1-6}$-alkyl, COOH, $CON(R^{81})_2$, CN, $NR^{81}$—$COR^{81}$, $C_{3-6}$-cycloalkyl and $C_{3-6}$-heterocycloalkyl;

$R^{55}$ is independently selected from H, $C_{1-6}$-alkyl and $C_{3-6}$-cycloalkyl, wherein alkyl and cycloalkyl is optionally substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

$R^{56}$ is independently selected from the group consisting of H, halogen, CN, $C_{1-6}$-alkyl, $C_{3-6}$-cycloalkyl, O—$C_{1-6}$-alkyl and $CONHR^{61}R^{62}$, wherein alkyl and cycloalkyl is unsubstituted or substituted with 1 to 5 substituents independently selected from the group consisting of halogen, OH, oxo, O—$C_{1-3}$-alkyl; O-halo-$C_{1-3}$-alkyl and $C_{3-6}$-cycloalkyl;

$R^{57}$ is $C_{1-10}$-alkyl, $C_{3-10}$-cycloalkyl, $C_{3-10}$-heterocycloalkyl, 6-10-membered mono- or bicyclic aryl or 6-10-membered mono- or bicyclic heteroaryl, wherein alkyl, cycloalkyl, heterocycloalkyl, aryl and heteroaryl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, $C_{3-10}$-cycloalkyl and 5 to 10-membered heterocycloalkyl;

$R^{61}$ and $R^{81}$ are independently selected from the group consisting of H, $C_{1-6}$-alkyl, $C_{3-10}$-cycloalkyl, $C_{3-10}$-heterocycloalkyl, phenyl, 5-6-membered heteroaryl containing 1 to 4 heteroatoms independently selected from the group consisting of N, O and S, wherein alkyl, cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 10-membered heteroaryl, halogen, $NH_2$, $NH(C_{1-6}$-alkyl), $N(C_{1-6}$-alkyl$)_2$, $C_{3-10}$-heterocycloalkyl, $C_{3-10}$-cycloalkyl, $SO_2$—$C_{1-3}$-alkyl, oxo, and CN, wherein cycloalkyl and heterocycloalkyl are unsubstituted or substituted with 1 to 3 substituents independently selected from the group consisting of $C_{1-6}$-alkyl, halo-$C_{1-6}$-alkyl, OH, O—$C_{1-6}$-alkyl, O-halo-$C_{1-6}$-alkyl, phenyl, 5 to 6-membered heteroaryl, halogen, $NH_2$, $NH(C_{1-6}$-alkyl), $N(C_{1-6}$-alkyl$)_2$ and $C_{3-10}$-cycloalkyl, wherein phenyl and heteroaryl are unsubstituted or substituted with 1 to 3 substituents independently selected from the group consisting of OH, O—$C_{1-6}$-alkyl, O-halo-$C_{1-6}$-alkyl, halogen, $C_{1-6}$-alkyl, halo-$C_{1-6}$-alkyl, $NH_2$, $NH(C_{1-6}$-alkyl), $N(C_{1-6}$-alkyl$)_2$ and $C_{3-10}$-cycloalkyl;

$R^{62}$ and $R^{82}$ are independently selected from the group consisting of H, $C_{1-6}$-alkyl, halo-$C_{1-6}$-alkyl and $C_{3-10}$-cycloalkyl;

$R^{91}$ is H, $C_{1-6}$-alkyl, $C_{3-6}$-cycloalkyl or $C_{3-6}$-heterocycloalkyl, wherein alkyl, cycloalkyl and heterocycloalkyl are unsubstituted or substituted with 1 to 3 substituents independently selected from the group consisting of OH, oxo, CN, halogen, O—$C_{1-6}$-alkyl, O-halo-$C_{1-6}$-alkyl, $C_{3-6}$-heterocycloalkyl and $C_{3-6}$-cycloalkyl;

x is independently selected from 0, 1 and 2.

20. A pharmaceutical composition comprising a compound according to claim 1, or an enantiomer, a diastereomer, a tautomer, an N-oxide or a pharmaceutically acceptable salt thereof, and a pharmaceutically acceptable carrier or excipient.

21. A method for the treatment of a disease or disorder in a mammal associated with the inhibition or activation of the RORγ receptor, wherein the method comprises administering to the mammal an effective amount of a compound according to claim 1, or an enantiomer, a diastereomer, a tautomer, an N-oxide, a formulation or a pharmaceutically acceptable salt thereof.

22. The method according to claim 21, wherein the disease or disorder is selected from rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, epidermal hyperplasia, glomerulonephritis, chronic obstructive pulmonary disease and amyotrophic lateral sclerosis.

23. A method for the treatment of a disease or disorder in a mammal associated with the inhibition or activation of the RORγ receptor, wherein the method comprises administering to the mammal an effective amount of a pharmaceutical composition according to claim 19 or claim 20.

* * * * *

UNITED STATES PATENT AND TRADEMARK OFFICE
CERTIFICATE OF CORRECTION

PATENT NO. : 9,458,104 B2
APPLICATION NO. : 14/419468
DATED : October 4, 2016
INVENTOR(S) : Christian Gege et al.

It is certified that error appears in the above-identified patent and that said Letters Patent is hereby corrected as shown below:

In the Claims

Column 249, Lines 36-37:
"$SO_2NR^{11}R^{12}$; $NR^{11}COR^{11}$; $NR^{11}SO_2R^{11}$; $NR^{11}$-CO-$NR^{11}R^{12}$," should read --$SO_2NR^{11}R^{12}$, $NR^{11}COR^{11}$, $NR^{11}SO_2R^{11}$, $NR^{11}$-CO-$NR^{11}R^{12}$,--.

Column 251, Line 65:
"$NR^{11}$-CO-$NR^{11}R^{12}$, $SO_2$-$NR^{11}R^{12}$," should read --$NR^{11}$-CO-$NR^{11}R^{12}$, $NR^{11}$-$SO_2$-$NR^{11}R^{12}$,--.

Column 264, Lines 43-51:
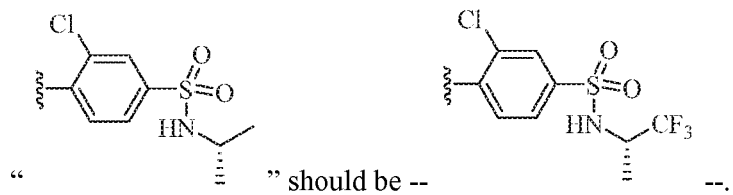

Column 264, Lines 52-58:
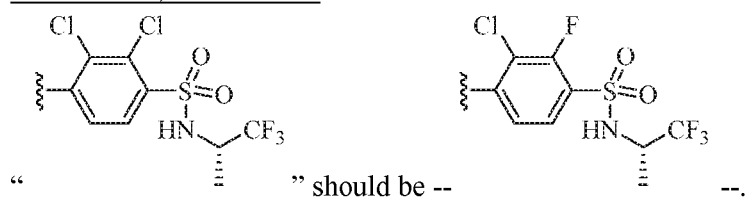

Column 277, Line 59:
"$OR_{61}$, $SO_xR_{61}$, $SO_3H$," should read --$OR^{61}$, $SO_xR^{61}$, $SO_3H$,--.

Column 279, Lines 62-63:
"$C_{1-3}$-alkyl, cycloalkyl and heterocycloalkyl." should read --$C_{1-3}$-alkyl, halo-$C_{1-3}$-alkyl, cycloalkyl and heterocycloalkyl.--.

Signed and Sealed this
Fourteenth Day of November, 2017

Joseph Matal
*Performing the Functions and Duties of the
Under Secretary of Commerce for Intellectual Property and
Director of the United States Patent and Trademark Office*

Column 280, Lines 64-65:
"$NR^{61}$-$SO_2$-$NR^{61}R^{62}$, $O_{3-6}$-cycloalkyl, $O$-$C_{3-6}$-cycloalkyl," should read --$NR^{61}$-$SO_2$-$NR^{61}R^{62}$, $C_{3-6}$-cycloalkyl, $O$-$C_{3-6}$-cycloalkyl,--.